US008901139B2

(12) United States Patent
Venkatraman et al.

(10) Patent No.: US 8,901,139 B2
(45) Date of Patent: Dec. 2, 2014

(54) TRICYCLIC INDOLE DERIVATIVES AND METHODS OF USE THEREOF

(75) Inventors: Srikanth Venkatraman, Edison, NJ (US); Anilkumar Gopinadhan Nair, Edison, NJ (US); Kevin X. Chen, Edison, NJ (US); Francisco Velazquez, Clinton, NJ (US); Qingbei Zeng, Edison, NJ (US); Duan Liu, Arlington, MA (US); Yueheng Jiang, Whitehouse Station, NJ (US); Joseph A. Kozlowski, Princeton, NJ (US); F. George Njoroge, Warren, NJ (US); Stuart B. Rosenblum, West Orange, NJ (US); Stephen J. Gavalas, Manhasset, NY (US); Patrick A. Pinto, Morris Plains, NJ (US); Oleg B. Selyutin, West Windsor, NJ (US); Bancha Vibulbhan, Kenilworth, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 681 days.

(21) Appl. No.: 12/997,654

(22) PCT Filed: Jun. 10, 2009

(86) PCT No.: PCT/US2009/046822

§ 371 (c)(1),
(2), (4) Date: Apr. 11, 2011

(87) PCT Pub. No.: WO2009/152200

PCT Pub. Date: Dec. 17, 2009

(65) Prior Publication Data

US 2011/0189127 A1 Aug. 4, 2011

Related U.S. Application Data

(60) Provisional application No. 61/061,344, filed on Jun. 13, 2008.

(51) Int. Cl.

| | |
|---|---|
| ***C07D 491/04*** | (2006.01) |
| ***C07D 519/00*** | (2006.01) |
| ***C07D 491/048*** | (2006.01) |
| *A61K 31/517* | (2006.01) |
| *A61P 31/12* | (2006.01) |
| *C07D 401/14* | (2006.01) |

(52) U.S. Cl.

CPC .......... *C07D 491/048* (2013.01); *C07D 491/04* (2013.01); *C07D 519/00* (2013.01)

USPC ...... 514/266.21; 514/280; 514/314; 514/338; 544/284; 546/174; 546/276.7; 546/48

(58) Field of Classification Search

CPC . C07D 491/04; C07D 519/00; C07D 491/048

USPC ....................................... 546/276.7; 514/338

See application file for complete search history.

(56) References Cited

U.S. PATENT DOCUMENTS

| | | | |
|---|---|---|---|
| 3,632,805 | A | 1/1972 | Yamamoto et al. |
| 4,634,697 | A | 1/1987 | Hamashima |
| 4,812,561 | A | 3/1989 | Hamashima et al. |
| 4,933,443 | A | 6/1990 | Hamashima et al. |
| 5,017,380 | A | 5/1991 | Hamashima et al. |
| 6,800,434 | B2 | 10/2004 | Saksena et al. |
| 6,838,475 | B2 | 1/2005 | Arasappan et al. |
| 6,846,802 | B2 | 1/2005 | Chen et al. |
| 6,911,428 | B2 | 6/2005 | Zhu et al. |
| 6,914,122 | B2 | 7/2005 | Venkatraman et al. |
| 7,012,066 | B2 | 3/2006 | Saksena et al. |
| 2002/0160962 | A1 | 10/2002 | Saksena et al. |
| 2004/0077704 | A1 | 4/2004 | Beight et al. |

(Continued)

FOREIGN PATENT DOCUMENTS

| | | |
|---|---|---|
| AU | 2002313410 B2 | 7/2002 |
| DE | 648639 C | 8/1937 |

(Continued)

OTHER PUBLICATIONS

Tan et al., "Hepatitis C Therapeutics: Current Status and Emerging Strategies", Nature Reviews, 2002, vol. 1, pp. 867-881.
Beaulieu et al., "Inhibitors of the HCV NS5B polymerase: New hope for the treatment of hepatitis C infections", Current Opinion in Investigational Drugs, 2004, vol. 5, pp. 838-850, No. 8.
Behrens et al., "Identification and properties of the RNA-dependent RNA polymerase of hepatitis C virus", The EMBO Journal, 1996, vol. 15, pp. 12-22, No. 1.
Bioworld Today, 9 (217):4 Nov. 10, 1998, pp. 1-5.
Birnbock et al., "Sulfate Derivatives of 2-Phenylindols as Novel Steroid Sulfatase Inhibitors", Biochemical Pharmacology, 1990, vol. 39, pp. 1709-1713, No. 11.

(Continued)

*Primary Examiner* — Susanna Moore

(74) *Attorney, Agent, or Firm* — Henry P. Wu; Sheldon O. Heber

(57) ABSTRACT

The present invention relates to Tricyclic Indole Derivatives, compositions comprising at least one Tricyclic Indole Derivatives, and methods of using the Tricyclic Indole Derivatives for treating or preventing a viral infection or a virus-related disorder in a patient.

(I)

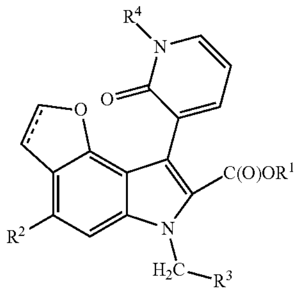

19 Claims, No Drawings

(56) References Cited

U.S. PATENT DOCUMENTS

| | | | | |
|---|---|---|---|---|
| 2005/0075331 | A1 | 4/2005 | Pratt et al. | |
| 2005/0101770 | A1 | 5/2005 | Presta | |
| 2005/0176648 | A1 | 8/2005 | Saksena et al. | |
| 2005/0249702 | A1 | 11/2005 | Njoroge et al. | |
| 2007/0274951 | A1 | 11/2007 | Tong et al. | |
| 2010/0098661 | A1* | 4/2010 | Chen et al. | 424/85.7 |
| 2010/0196319 | A1 | 8/2010 | Anilkumar et al. | |
| 2010/0239527 | A1 | 9/2010 | Anilkumar et al. | |
| 2010/0260711 | A1 | 10/2010 | Chen et al. | |
| 2010/0322901 | A1 | 12/2010 | Bennett et al. | |
| 2011/0033417 | A1 | 2/2011 | Anilkumar et al. | |
| 2011/0104109 | A1 | 5/2011 | Bennett et al. | |
| 2011/0104110 | A1 | 5/2011 | Anikumar et al. | |
| 2011/0165118 | A1 | 7/2011 | Chan et al. | |

FOREIGN PATENT DOCUMENTS

| | | | |
|---|---|---|---|
| EP | 0449196 | A2 | 10/1991 |
| FR | 2768146 | A1 | 3/1999 |
| JP | 4-149429 | | 5/2004 |
| WO | 96/37619 | A1 | 11/1996 |
| WO | 98/14181 | A1 | 4/1998 |
| WO | 98/17679 | A1 | 4/1998 |
| WO | 98/22496 | A2 | 5/1998 |
| WO | 99/07734 | A2 | 2/1999 |
| WO | 02/30895 | A1 | 4/2002 |
| WO | 02/068412 | A1 | 9/2002 |
| WO | 2004/035571 | A1 | 4/2004 |
| WO | 2004/106328 | A1 | 12/2004 |
| WO | 2005/034941 | A1 | 4/2005 |
| WO | 2005/084315 | A2 | 9/2005 |
| WO | 2005/087731 | A1 | 9/2005 |
| WO | 2005/111018 | A1 | 11/2005 |
| WO | 2006/020082 | A1 | 2/2006 |
| WO | 2006/032541 | A1 | 3/2006 |
| WO | 2006/034337 | A2 | 3/2006 |
| WO | 2006/046030 | A2 | 5/2006 |
| WO | 2005/076529 | A1 | 7/2006 |
| WO | 2007/029029 | A2 | 3/2007 |
| WO | 2007/038209 | A2 | 4/2007 |
| WO | 2007/084413 | A2 | 7/2007 |
| WO | 2007/084435 | A2 | 7/2007 |
| WO | 2008/082484 | A1 | 7/2008 |

OTHER PUBLICATIONS

Bunker et al., "1,3-Diaryl-2-Carboxyindoles as Potent Non-Peptide Endothelin Antagonists", Bioorganic & Medicinal Chemistry Letters, 1996, vol. 6, pp. 1061-1066, No. 9.

Chemical and Pharmaceutical Bulletin, vol. 19, 1971, p. 263-270.

Denmark et al., "Palladium-Catalyzed Cross-Coupling Reactions of Silanolates: A Paradigm Shift in Silicon-Based Cross-Coupling Reactions", Chem. Eur. J., 2006, vol. 12. pp. 4954-4963.

Dimasi et al.. "Characterization of Engineered Hepatitis C Virus NS3 Protease Inhibitors Affinity Selected from Human Pancreatic Secretory Trypsin Inhibitor and Minibody Repertoires". Journal of Virology. 1997, vol. 71, pp. 7461-7469, No. 10.

Elzouki et al., "Senne protease inhibitors in patients with chronic viral hepatitis", Journal of Hepatology, 1997, vol. 27, pp. 42-48.

Ferrari et al., "Characterization of Soluble Hepatitis C Virus RNA-Dependent RNA Polymerase Expressed in *Escherichia coli*", Journal of Virology. 1999, vol. 73, pp. 1649-1654, No. 2.

Fonseca et al., "Synthesis and antiviral evaluation of benzimidazoles, quinoxalines and indoles from dehydroabietic acid", Bioorganic & Medicinal Chemistry, 2004, vol. 12. pp. 103-112.

Forbes et al., "Synthesis, Biological Activity, and Molecular Modeling Studies of Selective 5-HT2C/2B Receptor Antagonists", J. Med. Chem., 1996, vol. 39, pp. 4966-4977, No. 25.

Goldsmith et al., "Studies in the Benzindole Series", J. Org. Chem, 1952, vol. 18, pp. 507-514.

Gopalsamy et al., "Design and synthesis of 2,3,4,9-tetrahydro-1H-carbazole and 1,2,3,4-tetrahydro-cyclopenta[b] indole derivatives and non-nucleoside inhibitors of hepatitis C virus NS5B RNA-dependent RNA polymerase", Bioorganic & Medicinal Chemistry Letters, 2006, vol. 16, pp. 2532-2534.

Humphrey et al., "Practical Methodologies for the Synthesis of Indoles", Chem. Rev., 2006, vol. 106, pp. 2875-2911.

International Search Report for International Application No. PCT/US2007/025764, mailed May 13, 2008, (4 pages).

Written Opinion for PCT/US2007/025754, filed Dec. 17, 2007, (7 pages).

International Search Report for International Application No. PCT/US2007/025765, mailed May 13, 2008, (6 pages).

Written Opinion for PCT/US2007/025765, filed Dec. 17, 2007, (8 pages).

International Search Report for International Application No. PCT/US2007/025757, mailed Mar. 6, 2009, (8 pages).

Written Opinion for PCT/US20074/025757, filed Dec. 17, 2007 (12 pages).

International Search Report for International Application No. PCT/US2008/010130, mailed Jan. 22, 2009, (5 pages).

Written Opinion for PCT/US2008/010130, filed Aug. 27, 2008 (9 pages).

International Search Report for International Application No. PCT/US2008/010149, mailed Feb. 2, 2009, (5 pages).

Written Opinion for PCT/US2008/010149, filed Aug. 27, 2008 (6 pages).

International Search Report for International Application No. PCT/US2008/083351, mailed Feb. 27, 2009, (3 pages).

Written Opinion for PCT/US2008/083351, filed Nov. 13, 2008 (5 pages).

International Search Report for International Application No. PCT/US2008/010147, mailed May 4, 2009, (3 pages).

Written Opinion for PCT/US2008/010147, filed Aug. 27, 2008 (6 pages).

International Search Report for International Application No. PCT/US2008/083358, mailed Mar. 6, 2009, (2 pages).

Written Opinion for PCT/US2008/083358, filed Nov. 13, 2008 (5 pages).

International Search Report for International Application No. PCT/US2008/010148, mailed Dec. 9, 2008, (3 pages).

Written Opinion for PCT/US2008/010148, filed Aug. 27, 2008 (7 pages).

International Search Report for International Application No. PCT/US2009/046822, mailed Oct. 7, 2009, (5 pages).

Written Opinion for PCT/US2009/046822, filed Jun. 10, 2009 (8 pages).

Ingallinella et al., "Potent Peptide Inhibitors of Human Hepatitis C Virus NS3 Protease are Obtained by Optimizing the Cleavage Products", Biochemistry, 1998, vol. 37, pp. 8906-8914.

Journal of Heterocyclic Chemistry, vol. 12, 1975, pp. 351-358.

Journal of Medicinal Chemistry, vol. 23, No. 7, 1960, pp. 764-773.

Journal of Organic Chemistry, vol. 27, 1962, pp. 3782-3786.

Landro et al., "Mechanistic Role of an NS4A Peptide Cofactor with the Truncated NS3 Protease of Hepatitis C Virus: Elucidation of the NS4A Stimulatory Effect via Kinetic Analysis and Inhibitor Mapping", Biochemistry, 1997, vol. 36, pp. 9340-9348.

Lindsay et al., "Sml2-Promoted Radical Addition Reactions with N-(2-Indolylacyl)oxazolidinones: Synthesis of Bisindole Compounds", Journal of Organic Chemistry, 2007, vol. 72, pp. 4181-4188, No. 11.

Llinas-Brunet et al., "Peptide-Based Inhibitors of the Hepatitis C Virus Serine Protease", Bioorganic & Medicinal Chemistry Letters, 1998, vol. 8, pp. 1713-1718.

Malcolm et al., "SCH 503034, a Mechanism-Based Inhibitor of Hepatitis C Virus NS3 Protease, Suppresses Polyprotein Maturation and Enhances the Antiviral Activity of Alpha Interferon in Replicon Cells", Antimicrobial Agents and Chemotherapy, 2006, vol. 50, pp. 1013-1020, No. 3.

Martin, et al., "Affinity selection of a camelized VH domain antibody of hepatitis C virus NS3 protease", Protein Engineering, 1997, vol. 10, pp. 607-614, No. 5.

Martin et al., "Design of Selective Eglin Inhibitors of HCV NS3 Proteinase", Biochemistry, 1998, vol. 37, pp. 11459-11468.

(56) References Cited

OTHER PUBLICATIONS

Muratake et al., "Synthesis of Duocarmuycin SA by Way of Methyl 4-(Methoxycarbonyl)oxy-3H-pyrrolo[3,2-f] quinoline-2-carboxylate as a Tricyclic Heteroaromatic Intermediate", Chem. Pharm. Bulleting, 1998, vol. 46, pp. 400-412, No. 3.

Ni et al., "Progress and development of small molecule HCV antivirals", Current Opinion in Drug Discovery & Development, 2004, vol. 7, pp. 446-459, No. 4.

Rawal et al., "Photocyclization of Pyrrole Analogues of Stilbene: an Expedient Approach to Anti-tumour Agent CC-1065", Journal Chem. Soc., Chem. Commun., 1984, pp. 1526-1527.

Sechi et al.; "Design and Synthesis of Novel Indole β-Diketo Acid Derivatives as HIV-1 Integrase Inhibitors", J. Med. Chem., 2004, vol. 47, pp. 5298-5310, No. 21.

Silvestri et al., "Synthesis and biological evaluation of 5H-indolo [3,2-b][1,5]benzothiazepine derivatives, designed as conformationally constrained analogues of the human immunodeficiency virus type 1 reverse transcriptase inhibitor L-737, 126", Antiviral Chemistry & Chemotherapy, 1998, vol. 9, pp. 139-148.

* cited by examiner

SEQUENCE LISTING

<160> NUMBER OF SEQ ID NOS: 4

<210> SEQ ID NO 1
<211> LENGTH: 75
<212> TYPE: RNA
<213> ORGANISM: Artificial Sequence
<220> FEATURE:
<223> OTHER INFORMATION: RNA template

<400> SEQUENCE: 1
ugugccgguc uuucugaacg ggauauaaac cuggccagcu ucaucgaaca aguugccgug 60
ucuaugacau agauc 75

<210> SEQ ID NO 2
<211> LENGTH: 17
<212> TYPE: DNA
<213> ORGANISM: Artificial Sequence
<220> FEATURE:
<223> OTHER INFORMATION: PCR primer 5B.2F

<400> SEQUENCE: 2
atggacaggc gccctga 17

<210> SEQ ID NO 3
<211> LENGTH: 20
<212> TYPE: DNA
<213> ORGANISM: Artificial Sequence
<220> FEATURE:
<223> OTHER INFORMATION: PCR primer 5B.2R

<400> SEQUENCE: 3
ttgatgggca gcttggtttc 20

-continued

```
<210> SEQ ID NO 4
<211> LENGTH: 17
<212> TYPE: DNA
<213> ORGANISM: Artificial Sequence
<220> FEATURE:
<223> OTHER INFORMATION: FAM labeled probe

<400> SEQUENCE: 4

cacgccatgc gctgcgg                                                17
```

TRICYCLIC INDOLE DERIVATIVES AND METHODS OF USE THEREOF

CROSS-REFERENCE TO RELATED APPLICATIONS

This application is the National Stage of International Application No. PCT/US2009/046822, filed Jun. 10, 2009. This application also claims the benefit of U.S. Provisional Application No. 61/061.344, filed Jun. 13, 2008.

REFERENCE TO SEQUENCE LISTING SUBMITTED ELECTRONICALLY

The sequence listing of the present application is submitted electronically via EFS-Web as an ASCII formatted sequence listing with a file name "IN06831-US-PCT _SEQ_LIST-.TXT," creation date of Apr. 8, 2010, and a size of 2.0 KB. This sequence listing submitted via EFS-Web is part of the specification and is herein incorporated by reference in its entirety.

FIELD OF THE INVENTION

The present invention relates to Tricyclic Indole Derivatives, compositions comprising at least one Tricyclic Indole Derivatives, and methods of using the Tricyclic Indole Derivatives for treating or preventing a viral infection or a virus-related disorder in a patient.

BACKGROUND OF THE INVENTION

HCV is a (+)-sense single-stranded RNA virus that has been implicated as the major causative agent in non-A, non-B hepatitis (NANBH). NANBH is distinguished from other types of viral-induced liver disease, such as hepatitis A virus (HAV), hepatitis B virus (HBV), hepatitis delta virus (HDV), as well as from other forms of liver disease such as alcoholism and primary biliary cirrhosis.

Hepatitis C virus is a member of the hepacivirus genus in the family Flaviviridae. It is the major causative agent of non-A, non-B viral hepatitis and is the major cause of transfusion-associated hepatitis and accounts for a significant proportion of hepatitis cases worldwide. Although acute HCV infection is often asymptomatic, nearly 80% of cases resolve to chronic hepatitis. About 60% of patients develop liver disease with various clinical outcomes ranging from an asymptomatic carrier state to chronic active hepatitis and liver cirrhosis (occurring in about 20% of patients), which is strongly associated with the development of hepatocellular carcinoma (occurring in about 1-5% of patients). The World Health Organization estimates that 170 million people are chronically infected with HCV, with an estimated 4 million living in the United States.

HCV has been implicated in cirrhosis of the liver and in induction of hepatocellular carcinoma. The prognosis for patients suffering from HCV infection remains poor as HCV infection is more difficult to treat than other forms of hepatitis. Current data indicates a four-year survival rate of below 50% for patients suffering from cirrhosis and a five-year survival rate of below 30% for patients diagnosed with localized resectable hepatocellular carcinoma. Patients diagnosed with localized unresectable hepatocellular carcinoma fare even worse, having a five-year survival rate of less than 1%.

HCV is an enveloped RNA virus containing a single-stranded positive-sense RNA genome approximately 9.5 kb in length. The RNA genome contains a 5'-nontranslated region (5' NTR) of 341 nucleotides, a large open reading frame (ORF) encoding a single polypeptide of 3,010 to 3,040 amino acids, and a 3'-nontranslated region (3'-NTR) of variable length of about 230 nucleotides. HCV is similar in amino acid sequence and genome organization to Flaviviruses and pestiviruses, and therefore HCV has been classified as a third genus of the family Flaviviridae.

The 5' NTR, one of the most conserved regions of the viral genome, contains an internal ribosome entry site (IRES) which plays a pivotal role in the initiation of translation of the viral polyprotein. A single long open reading frame encodes a polyprotein, which is co- or post-translationally processed into structural (core, E1, E2 and p7) and nonstructural (NS2, NS3, NS4A, NS4B, NS5A, and NS5B) viral proteins by either cellular or viral proteinases. The 3' NTR consists of three distinct regions: a variable region of about 38 nucleotides following the stop codon of the polyprotein, a polyuridine tract of variable length with interspersed substitutions of cytidines, and 98 nucleotides (nt) at the very 3' end which are highly conserved among various HCV isolates. By analogy to other plus-strand RNA viruses, the 3'-NTR is thought to play an important role in viral RNA synthesis. The order of the genes within the genome is: $NH_2$—C-E1-E2-p7-NS2-NS3-NS4A-NS4B-NS5A-NS5B-COOH.

Processing of the structural proteins core (C), envelope protein 1 and (E1, E2), and the p7 region is mediated by host signal peptidases. In contrast, maturation of the nonstructural (NS) region is accomplished by two viral enzymes. The HCV polyprotein is first cleaved by a host signal peptidase generating the structural proteins C/E1, E1/E2, E2/p7, and p7/NS2. The NS2-3 proteinase, which is a metalloprotease, then cleaves at the NS2/NS3 junction. The NS3/4A proteinase complex (NS3 being a serine protease and NS4A acting as a cofactor of the NS3 protease), is then responsible for processing all the remaining cleavage junctions. RNA helicase and NTPase activities have also been identified in the NS3 protein. One-third of the NS3 protein functions as a protease, and the remaining two-thirds of the molecule acts as the helicase/ATPase that is thought to be involved in HCV replication. NS5A may be phosphorylated and acts as a putative cofactor of NS5B. The fourth viral enzyme, NS5B, is a membrane-associated RNA-dependent RNA polymerase (RdRp) and a key component responsible for replication of the viral RNA genome. NS5B contains the "GDD" sequence motif, which is highly conserved among all RdRps characterized to date.

Replication of HCV is thought to occur in membrane-associated replication complexes. Within these, the genomic plus-strand RNA is transcribed into minus-strand RNA, which in turn can be used as a template for synthesis of progeny genomic plus-strands. At least two viral enzymes appear to be involved in this reaction: the NS3 helicase/NTPase, and the NS5B RNA-dependent RNA polymerase. While the role of NS3 in RNA replication is less clear, NS5B is the key enzyme responsible for synthesis of progeny RNA strands. Using recombinant baculoviruses to express NS5B in insect cells and a synthetic nonviral RNA as a substrate, two enzymatic activities have been identified as being associated with it: a primer-dependent RdRp and a terminal transferase (TNTase) activity. It was subsequently continued and further characterized through the use of the HCV RNA genome as a substrate. Other studies have shown that NS5B with a C-terminal 21 amino-acid truncation expressed in *Escherichia coli* is also active for in vitro RNA synthesis. On certain RNA templates, NS5B has been shown to catalyze RNA synthesis via a de novo initiation mechanism, which has been postulated to be the mode of viral replication in vivo. Templates with single-stranded 3' termini, especially those containing a 3'-terminal cytidylate moiety, have been found to direct de novo synthesis efficiently. There has also been evidence for NS5B to utilize di- or tri-nucleotides as short primers to initiate replication.

It is well-established that persistent infection of HCV is related to chronic hepatitis, and as such, inhibition of HCV replication is a viable strategy for the prevention of hepatocellular carcinoma. Present treatment approaches for HCV infection suffer from poor efficacy and unfavorable side-effects and there is currently a strong effort directed to the discovery of HCV replication inhibitors that are useful for the treatment and prevention of HCV related disorders. New approaches currently under investigation include the development of prophylactic and therapeutic vaccines, the identification of interferons with improved pharmacokinetic characteristics, and the discovery of agents designed to inhibit the function of three major viral proteins: protease, helicase and polymerase. In addition, the HCV RNA genome itself, particularly the IRES element, is being actively exploited as an antiviral target using antisense molecules and catalytic ribozymes.

Particular therapies for HCV infection include α-interferon monotherapy and combination therapy comprising α-interferon and ribavirin. These therapies have been shown to be effective in some patients with chronic HCV infection. The use of antisense oligonucleotides for treatment of HCV infection has also been proposed as has the use of free bile acids, such as ursodeoxycholic acid and chenodeoxycholic acid, and conjugated bile acids, such as tauroursodeoxycholic acid. Phosphonoformic acid esters have also been proposed as potentially for the treatment of various viral infections including HCV. Vaccine development, however, has been hampered by the high degree of viral strain heterogeneity and immune evasion and the lack of protection against reinfection, even with the same inoculum.

The development of small-molecule inhibitors directed against specific viral targets has become a major focus of anti-HCV research. The determination of crystal structures for NS3 protease, NS3 RNA helicase, and NS5B polymerase, with and without bound ligands, has provided important structural insights useful for the rational design of specific inhibitors.

NS5B, the RNA-dependent RNA polymerase, is an important and attractive target for small-molecule inhibitors. Studies with pestiviruses have shown that the small molecule compound VP32947 (3-[((2-dipropylamino)ethyl)thio]-5H-1,2,4-triazino[5,6-b]indole) is a potent inhibitor of pestivirus replication and most likely inhibits the NS5B enzyme since resistant strains are mutated in this gene. Inhibition of RdRp activity by (−)β-L-2',3'-dideoxy-3'-thiacytidine 5'-triphosphate (3TC; lamivudine triphosphate) and phosphonoacetic acid also has been observed.

Despite the intensive effort directed at the treatment and prevention of HCV and related viral infections, there exists a need in the art for non-peptide, small-molecule compounds having desirable or improved physicochemical properties that are useful for inhibiting viruses and treating viral infections and virus-related disorders.

SUMMARY OF THE INVENTION

In one aspect, the present invention provides compounds having the formula:

(I)

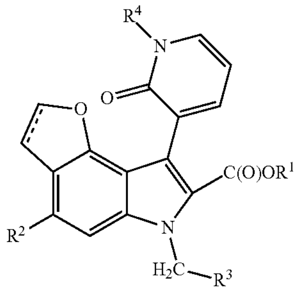

and pharmaceutically acceptable salts, solvates, esters and prodrugs thereof, wherein the dotted line represents an optional and additional bond, and wherein:

$R^1$ is H, alkyl, alkenyl, -alkylene-OC(O)-alkyl, -alkylene-aryl, aminoalkyl or -alkylene-heterocycloalkyl;

$R^2$ is H, F, Cl or $—CH_3$;

$R^3$ is phenyl, naphthyl, nitrogen-containing heterocycloalkyl, nitrogen-containing heterocycloalkenyl or nitrogen-containing heteroaryl, any of which can be optionally substituted with up to 3 groups, which can be the same or different, and are selected from methyl, t-butyl, allyl, F, Cl, Br, —CN, $—O—CH_2CH_3$, $—S(O)CH_3$, $—S(O)_2CH_3$, $—NH_2$, —OH, $—CH_2NH_2$, $—C(O)NH_2$, $—C(O)NHCH_3$, —C(O)NH-cyclopropyl, hydroxyalkyl, —C(O)H, $—C(O)CH_3$, —C(O)O-isopropyl, —C(O)O-t-butyl, $—CH_2C(O)$-t-butyl, $—OCH_3$, $—NHCH_3$, $—SCH_3$, $—C(O)NHCH_3$, $—NHC(O)OCH_3$, —NHC(O)O-isopropyl, $—CH_2N(CH_3)_2$, $—OC(O)CH(CH_3)NHC(O)O$-t-butyl, $—OC(O)CH(CH_3)NH_2$, —C(O)O-t-butyl, $—CH_2C(O)O$-t-butyl, $—OCH_2CH_2N(CH_3)_2$, morpholinyl, $—CH_2OC(O)$-t-butyl, —CH(=NOH), $—CH(=NOCH_3)$, $—NHC(O)CH_2N(CH_3)_2$ and —NHC(O)O-t-butyl; and $R^4$ is H or —C(O)O-alkyl.

The Compounds of Formula (I) (also referred to herein as the "Tricyclic Indole Derivatives") and pharmaceutically acceptable salts, solvates, esters and prodrugs thereof can be useful for treating or preventing a viral infection in a patient.

The Tricyclic Indole Derivatives or pharmaceutically acceptable salts, solvates, prodrugs or esters thereof can also be useful for treating or preventing a virus-related disorder in a patient.

Also provided by the invention are methods for treating or preventing a viral infection or a virus-related disorder in a patient, comprising administering to the patient an effective amount of at least one Tricyclic Indole Derivative.

The present invention further provides pharmaceutical compositions comprising an effective amount of at least one Tricyclic Indole Derivative or a pharmaceutically acceptable salt, solvate, ester or prodrug thereof, and a pharmaceutically acceptable carrier. The compositions can be useful for treating or preventing a viral infection or a virus-related disorder in a patient.

The details of the invention are set forth in the accompanying detailed description below.

Although any methods and materials similar to those described herein can be used in the practice or testing of the present invention, illustrative methods and materials are now described. Other features, objects, and advantages of the invention will be apparent from the description and the claims. All patents and publications cited in this specification are incorporated herein by reference.

DETAILED DESCRIPTION OF THE INVENTION

The present invention provides Tricyclic Indole Derivatives, pharmaceutical compositions comprising at least one Tricyclic Indole Derivative, and methods of using the Tricyclic Indole Derivatives for treating or preventing a viral infection or a virus-related disorder in a patient.

Definitions and Abbreviations

The terms used herein have their ordinary meaning and the meaning of such terms is independent at each occurrence thereof. That notwithstanding and except where stated otherwise, the following definitions apply throughout the specification and claims. Chemical names, common names, and chemical structures may be used interchangeably to describe the same structure. If a chemical compound is referred to using both a chemical structure and a chemical name and an ambiguity exists between the structure and the name, the structure predominates. These definitions apply regardless of whether a terms is used by itself or in combination with other terms, unless otherwise indicated. Hence, the definition of "alkyl" applies to "alkyl" as well as the "alkyl" portions of "aminoalkyl," "haloalkyl," "alkoxy," etc. . . .

As used herein, and throughout this disclosure, the following terms, unless otherwise indicated, shall be understood to have the following meanings:

A "patient" is a human or non-human mammal. In one embodiment, a patient is a human. In another embodiment, a patient is a non-human mammal, including, but not limited to, a monkey, dog, baboon, rhesus, mouse, rat, horse, cat or rabbit. In another embodiment, a patient is a companion animal, including but not limited to a dog, cat, rabbit, horse or ferret. In one embodiment, a patient is a dog. In another embodiment, a patient is a cat.

The term "alkyl" as used herein, refers to an aliphatic hydrocarbon group, wherein one of the aliphatic hydrocarbon group's hydrogen atoms is replaced with a single bond. An alkyl group can be straight or branched and can contain from about 1 to about 20 carbon atoms. In one embodiment, an alkyl group contains from about 1 to about 12 carbon atoms. In another embodiment, an alkyl group contains from about 1 to about 6 carbon atoms. Non-limiting examples of alkyl groups include methyl, ethyl, n-propyl, isopropyl, n-butyl, sec-butyl, isobutyl, tert-butyl, n-pentyl, neopentyl, isopentyl, n-hexyl, isohexyl and neohexyl. An alkyl group may be unsubstituted or optionally substituted by one or more substituents which may be the same or different, each substituent being independently selected from the group consisting of halo, alkenyl, alkynyl, —O-aryl, aryl, heteroaryl, cycloalkyl, cycloalkenyl, cyano, —OH, —O-alkyl, —O-haloalkyl, -alkylene-O-alkyl, alkylthio, $—NH_2$, —NH(alkyl), $—N(alkyl)_2$, —NH-aryl, —NH-heteroaryl, —NHC(O)-alkyl, —NHC(O)NH-alkyl, $—NHSO_2$-alkyl, $—NHSO_2$-aryl, $—NHSO_2$-heteroaryl, —NH(cycloalkyl), —OC(O)-alkyl, —OC(O)-aryl, —OC(O)-cycloalkyl, —C(O)alkyl, $—C(O)NH_2$, —C(O)NH-alkyl, —C(O)OH and —C(O)O-alkyl. In one embodiment, an alkyl group is unsubstituted. In another embodiment, an alkyl group is a straight chain alkyl group. In another embodiment, an alkyl group is a branched alkyl group.

The term "aminoalkyl" as used herein, refers to an alkyl group, as defined above, wherein at least one of the alkyl group's hydrogen atoms is replaced with a group having the formula $—N(R')_2$, wherein each occurrence of R' is independently selected from H and alkyl. In one embodiment, an aminoalkyl group's alkyl moiety is linear. In another embodiment, an aminoalkyl group's alkyl moiety is branched. Illustrative examples of aminoalkyl groups include, but are not limited to, $—CH_2CH_2NH_2$, $—CH_2CH(NH_2)CH_3$, $—CH_2CH_2CH_2NH_2$, $—CH_2CH_2NHCH_3$, $—CH_2CH_2N(CH_3)_2$, $—CH_2CH(N(CH_3)_2)CH_3$ and $—CH_2CH_2CH_2N(CH_3)_2$.

The term "alkylene" as used herein, refers to an alkyl group, as defined above, wherein one of the alkyl group's hydrogen atoms is replaced with a bond. Illustrative examples of alkylene include, but are not limited to, $—CH_2—$, $—CH_2CH_2—$, $—CH_2CH_2CH_2—$, $—CH_2CH_2CH_2CH_2—$, $—CH(CH_3)CH_2CH_2—$, $—CH_2CH(CH_3)CH_2—$ and $—CH_2CH_2CH(CH_3)—$. In one embodiment, an alkylene group is a straight chain alkylene group. In another embodiment, an alkylene group is a branched alkylene group.

The term "nitrogen-containing heteroaryl" as used herein, refers to an aromatic monocyclic or multicyclic ring system comprising about 5 to about 14 ring atoms, wherein one of the ring atoms is nitrogen, up to 3 remaining ring atoms can independently O, N or S, and the remaining ring atoms are carbon atoms. In one embodiment, a nitrogen-containing heteroaryl group has 5 to 10 ring atoms. In another embodiment, a nitrogen-containing heteroaryl group is monocyclic and has 5 or 6 ring atoms. In another embodiment, a nitrogen-containing heteroaryl group is bicyclic and has 9 or 10 ring atoms. A nitrogen-containing heteroaryl group can be joined via a ring carbon or ring nitrogen atom. A nitrogen or sulfur atom of a nitrogen-containing heteroaryl group can be optionally oxidized to the corresponding N-oxide, S-oxide or S,S-dioxide. The term "nitrogen-containing heteroaryl" also encompasses a nitrogen-containing heteroaryl group, as defined above, which has been fused to a benzene ring. Non-limiting examples of illustrative nitrogen-containing heteroaryls include pyridyl, pyrazinyl, pyrimidinyl, isoxazolyl, isothiazolyl, oxazolyl, thiazolyl, pyrazolyl, indazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, indolyl, azaindolyl, benzimidazolyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "nitrogen-containing heteroaryl" also refers to partially saturated nitrogen-containing multicyclic heteroaryl moieties such as, for example, tetrahydroisoquinolyl, tetrahydroquinolyl and the like. In one embodiment, a nitrogen-containing heteroaryl group is a 6-membered monocyclic nitrogen-containing heteroaryl group. In another embodiment, a nitrogen-containing heteroaryl group is a 5-membered monocyclic nitrogen-containing heteroaryl group. In another embodiment, a nitrogen-containing heteroaryl group is a 9-membered bicyclic nitrogen-containing heteroaryl group. In another embodiment, a nitrogen-containing heteroaryl group is a 10-membered bicyclic nitrogen-containing heteroaryl group.

The term "nitrogen-containing heterocycloalkyl" as used herein, refers to a non-aromatic saturated monocyclic or multicyclic ring system comprising 3 to about 10 ring atoms, wherein one of the ring atoms is nitrogen, up to 3 remaining ring atoms can independently O, N or S, and the remaining ring atoms are carbon atoms. In one embodiment, a nitrogen-containing heterocycloalkyl group has from about 5 to about 10 ring atoms. In another embodiment, a nitrogen-containing heterocycloalkyl group has 5 or 6 ring atoms. There are no adjacent oxygen and/or sulfur atoms present in the ring system. Any —NH group in a nitrogen-containing heterocycloalkyl ring may exist protected such as, for example, as an —N(Boc), —N(CBz), —N(Tos) group and the like; such protected nitrogen-containing heterocycloalkyl groups are considered part of this invention. The nitrogen or sulfur atom of a nitrogen-containing heterocycloalkyl group can be optionally oxidized to the corresponding N-oxide, S-oxide or S,S-dioxide. Non-limiting examples of illustrative monocyclic nitrogen-containing heterocycloalkyl rings include piperidyl, pyrrolidinyl, piperazinyl, morpholinyl, thiomorpholinyl, thiazolidinyl, lactam, and the like. A ring carbon atom of a nitrogen-containing heterocycloalkyl group may be functionalized as a carbonyl group. An illustrative example of such a nitrogen-containing heterocycloalkyl group is pyrrolidonyl:

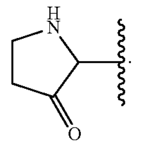 [SMILES: *C1NCCC1=O]

In one embodiment, a nitrogen-containing heterocycloalkyl group is a monocycle 6-membered nitrogen-containing monocyclic nitrogen-containing heterocycloalkyl group. In another embodiment, a nitrogen-containing heterocycloalkyl group is a 5-membered monocyclic nitrogen-containing heterocycloalkyl group. In another embodiment, a nitrogen-containing heterocycloalkyl group is a 9-membered bicyclic nitrogen-containing heterocycloalkyl group. In another embodiment, a nitrogen-containing heterocycloalkyl group is a 10-membered bicyclic nitrogen-containing heterocycloalkyl group.

The term "nitrogen-containing heterocycloalkenyl" as used herein, refers to a nitrogen-containing heterocycloalkyl group, as defined above, wherein the nitrogen-containing heterocycloalkyl group contains from 3 to 10 ring atoms, and at least one endocyclic carbon-carbon or carbon-nitrogen double bond. In one embodiment, a nitrogen-containing heterocycloalkenyl group is bicycle and has from 5 to 10 ring atoms. In another embodiment, a nitrogen-containing heterocycloalkenyl group is monocyclic and has 5 or 6 ring atoms. A nitrogen or sulfur atom of the nitrogen-containing heterocycloalkenyl can be optionally oxidized to the corresponding N-oxide, S-oxide or S,S-dioxide. Non-limiting examples of illustrative nitrogen-containing heterocycloalkenyl groups include 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, pyridone, 2-pyridone, dihydrothiopyranyl, and the like. A ring carbon atom of a nitrogen-containing heterocycloalkenyl group may be functionalized as a carbonyl group. An illustrative example of such a nitrogen-containing heterocycloalkenyl group is:

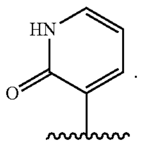 [SMILES: *c1ccc[nH]c1=O]

In one embodiment, a nitrogen-containing heterocycloalkenyl group is a 6-membered nitrogen-containing monocyclic heterocycloalkenyl group. In another embodiment, a nitrogen-containing heterocycloalkenyl group is a 5-membered nitrogen-containing monocyclic heterocycloalkenyl group. In another embodiment, a nitrogen-containing heterocycloalkenyl group is a 9-membered bicyclic nitrogen-containing heterocycloalkenyl group. In another embodiment, a nitrogen-containing heterocycloalkenyl group is a 10-membered nitrogen-containing bicyclic heterocycloalkenyl group.

The term "substituted," as used herein, means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound' or "stable structure" is meant a compound that is sufficiently robust to survive isolation to a useful degree of purity from a reaction mixture, and formulation into an efficacious therapeutic agent.

The term "optionally substituted" as used herein, means optional substitution with the specified groups, radicals or moieties.

The terms "purified", "in purified form" or "in isolated and purified form" as used herein, for a compound refers to the physical state of said compound after being isolated from a synthetic process (e.g. from a reaction mixture), or natural source or combination thereof. Thus, the term "purified", "in purified form" or "in isolated and purified form" for a compound refers to the physical state of said compound after being obtained from a purification process or processes described herein or well known to the skilled artisan (e.g., chromatography, recrystallization and the like), in sufficient purity to be characterizable by standard analytical techniques described herein or well known to the skilled artisan.

It should also be noted that any carbon as well as heteroatom with unsatisfied valences in the text, schemes, examples and tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" as used herein, refers to a compound (e.g., a drug precursor) that is transformed in vivo to provide a Tricyclic Indole Derivative or a pharmaceutically acceptable salt, hydrate or solvate thereof. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a Tricyclic Indole Derivative or a pharmaceutically acceptable salt, hydrate or solvate of the compound contains a carboxylic acid functional group, a prodrug can comprise an ester formed by the replacement of the hydrogen atom of the acid group with a group such as, for example, ($C_1$-$C_8$)alkyl, ($C_2$-$C_{12}$)alkanoyloxymethyl, 1-(alkanoyloxy) ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—($C_1$-$C_2$)aminoalkyl($C_2$-$C_3$)alkyl (such as β-dimethylaminoethyl), carbamoyl-($C_1$-$C_2$)alkyl, N,N-di($C_1$-$C_2$)alkylcarbamoyl-($C_1$-$C_2$)alkyl and piperidino-, pyrrolidino- or morpholino($C_2$-$C_3$) alkyl, and the like.

Similarly, if a Tricyclic Indole Derivative contains an alcohol functional group, a prodrug can be formed by the replacement of the hydrogen atom of the alcohol group with a group such as, for example, ($C_1$-$C_6$)alkanoyloxymethyl, 1-(($C_2$-$C_6$) alkanoyloxy)ethyl, 1-methyl-1-(($C_1$-$C_6$)alkanoyloxy)ethyl, ($C_1$-$C_6$)alkoxycarbonyloxymethyl, N—($C_1$-$C_6$)alkoxycarbonylaminomethyl, succinoyl, ($C_1$-$C_6$)alkanoyl, α-amino ($C_1$-$C_4$)alkanyl, arylacyl and α-aminoacyl, or α-aminoacyl-α-aminoacyl, where each α-aminoacyl group is independently selected from the naturally occurring L-amino acids, $P(O)(OH)_2$, —$P(O)(O(C_1\text{-}C_6)alkyl)_2$ or glycosyl (the radical resulting from the removal of a hydroxyl group of the hemiacetal form of a carbohydrate), and the like.

If a Tricyclic Indole Derivative incorporates an amine functional group, a prodrug can be formed by the replacement of a hydrogen atom in the amine group with a group such as, for example, R-carbonyl, RO-carbonyl, NRR'-carbonyl where R and R' are each independently ($C_1$-$C_{10}$)alkyl, ($C_3$-$C_7$)cycloalkyl, benzyl, or R-carbonyl is a natural α-aminoacyl or natural α-aminoacyl, —C(OH)C(O)O$Y^1$ wherein $Y^1$ is H, ($C_1$-$C_6$)alkyl or benzyl, —C(O$Y^2$)$Y^3$ wherein $Y^2$ is ($C_1$-$C_4$) alkyl and $Y^3$ is ($C_1$-$C_6$)alkyl, carboxy ($C_1$-$C_6$)alkyl, amino ($C_1$-$C_4$)alkyl or mono-N- or di-N,N—($C_1$-$C_6$)aminoalkylalkyl, —C($Y^4$)$Y^5$ wherein $Y^4$ is H or methyl and $Y^5$ is mono-N or di-N,N—($C_1$-$C_6$)aminoalkyl morpholino, piperidin-1-yl or pyrrolidin-1-yl, and the like.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of illustrative solvates include ethanolates, methanolates, and the like. "Hydrate" is a solvate wherein the solvent molecule is $H_2O$.

One or more compounds of the invention may optionally be converted to a solvate. Preparation of Solvates is Generally Known. Thus, for Example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods, Analytical techniques such as, for example I. R. spectroscopy, show the presence of the solvent (or water) in the crystals as a solvate (or hydrate).

The term "effective amount" as used herein, refers to an amount of Tricyclic Indole Derivative and/or an additional therapeutic agent, or a composition thereof that is effective in producing the desired therapeutic, ameliorative, inhibitory or preventative effect when administered to a patient suffering from a viral infection or virus-related disorder. In the combination therapies of the present invention, an effective amount can refer to each individual agent or to the combination as a whole, wherein the amounts of all agents administered are together effective, but wherein the component agent of the combination may not be present individually in an effective amount.

Metabolic conjugates, such as glucuronides and sulfates which can undergo reversible conversion to the Tricyclic Indole Derivatives are contemplated in the present invention.

The Tricyclic Indole Derivatives may form salts, and all such salts are contemplated within the scope of this invention. Reference to a Tricyclic Indole Derivative herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a Tricyclic Indole Derivative contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula I may be formed, for example, by reacting a Tricyclic Indole Derivative with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 660) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamine, t-butyl amine, choline, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the present compounds which can be metabolically converted to the compounds to the present invention include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl-, aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) carboxylic acid esters obtained by esterification of a indole 2-carboxylic with a hydroxyl group of an alcohol, in which the alcohol is selected from from straight or branched chain alkylalcohols (for example, ethanol, n-propanol, t-butanol, or n-butanol), alkoxyalkanols (for example, methoxyethanol-), aminoalkanols (for example, aminoethanol, methylaminoethanol, dimethylaminoethanol, dimethylaminopropanol), aralkanols (for example, benzyl alcohol), aryloxyalkanols (for example, phenoxymethanol), aryl alcohols (for example, phenol optionally substituted with, for example, halogen, $C_{1-4}$alkyl, or $C_{1-4}$alkoxy or amino); (3) sulfonate esters, such as alkyl- or aralkylsulfonyl (for example, methanesulfonyl); (4) amino acid esters (for example, L-valyl or L-isoleucyl); (5) phosphonate esters and (6) mono-, di- or triphosphate esters. The phosphate esters may be further esterified by, for example, a $C_{1-20}$ alcohol or reactive derivative thereof, or by a 2,3-di($C_{6-24}$)acyl glycerol.

The Tricyclic indole Derivatives may contain asymmetric or chiral centers, and, therefore, exist in different stereoisomeric forms. It is intended that all stereoisomeric forms of the Tricyclic Indole Derivatives as well as mixtures thereof, including racemic mixtures, form part of the present invention. In addition, the present invention embraces all geometric and positional isomers. For example, if a Tricyclic Indole Derivative incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the Tricyclic Indole Derivatives may be atropisomers (e.g., substituted biaryls) and are considered as part of this invention. Enantiomers can also be separated by use of chiral HPLC column.

The straight line ——— as a bond generally indicates a mixture of, or either of, the possible isomers, non-limiting example(s) include, containing (R)- and (S)-stereochemistry. For example,

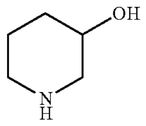

means containing both

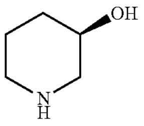

and

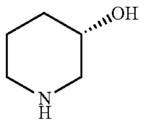

A dashed line (- - - - -) represents an optional and additional bond.

As well known in the art, a bond drawn from a particular atom wherein no moiety is depicted at the terminal end of the bond indicates a methyl group bound through that bond to the atom, unless stated otherwise. For example:

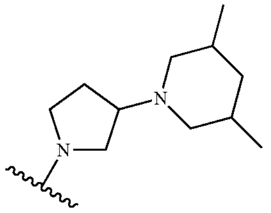

represents

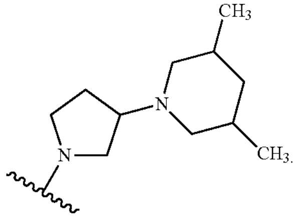

All stereoisomers (for example, geometric isomers, optical isomers and the like) of the present compounds (including those of the salts, solvates, hydrates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). For example, if a Tricyclic Indole Derivative incorporates a double bond or a fused ring, both the cis- and trans-forms, as well as mixtures, are embraced within the scope of the invention.

Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate", "ester", "prodrug" and the like, is intended to equally apply to the salt, solvate, ester and prodrug of enantiomers, stereoisomers, rotamers, positional isomers, racemates or prodrugs of the inventive compounds.

The present invention also embraces isotopically-labelled compounds of the present invention which are identical to those recited herein, but for the fact that one or more atoms are replaced by an atom having an atomic mass or mass number different from the atomic mass or mass number usually found in nature. Such compounds are useful as therapeutic, diagnostic or research reagents. Examples of isotopes that can be incorporated into compounds of the invention include isotopes of hydrogen, carbon, nitrogen, oxygen, phosphorus, fluorine and chlorine, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

Certain isotopically-labelled Tricyclic Indole Derivatives (e.g., those labeled with $^{3}H$ and $^{14}C$) are useful in compound and/or substrate tissue distribution assays. Tritiated (i.e., $^{3}H$) and carbon-14 (i.e., $^{14}C$) isotopes are particularly preferred for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances. In one embodiment, one or more hydrogen atoms of a Compound of Formula (I) is replaced with a deuterium atom. Isotopically labelled Tricyclic Indole Derivatives can generally be prepared by following procedures analogous to those disclosed in the Schemes and/or in the Examples herein below, by substituting an appropriate isotopically labelled reagent for a non-isotopically labelled reagent.

Polymorphic forms of the Tricyclic Indole Derivatives, and of the salts, solvates, hydrates, esters and prodrugs of the Tricyclic Indole Derivatives, are intended to be included in the present invention.

The following abbreviations are used below and have the following meanings: BINAP is racemic-2,2'-bis(diphenylphosphino)-1,1'-binaphthyl; CSA is camphorsulfonic acid; DBPD is 2-(Di-t-butylphosphino)biphenyl, DBU is 1,8-diazabicyclo[5.4.0]undec-7-ene, DBN is 1,5-diazabicyclo[4.3.0]non-5-ene; DCC is dicyclohexylcarbodiimide; DCM is dichloromethane; Dibal-His diisobutylaluminum hydride; DMF is dimethylformamide; EDCI is 1-(3-dimethylaminopropyl)-3-ethylcarbodiimide; HATU is N-(diethylamino)-1H-1,2,3-triazolo[4,5-b]pyridine-1-ylmethyl enej-N-methylmethanaminium Hexafluorophosphate N-oxide; HOBT is 1-hydroxybenzotriazole; LAH is lithium aluminum hydride; LDA is lithium diisopropylamide; m-CPBA is m-chloroperbenzoic acid; $NaBH(OAc)_3$ is sodium triacetoxyborohydride; $NaBH_4$ is sodium borohydride; $NaBH_3CN$ is sodium cyanoborohydride; NaHMDS is sodium hexamethyl disilylazide; p-TsOH is p-toluenesulfonic acid; p-TsCl is p-toluenesulfonyl chloride; PPTS is pyridinium p-toluenesulfonate; TMAD is N,N,N',N'-tetramethylazodicarboxamide; HRMS is high resolution mass spectrometry; HPLC is high performance liquid chromatography; LRMS is low resolution mass spectrometry; Tr is triphenylmethyl; Tris is tris (hydroxymethyl)aminomethane; THF is tetrahydrofuran; TFA is trifluoroacetic acid; Ci/mmol is Curie/mmol (a measure of specific activity); and Ki represents the dissociation constant for a substrate/receptor complex.

The Tricyclic Indole Derivatives of Formula (I)

The present invention provides Tricyclic Indole Derivatives of Formula (I):

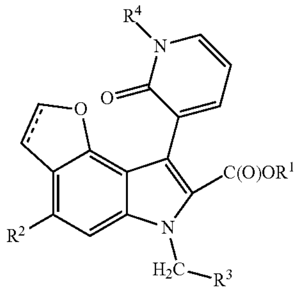

(I)

and pharmaceutically acceptable salts, solvates, esters and prodrugs thereof, wherein the dotted line represents an optional and additional bond and $R^1$, $R^2$, $R^3$ and $R^4$ are defined above.

In one embodiment, the optional and additional bond is present.

In another embodiment, the optional and additional bond is absent.

In one embodiment, $R^1$ is H or aminoalkyl.

In another embodiment, $R^1$ is H.

In another embodiment, $R^1$ is aminoalkyl.

In another embodiment, $R^1$ is alkylene-heterocycloalkyl.

In still another embodiment, $R^1$ is alkyl.

In one embodiment, $R^1$ is H, methyl, ethyl, n-propyl, $-CH_2CH_2NH_2$, $-CH_2CH(NH_2)CH_3$, $-CH_2CH_2CH_2NH_2$, $-CH_2CH_2NHCH_3$, $-CH_2CH_2N(CH_3)_2$, $-CH_2CH(N(CH_3)_2)CH_3$ or $-CH_2CH_2CH_2N(CH_3)_2$.

In another embodiment, $R^1$ is methyl, ethyl, n-propyl, $-CH_2CH_2NH_2$, $-CH_2CH(NH_2)CH_3$, $-CH_2CH_2CH_2NH_2$, $-CH_2CH_2NHCH_3$, $-CH_2CH_2N(CH_3)_2$, $-CH_2CH(N(CH_3)_2)CH_3$ or $-CH_2CH_2CH_2N(CH_3)_2$.

In another embodiment, $R^1$ is $-CH_2CH_2NH_2$, $-CH_2CH(NH_2)CH_3$, $-CH_2CH_2CH_2NH_2$, $-CH_2CH_2NHCH_3$, $-CH_2CH_2N(CH_3)_2$, $-CH_2CH(N(CH_3)_2)CH_3$ or $-CH_2CH_2CH_2N(CH_3)_2$.

In still another embodiment, $R^1$ is $-CH_2CH_2N(CH_3)_2$.

In another embodiment, $R^1$ is other than H.

In another embodiment, $R^2$ is H or F.

In another embodiment, $R^2$ is F.

In still another embodiment, $R^2$ is H.

In one embodiment, $R^3$ is phenyl.

In another embodiment, $R^3$ is naphthyl.

In another embodiment, $R^3$ is nitrogen-containing heteroaryl or nitrogen-containing heterocycloalkenyl.

In yet another embodiment, $R^3$ is nitrogen-containing heteroaryl.

In another embodiment, $R^3$ is nitrogen-containing heterocycloalkyl.

In another embodiment, $R^3$ is nitrogen-containing heterocycloalkenyl.

In one embodiment, $R^3$ is phenyl.

In another embodiment, $R^3$ is quinoline.

In another embodiment, $R^3$ is isoquinoline.

In still another embodiment, $R^3$ is 1,8-naphthyridine.

In another embodiment, $R^3$ is quinazoline.

In yet another embodiment, $R^3$ is benzimidazole.

In another embodiment, $R^3$ is indazole.

In a further embodiment, $R^3$ is quinolin-2-one.

In one embodiment, $R^3$ is:

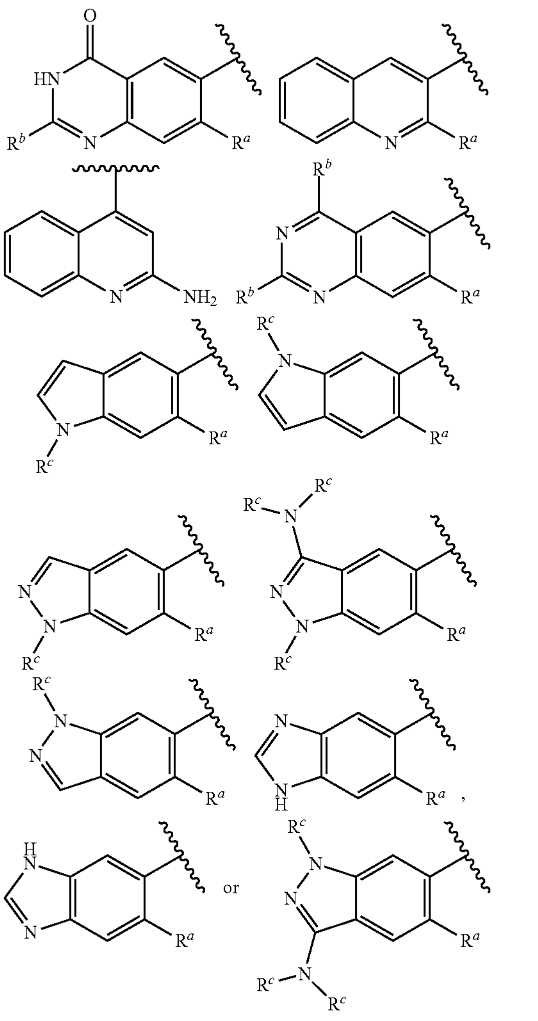

or wherein $R^a$ is F, Cl or methyl; $R^b$ is H, —OH, —$NH_2$ or methyl; and $R^c$ is H or methyl.

In another embodiment, $R^3$ is:

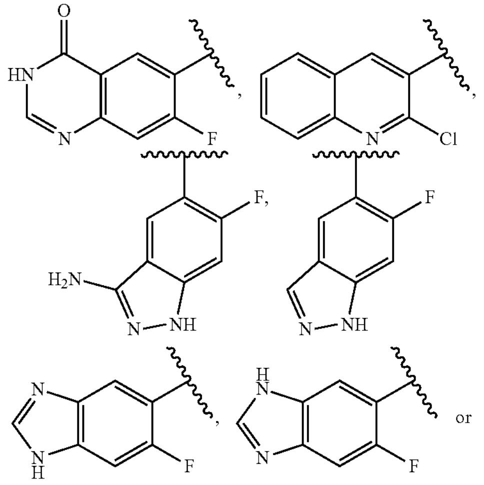

or

-continued

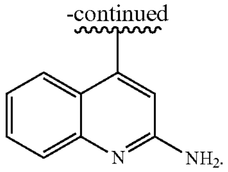

In one embodiment, $R^4$ is H.

In another embodiment, $R^4$ is —C(O)O-alkyl.

In another embodiment, $R^4$ is —$C(O)OCH_3$.

In still another embodiment, $R^4$ is —C(O)O-t-butyl.

In one embodiment, $R^1$ is H or aminoalkyl and $R^2$ is H or F.

In another embodiment, $R^1$ is H or aminoalkyl and $R^2$ is F.

In another embodiment, $R^1$ is H or aminoalkyl and $R^2$ is H.

In one embodiment, $R^1$ is H or aminoalkyl; $R^2$ is H or F; and the optional and additional bond is present.

In one embodiment, $R^1$ is H or aminoalkyl; $R^2$ is H or F; and the optional and additional bond is absent.

In one embodiment, $R^1$ is H or aminoalkyl; $R^2$ is H or F; and $R^3$ is nitrogen-containing heteroaryl or nitrogen-containing heterocycloalkenyl.

In another embodiment, $R^1$ is H or aminoalkyl; $R^2$ is H or F; and $R^3$ is nitrogen-containing heteroaryl.

In another embodiment, $R^1$ is H or aminoalkyl; $R^2$ is H or F; and $R^3$ is:

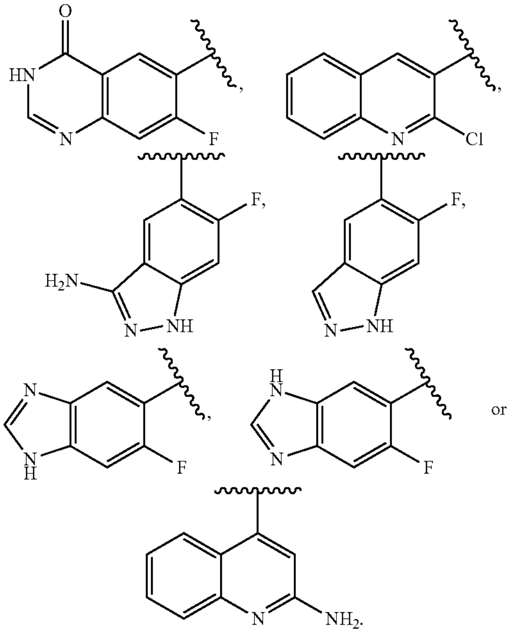

or

In another embodiment, $R^1$ is H or aminoalkyl; $R^2$ is H or F; $R^3$ is nitrogen-containing heteroaryl or nitrogen-containing heterocycloalkenyl; and the optional and additional bond is present.

In another embodiment, $R^1$ is H or aminoalkyl; $R^2$ is H or F; $R^3$ is nitrogen-containing heteroaryl or nitrogen-containing heterocycloalkenyl; and the optional and additional bond is absent.

In another embodiment, $R^1$ is H or aminoalkyl; $R^2$ is H or F; $R^3$ is nitrogen-containing heteroaryl; and the optional and additional bond is present.

In another embodiment, $R^1$ is H or aminoalkyl; $R^2$ is H or F; $R^3$ is nitrogen-containing heteroaryl; and the optional and additional bond is absent.

In another embodiment $R^1$ is H or aminoalkyl; $R^2$ is H or F; the optional and additional bond is present; and $R^3$ is:

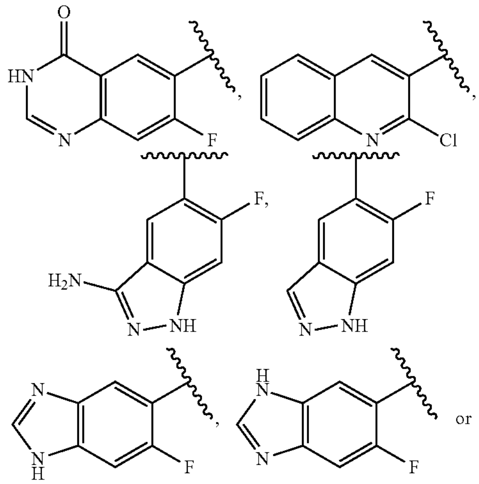

or

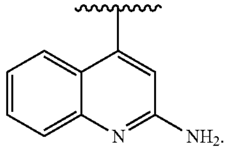

In another embodiment, $R^1$ is H or aminoalkyl; $R^2$ is H or F; the optional and additional bond is absent; and $R^3$ is:

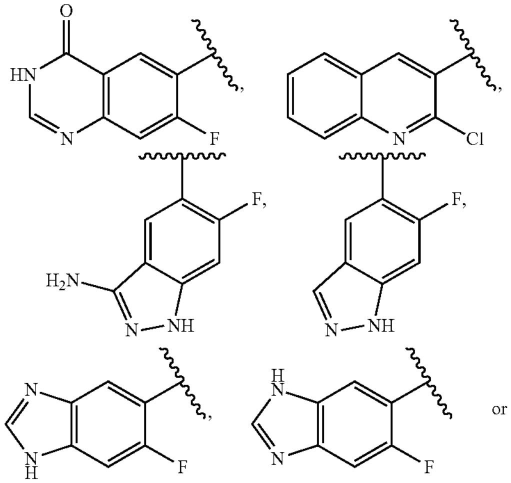

or

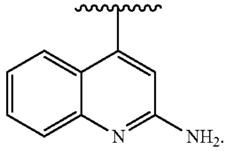

In one embodiment, $R^1$ is aminoalkyl and $R^2$ is H or F.

In another embodiment, $R^1$ is aminoalkyl and $R^2$ is F.

In another embodiment, $R^1$ is aminoalkyl and $R^2$ is H.

In one embodiment, $R^1$ is aminoalkyl; $R^2$ is H or F; and the optional and additional bond is present.

In one embodiment, $R^1$ is aminoalkyl; $R^2$ is H or F; and the optional and additional bond is absent.

In one embodiment, $R^1$ is aminoalkyl; $R^2$ is H or F; and $R^3$ is nitrogen-containing heteroaryl or nitrogen-containing heterocycloalkenyl.

In another embodiment, $R^1$ is aminoalkyl; $R^2$ is H or F; and $R^3$ is nitrogen-containing heteroaryl.

In another embodiment, $R^1$ is aminoalkyl; $R^2$ is H or F; and $R^3$ is:

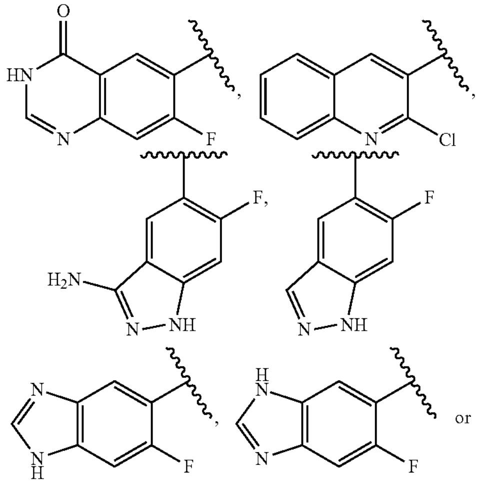

or

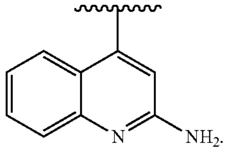

In another embodiment, $R^1$ is aminoalkyl; $R^2$ is H or F; $R^3$ is nitrogen-containing heteroaryl or nitrogen-containing heterocycloalkenyl; and the optional and additional bond is present.

In another embodiment, $R^1$ is aminoalkyl; $R^2$ is H or F; $R^3$ is nitrogen-containing heteroaryl or nitrogen-containing heterocycloalkenyl; and the optional and additional bond is absent.

In another embodiment, $R^1$ is aminoalkyl; $R^2$ is H or F; R nitrogen-containing heteroaryl; and the optional and additional bond is present.

In another embodiment, $R^1$ is aminoalkyl; $R^2$ is H or F; $R^3$ is nitrogen-containing heteroaryl; and the optional and additional bond is absent.

In another embodiment $R^1$ is aminoalkyl; $R^2$ is Har F; the optional and additional bond is present; and $R^3$ is:

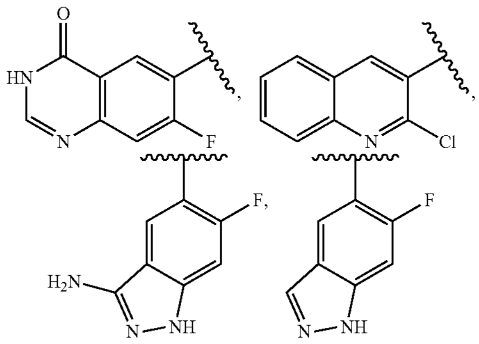

-continued

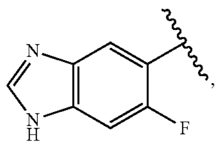,
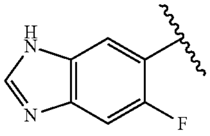 or
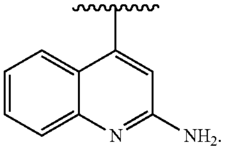

In another embodiment, $R^1$ is aminoalkyl; $R^2$ is H or F; the optional and additional bond is absent; and $R^3$ is:

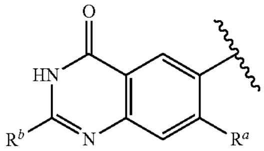
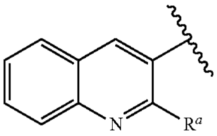
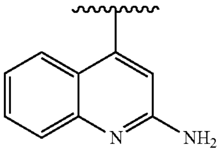
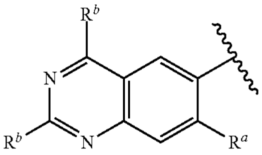
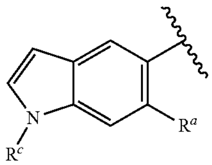
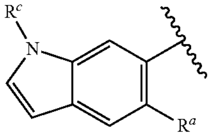
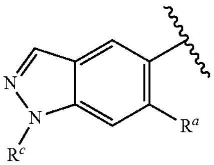
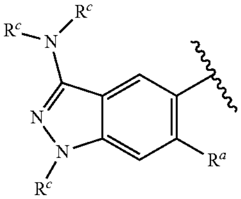
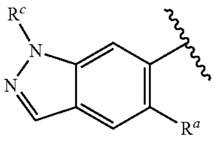
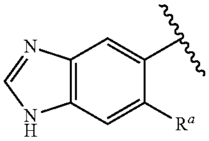,
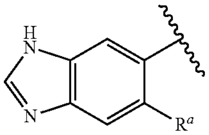 or
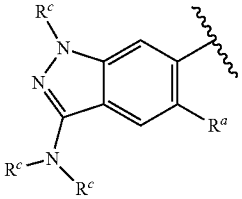

wherein $R^a$ is F, Cl or methyl; $R^b$ is H, —OH, —$NH_2$ or methyl; and $R^c$ is H or methyl.

In another embodiment, $R^1$ is aminoalkyl; $R^2$ is H or F; the optional and additional bond is absent; and $R^3$ is:

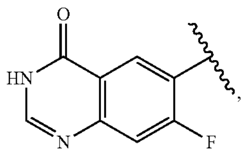,
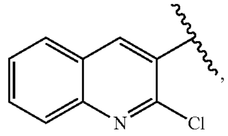,
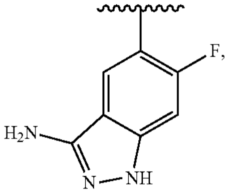
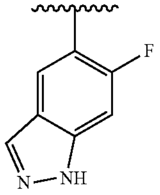
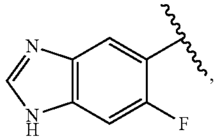,
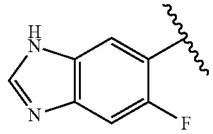 or
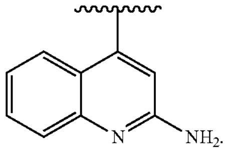

In one embodiment, $R^1$ is —$CH_2CH_2N(CH_3)_2$ and $R^2$ is F.

In another embodiment, $R^1$ is —$CH_2CH_2N(CH_3)_2$, $R^2$ is F, and $R^3$ is:

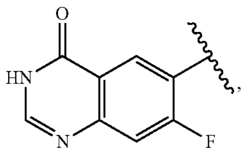,
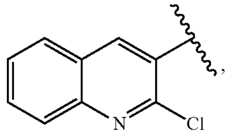,
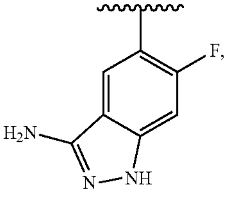
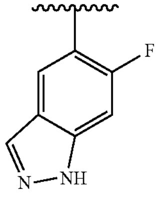
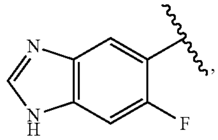,
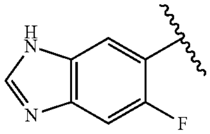 or
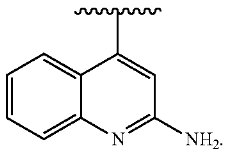

In another embodiment, $R^1$ is —$CH_2CH_2N(CH_3)_2$; $R^2$ is H; the optional and additional bond is absent; and $R^3$ is:

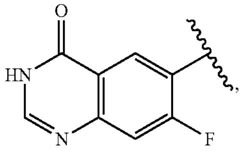, 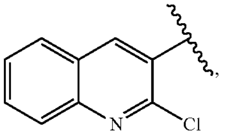,
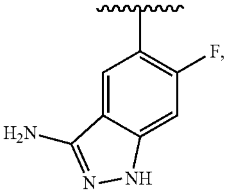 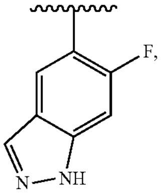
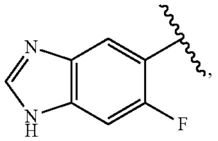, 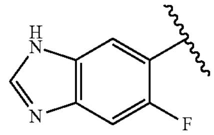 or
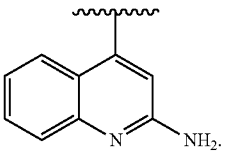
In still another embodiment, $R^1$ is $—CH_2CH_2CH_2N(CH_3)_2$; $R^2$ is F; the optional and additional bond is absent; and $R^3$ is:
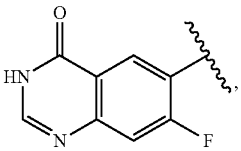, 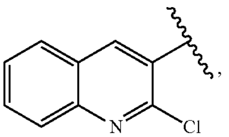,
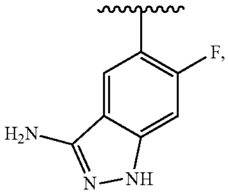 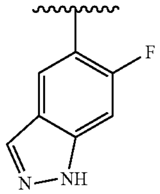
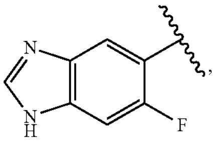, 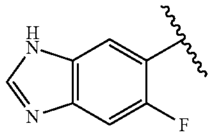 or
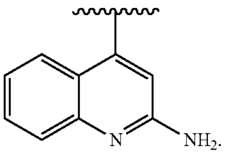
In another embodiment, $R^1$ is $—CH_2CH_2N(CH_3)_2$; $R^2$ is F; the optional and additional bond is present; and $R^3$ is:
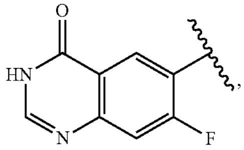, 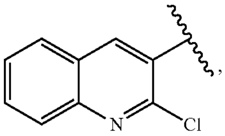,
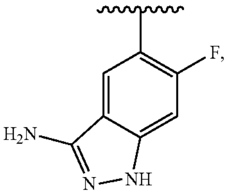 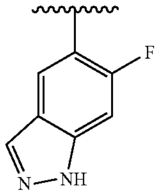
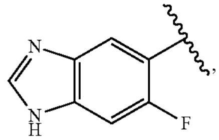, 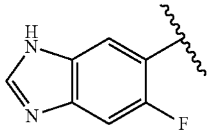 or
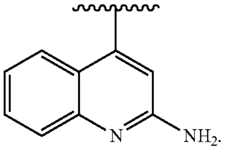
In one embodiment, the Compounds of Formula (I) have the formula:
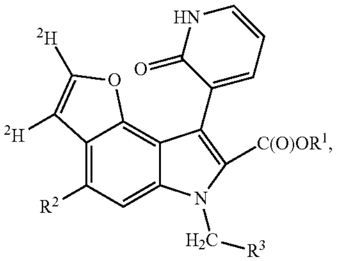
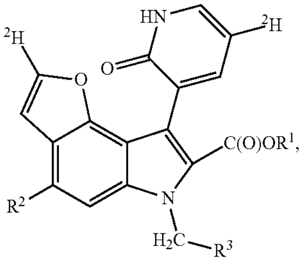
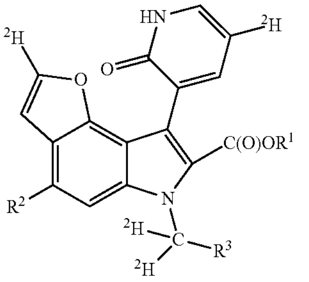 or -continued

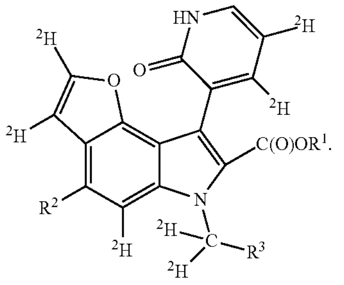

In one embodiment, one or more hydrogen atoms of a Compound of Formula (I) is replaced with a deuterium atom.

In another embodiment, for the Compounds of Formula (I), variables $R^1$, $R^2$ and $R^3$ are selected independently from each other.

In another embodiment, a Compound of Formula (I) is in purified form.

Non-limiting examples of the Compounds of Formula (I) include compounds 1-209 as set forth in the following table:

| Cpd No. | Structure |
|---|---|
| 1 | 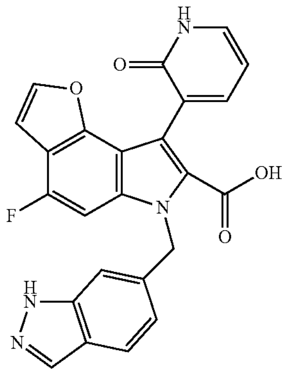 [SMILES: O=C(O)c1c(-c2ccc[nH]c2=O)c2c3occc3c(F)cc2n1Cc1ccc2cn[nH]c2c1] |
| 2 | 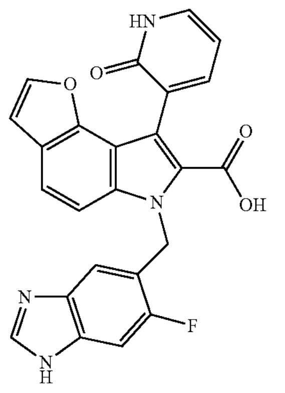 [SMILES: O=C(O)c1c(-c2ccc[nH]c2=O)c2c3occc3ccc2n1Cc1cc2nc[nH]c2cc1F] |

-continued

| Cpd No. | Structure |
|---|---|
| 3 | 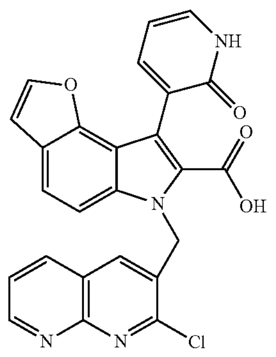 [SMILES: O=C(O)c1c(-c2ccc[nH]c2=O)c2c3occc3ccc2n1Cc1cc2cccnc2nc1Cl] |
| 4 | 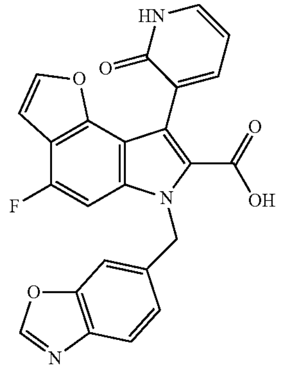 [SMILES: O=C(O)c1c(-c2ccc[nH]c2=O)c2c3occc3c(F)cc2n1Cc1ccc2ncoc2c1] |
| 5 | 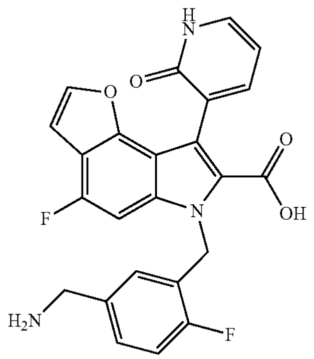 [SMILES: NCc1ccc(F)c(Cn2c(C(=O)O)c(-c3ccc[nH]c3=O)c3c4occc4c(F)cc32)c1] |
| 6 | 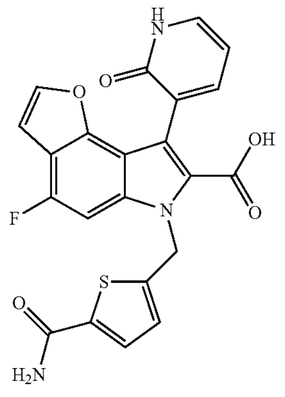 [SMILES: NC(=O)c1ccc(Cn2c(C(=O)O)c(-c3ccc[nH]c3=O)c3c4occc4c(F)cc32)s1] |

-continued
| Cpd No. | Structure |
|---|---|
| 7 | 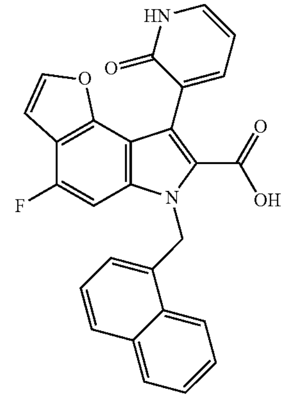 [SMILES: O=C(O)c1c(-c2ccc[nH]c2=O)c2c3occc3c(F)cc2n1Cc1cccc2ccccc12] |
| 8 | 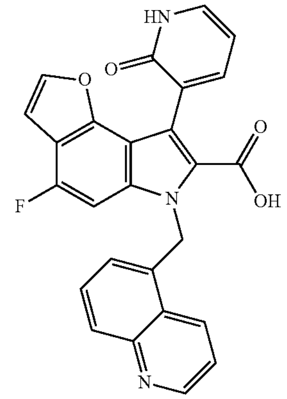 [SMILES: O=C(O)c1c(-c2ccc[nH]c2=O)c2c3occc3c(F)cc2n1Cc1cccc2ncccc12] |
| 9 | 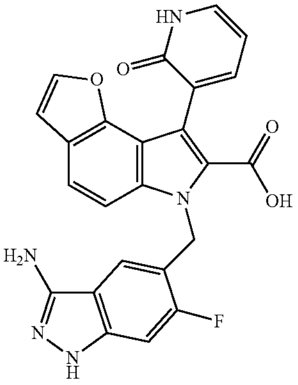 [SMILES: Nc1n[nH]c2cc(F)c(Cn3c(C(=O)O)c(-c4ccc[nH]c4=O)c4c5occc5ccc43)cc12] |
| 10 | 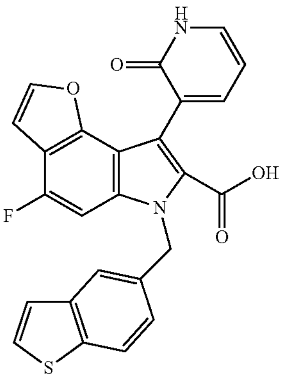 [SMILES: O=C(O)c1c(-c2ccc[nH]c2=O)c2c3occc3c(F)cc2n1Cc1ccc2sccc2c1] |
-continued
| Cpd No. | Structure |
|---|---|
| 11 | 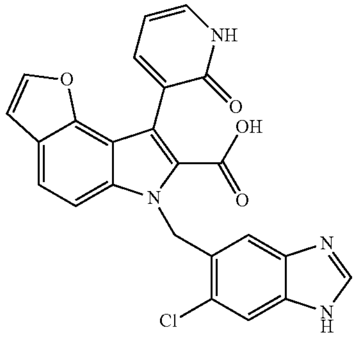 [SMILES: O=C(O)c1c(-c2ccc[nH]c2=O)c2c3occc3ccc2n1Cc1cc2nc[nH]c2cc1Cl] |
| 12 | 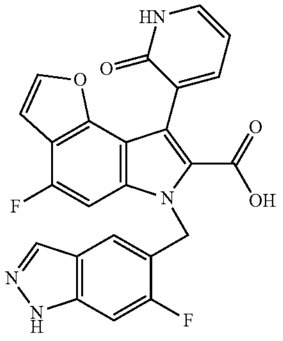 [SMILES: O=C(O)c1c(-c2ccc[nH]c2=O)c2c3occc3c(F)cc2n1Cc1cc2cn[nH]c2cc1F] |
| 13 | 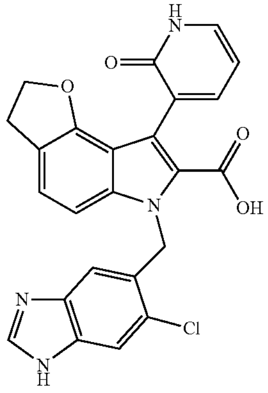 [SMILES: O=C(O)c1c(-c2ccc[nH]c2=O)c2c3c(ccc2n1Cc1cc2nc[nH]c2cc1Cl)CCO3] |
| 14 | 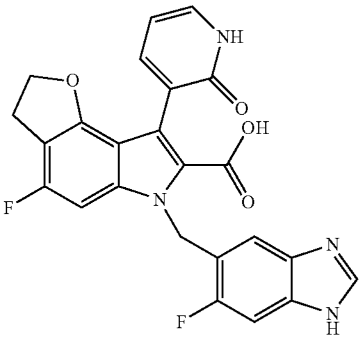 [SMILES: O=C(O)c1c(-c2ccc[nH]c2=O)c2c3c(c(F)cc2n1Cc1cc2nc[nH]c2cc1F)CCO3] |

-continued
| Cpd No. | Structure |
|---|---|
| 15 | 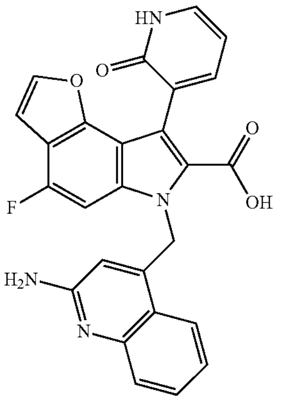 [SMILES: Nc1cc(Cn2c(C(=O)O)c(-c3ccc[nH]c3=O)c3c4occc4c(F)cc32)c2ccccc2n1] |
| 16 | 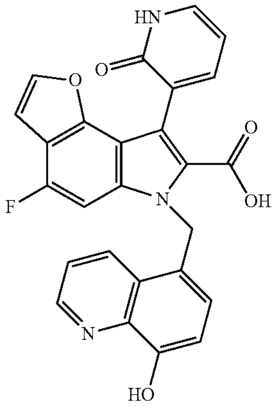 [SMILES: O=C(O)c1c(-c2ccc[nH]c2=O)c2c3occc3c(F)cc2n1Cc1ccc(O)c2ncccc12] |
| 17 | 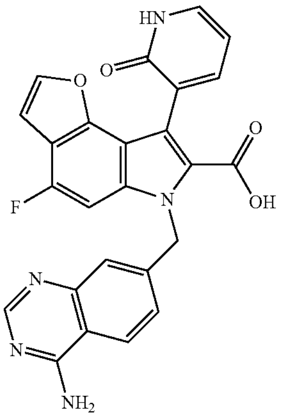 [SMILES: Nc1ncnc2cc(Cn3c(C(=O)O)c(-c4ccc[nH]c4=O)c4c5occc5c(F)cc43)ccc12] |
-continued
| Cpd No. | Structure |
|---|---|
| 18 | 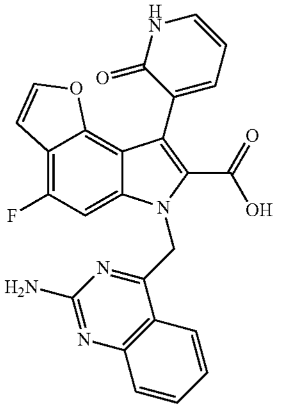 [SMILES: Nc1nc(Cn2c(C(=O)O)c(-c3ccc[nH]c3=O)c3c4occc4c(F)cc32)c2ccccc2n1] |
| 19 | 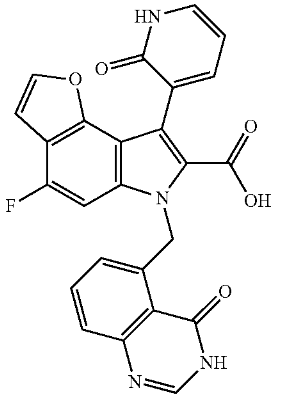 [SMILES: O=C(O)c1c(-c2ccc[nH]c2=O)c2c3occc3c(F)cc2n1Cc1cccc2nc[nH]c(=O)c12] |
| 20 | 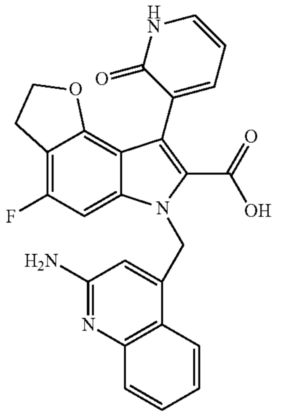 [SMILES: Nc1cc(Cn2c(C(=O)O)c(-c3ccc[nH]c3=O)c3c4c(c(F)cc32)CCO4)c2ccccc2n1] |

-continued
| Cpd No. | Structure |
|---|---|
| 21 | 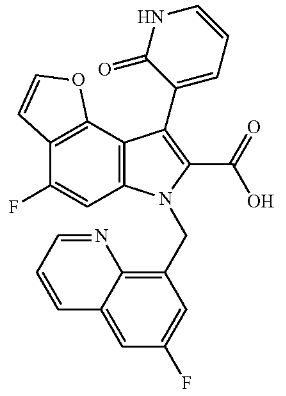 [SMILES: O=C(O)c1c(-c2ccc[nH]c2=O)c2c3occc3c(F)cc2n1Cc1cc(F)cc2cccnc12] |
| 22 | 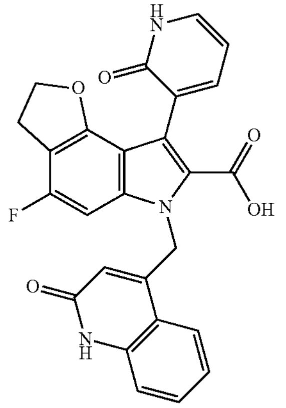 [SMILES: O=C(O)c1c(-c2ccc[nH]c2=O)c2c3c(c(F)cc2n1Cc1cc(=O)[nH]c2ccccc12)CCO3] |
| 23 | 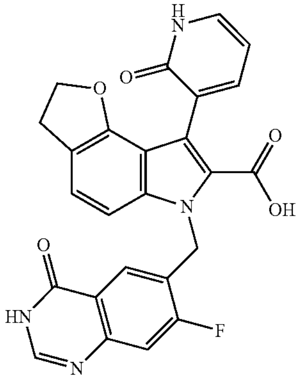 [SMILES: O=C(O)c1c(-c2ccc[nH]c2=O)c2c3c(ccc2n1Cc1cc2c(=O)[nH]cnc2cc1F)CCO3] |
| 24 | 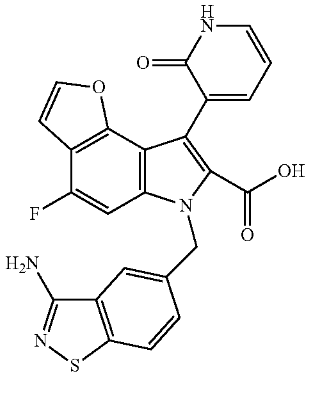 [SMILES: Nc1nsc2ccc(Cn3c(C(=O)O)c(-c4ccc[nH]c4=O)c4c5occc5c(F)cc43)cc12] |
-continued
| Cpd No. | Structure |
|---|---|
| 25 | 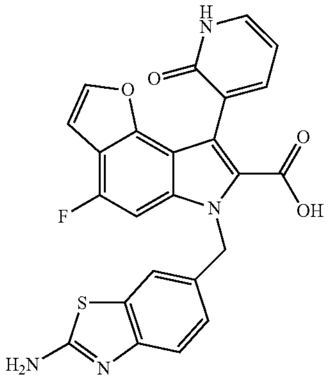 [SMILES: Nc1nc2ccc(Cn3c(C(=O)O)c(-c4ccc[nH]c4=O)c4c5occc5c(F)cc43)cc2s1] |
| 26 | 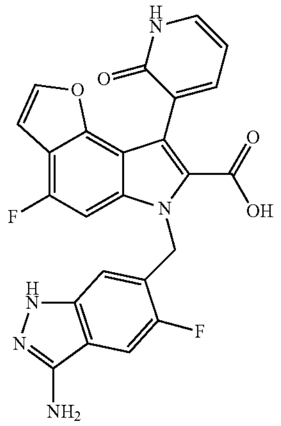 [SMILES: Nc1n[nH]c2cc(Cn3c(C(=O)O)c(-c4ccc[nH]c4=O)c4c5occc5c(F)cc43)c(F)cc12] |
| 27 | 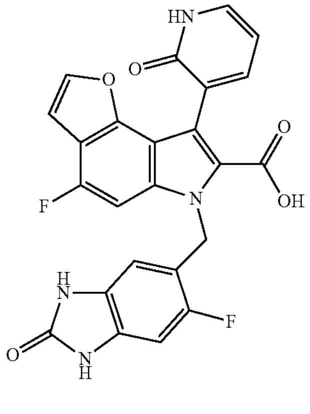 [SMILES: O=C(O)c1c(-c2ccc[nH]c2=O)c2c3occc3c(F)cc2n1Cc1cc2[nH]c(=O)[nH]c2cc1F] |

-continued
| Cpd No. | Structure |
|---|---|
| 28 | 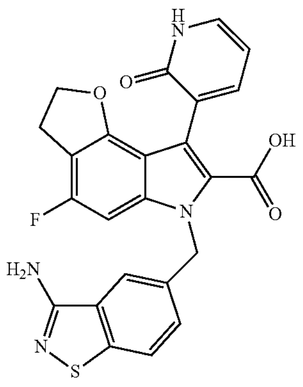 [SMILES: Nc1nsc2ccc(Cn3c(C(=O)O)c(-c4ccc[nH]c4=O)c4c5c(c(F)cc43)CCO5)cc12] |
| 29 | 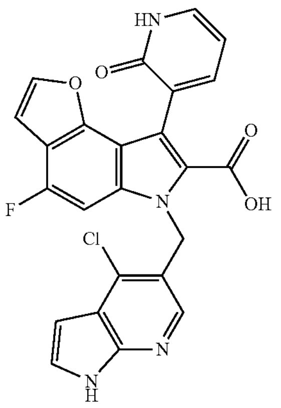 [SMILES: O=C(O)c1c(-c2ccc[nH]c2=O)c2c3occc3c(F)cc2n1Cc1cnc2[nH]ccc2c1Cl] |
| 30 | 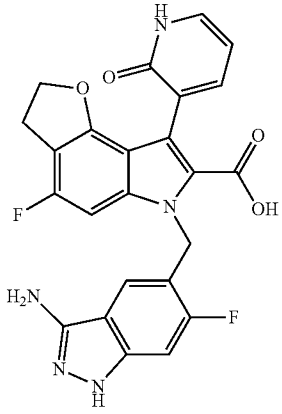 [SMILES: Nc1n[nH]c2cc(F)c(Cn3c(C(=O)O)c(-c4ccc[nH]c4=O)c4c5c(c(F)cc43)CCO5)cc12] |
-continued
| Cpd No. | Structure |
|---|---|
| 31 | 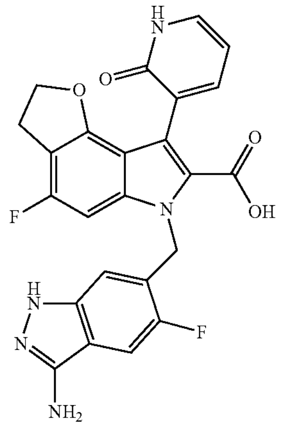 [SMILES: Nc1n[nH]c2cc(Cn3c(C(=O)O)c(-c4ccc[nH]c4=O)c4c5c(c(F)cc43)CCO5)c(F)cc12] |
| 32 | 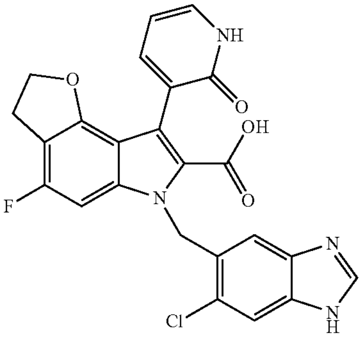 [SMILES: O=C(O)c1c(-c2ccc[nH]c2=O)c2c3c(c(F)cc2n1Cc1cc2nc[nH]c2cc1Cl)CCO3] |
| 33 | 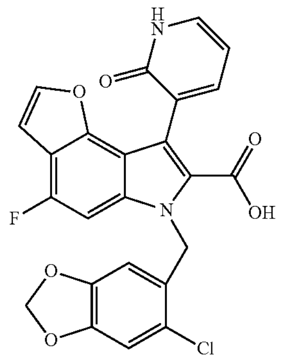 [SMILES: O=C(O)c1c(-c2ccc[nH]c2=O)c2c3occc3c(F)cc2n1Cc1cc2c(cc1Cl)OCO2] |
| 34 | 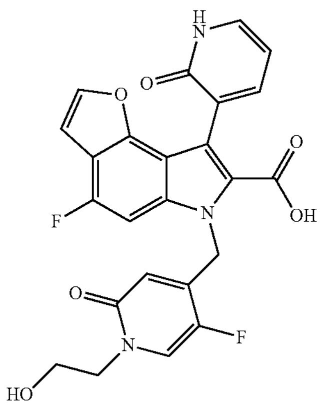 [SMILES: O=C(O)c1c(-c2ccc[nH]c2=O)c2c3occc3c(F)cc2n1Cc1cc(=O)n(CCO)cc1F] |

-continued
| Cpd No. | Structure |
|---|---|
| 35 | 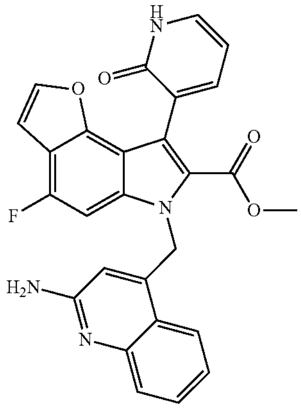 [SMILES: COC(=O)c1c(-c2ccc[nH]c2=O)c2c3occc3c(F)cc2n1Cc1cc(N)nc2ccccc12] |
| 36 | 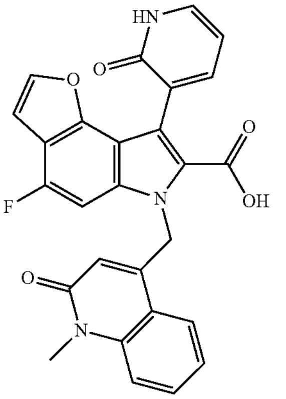 [SMILES: Cn1c(=O)cc(Cn2c(C(=O)O)c(-c3ccc[nH]c3=O)c3c4occc4c(F)cc32)c2ccccc21] |
| 37 | 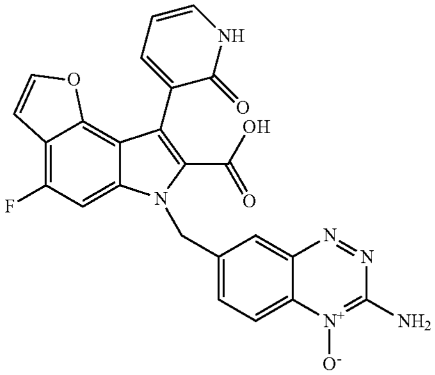 [SMILES: Nc1nnc2cc(Cn3c(C(=O)O)c(-c4ccc[nH]c4=O)c4c5occc5c(F)cc43)ccc2[n+]1[O-]] |
| 38 | 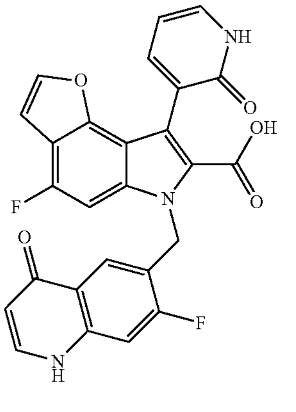 [SMILES: O=C(O)c1c(-c2ccc[nH]c2=O)c2c3occc3c(F)cc2n1Cc1cc2c(=O)cc[nH]c2cc1F] |
-continued
| Cpd No. | Structure |
|---|---|
| 39 | 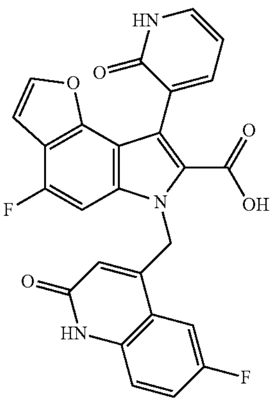 [SMILES: O=C(O)c1c(-c2ccc[nH]c2=O)c2c3occc3c(F)cc2n1Cc1cc(=O)[nH]c2ccc(F)cc12] |
| 40 | 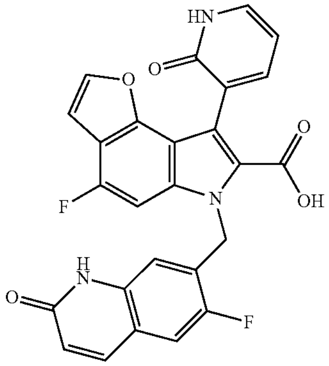 [SMILES: O=C(O)c1c(-c2ccc[nH]c2=O)c2c3occc3c(F)cc2n1Cc1cc2[nH]c(=O)ccc2cc1F] |
| 41 | 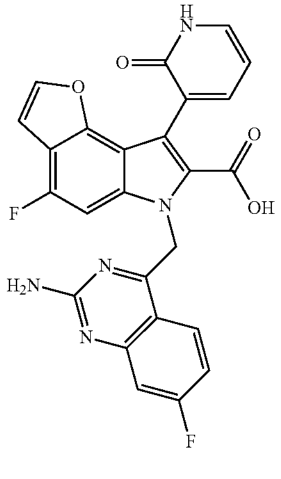 [SMILES: Nc1nc(Cn2c(C(=O)O)c(-c3ccc[nH]c3=O)c3c4occc4c(F)cc32)c2ccc(F)cc2n1] |

-continued
| Cpd No. | Structure |
|---|---|
| 42 | 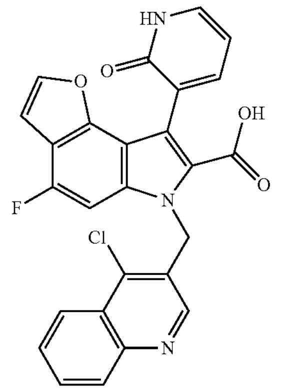 [SMILES: O=C(O)c1c(-c2ccc[nH]c2=O)c2c3occc3c(F)cc2n1Cc1cnc2ccccc2c1Cl] |
| 43 | 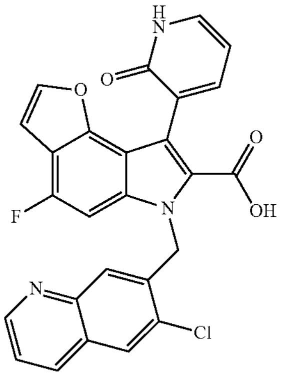 [SMILES: O=C(O)c1c(-c2ccc[nH]c2=O)c2c3occc3c(F)cc2n1Cc1cc2ncccc2cc1Cl] |
| 44 | 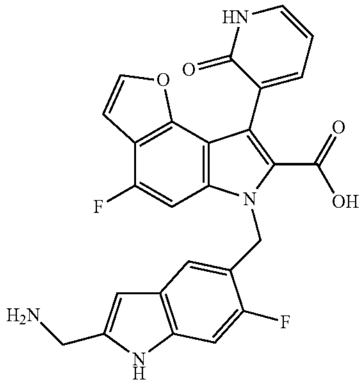 [SMILES: NCc1cc2cc(Cn3c(C(=O)O)c(-c4ccc[nH]c4=O)c4c5occc5c(F)cc43)c(F)cc2[nH]1] |
| 45 | 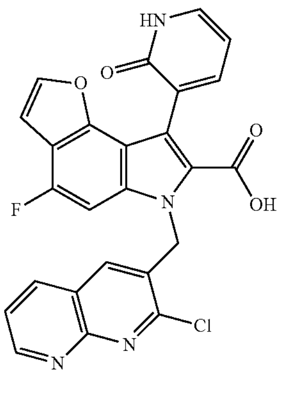 [SMILES: O=C(O)c1c(-c2ccc[nH]c2=O)c2c3occc3c(F)cc2n1Cc1cc2cccnc2nc1Cl] |
-continued
| Cpd No. | Structure |
|---|---|
| 46 | 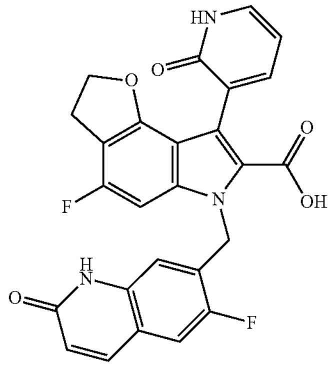 [SMILES: O=C(O)c1c(-c2ccc[nH]c2=O)c2c3c(c(F)cc2n1Cc1cc2[nH]c(=O)ccc2cc1F)CCO3] |
| 47 | 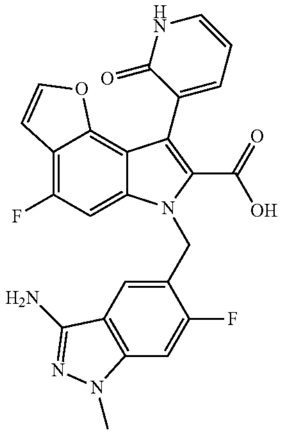 [SMILES: Cn1nc(N)c2cc(Cn3c(C(=O)O)c(-c4ccc[nH]c4=O)c4c5occc5c(F)cc43)c(F)cc21] |
| 48 | 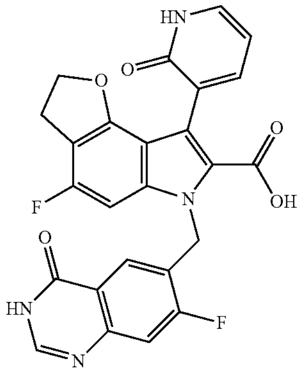 [SMILES: O=C(O)c1c(-c2ccc[nH]c2=O)c2c3c(c(F)cc2n1Cc1cc2c(=O)[nH]cnc2cc1F)CCO3] |
| 49 | 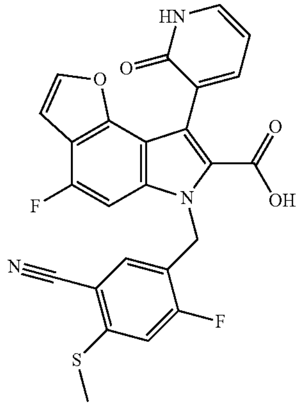 [SMILES: CSc1cc(F)c(Cn2c(C(=O)O)c(-c3ccc[nH]c3=O)c3c4occc4c(F)cc32)cc1C#N]

-continued
| Cpd No. | Structure |
|---|---|
| 50 | 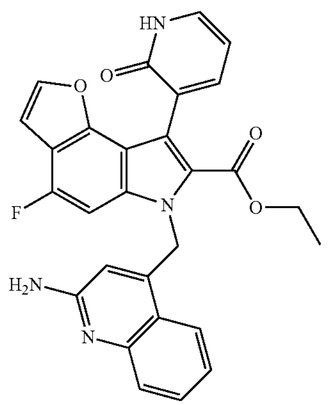 [SMILES: CCOC(=O)c1c(-c2ccc[nH]c2=O)c2c3occc3c(F)cc2n1Cc1cc(N)nc2ccccc12] |
| 51 | 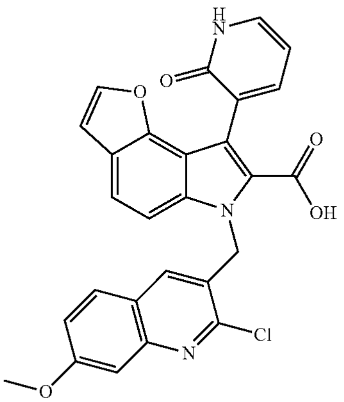 [SMILES: COc1ccc2cc(Cn3c(C(=O)O)c(-c4ccc[nH]c4=O)c4c5occc5ccc43)c(Cl)nc2c1] |
| 52 | 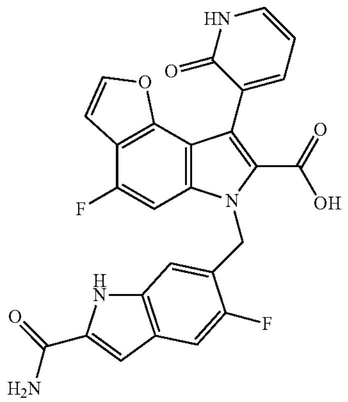 [SMILES: NC(=O)c1cc2cc(F)c(Cn3c(C(=O)O)c(-c4ccc[nH]c4=O)c4c5occc5c(F)cc43)cc2[nH]1] |
-continued
| Cpd No. | Structure |
|---|---|
| 53 | 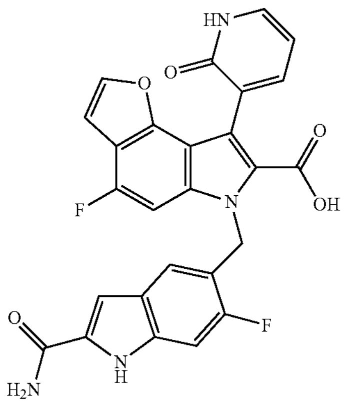 [SMILES: NC(=O)c1cc2cc(Cn3c(C(=O)O)c(-c4ccc[nH]c4=O)c4c5occc5c(F)cc43)c(F)cc2[nH]1] |
| 54 | 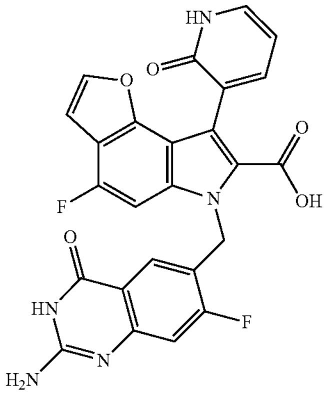 [SMILES: Nc1nc2cc(F)c(Cn3c(C(=O)O)c(-c4ccc[nH]c4=O)c4c5occc5c(F)cc43)cc2c(=O)[nH]1] |
| 55 | 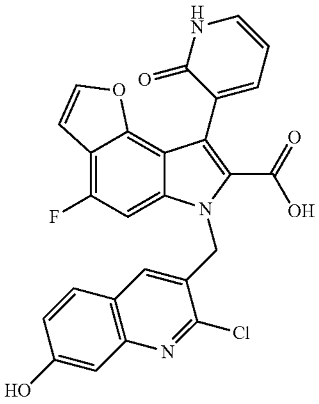 [SMILES: O=C(O)c1c(-c2ccc[nH]c2=O)c2c3occc3c(F)cc2n1Cc1cc2ccc(O)cc2nc1Cl] |

-continued
| Cpd No. | Structure |
|---|---|
| 56 | 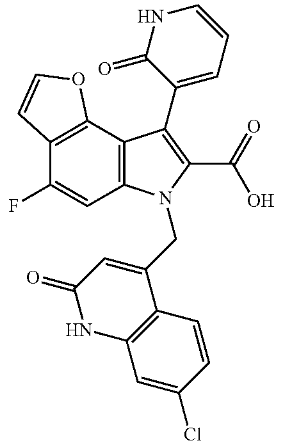 [SMILES: O=C(O)c1c(-c2ccc[nH]c2=O)c2c3occc3c(F)cc2n1Cc1cc(=O)[nH]c2cc(Cl)ccc12] |
| 57 | 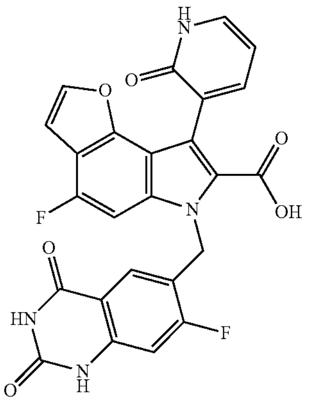 [SMILES: O=C(O)c1c(-c2ccc[nH]c2=O)c2c3occc3c(F)cc2n1Cc1cc2c(=O)[nH]c(=O)[nH]c2cc1F] |
| 58 | 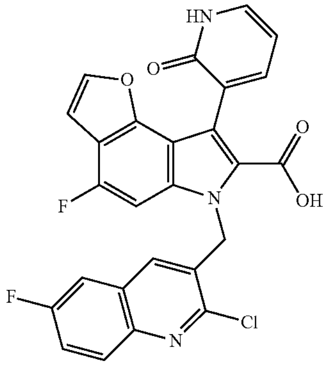 [SMILES: O=C(O)c1c(-c2ccc[nH]c2=O)c2c3occc3c(F)cc2n1Cc1cc2cc(F)ccc2nc1Cl] |
| 59 | 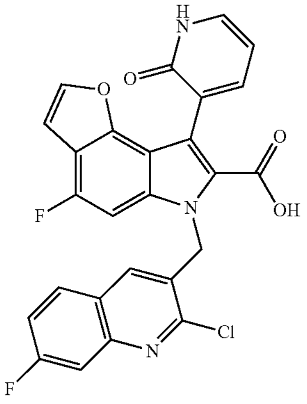 [SMILES: O=C(O)c1c(-c2ccc[nH]c2=O)c2c3occc3c(F)cc2n1Cc1cc2ccc(F)cc2nc1Cl] |
| 60 | 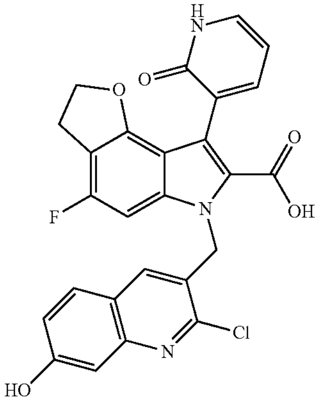 [SMILES: O=C(O)c1c(-c2ccc[nH]c2=O)c2c3c(c(F)cc2n1Cc1cc2ccc(O)cc2nc1Cl)CCO3] |
| 61 | 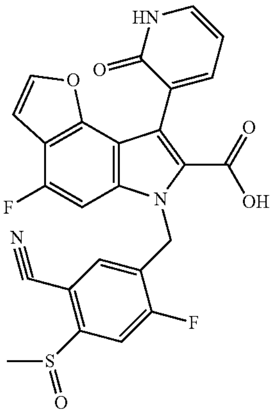 [SMILES: CS(=O)c1cc(F)c(Cn2c(C(=O)O)c(-c3ccc[nH]c3=O)c3c4occc4c(F)cc32)cc1C#N] |

-continued
| Cpd No. | Structure |
| --- | --- |
| 62 | 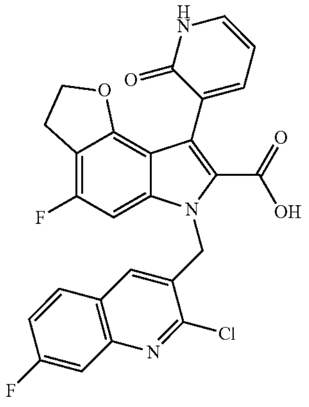 [SMILES: O=C(O)c1c(-c2ccc[nH]c2=O)c2c3c(c(F)cc2n1Cc1cc2ccc(F)cc2nc1Cl)CCO3] |
| 63 | 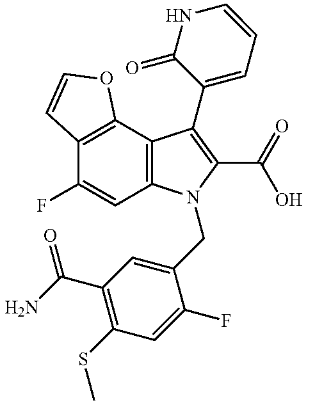 [SMILES: CSc1cc(F)c(Cn2c(C(=O)O)c(-c3ccc[nH]c3=O)c3c4occc4c(F)cc32)cc1C(N)=O] |
| 64 | 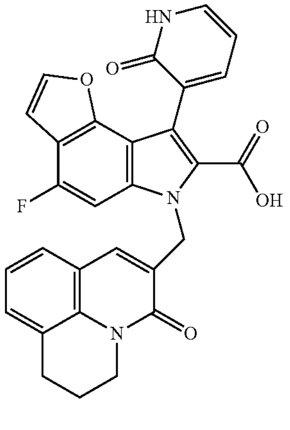 [SMILES: O=C(O)c1c(-c2ccc[nH]c2=O)c2c3occc3c(F)cc2n1Cc1cc2cccc3c2n(c1=O)CCC3] |
-continued
| Cpd No. | Structure |
| --- | --- |
| 65 | 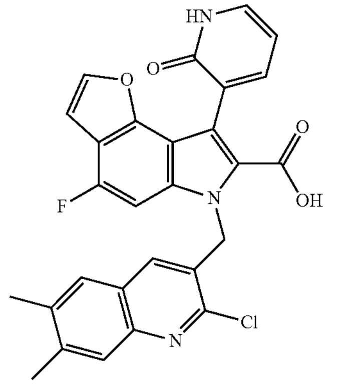 [SMILES: Cc1cc2cc(Cn3c(C(=O)O)c(-c4ccc[nH]c4=O)c4c5occc5c(F)cc43)c(Cl)nc2cc1C] |
| 66 | 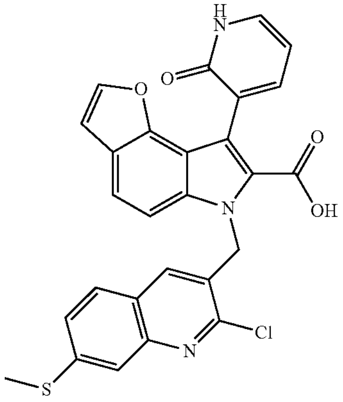 [SMILES: CSc1ccc2cc(Cn3c(C(=O)O)c(-c4ccc[nH]c4=O)c4c5occc5ccc43)c(Cl)nc2c1] |
| 67 | 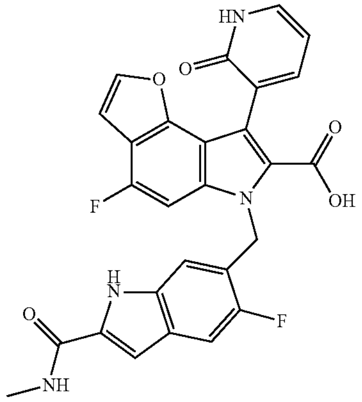 [SMILES: CNC(=O)c1cc2cc(F)c(Cn3c(C(=O)O)c(-c4ccc[nH]c4=O)c4c5occc5c(F)cc43)cc2[nH]1] |

-continued
| Cpd No. | Structure |
|---|---|
| 68 | 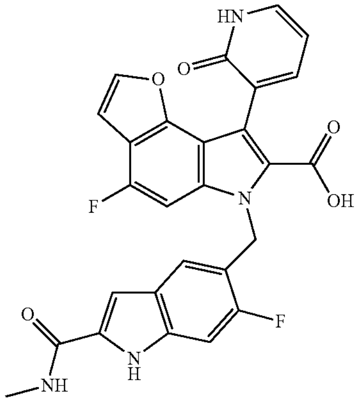 [SMILES: CNC(=O)c1cc2cc(Cn3c(C(=O)O)c(-c4ccc[nH]c4=O)c4c5occc5c(F)cc43)c(F)cc2[nH]1] |
| 69 | 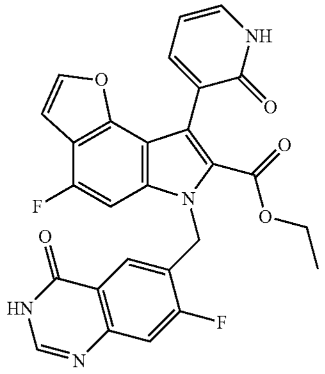 [SMILES: CCOC(=O)c1c(-c2ccc[nH]c2=O)c2c3occc3c(F)cc2n1Cc1cc2c(=O)[nH]cnc2cc1F] |
| 70 | 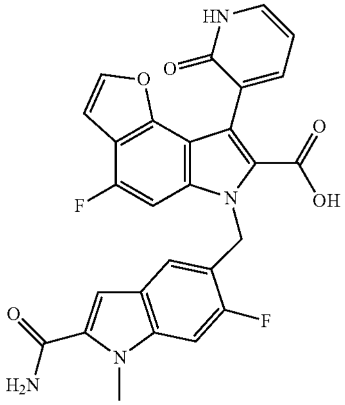 [SMILES: Cn1c(C(N)=O)cc2cc(Cn3c(C(=O)O)c(-c4ccc[nH]c4=O)c4c5occc5c(F)cc43)c(F)cc21] |
| 71 | 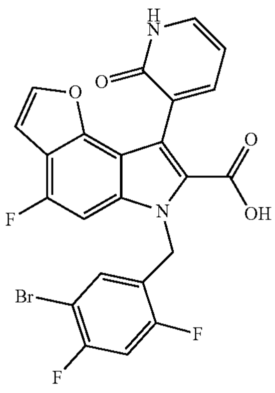 [SMILES: O=C(O)c1c(-c2ccc[nH]c2=O)c2c3occc3c(F)cc2n1Cc1cc(Br)c(F)cc1F] |
-continued
| Cpd No. | Structure |
|---|---|
| 72 | 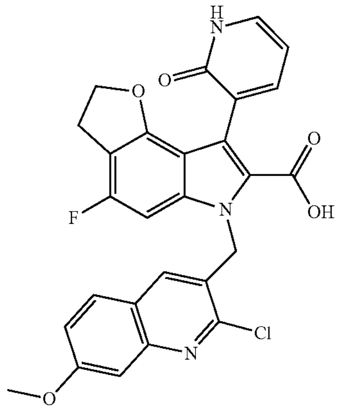 [SMILES: COc1ccc2cc(Cn3c(C(=O)O)c(-c4ccc[nH]c4=O)c4c5c(c(F)cc43)CCO5)c(Cl)nc2c1] |
| 73 | 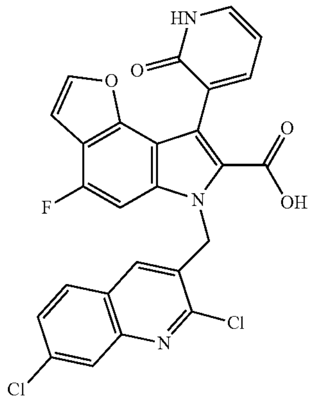 [SMILES: O=C(O)c1c(-c2ccc[nH]c2=O)c2c3occc3c(F)cc2n1Cc1cc2ccc(Cl)cc2nc1Cl] |
| 74 | 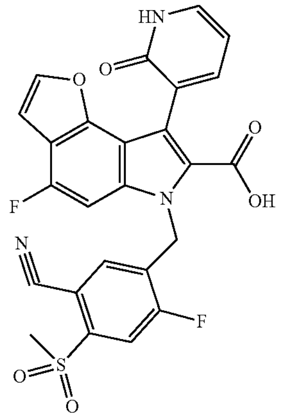 [SMILES: CS(=O)(=O)c1cc(F)c(Cn2c(C(=O)O)c(-c3ccc[nH]c3=O)c3c4occc4c(F)cc32)cc1C#N] |

| Cpd No. | Structure |
|---|---|
| 75 | 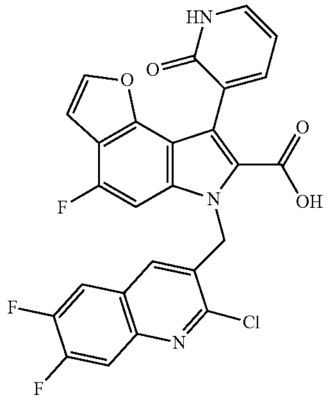 [SMILES: O=C(O)c1c(-c2ccc[nH]c2=O)c2c3occc3c(F)cc2n1Cc1cc2cc(F)c(F)cc2nc1Cl] |
| 76 | 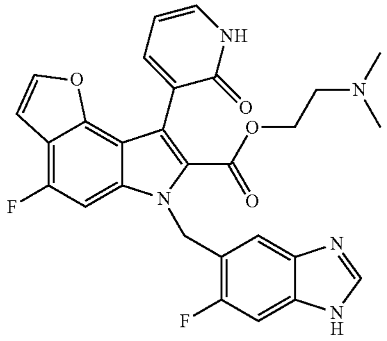 [SMILES: CN(C)CCOC(=O)c1c(-c2ccc[nH]c2=O)c2c3occc3c(F)cc2n1Cc1cc2nc[nH]c2cc1F] |
| 77 | 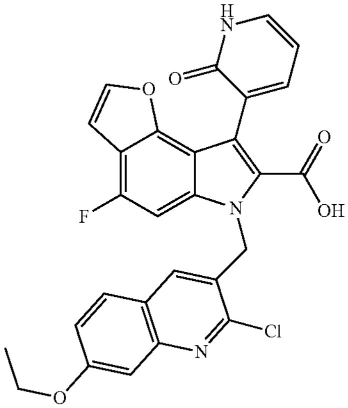 [SMILES: CCOc1ccc2cc(Cn3c(C(=O)O)c(-c4ccc[nH]c4=O)c4c5occc5c(F)cc43)c(Cl)nc2c1] |
| 78 | 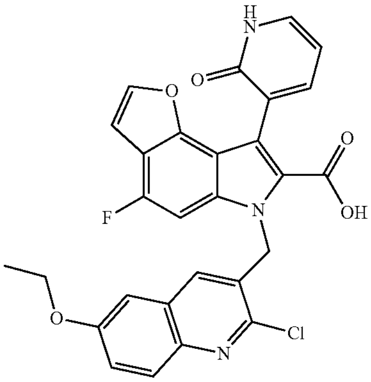 [SMILES: CCOc1ccc2nc(Cl)c(Cn3c(C(=O)O)c(-c4ccc[nH]c4=O)c4c5occc5c(F)cc43)cc2c1] |
| Cpd No. | Structure |
|---|---|
| 79 | 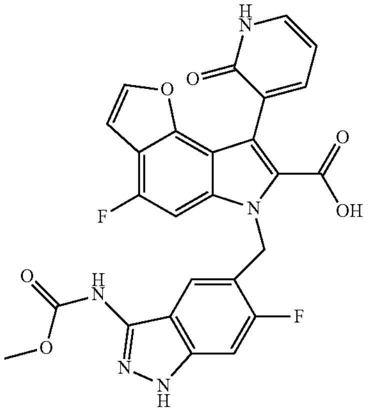 [SMILES: COC(=O)Nc1n[nH]c2cc(F)c(Cn3c(C(=O)O)c(-c4ccc[nH]c4=O)c4c5occc5c(F)cc43)cc12] |
| 80 | 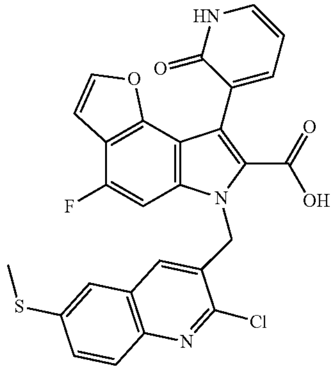 [SMILES: CSc1ccc2nc(Cl)c(Cn3c(C(=O)O)c(-c4ccc[nH]c4=O)c4c5occc5c(F)cc43)cc2c1] |
| 81 | 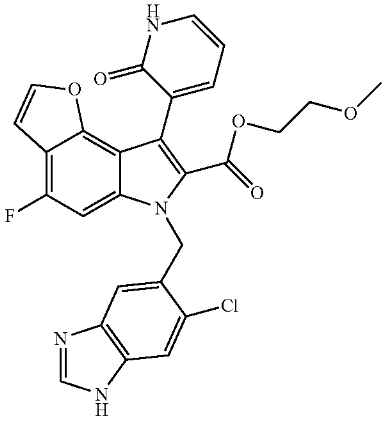 [SMILES: COCCOC(=O)c1c(-c2ccc[nH]c2=O)c2c3occc3c(F)cc2n1Cc1cc2nc[nH]c2cc1Cl] |

| Cpd No. | Structure |
|---|---|
| 82 | 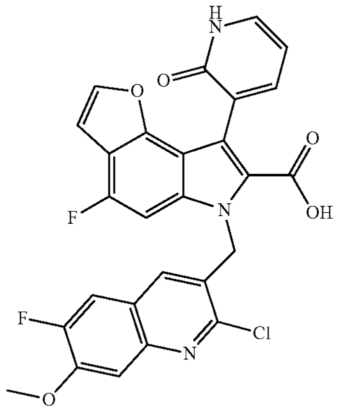 [SMILES: COc1cc2nc(Cl)c(Cn3c(C(=O)O)c(-c4ccc[nH]c4=O)c4c5occc5c(F)cc43)cc2cc1F] |
| 83 | 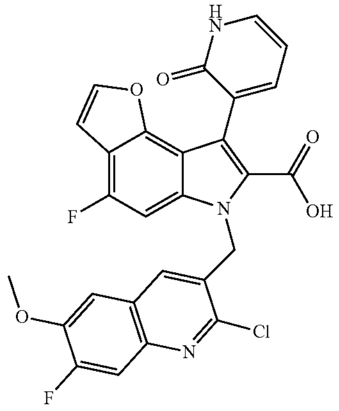 [SMILES: COc1cc2cc(Cn3c(C(=O)O)c(-c4ccc[nH]c4=O)c4c5occc5c(F)cc43)c(Cl)nc2cc1F] |
| 84 | 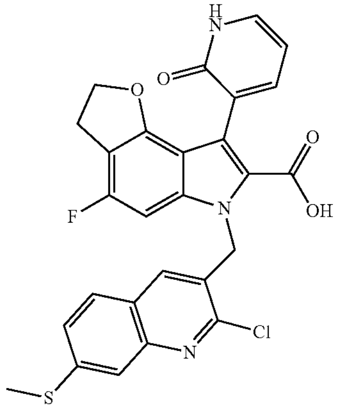 [SMILES: CSc1ccc2cc(Cn3c(C(=O)O)c(-c4ccc[nH]c4=O)c4c5c(c(F)cc43)CCO5)c(Cl)nc2c1] |
| Cpd No. | Structure |
|---|---|
| 85 | 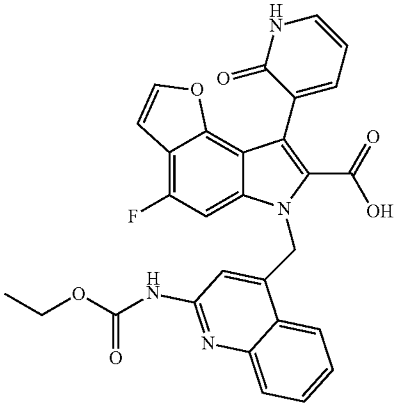 [SMILES: CCOC(=O)Nc1cc(Cn2c(C(=O)O)c(-c3ccc[nH]c3=O)c3c4occc4c(F)cc32)c2ccccc2n1] |
| 86 | 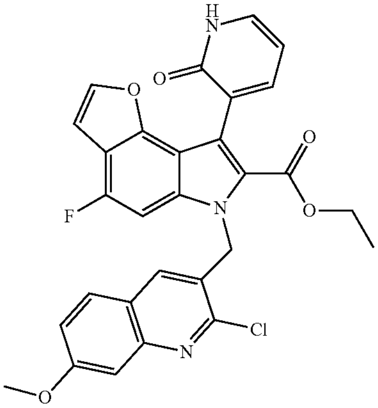 [SMILES: CCOC(=O)c1c(-c2ccc[nH]c2=O)c2c3occc3c(F)cc2n1Cc1cc2ccc(OC)cc2nc1Cl] |
| 87 | 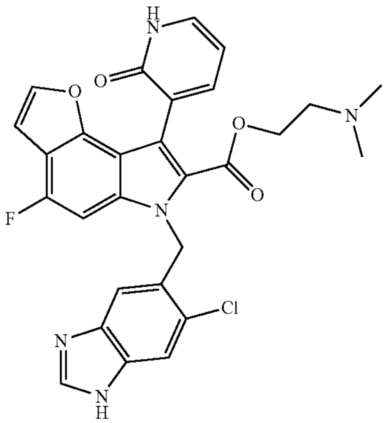 [SMILES: CN(C)CCOC(=O)c1c(-c2ccc[nH]c2=O)c2c3occc3c(F)cc2n1Cc1cc2nc[nH]c2cc1Cl] |

-continued
| Cpd No. | Structure |
|---|---|
| 88 | 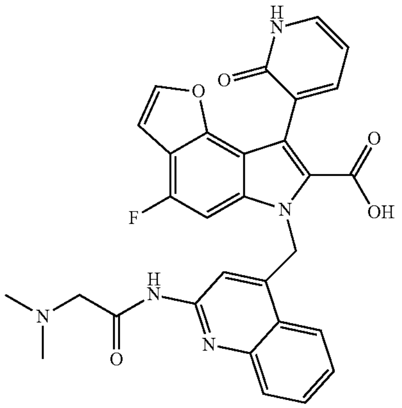 [SMILES: CN(C)CC(=O)Nc1cc(Cn2c(C(=O)O)c(-c3ccc[nH]c3=O)c3c4occc4c(F)cc32)c2ccccc2n1] |
| 89 | 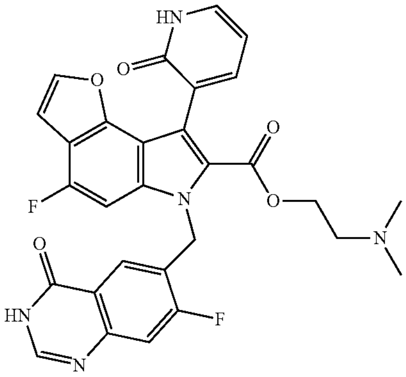 [SMILES: CN(C)CCOC(=O)c1c(-c2ccc[nH]c2=O)c2c3occc3c(F)cc2n1Cc1cc2c(=O)[nH]cnc2cc1F] |
| 90 | 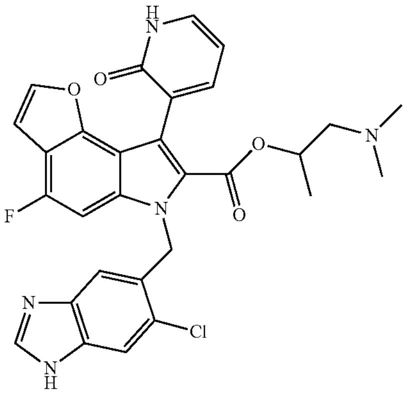 [SMILES: CC(CN(C)C)OC(=O)c1c(-c2ccc[nH]c2=O)c2c3occc3c(F)cc2n1Cc1cc2nc[nH]c2cc1Cl] |
-continued
| Cpd No. | Structure |
|---|---|
| 91 | 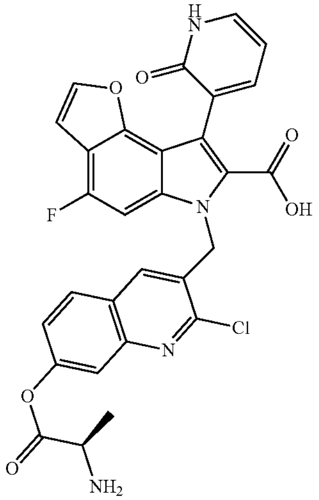 [SMILES: C[C@@H](N)C(=O)Oc1ccc2cc(Cn3c(C(=O)O)c(-c4ccc[nH]c4=O)c4c5occc5c(F)cc43)c(Cl)nc2c1] |
| 92 | 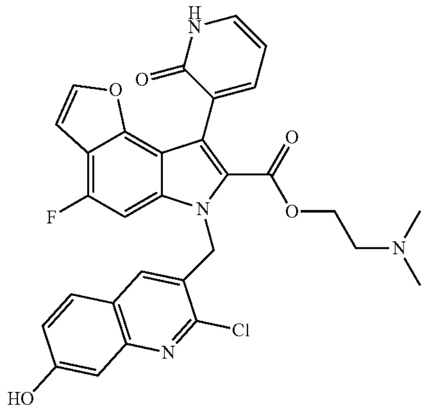 [SMILES: CN(C)CCOC(=O)c1c(-c2ccc[nH]c2=O)c2c3occc3c(F)cc2n1Cc1cc2ccc(O)cc2nc1Cl] |
| 93 | 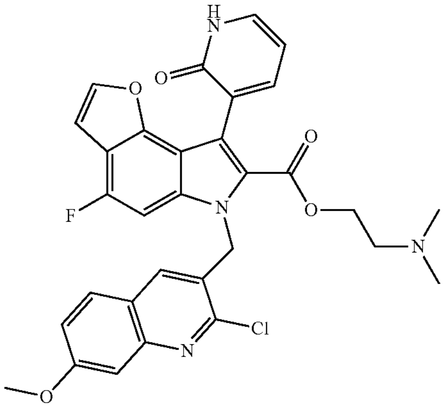 |

-continued
| Cpd No. | Structure |
|---|---|
| 94 | 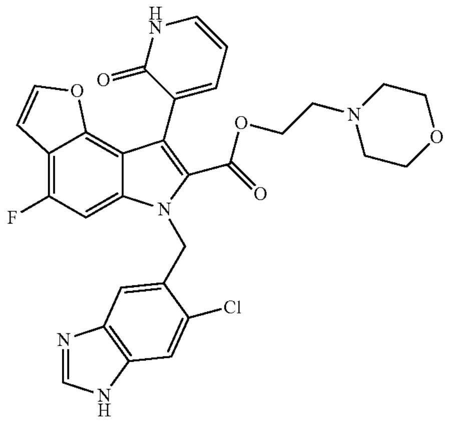 [SMILES: O=C(OCCN1CCOCC1)c1c(-c2ccc[nH]c2=O)c2c3occc3c(F)cc2n1Cc1cc2nc[nH]c2cc1Cl] |
| 95 | 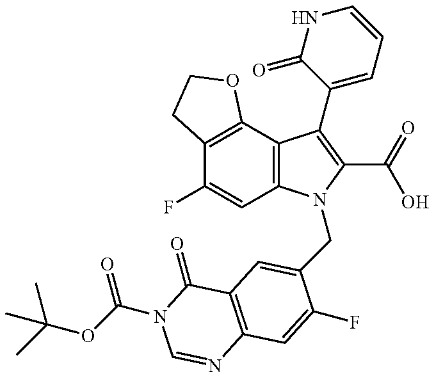 [SMILES: CC(C)(C)OC(=O)n1cnc2cc(F)c(Cn3c(C(=O)O)c(-c4ccc[nH]c4=O)c4c5c(c(F)cc43)CCO5)cc2c1=O] |
| 96 | 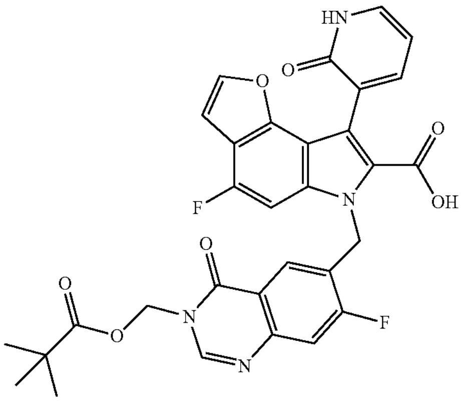 [SMILES: CC(C)(C)C(=O)OCn1cnc2cc(F)c(Cn3c(C(=O)O)c(-c4ccc[nH]c4=O)c4c5occc5c(F)cc43)cc2c1=O] |
-continued
| Cpd No. | Structure |
|---|---|
| 97 | 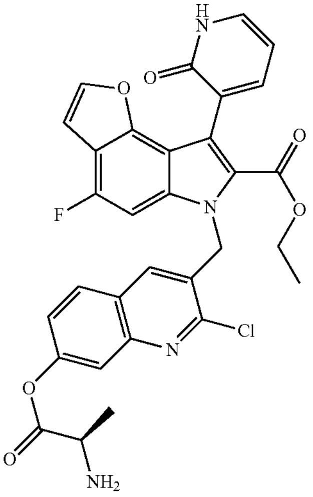 [SMILES: CCOC(=O)c1c(-c2ccc[nH]c2=O)c2c3occc3c(F)cc2n1Cc1cc2ccc(OC(=O)[C@@H](C)N)cc2nc1Cl] |
| 98 | 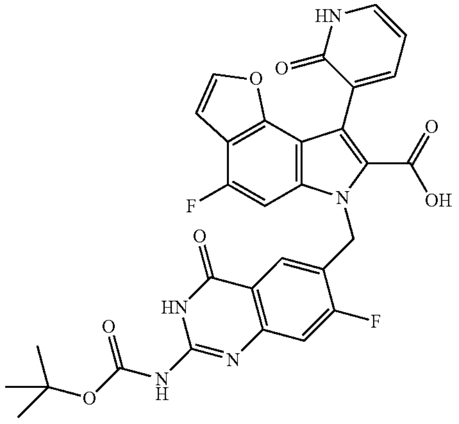 [SMILES: CC(C)(C)OC(=O)Nc1nc2cc(F)c(Cn3c(C(=O)O)c(-c4ccc[nH]c4=O)c4c5occc5c(F)cc43)cc2c(=O)[nH]1] |
| 99 | 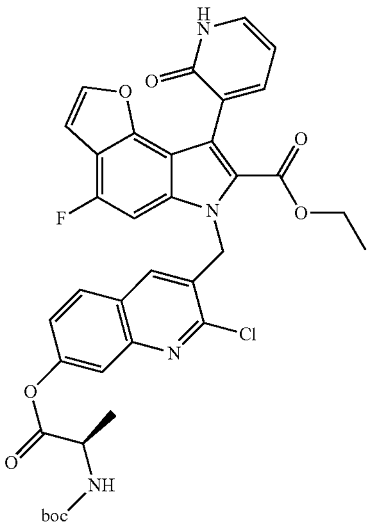 |

-continued
| Cpd No. | Structure |
| --- | --- |
| 100 | 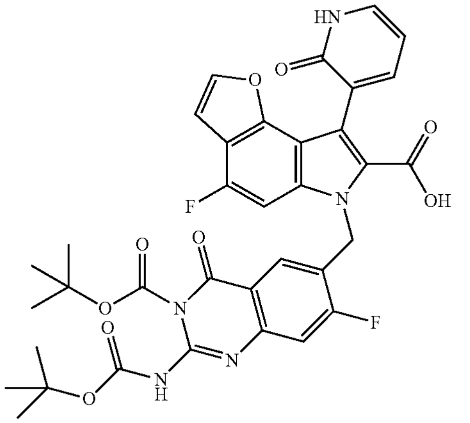 [SMILES: CC(C)(C)OC(=O)Nc1nc2cc(F)c(Cn3c(C(=O)O)c(-c4ccc[nH]c4=O)c4c5occc5c(F)cc43)cc2c(=O)n1C(=O)OC(C)(C)C] |
| 101 | 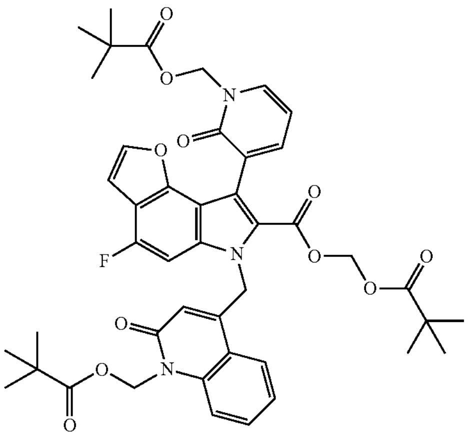 [SMILES: CC(C)(C)C(=O)OCOC(=O)c1c(-c2cccn(COC(=O)C(C)(C)C)c2=O)c2c3occc3c(F)cc2n1Cc1cc(=O)n(COC(=O)C(C)(C)C)c2ccccc12] |
| 102 | 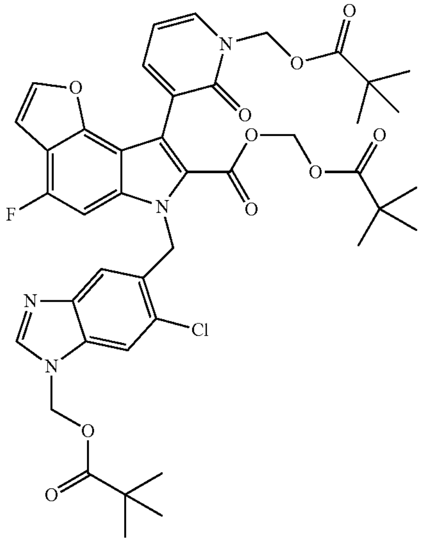 [SMILES: CC(C)(C)C(=O)OCOC(=O)c1c(-c2cccn(COC(=O)C(C)(C)C)c2=O)c2c3occc3c(F)cc2n1Cc1cc2ncn(COC(=O)C(C)(C)C)c2cc1Cl] |
-continued
| Cpd No. | Structure |
| --- | --- |
| 103 | 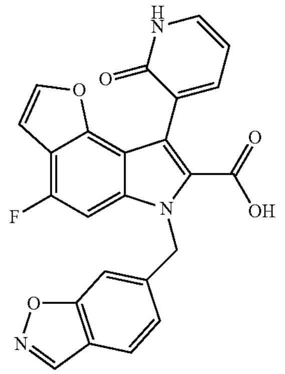 [SMILES: O=C(O)c1c(-c2ccc[nH]c2=O)c2c3occc3c(F)cc2n1Cc1ccc2cnoc2c1] |
| 104 | 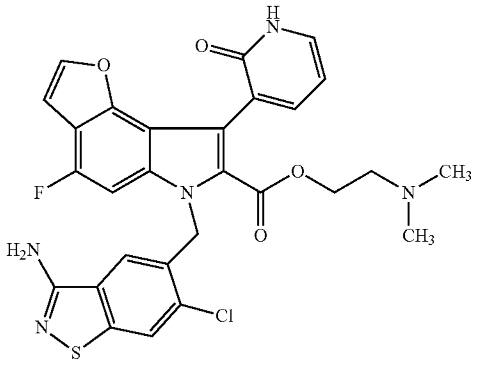 [SMILES: CN(C)CCOC(=O)c1c(-c2ccc[nH]c2=O)c2c3occc3c(F)cc2n1Cc1cc2c(N)nsc2cc1Cl] |
| 105 | 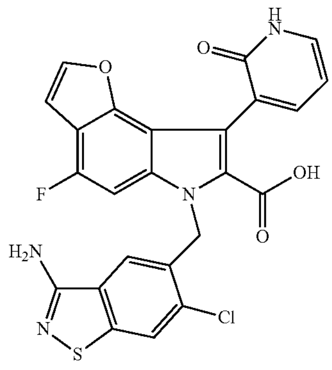 [SMILES: Nc1nsc2cc(Cl)c(Cn3c(C(=O)O)c(-c4ccc[nH]c4=O)c4c5occc5c(F)cc43)cc12] |
| 106 | 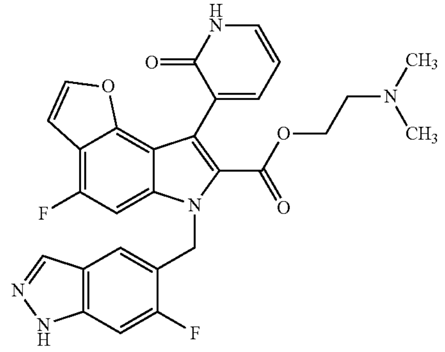 [SMILES: CN(C)CCOC(=O)c1c(-c2ccc[nH]c2=O)c2c3occc3c(F)cc2n1Cc1cc2cn[nH]c2cc1F] |

-continued
| Cpd No. | Structure |
|---|---|
| 107 | 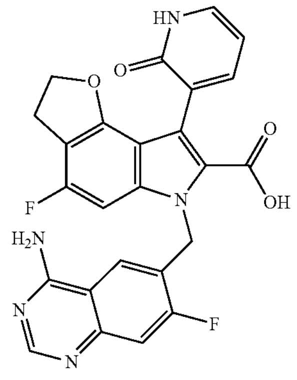 [SMILES: Nc1ncnc2cc(F)c(Cn3c(C(=O)O)c(-c4ccc[nH]c4=O)c4c5c(c(F)cc43)CCO5)cc12] |
| 108 | 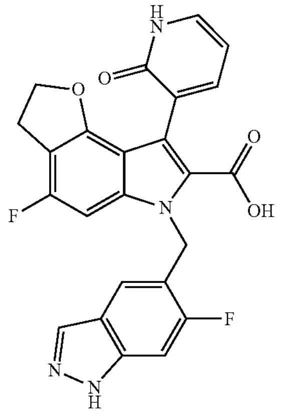 [SMILES: O=C(O)c1c(-c2ccc[nH]c2=O)c2c3c(c(F)cc2n1Cc1cc2cn[nH]c2cc1F)CCO3] |
| 109 | 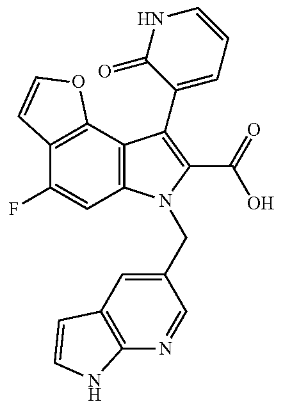 [SMILES: O=C(O)c1c(-c2ccc[nH]c2=O)c2c3occc3c(F)cc2n1Cc1cnc2[nH]ccc2c1] |
| 110 | 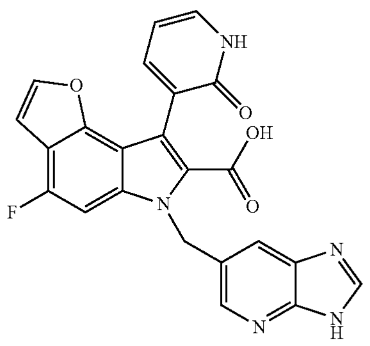 [SMILES: O=C(O)c1c(-c2ccc[nH]c2=O)c2c3occc3c(F)cc2n1Cc1cnc2[nH]cnc2c1] |
-continued
| Cpd No. | Structure |
|---|---|
| 111 | 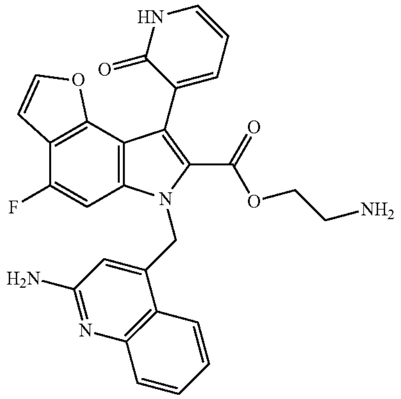 [SMILES: NCCOC(=O)c1c(-c2ccc[nH]c2=O)c2c3occc3c(F)cc2n1Cc1cc(N)nc2ccccc12] |
| 112 | 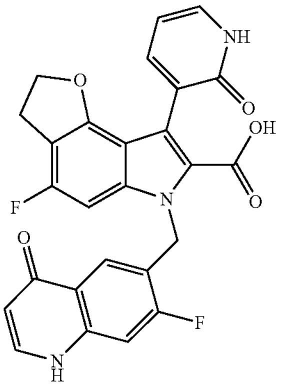 [SMILES: O=C(O)c1c(-c2ccc[nH]c2=O)c2c3c(c(F)cc2n1Cc1cc2c(=O)cc[nH]c2cc1F)CCO3] |
| 113 | 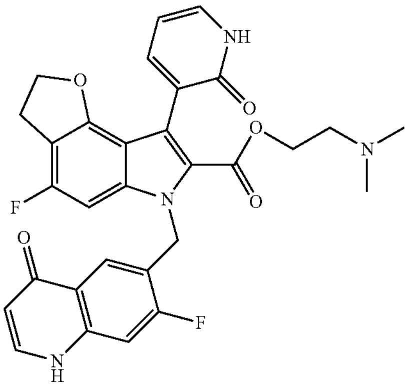 [SMILES: CN(C)CCOC(=O)c1c(-c2ccc[nH]c2=O)c2c3c(c(F)cc2n1Cc1cc2c(=O)cc[nH]c2cc1F)CCO3] |
| 114 | 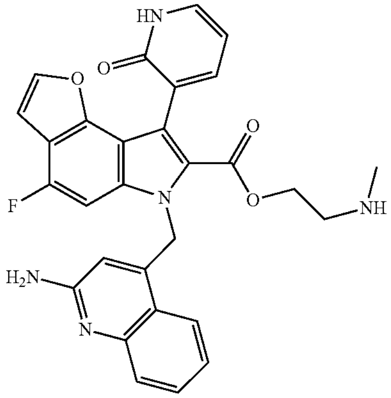 [SMILES: CNCCOC(=O)c1c(-c2ccc[nH]c2=O)c2c3occc3c(F)cc2n1Cc1cc(N)nc2ccccc12] |

-continued
| Cpd No. | Structure |
| --- | --- |
| 115 | 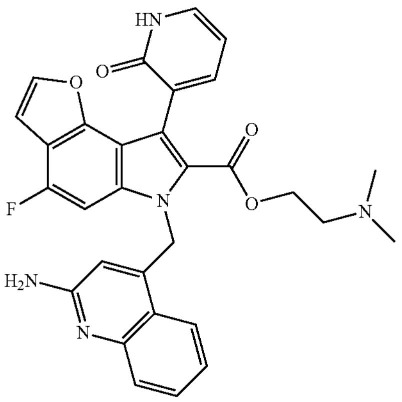 [SMILES: CN(C)CCOC(=O)c1c(-c2ccc[nH]c2=O)c2c3occc3c(F)cc2n1Cc1cc(N)nc2ccccc12] |
| 116 | 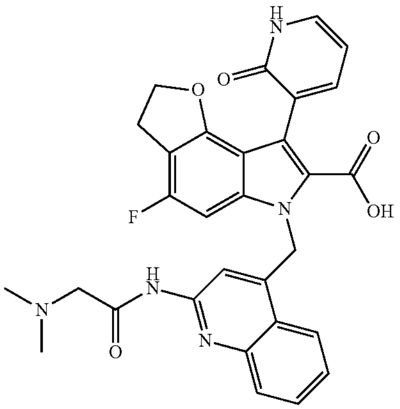 [SMILES: CN(C)CC(=O)Nc1cc(Cn2c(C(=O)O)c(-c3ccc[nH]c3=O)c3c4c(c(F)cc32)CCO4)c2ccccc2n1] |
| 117 | 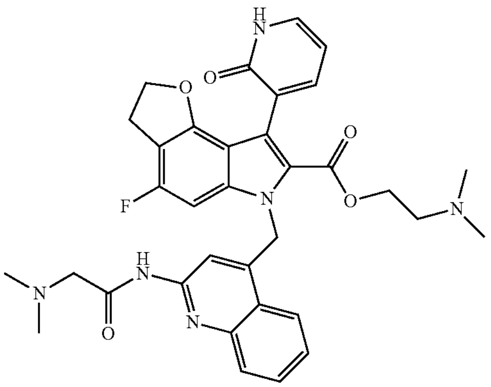 |
-continued
| Cpd No. | Structure |
| --- | --- |
| 118 | 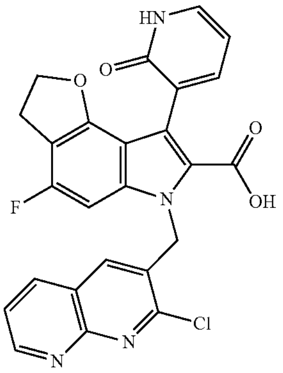 [SMILES: O=C(O)c1c(-c2ccc[nH]c2=O)c2c3c(c(F)cc2n1Cc1cc2cccnc2nc1Cl)CCO3] |
| 119 | 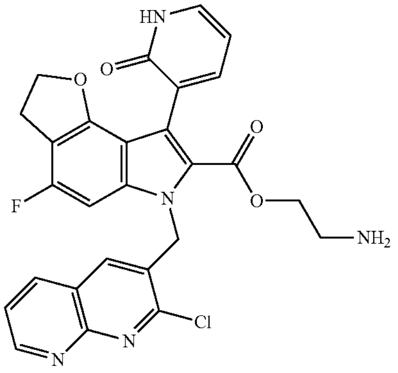 [SMILES: NCCOC(=O)c1c(-c2ccc[nH]c2=O)c2c3c(c(F)cc2n1Cc1cc2cccnc2nc1Cl)CCO3] |
| 120 | 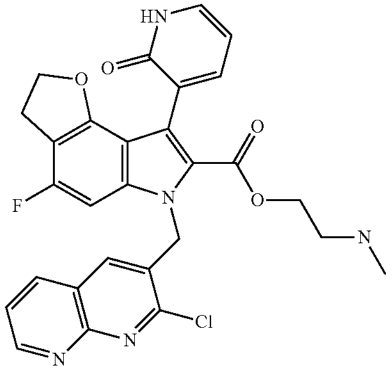 [SMILES: CNCCOC(=O)c1c(-c2ccc[nH]c2=O)c2c3c(c(F)cc2n1Cc1cc2cccnc2nc1Cl)CCO3] |
| 121 | 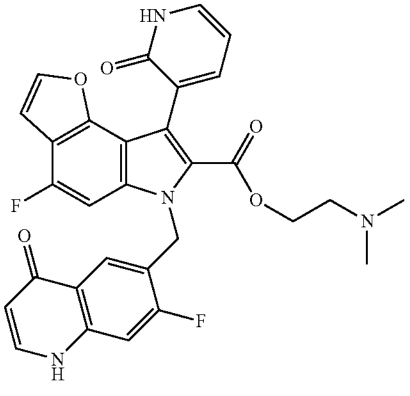 [SMILES: CN(C)CCOC(=O)c1c(-c2ccc[nH]c2=O)c2c3occc3c(F)cc2n1Cc1cc2c(=O)cc[nH]c2cc1F] |

-continued
| Cpd No. | Structure |
|---|---|
| 122 | 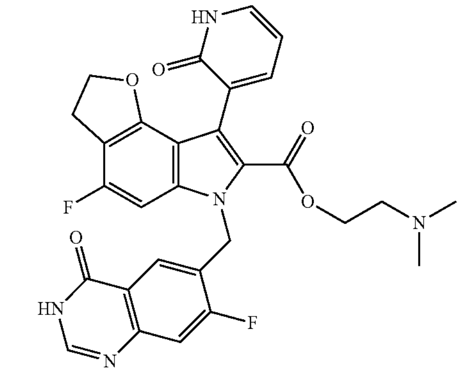 [SMILES: CN(C)CCOC(=O)c1c(-c2ccc[nH]c2=O)c2c3c(c(F)cc2n1Cc1cc2c(=O)[nH]cnc2cc1F)CCO3] |
| 123 | 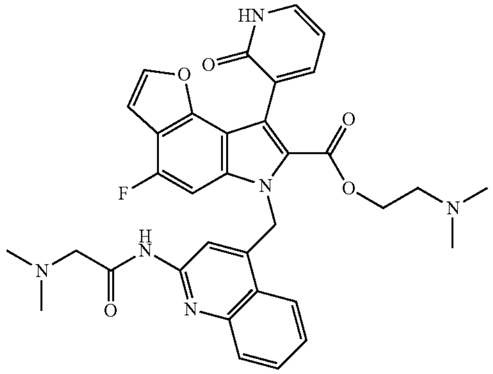 |
| 124 | 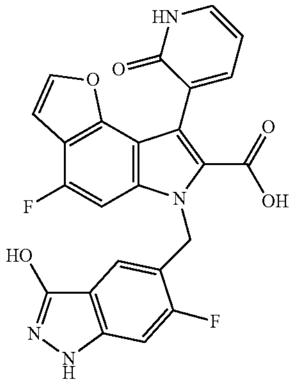 [SMILES: O=C(O)c1c(-c2ccc[nH]c2=O)c2c3occc3c(F)cc2n1Cc1cc2c(O)n[nH]c2cc1F] |
| 125 | 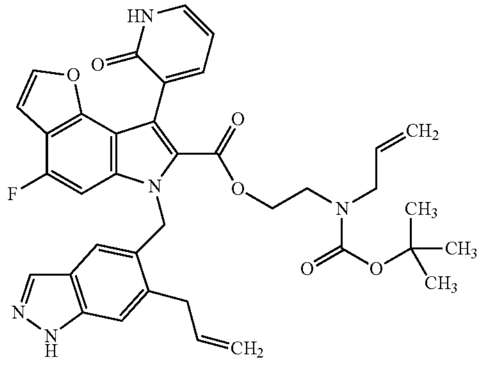 [SMILES: C=CCc1cc2[nH]ncc2cc1Cn1c(C(=O)OCCN(CC=C)C(=O)OC(C)(C)C)c(-c2ccc[nH]c2=O)c2c3occc3c(F)cc21] |
-continued
| Cpd No. | Structure |
|---|---|
| 126 | 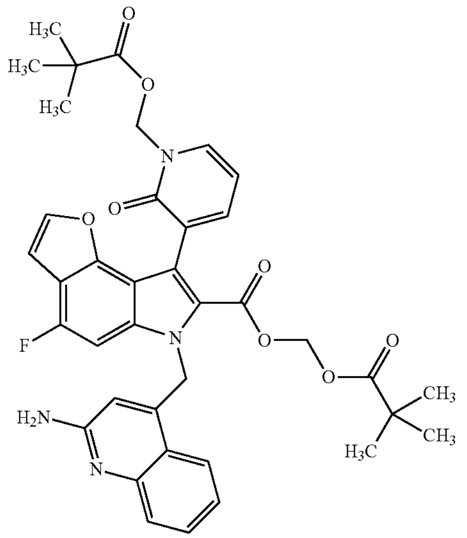 [SMILES: CC(C)(C)C(=O)OCOC(=O)c1c(-c2cccn(COC(=O)C(C)(C)C)c2=O)c2c3occc3c(F)cc2n1Cc1cc(N)nc2ccccc12] |
| 127 | 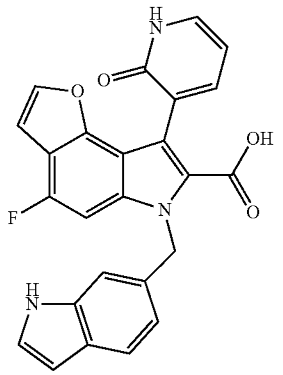 [SMILES: O=C(O)c1c(-c2ccc[nH]c2=O)c2c3occc3c(F)cc2n1Cc1ccc2cc[nH]c2c1] |
| 128 | 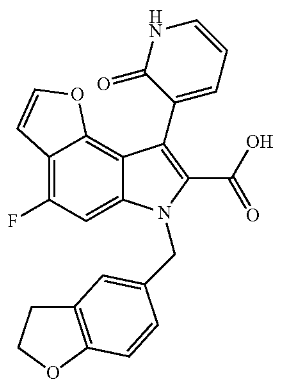 [SMILES: O=C(O)c1c(-c2ccc[nH]c2=O)c2c3occc3c(F)cc2n1Cc1ccc2c(c1)CCO2] |

-continued
| Cpd No. | Structure |
|---|---|
| 129 | 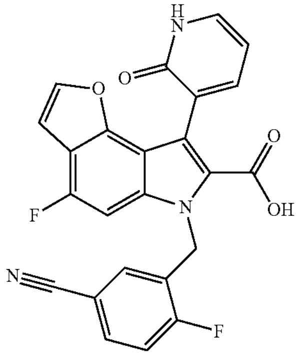 [SMILES: N#Cc1ccc(F)c(Cn2c(C(=O)O)c(-c3ccc[nH]c3=O)c3c4occc4c(F)cc32)c1] |
| 130 | 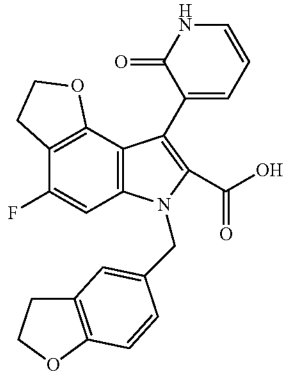 [SMILES: O=C(O)c1c(-c2ccc[nH]c2=O)c2c3c(c(F)cc2n1Cc1ccc2c(c1)CCO2)CCO3] |
| 131 | 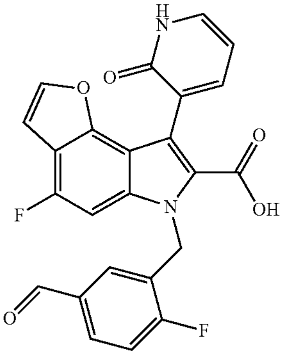 [SMILES: O=Cc1ccc(F)c(Cn2c(C(=O)O)c(-c3ccc[nH]c3=O)c3c4occc4c(F)cc32)c1] |
| 132 | 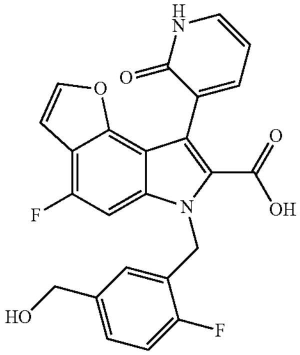 [SMILES: O=C(O)c1c(-c2ccc[nH]c2=O)c2c3occc3c(F)cc2n1Cc1cc(CO)ccc1F] |
-continued
| Cpd No. | Structure |
|---|---|
| 133 | 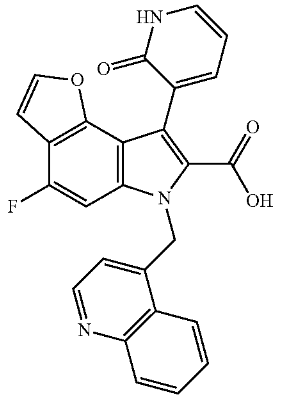 [SMILES: O=C(O)c1c(-c2ccc[nH]c2=O)c2c3occc3c(F)cc2n1Cc1ccnc2ccccc12] |
| 134 | 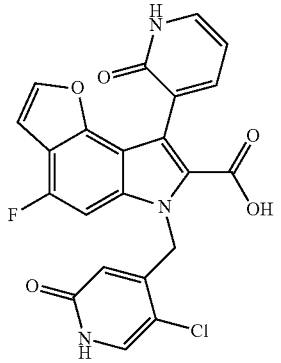 [SMILES: O=C(O)c1c(-c2ccc[nH]c2=O)c2c3occc3c(F)cc2n1Cc1cc(=O)[nH]cc1Cl] |
| 135 | 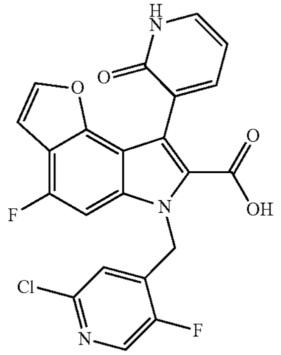 [SMILES: O=C(O)c1c(-c2ccc[nH]c2=O)c2c3occc3c(F)cc2n1Cc1cc(Cl)ncc1F] |
| 136 | 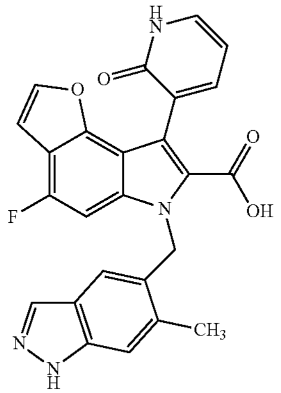 [SMILES: Cc1cc2[nH]ncc2cc1Cn1c(C(=O)O)c(-c2ccc[nH]c2=O)c2c3occc3c(F)cc21] |

-continued
| Cpd No. | Structure |
|---|---|
| 137 | 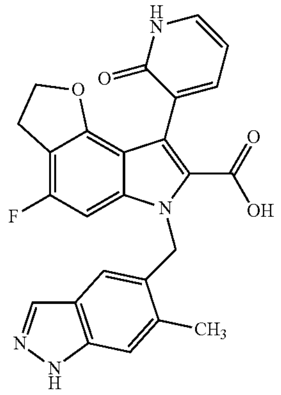 [SMILES: Cc1cc2[nH]ncc2cc1Cn1c(C(=O)O)c(-c2ccc[nH]c2=O)c2c3c(c(F)cc21)CCO3] |
| 138 | 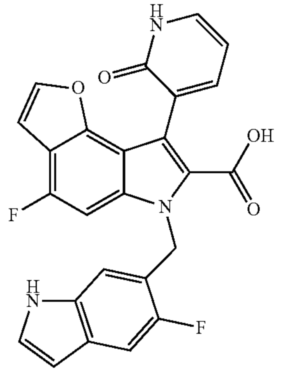 [SMILES: O=C(O)c1c(-c2ccc[nH]c2=O)c2c3occc3c(F)cc2n1Cc1cc2[nH]ccc2cc1F] |
| 139 | 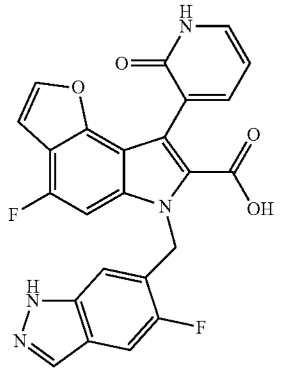 [SMILES: O=C(O)c1c(-c2ccc[nH]c2=O)c2c3occc3c(F)cc2n1Cc1cc2[nH]ncc2cc1F] |
| 140 | 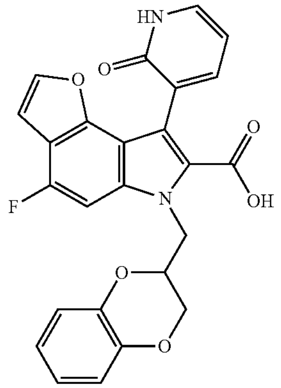 |
-continued
| Cpd No. | Structure |
|---|---|
| 141 | 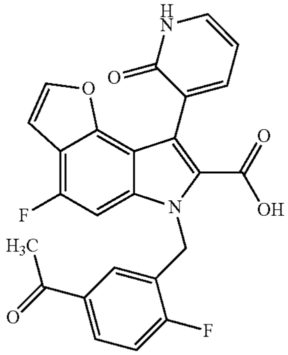 [SMILES: CC(=O)c1ccc(F)c(Cn2c(C(=O)O)c(-c3ccc[nH]c3=O)c3c4occc4c(F)cc32)c1] |
| 142 | 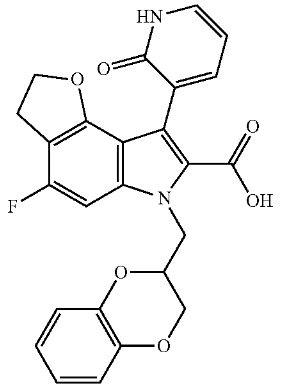 [SMILES: O=C(O)c1c(-c2ccc[nH]c2=O)c2c3c(c(F)cc2n1CC1COc2ccccc2O1)CCO3] |
| 143 | 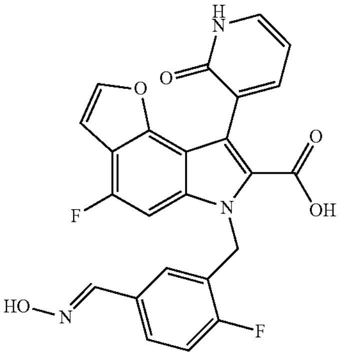 [SMILES: O=C(O)c1c(-c2ccc[nH]c2=O)c2c3occc3c(F)cc2n1Cc1cc(/C=N/O)ccc1F] |
| 144 | 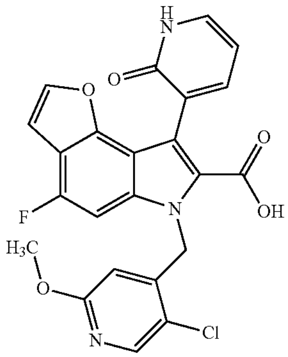 [SMILES: COc1cc(Cn2c(C(=O)O)c(-c3ccc[nH]c3=O)c3c4occc4c(F)cc32)c(Cl)cn1] |

-continued
| Cpd No. | Structure |
|---|---|
| 145 | 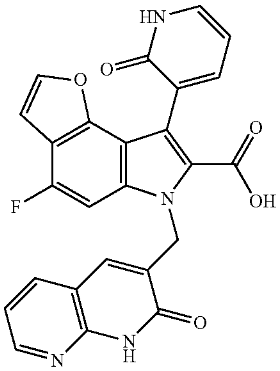 [SMILES: O=C(O)c1c(-c2ccc[nH]c2=O)c2c3occc3c(F)cc2n1Cc1cc2cccnc2[nH]c1=O] |
| 146 | 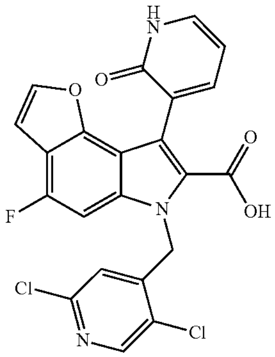 [SMILES: O=C(O)c1c(-c2ccc[nH]c2=O)c2c3occc3c(F)cc2n1Cc1cc(Cl)ncc1Cl] |
| 147 | 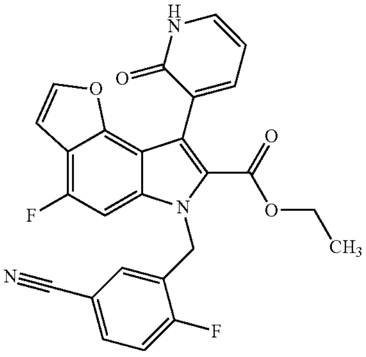 [SMILES: CCOC(=O)c1c(-c2ccc[nH]c2=O)c2c3occc3c(F)cc2n1Cc1cc(C#N)ccc1F] |
| 148 | 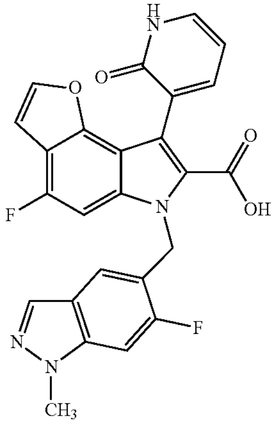 [SMILES: Cn1ncc2cc(Cn3c(C(=O)O)c(-c4ccc[nH]c4=O)c4c5occc5c(F)cc43)c(F)cc21] |
-continued
| Cpd No. | Structure |
|---|---|
| 149 | 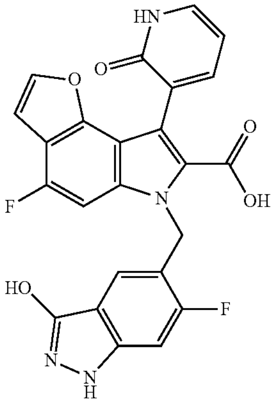 [SMILES: O=C(O)c1c(-c2ccc[nH]c2=O)c2c3occc3c(F)cc2n1Cc1cc2c(O)n[nH]c2cc1F] |
| 150 | 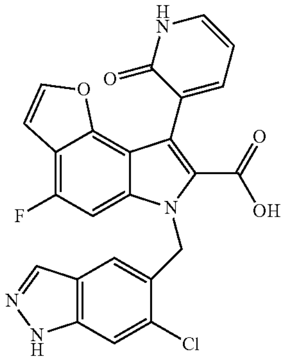 [SMILES: O=C(O)c1c(-c2ccc[nH]c2=O)c2c3occc3c(F)cc2n1Cc1cc2cn[nH]c2cc1Cl] |
| 151 | 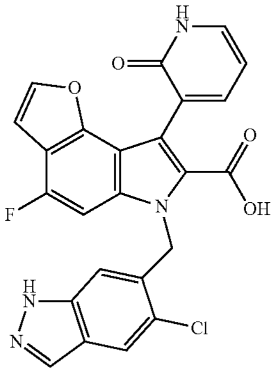 [SMILES: O=C(O)c1c(-c2ccc[nH]c2=O)c2c3occc3c(F)cc2n1Cc1cc2[nH]ncc2cc1Cl] |
| 152 | 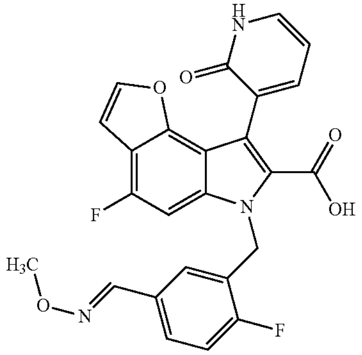 [SMILES: CO/N=C/c1ccc(F)c(Cn2c(C(=O)O)c(-c3ccc[nH]c3=O)c3c4occc4c(F)cc32)c1] |

-continued
| Cpd No. | Structure |
|---|---|
| 153 | 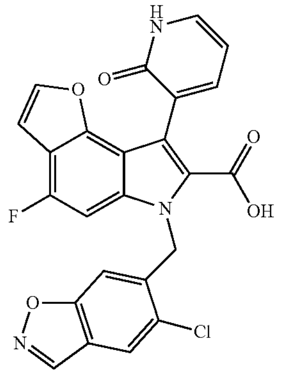 [SMILES: O=C(O)c1c(-c2ccc[nH]c2=O)c2c3occc3c(F)cc2n1Cc1cc2oncc2cc1Cl] |
| 154 | 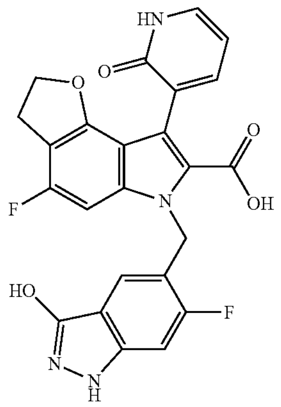 [SMILES: O=C(O)c1c(-c2ccc[nH]c2=O)c2c3c(c(F)cc2n1Cc1cc2c(O)n[nH]c2cc1F)CCO3] |
| 155 | 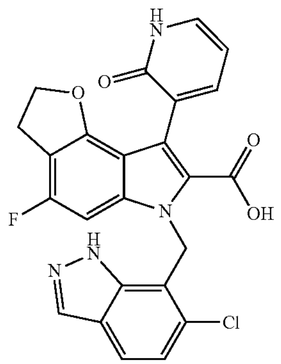 [SMILES: O=C(O)c1c(-c2ccc[nH]c2=O)c2c3c(c(F)cc2n1Cc1c(Cl)ccc2cn[nH]c12)CCO3] |
| 156 | 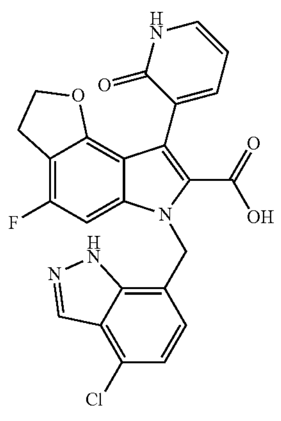 [SMILES: O=C(O)c1c(-c2ccc[nH]c2=O)c2c3c(c(F)cc2n1Cc1ccc(Cl)c2cn[nH]c12)CCO3] |
-continued
| Cpd No. | Structure |
|---|---|
| 157 | 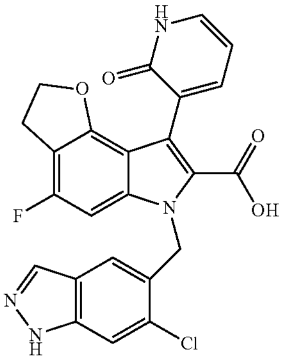 [SMILES: O=C(O)c1c(-c2ccc[nH]c2=O)c2c3c(c(F)cc2n1Cc1cc2cn[nH]c2cc1Cl)CCO3] |
| 158 | 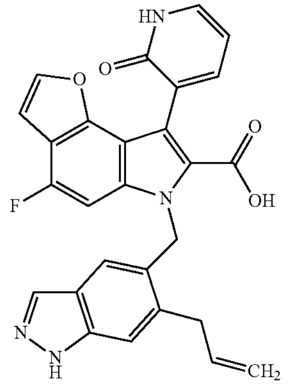 [SMILES: C=CCc1cc2[nH]ncc2cc1Cn1c(C(=O)O)c(-c2ccc[nH]c2=O)c2c3occc3c(F)cc21] |
| 159 | 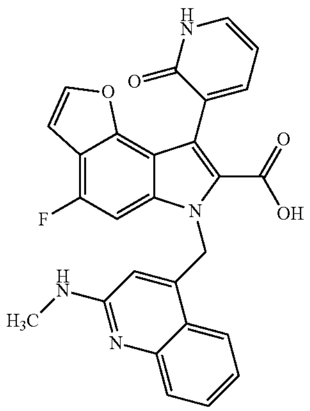 [SMILES: CNc1cc(Cn2c(C(=O)O)c(-c3ccc[nH]c3=O)c3c4occc4c(F)cc32)c2ccccc2n1] |
| 160 | 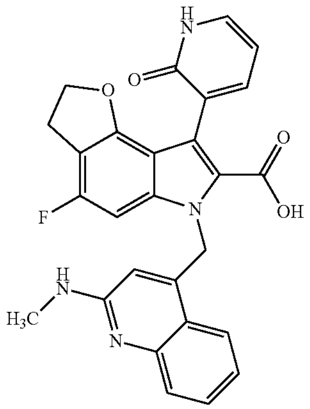 [SMILES: CNc1cc(Cn2c(C(=O)O)c(-c3ccc[nH]c3=O)c3c4c(c(F)cc32)CCO4)c2ccccc2n1] |

-continued
| Cpd No. | Structure |
|---|---|
| 161 | 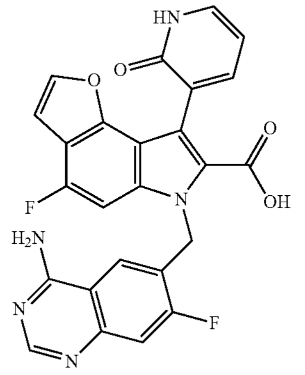 [SMILES: Nc1ncnc2cc(F)c(Cn3c(C(=O)O)c(-c4ccc[nH]c4=O)c4c5occc5c(F)cc43)cc12] |
| 162 | 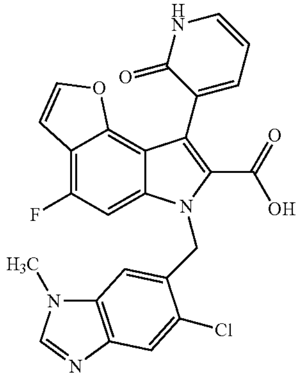 [SMILES: Cn1cnc2cc(Cl)c(Cn3c(C(=O)O)c(-c4ccc[nH]c4=O)c4c5occc5c(F)cc43)cc21] |
| 163 | 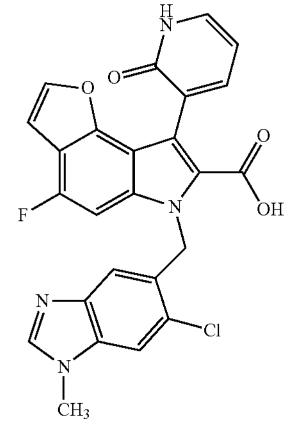 [SMILES: Cn1cnc2cc(Cn3c(C(=O)O)c(-c4ccc[nH]c4=O)c4c5occc5c(F)cc43)c(Cl)cc21] |
| 164 | 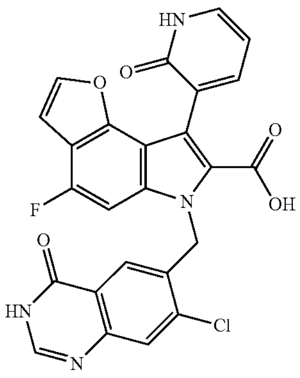 [SMILES: O=C(O)c1c(-c2ccc[nH]c2=O)c2c3occc3c(F)cc2n1Cc1cc2c(=O)[nH]cnc2cc1Cl] |
-continued
| Cpd No. | Structure |
|---|---|
| 165 | 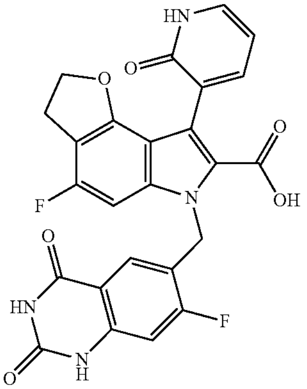 [SMILES: O=C(O)c1c(-c2ccc[nH]c2=O)c2c3c(c(F)cc2n1Cc1cc2c(=O)[nH]c(=O)[nH]c2cc1F)CCO3] |
| 166 | 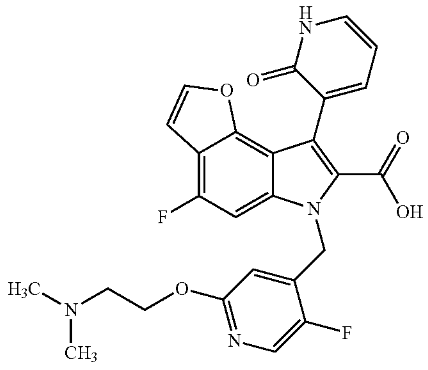 [SMILES: CN(C)CCOc1cc(Cn2c(C(=O)O)c(-c3ccc[nH]c3=O)c3c4occc4c(F)cc32)c(F)cn1] |
| 167 | 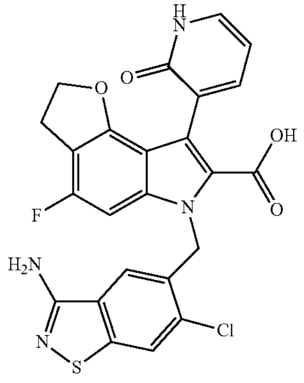 [SMILES: Nc1nsc2cc(Cl)c(Cn3c(C(=O)O)c(-c4ccc[nH]c4=O)c4c5c(c(F)cc43)CCO5)cc12] |
| 168 | 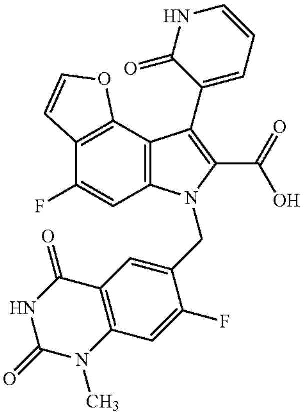 [SMILES: Cn1c(=O)[nH]c(=O)c2cc(Cn3c(C(=O)O)c(-c4ccc[nH]c4=O)c4c5occc5c(F)cc43)c(F)cc21] |

-continued
| Cpd No. | Structure |
|---|---|
| 169 | 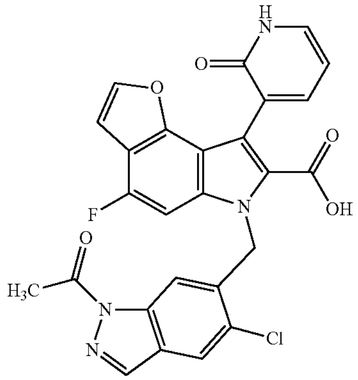 [SMILES: CC(=O)n1ncc2cc(Cl)c(Cn3c(C(=O)O)c(-c4ccc[nH]c4=O)c4c5occc5c(F)cc43)cc21] |
| 170 | 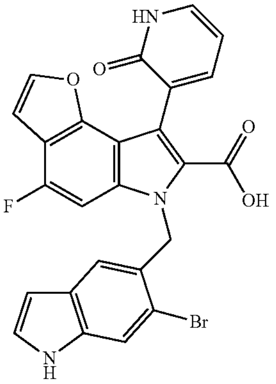 [SMILES: O=C(O)c1c(-c2ccc[nH]c2=O)c2c3occc3c(F)cc2n1Cc1cc2cc[nH]c2cc1Br] |
| 171 | 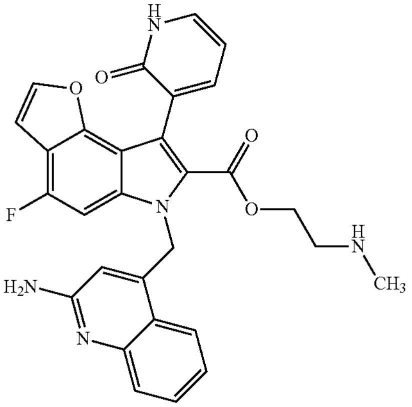 [SMILES: CNCCOC(=O)c1c(-c2ccc[nH]c2=O)c2c3occc3c(F)cc2n1Cc1cc(N)nc2ccccc12] |
-continued
| Cpd No. | Structure |
|---|---|
| 172 | 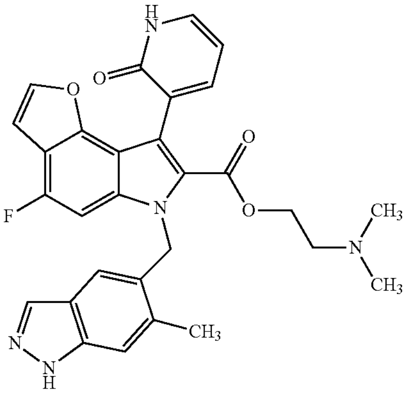 [SMILES: Cc1cc2[nH]ncc2cc1Cn1c(C(=O)OCCN(C)C)c(-c2ccc[nH]c2=O)c2c3occc3c(F)cc21] |
| 173 | 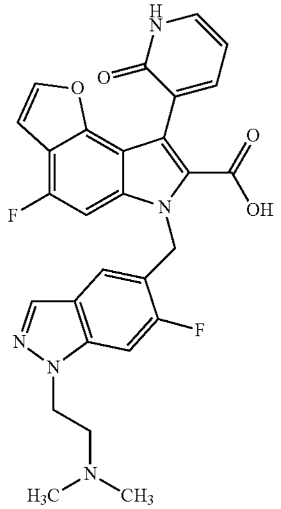 [SMILES: CN(C)CCn1ncc2cc(Cn3c(C(=O)O)c(-c4ccc[nH]c4=O)c4c5occc5c(F)cc43)c(F)cc21] |
| 174 | 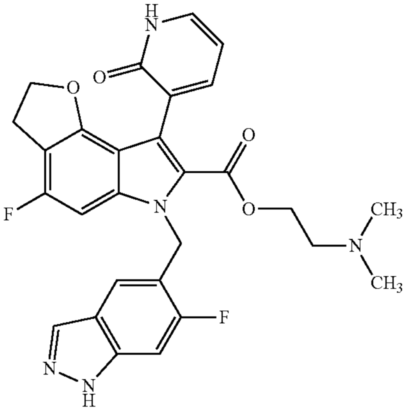 [SMILES: CN(C)CCOC(=O)c1c(-c2ccc[nH]c2=O)c2c3c(c(F)cc2n1Cc1cc2cn[nH]c2cc1F)CCO3]

-continued
| Cpd No. | Structure |
|---|---|
| 175 | 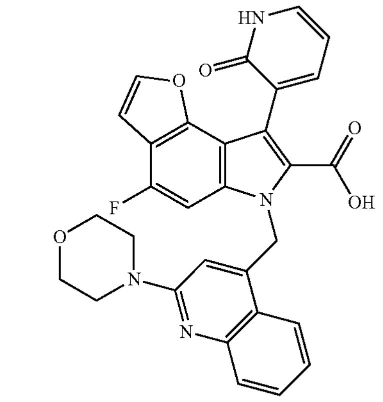 [SMILES: O=C(O)c1c(-c2ccc[nH]c2=O)c2c3occc3c(F)cc2n1Cc1cc(N2CCOCC2)nc2ccccc12] |
| 176 | 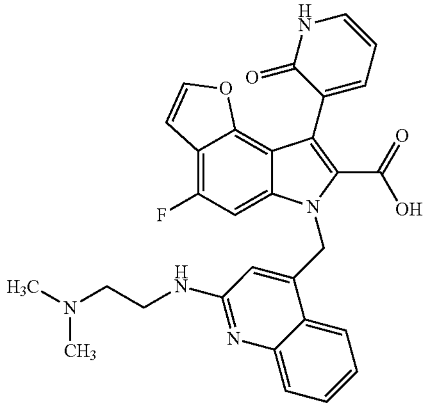 [SMILES: CN(C)CCNc1cc(Cn2c(C(=O)O)c(-c3ccc[nH]c3=O)c3c4occc4c(F)cc32)c2ccccc2n1] |
| 177 | 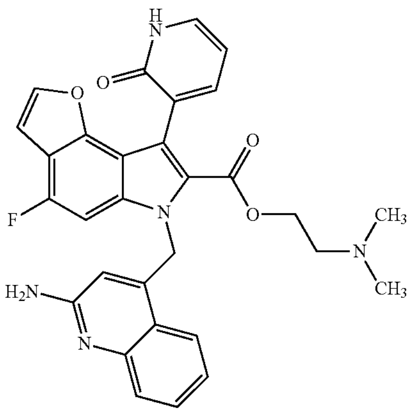 [SMILES: CN(C)CCOC(=O)c1c(-c2ccc[nH]c2=O)c2c3occc3c(F)cc2n1Cc1cc(N)nc2ccccc12] |
-continued
| Cpd No. | Structure |
|---|---|
| 178 | 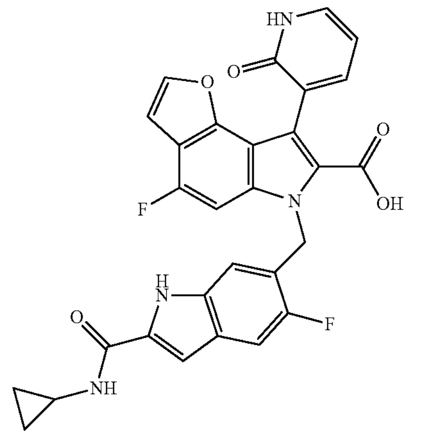 [SMILES: O=C(NC1CC1)c1cc2cc(F)c(Cn3c(C(=O)O)c(-c4ccc[nH]c4=O)c4c5occc5c(F)cc43)cc2[nH]1] |
| 179 | 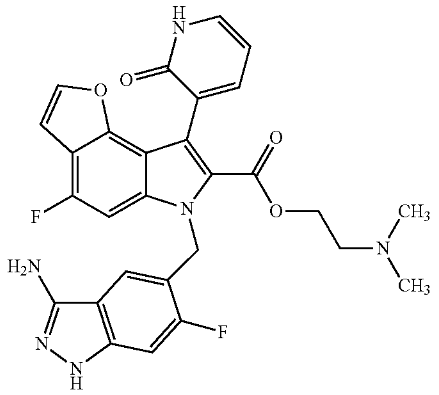 [SMILES: CN(C)CCOC(=O)c1c(-c2ccc[nH]c2=O)c2c3occc3c(F)cc2n1Cc1cc2c(N)n[nH]c2cc1F] |
| 180 | 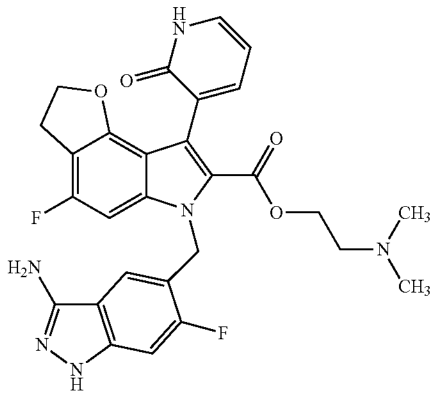 [SMILES: CN(C)CCOC(=O)c1c(-c2ccc[nH]c2=O)c2c3c(c(F)cc2n1Cc1cc2c(N)n[nH]c2cc1F)CCO3] |

-continued
| Cpd No. | Structure |
|---|---|
| 181 | 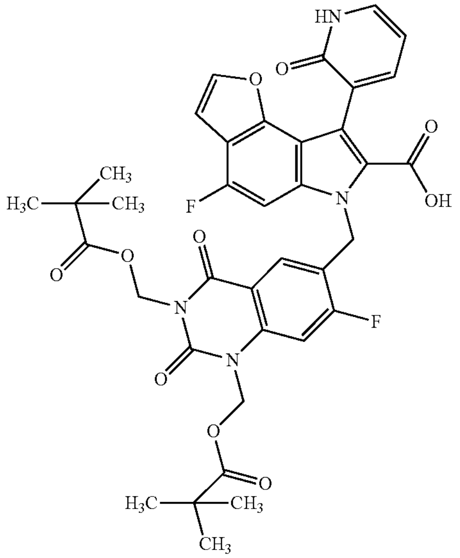 [SMILES: CC(C)(C)C(=O)OCn1c(=O)c2cc(Cn3c(C(=O)O)c(-c4ccc[nH]c4=O)c4c5occc5c(F)cc43)c(F)cc2n(COC(=O)C(C)(C)C)c1=O] |
| 182 | 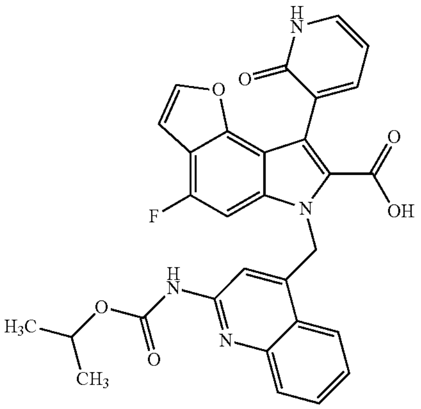 [SMILES: CC(C)OC(=O)Nc1cc(Cn2c(C(=O)O)c(-c3ccc[nH]c3=O)c3c4occc4c(F)cc32)c2ccccc2n1] |
| 183 | 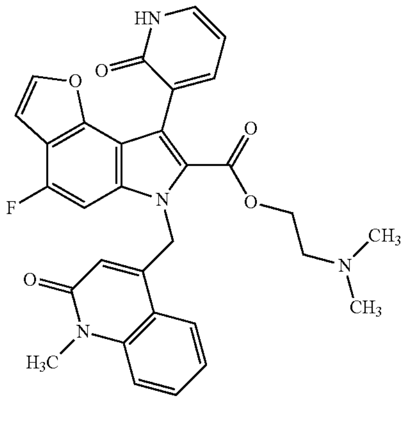 [SMILES: CN(C)CCOC(=O)c1c(-c2ccc[nH]c2=O)c2c3occc3c(F)cc2n1Cc1cc(=O)n(C)c2ccccc12] |
-continued
| Cpd No. | Structure |
|---|---|
| 184 | 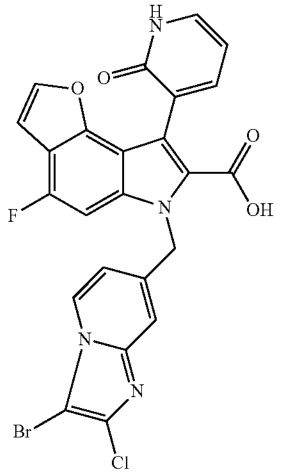 [SMILES: O=C(O)c1c(-c2ccc[nH]c2=O)c2c3occc3c(F)cc2n1Cc1ccn2c(Br)c(Cl)nc2c1] |
| 185 | 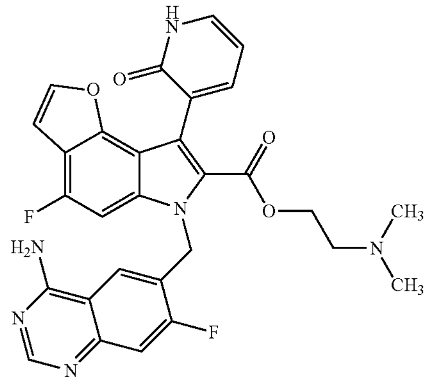 [SMILES: CN(C)CCOC(=O)c1c(-c2ccc[nH]c2=O)c2c3occc3c(F)cc2n1Cc1cc2c(N)ncnc2cc1F] |
| 186 | 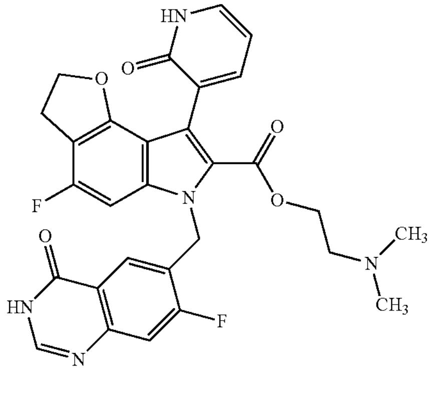 [SMILES: CN(C)CCOC(=O)c1c(-c2ccc[nH]c2=O)c2c3c(c(F)cc2n1Cc1cc2c(=O)[nH]cnc2cc1F)CCO3] |

-continued
| Cpd No. | Structure |
|---|---|
| 187 | 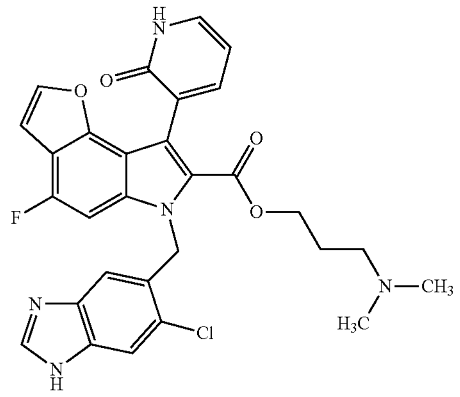 [SMILES: CN(C)CCCOC(=O)c1c(-c2ccc[nH]c2=O)c2c3occc3c(F)cc2n1Cc1cc2nc[nH]c2cc1Cl] |
| 188 | 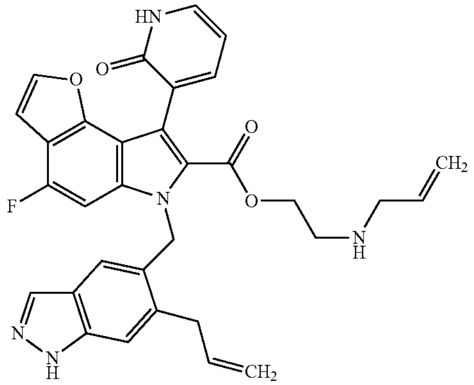 [SMILES: C=CCNCCOC(=O)c1c(-c2ccc[nH]c2=O)c2c3occc3c(F)cc2n1Cc1cc2cn[nH]c2cc1CC=C] |
| 189 | 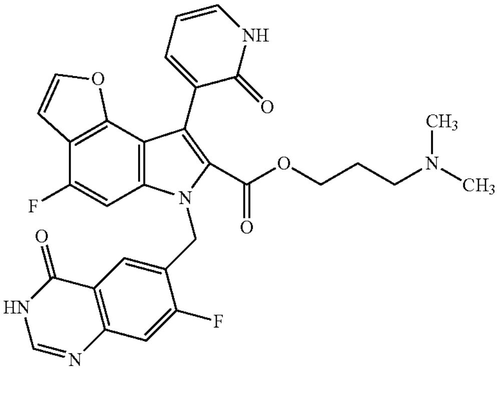 [SMILES: CN(C)CCCOC(=O)c1c(-c2ccc[nH]c2=O)c2c3occc3c(F)cc2n1Cc1cc2c(=O)[nH]cnc2cc1F] |
-continued
| Cpd No. | Structure |
|---|---|
| 190 | 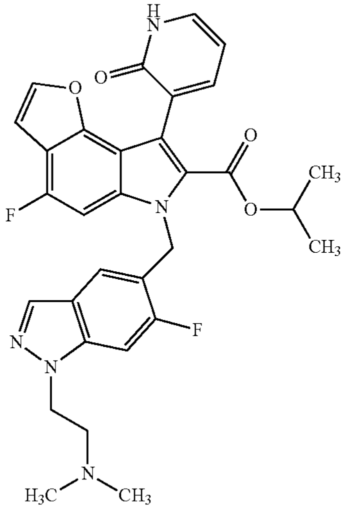 [SMILES: CC(C)OC(=O)c1c(-c2ccc[nH]c2=O)c2c3occc3c(F)cc2n1Cc1cc2cnn(CCN(C)C)c2cc1F] |
| 191 | 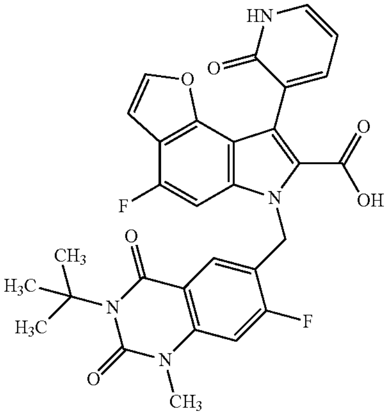 [SMILES: Cn1c(=O)n(C(C)(C)C)c(=O)c2cc(Cn3c(C(=O)O)c(-c4ccc[nH]c4=O)c4c5occc5c(F)cc43)c(F)cc21] |
| 192 | 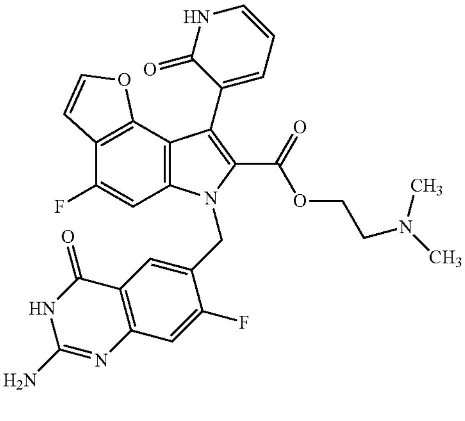 [SMILES: CN(C)CCOC(=O)c1c(-c2ccc[nH]c2=O)c2c3occc3c(F)cc2n1Cc1cc2c(=O)[nH]c(N)nc2cc1F] |

-continued
| Cpd No. | Structure |
|---|---|
| 193 | 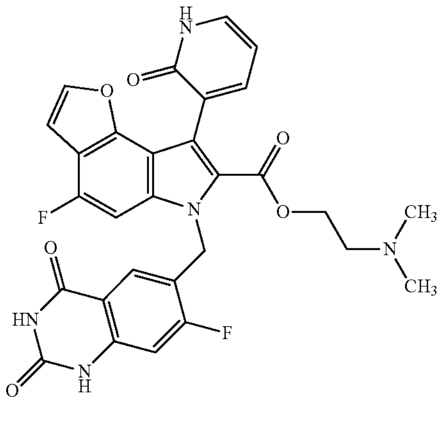 [SMILES: CN(C)CCOC(=O)c1c(-c2ccc[nH]c2=O)c2c3occc3c(F)cc2n1Cc1cc2c(=O)[nH]c(=O)[nH]c2cc1F] |
| 194 | 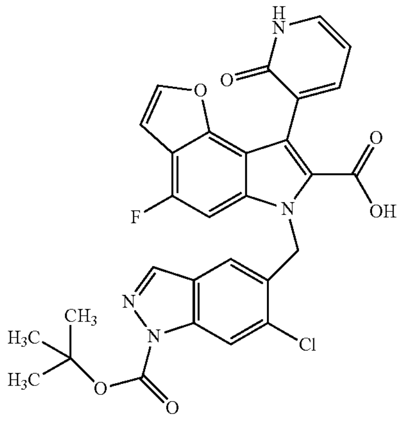 [SMILES: CC(C)(C)OC(=O)n1ncc2cc(Cn3c(C(=O)O)c(-c4ccc[nH]c4=O)c4c5occc5c(F)cc43)c(Cl)cc21] |
| 195 | 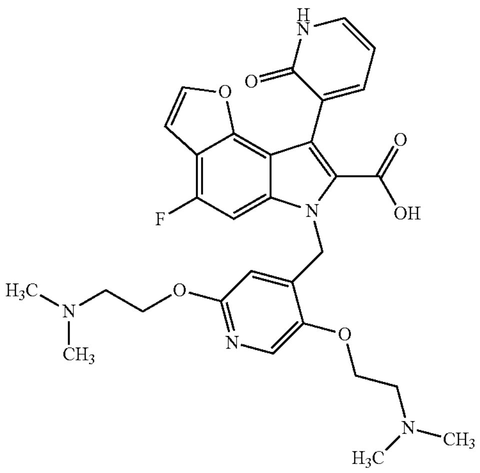 |
-continued
| Cpd No. | Structure |
|---|---|
| 196 | 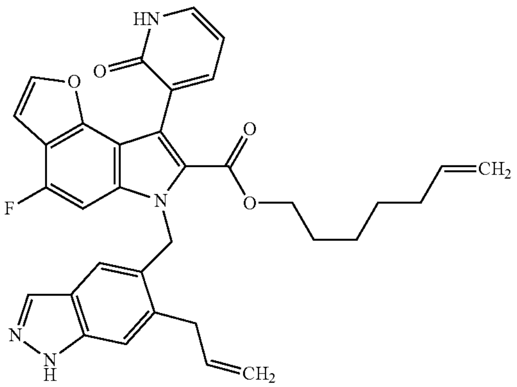 [SMILES: C=CCCCCCOC(=O)c1c(-c2ccc[nH]c2=O)c2c3occc3c(F)cc2n1Cc1cc2cn[nH]c2cc1CC=C] |
| 197 | 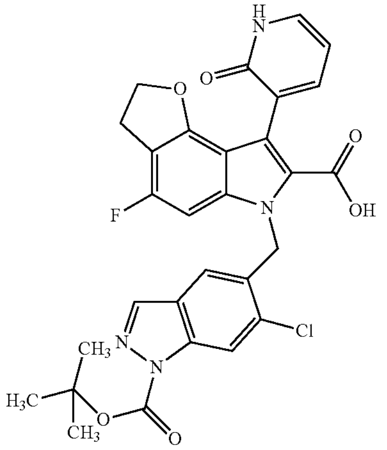 [SMILES: CC(C)(C)OC(=O)n1ncc2cc(Cn3c(C(=O)O)c(-c4ccc[nH]c4=O)c4c5c(c(F)cc43)CCO5)c(Cl)cc21] |
| 198 | 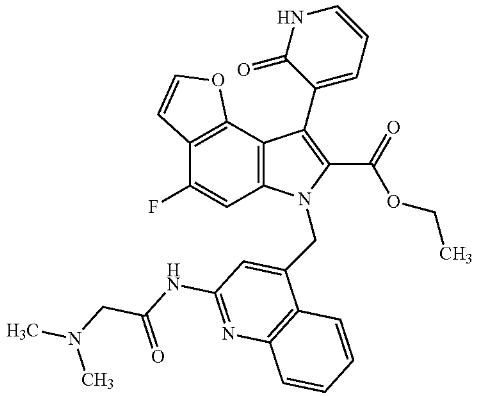 [SMILES: CCOC(=O)c1c(-c2ccc[nH]c2=O)c2c3occc3c(F)cc2n1Cc1cc(NC(=O)CN(C)C)nc2ccccc12] |

-continued
| Cpd No. | Structure |
| --- | --- |
| 199 | 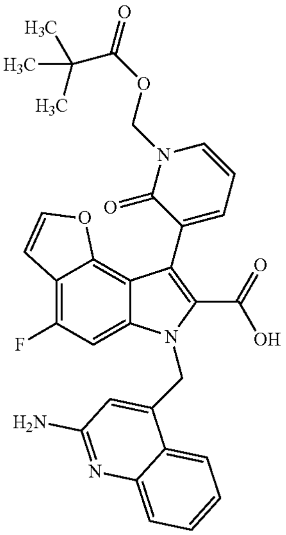 [SMILES: CC(C)(C)C(=O)OCn1cccc(-c2c(C(=O)O)n(Cc3cc(N)nc4ccccc34)c3cc(F)c4ccoc4c23)c1=O] |
| 200 | 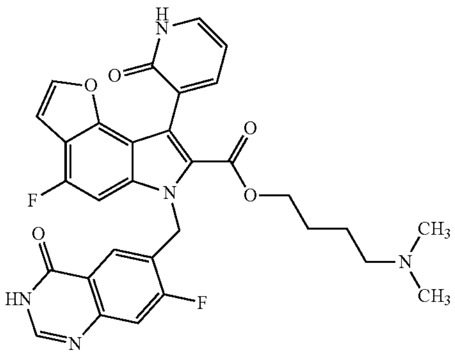 [SMILES: CN(C)CCCCOC(=O)c1c(-c2ccc[nH]c2=O)c2c3occc3c(F)cc2n1Cc1cc2c(=O)[nH]cnc2cc1F] |
| 201 | 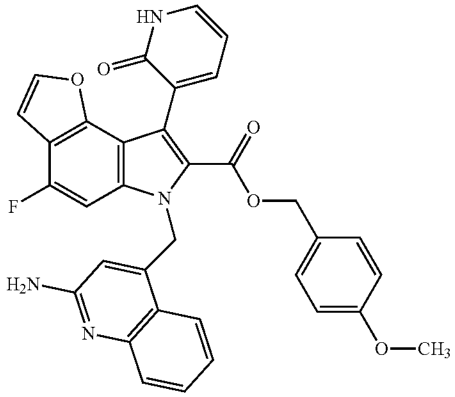 [SMILES: COc1ccc(COC(=O)c2c(-c3ccc[nH]c3=O)c3c4occc4c(F)cc3n2Cc2cc(N)nc3ccccc23)cc1] |
-continued
| Cpd No. | Structure |
| --- | --- |
| 202 | 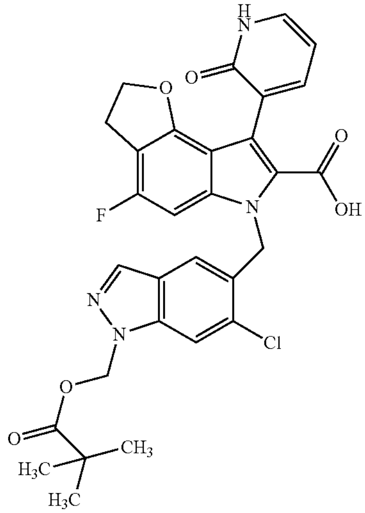 [SMILES: CC(C)(C)C(=O)OCn1ncc2cc(Cn3c(C(=O)O)c(-c4ccc[nH]c4=O)c4c5c(c(F)cc43)CCO5)c(Cl)cc21] |
| 203 | 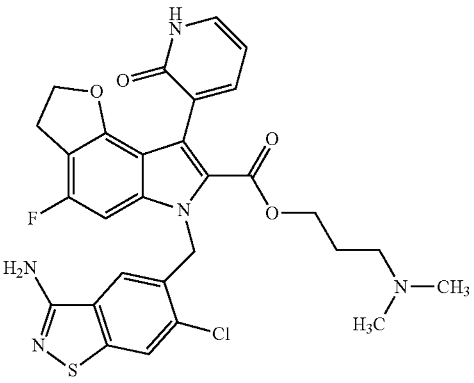 [SMILES: CN(C)CCCOC(=O)c1c(-c2ccc[nH]c2=O)c2c3c(c(F)cc2n1Cc1cc2c(N)nsc2cc1Cl)CCO3] |
| 204 | 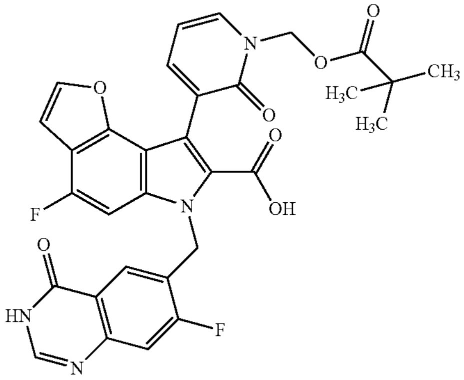 [SMILES: CC(C)(C)C(=O)OCn1cccc(-c2c(C(=O)O)n(Cc3cc4c(=O)[nH]cnc4cc3F)c3cc(F)c4ccoc4c23)c1=O] |

-continued

| Cpd No. | Structure |
|---|---|
| 205 | 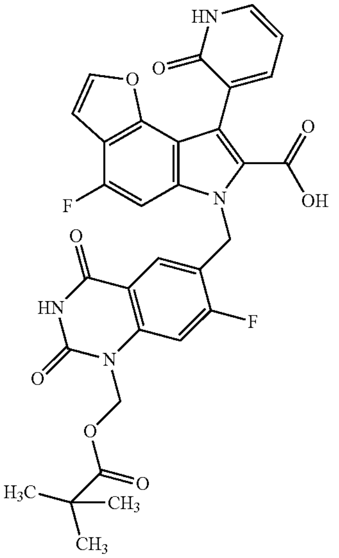 [SMILES: CC(C)(C)C(=O)OCn1c(=O)[nH]c(=O)c2cc(Cn3c(C(=O)O)c(-c4ccc[nH]c4=O)c4c5occc5c(F)cc43)c(F)cc21] |
| 206 | 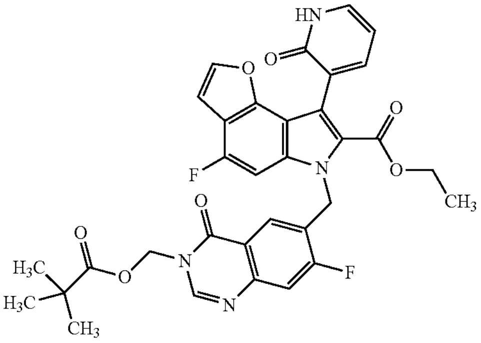 [SMILES: CCOC(=O)c1c(-c2ccc[nH]c2=O)c2c3occc3c(F)cc2n1Cc1cc2c(=O)n(COC(=O)C(C)(C)C)cnc2cc1F] |
| 207 | 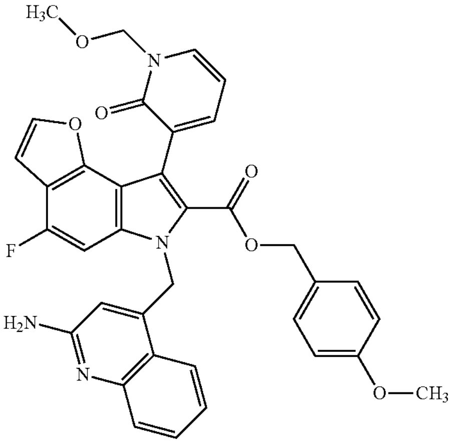 [SMILES: COCn1cccc(-c2c(C(=O)OCc3ccc(OC)cc3)n(Cc3cc(N)nc4ccccc34)c3cc(F)c4ccoc4c23)c1=O] |
| 208 | 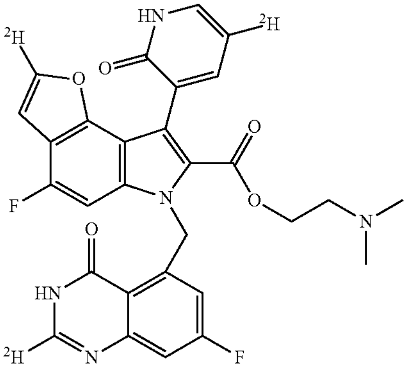 [SMILES: [2H]c1c[nH]c(=O)c(-c2c(C(=O)OCCN(C)C)n(Cc3cc(F)cc4nc([2H])[nH]c(=O)c34)c3cc(F)c4cc([2H])oc4c23)c1] |
| 209 | 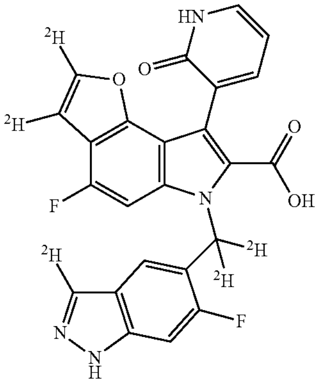 [SMILES: [2H]c1oc2c(c(F)cc3c2c(-c2ccc[nH]c2=O)c(C(=O)O)n3C([2H])([2H])c2cc3c([2H])n[nH]c3cc2F)c1[2H]] |

and pharmaceutically acceptable salts, solvates, esters and prodrugs thereof.

Methods for Making the Compounds of Formula (I)

The Compounds of Formula (I) may be prepared from known or readily prepared starting materials, following methods known to one skilled in the art of organic synthesis. Methods useful for making the Compounds of Formula (I) are set forth in the Examples below and generalized in Schemes 1-4. Alternative synthetic pathways and analogous structures will be apparent to those skilled in the art of organic synthesis. All stereoisomers and tautomeric forms of the compounds are contemplated.

Scheme 1 shows one method for preparing compounds of formula A4, which are useful intermediates for making of the Compounds of Formula (I).

Scheme 1

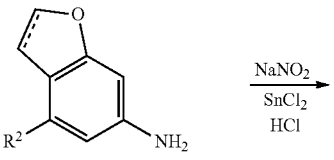

A1

-continued

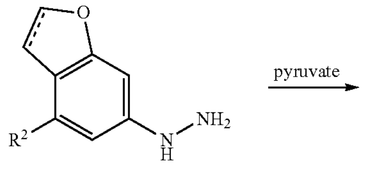

A2

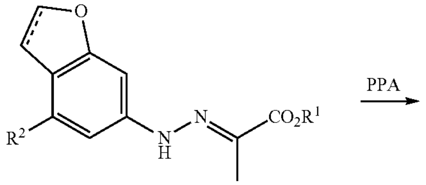

A3

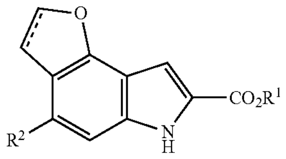

A4 wherein $R^1$ and $R^2$ are defined above for the Compounds of Formula (I).

A 3,4-ring fused aniline compound of formula A1 can be converted to an indole compound of formula A4 using various indole syntheses that are well-known to those skilled in the art of organic synthesis, including but not limited to, a Fischer indole synthesis through intermediates of type A2 and A3, using the method set forth in Nazare et al., *Angew. Chem.*, 116:4626-4629 (2004).

Scheme 2 shows alternative methods useful for making the compounds of formula A4, which are useful intermediates for making the Compounds of Formula (I).

Scheme 2

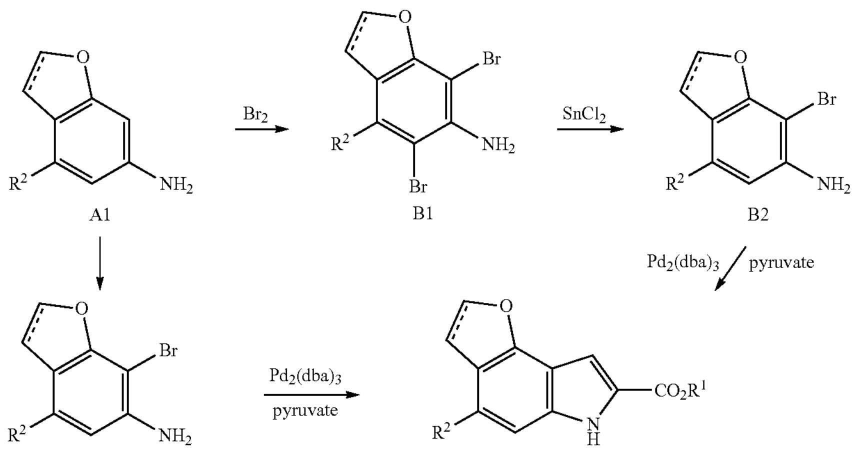

A1 B1 B2 B2 A4 wherein $R^1$ and $R^2$ are defined above for the Compounds of Formula (I).

A 3,4-ring fused aniline compound of formula A1 can be di-brominated to provide a compound of formula B1. Selective de-bromination of B1 using $SnCl_2$ provides the corresponding monobromo compounds of formula B2, which under palladium catalyzed cyclization conditions in the presence of an appropriately substituted pyruvate derivative, can provide the compounds of formula A4. Alternatively, a compound of formula A1 can be monobrominated to directly provide a compound of foiinula B2, which can then undergo a similar cyclization to provide a compound of formula A4.

Scheme 3 shows a method for making compounds of formula C5, which are useful intermediates for making of the Compounds of Formula (I), wherein the optional and additional bond is present and $R^1$ is methyl.

Scheme 3

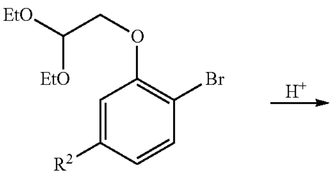

C1

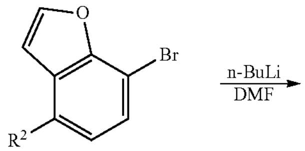

C2

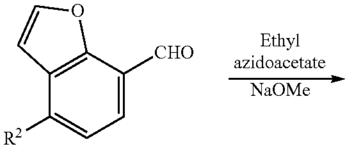

C3

-continued

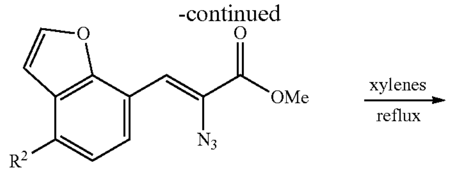

C4

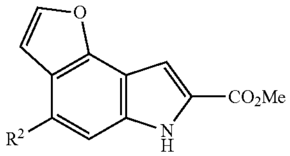

C5 wherein $R^1$ and $R^2$ are defined above for the Compounds of Formula (I).

An ethoxy ether compound of formula C1, can be ring closed under acidic conditions (e.g., polyphosphoric acid or Amberlyst-15) to provide the bicyclic compounds of formula C2. A compound of formula C2 can in turn be converted to an aromatic aldehyde of formula C3 using n-butyllitihium in DMF. A compound of formula C3 can then undergo a condensation reaction in the presence of an alkyl azidoacetate, such as ethylazidoacetate, to provide the azido compounds of formula C4 which can be subsequently cyclized under thermal conditions to provide the tricyclic indoles of formula C5.

Scheme 4 shows a method useful for making compounds of formula D3, which are useful intermediates for making of the Compounds of Formula (I).

Scheme 4

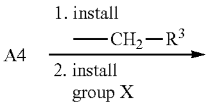

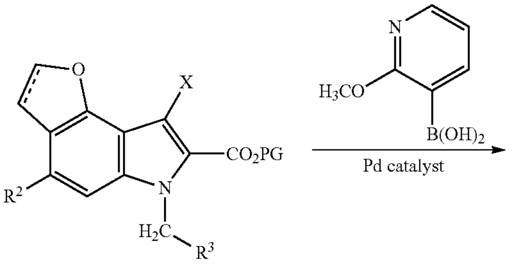

D1

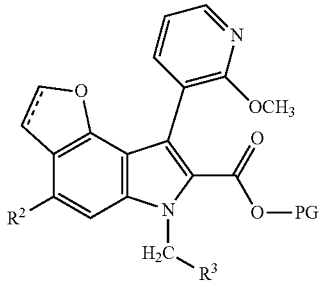

D2

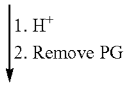

-continued

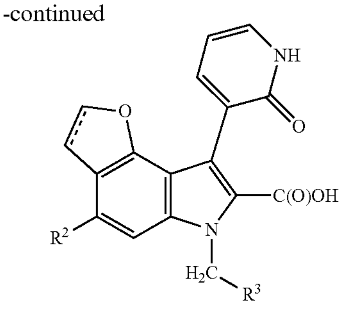

D3 wherein X is Br, I, —OTf, —$B(OH)_2$, —Sn(alkyl)$_3$, —MgBr, —MgCl, —ZnBr, —ZnCl, or any metal which can participate in an organometallic cross-coupling reaction PG is a carboxy protecting group; and $R^2$ and $R^3$ are defined above for the Compounds of Formula (I).

An intermediate compound of formula A4 can be converted to a 3-substituted indole of formula D1 using methods well-known to one skilled in the art of organic synthesis. A compound of formula D1, wherein X is Br, I or —OTf, can then be coupled with 2-methoxypyridine-3-boronic acid using a Suzuki coupling or a similar organometallic cross-coupling reaction. Alternatively, a compound of formula D1, wherein X is —$B(OH)_2$, —Sn(alkyl)$_3$, —MgBr, —MgCl, —ZnBr, —ZnCl; or any metal which can participate in an organometallic cross-coupling reaction with 3-halo-2-methoxypyridine or 3-triflyl-2-methoxypyridine using well known organometallic cross-coupling method. Suitable cross-coupling methods include, but not limited to, a Stine coupling (see Choshi et al., *J. Org. Chem.,* 62:2535-2543 (1997), and Scott et al., *J. Am. Chem. Soc.,* 106:4630 (1984)), a Suzuki coupling (see Miyaura et al., *Chem. Rev.,* 95:2457 (1995)), a Negishi coupling (see Zhou et al., *J. Am. Chem. Soc.,* 127:12537-12530 (2003)), and a Kumada coupling (see Kumada, *Pure Appl. Chem.,* 52:669 (1980) and Fu et al. *Angew. Chem.* 114:4363 (2002)) to provide a compound of formula D2. The methoxypyridyl group of E2 can be converted to the corresponding pyridine by treatment with acid, followed by removal of the protecting group of E2 to provide the compounds of formula D3, which correspond to the Compounds of Formula (I), wherein $R^1$ is H. The —C(O)OH group can be further derivatized to provide Compounds of Formula (I) wherein $R^2$ is other than H.

The starting material and reagents depicted above are either available from commercial suppliers such as Sigma-Aldrich (St. Louis, Mo.) and Acros Organics Co. (Fair Lawn, N.J.), or can be prepared using methods well-known to those of skill in the art of organic synthesis.

One skilled in the art of organic synthesis will recognize that the synthesis of the core of the Compounds of Formula (I) may require the need for the protection of certain functional groups (i.e., derivatization for the purpose of chemical compatibility with a particular reaction condition). Suitable protecting groups for the various functional groups of these compounds and methods for their installation and removal can be found in Greene et al., *Protective Groups in Organic Synthesis*, Wiley-Interscience, New York, (1999).

One skilled in the art of organic synthesis will also recognize that one route for the synthesis of the core of the Compounds of Formula (I) may be more desirable than others, depending on the choice of appendage substituents. Additionally, one skilled in the art will recognize that in some cases the order of reactions may differ from that presented herein to avoid functional group incompatibilities and amend the synthetic route accordingly.

One skilled in the art of organic synthesis will recognize that the synthesis of certain cores of the Compounds of Formula (I) require the construction of an amide bond. Methods useful for making such amide bonds, include but are not limited to, the use of a reactive carboxy derivative (e.g., acid halide, or ester at elevated temperatures) or the use of an acid with a coupling reagent (e.g., EDCI, DCC, HATU, PyBrop) with an amine.

The preparation of ring systems contemplated in this invention have been described in the literature and in compendia such as "Comprehensive Heterocyclic Chemistry" editions I, II and III, published by Elsevier and edited by A. R. Katritzky & R J K Taylor. Manipulations of the required substitution patterns have also been described in the available chemical literature as summarized in compendia such as, for example, "Comprehensive Organic Chemistry" published by Elsevier and edited by DH R. Barton and W. D. Ollis; "Comprehensive Organic Functional Group Transformations" edited by edited by A. R. Katritzky & R J K Taylor; and "Comprehensive Organic Transformation" published by Wily-CVH and edited by R. C. Larock.

The starting materials used and the intermediates prepared using the methods set forth in schemes 1-4 above may be isolated and purified if desired using conventional techniques, including but not limited to, filtration, distillation, crystallization, chromatography and alike. Such materials can be characterized using conventional means, including physical constants and spectral data.

EXAMPLES

General Methods

Solvents, reagents, and intermediates that are commercially available were used as received, Reagents and intermediates that are not commercially available were prepared in the manner as described below. $^{1}H$ NMR spectra were obtained on a Bruker Avance 500 (500 MHz) and are reported as ppm down field from $Me_4Si$ with number of protons, multiplicities, and coupling constants in Hertz indicated parenthetically. Where LC/MS data are presented, analyses was performed using an Applied Biosystems API-100 mass spectrometer and Shimadzu SCL-10A LC column: Altech platinum C18, 3 micron, 33 mm×7 mm ID; gradient flow: 0 minutes—10% $CH_3CN$, 5 minutes—95% $CH_3CN$, 5-7 minutes—95% $CH_3CN$, 7 minutes—stop. The retention time and observed parent ion are given. Flash column chromatography was perfoi uied using pre-packed normal phase silica from Biotage, Inc. or bulk silica from Fisher Scientific. Unless otherwise indicated, column chromatography was performed using a gradient elution of hexanes; ethyl acetate, from 100% hexanes to 100% ethyl acetate.

Example 1

Preparation of Intermediate Compound 1E

Step A—Synthesis of compound 1A

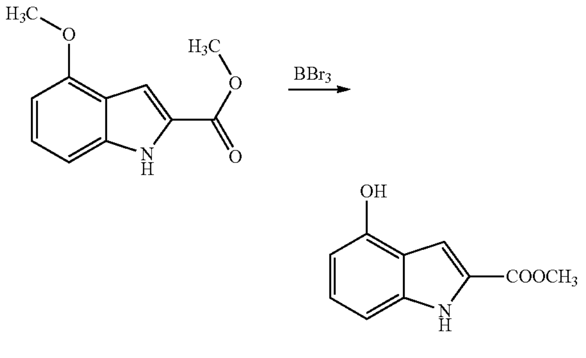

1A

A solution of 4-methoxy-1H-indole-2-carboxylic acid methyl ester (410 mg, 2.00 mmol) in $CH_2Cl_2$ (5 mL) was cooled to −78° C. and $BBr_3$ (6 mL solution, 1M) was added. The resulting reaction was then allowed to stir at 0° C. for 3 hours. The reaction mixture was then quenched using water and the resulting solution was extracted with EtOAc (200 mL). The combined organic layers were dried ($MgSO_4$), filtered, concentrated in vacuo and purified using flash column chromatography to provide compound 1A.

Step B—Synthesis of Compound 1B

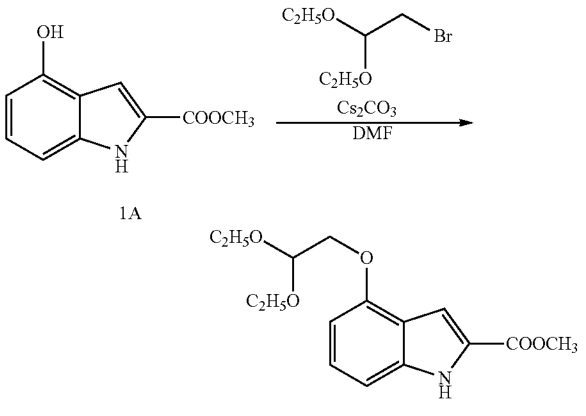

1A

1B

To a solution of compound 1A (2.5 g, 13.10 mmol) in DMF (50 mL) was added $Cs_2CO_3$ (5.12 g, 15.72 mmol), then bromoacetaldehyde-diethylacetal (12.90 g, 65.6 mmol), and the resulting reaction was allowed to stir at reflux for 2 hours. The reaction mixture was cooled to room temperature, treated with aqueous NaOH (1M, 50 mL) and extracted into EtOAc (250 mL). The organic layers were combined, dried ($MgSO_4$), filtered, and concentrated in vacuo to provide a crude residue which was purified using flash column chromatography (Hexanes/EtOAc 0 to 100%) to provide compound 1B as a colorless solid.

Step C—Synthesis of Compound 1C

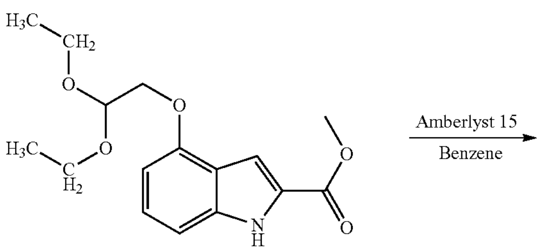

1B

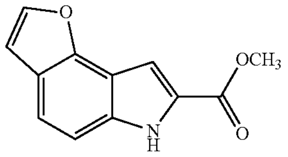

1C

To a solution of compound 1B in benzene (60 mL) was added Amberlyst-15 strongly acidic resin (4.5 g) and the resulting reaction was heated to 70° C. and allowed to stir at this temperature for 4 hours. The reaction mixture was then cooled to room temperature, diluted with EtOAc (300 mL) and washed with aqueous $NaHCO_3$. The combined organic layers were dried ($MgSO_4$), filtered, concentrated in vacuo and purified using flash column chromatography on silica gel (EtOAc/Hexanes, 0-30% EtOAc) to provide compound 1C (1.2 g).

Step D—Synthesis of Compound 1D

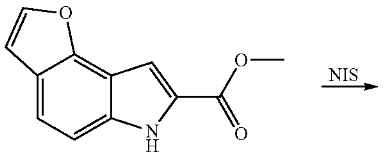

1C

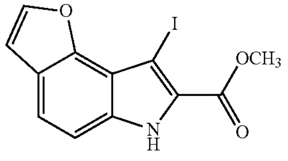

1D

To a solution of compound 1C (2.00 g, 9.3 mmol) in DMF (20 mL) was added N-iodosuccinimide (2.29 g, 10.2 mmol) and the resulting reaction was allowed to stir at room temperature for 12 hours. The reaction mixture was then concentrated in vacuo, diluted with water and extracted into EtOAc (300 mL). The combined organic layers were dried ($MgSO_4$), filtered, and concentrated in vacuo. The resulting brown residue was diluted with a minimum amount of $CH_2Cl^2$ and triturated using hexanes. Compound 1D separated out as a brown solid, which was filtered, then dried in vacuo. (Yield 2.6 g, 84%).

Step E—Synthesis of Compound

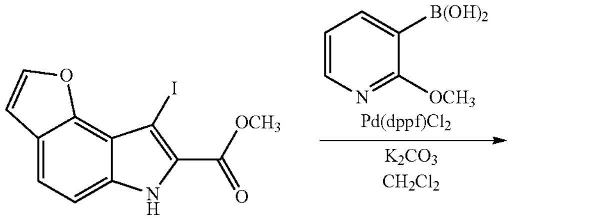

1D

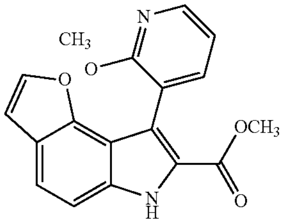

1E

To a solution of compound 1D (2.6 g, 7.6 mmol) in DME (40 mL) under nitrogen atmosphere was added with 2-methoxy-3-pyridyl boronic acid (3.5 g, 22.8 mmol) and Pd $(dppf)_2 Cl_2$ (616 mg) and the resulting reaction was allowed to stir at room temperature under nitrogen for 0.5 hours. The reaction mixture was then treated with a solution of potassium carbonate (6.3 g, 45.6 mmol) in water (40 mL) and the resulting solution was heated to 90° C. and allowed to stir at this temperature for 1 hour. The reaction mixture was then diluted with EtOAc (300 mL) and the resulting solution was concentrated in vacuo to provide a crude residue which was purified using flash column chromatography (EtOAc/Hexanes, 0 to 50% EtOAc) to provide compound 1E as a solid (2.0 g).

Example 2

Preparation of Intermediate Compound 2F

Step A—Synthesis of Compound 2A

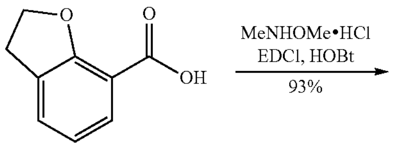

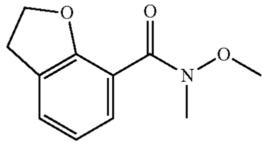

2A

A suspension of 2,3-dihydro-benzofuran-7-carboxylic acid, (TCI, 20.0 g, 121.8 mmol) in 600 mL of dry acetonitrile was cooled to 0° C. and treated with N,O-dimethylhydroxylamine hydrochloride (14.25 g, 146.1 mmol). The reaction was allowed to stir for 10 minutes and EDCI (24.6 g, 158.3 mmol) was added, followed by HOBT (3.2 g, 24.2 mmol) and the resulting mixture was allowed to stir for 5 minutes. Triethylamine (365.4 mmol) was then added and the reaction mixture was allowed to stir for 18 hours at room temperature, then diluted with aqueous 1N HCl (250 mL) and extracted with ethyl acetate (1.0 L). The organic layer was sequentially washed with aqueous 10% potassium carbonate (200 mL), aqueous 1N HCl (200 mL), and brine (200 mL). The organic layer was then dried over magnesium sulfate, filtered and concentrated in vacuo to provide compound 2A (23.37 g, 93%) as a colorless oil. M.S. found for $CH_{11}H_{13}NO_3$: 230.11 $(M+Na)^+$.

Step B—Synthesis of Compound 2B

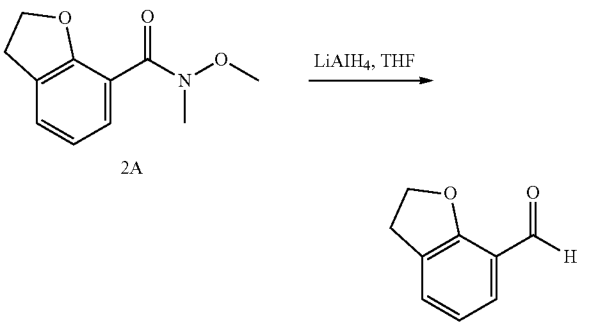

2A

2B

A suspension of lithium aluminum hydride (pellets, 5.56 g, 146.5 mmol) in 500 mL of dry THF was allowed to stir at 55° C. for 18 hours under anhydrous atmosphere, then cooled to 0° C., and a solution of compound 2A (23.37 g, 112.7 mmol) in 500 mL of dry THF was added over 45 minutes. The reaction mixture was allowed to stir at 0° C. for 30 minutes, then quenched by careful addition of aqueous 20% sodium hydrogen sulfate until gas evolution stopped. Additional aqueous 20% sodium hydrogen sulfate (approx. 5 mL) was added, and the resulting solution was vigorously allowed to stir for 15 minutes. The reaction mixture wsa diluted with ether (500 mL) and hexanes (500 mL) and filtered through a short path of celite. The filtrate was concentrated in vacuo to provide a crude residue which was purified using medium pressure liquid chromatography (Biotage 75-M silica gel column, gradient: 0 to 30% ethyl acetate in hexanes) to provide compound 2B (9.00 g, 54%) as a white solid. $^1H$ NMR (400 MHz, $d_6$-DMSO): δ 10.10 (s, 1H), 7.51 (q, J=7.32 Hz & 5.13 Hz, 2H), 6.95 (t, J=7.69 Hz, 1H), 4.69 (t, J=8.79 Hz, 2H), 3.22 (t, J=8.42 Hz, 2H).

Step C—Synthesis of Compound 2C

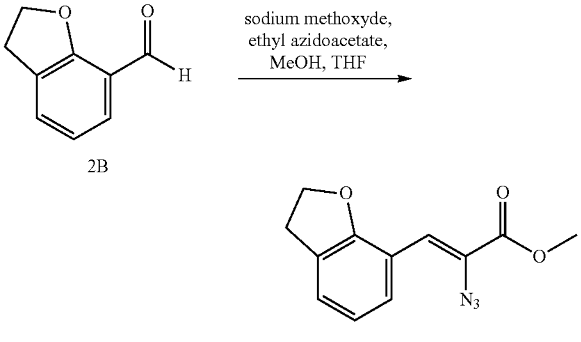

2B

2C

A solution of freshly prepared sodium methoxyde in methanol (2.5 eq, prepared by dissolving 1.94 g of sodium in 80 mL of methanol) was added dropwise (over 20 minutes) to a cooled (−20° C., internal temperature) solution of compound 2B (5.0 g, 33.74 mmol) and ethyl azidoacetate (10.9 g, 84.36 mmol) in 20 mL of dry methanol and 20 mL of dry THF. The addition was carried such that the internal reaction temperature was not permitted to rise above −10° C. The reaction was then allowed to stir at −10° C. for 1 hour, then allowed to warm to room temperature over 1 hour. The reaction mixture was then allowed to stir at room temperature for 1 hour (a white precipitate formed), and was then quenched with aqueous saturated ammonium chloride solution (10 mL). The resulting solution mixture was partitioned between ethyl acetate (500 mL) and water (100 mL). The organic layer was washed with brine (80 mL), dried over magnesium sulfate, filtered, and concentrated in vacuo. The resulting residue was purified using column chromatography on silica gel (Biotage 75-M column; gradient: 0 to 25% ethyl acetate in hexanes) to provide compound 2C (4.20 g, 52%) as a slightly yellow solid. $^1H$ NMR (400 MHz, $d_6$-DMSO): δ 7.96 (d, J=8.06 Hz, 1H), 7.24 (d, J=6.59 Hz, 1H), 7.01 (s, 1H), 6.88 (t, J=7.69 Hz, 1H), 4.58 (t, J=8.79 Hz, 2H), 3.84 (s, 3H), 3.21 (t, J=8.79 Hz, 2H).

Step D—Synthesis of Compound 2D

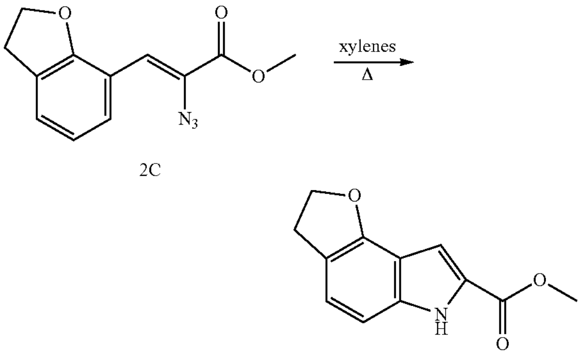

2C

2D

A solution of compound 2C (4.0 g, 16.31 mmol) in 60 mL of xylenes was heated to 150° C. and allowed to stir at this temperature for 10 minutes, then was cooled to room temperature, during which time a white solid formed. The suspension was stored as −20° C. in freezer for 1 hour, then filtered to provide compound 20 as a white solid (1.0 g). The filtrate was concentrated in vacuo, and the resulting residue was purified using column chromatography on silica gel (Biotage 40-S column; gradient: 0 to 35% ethyl acetate in hexanes) to provide an additional amount of compound 20 (290 mg). (Total yield=1.29 g, 37%). $^1H$ NMR (400 MHz, $d_6$-DMSO): δ 11.91 (s, 1H), 7.12 (d, J=8.06 Hz, 1H), 6.96 (s, 1H), 6.95 (d, J=8.06 Hz, 1H), 4.65 (t, J=8.79 Hz, 2H), 3.85 (s, 3H), 3.22 (t, J=8.79 Hz, 2H).

Step E—Synthesis of Compound 2E

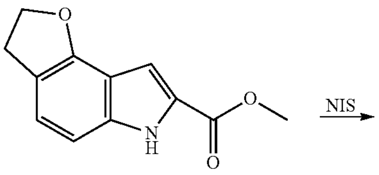

2D

-continued

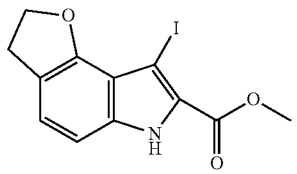

2E

To a solution of compound 590 (1.45 g, 6.67 mmol) in 50 mL of chloroform and 20 mL of THF at 0° C. was added N-iodosuccinimide (1.65 g, 7.34 mmol). The resulting reaction was allowed to stir at 0° C. for 30 minutes, then warmed to room temperature and allowed to stir at this temperature for 30 minutes. The reaction mixture was then diluted with ethyl acetate (100 mL), and the resulting solution was sequentially washed with aqueous saturated sodium thiosulfate (20 mL), aqueous saturated sodium bicarbonate (20 mL) and brine (20 mL). The organic layer was dried over magnesium sulfate, filtered, and concentrated in vacuo. The crude product was purified using column chromatography on silica gel (Biotage 40-S column; gradient: 0 to 40% ethyl acetate in hexanes) to provide compound 59E (190 mg, 10%) as a white solid. M.S. found for $C_{12}H_{10}INO_3$: 343.87 $(M+H)^+$.

Step F—Synthesis of Compound 2F

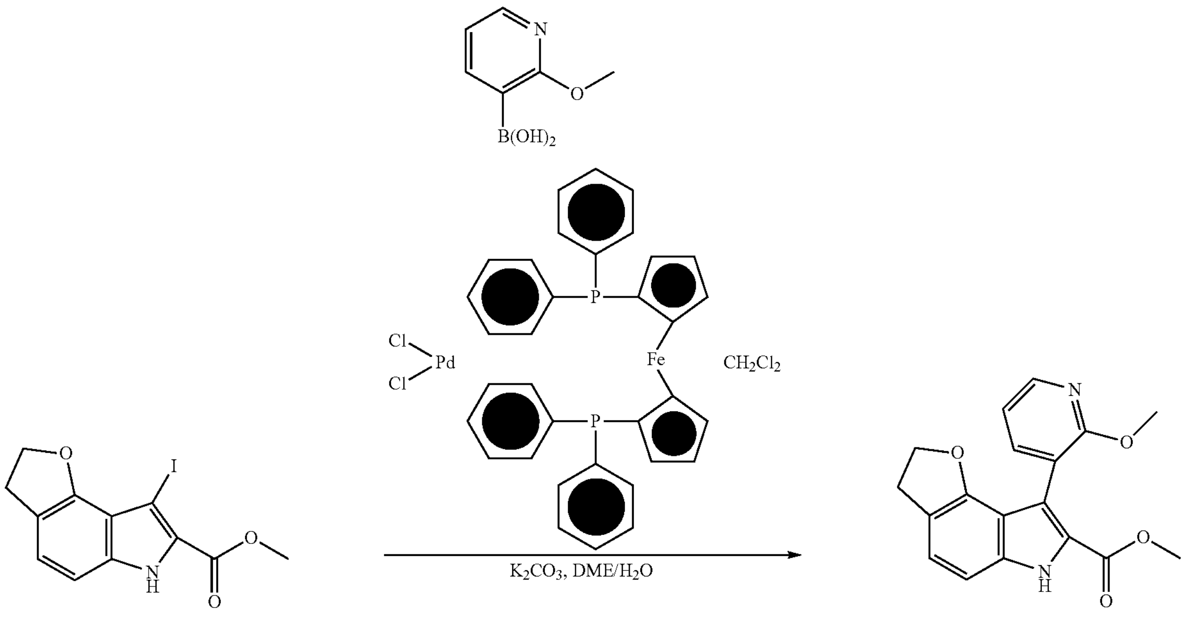

2E 2F

To a solution of compound 2E (180 mg, 0.524 mmol) in 10 mL of 1,2-dimethoxyethane was added 2-methoxy-3-pyridine boronic acid (240 mg, 1.573 mmol) and the resulting mixture was de-gassed (vacuum/argon flush), and $PdCl_2(dppf)_2$ (10 mol %, 42 mg) was added. The resulting mixture was allowed to stir for 15 minutes at room temperature and a solution of potassium carbonate (434 mg, 3.144 mmol) was added. The resulting brown reaction was heated to 90° C. and allowed to stir at this temperature for 45 minutes. The reaction mixture was then cooled to room temperature, and diluted with ethyl acetate (80 mL). The organic layer was washed sequentially with aqueous saturated sodium bicarbonate (10 mL) and brine (10 mL), then dried over magnesium sulfate, filtered, and concentrated in vacuo. The resulting residue was purified using column chromatography on silica gel (Biotage 25-S column; gradient: 10 to 50% ethyl acetate in hexanes) to provide compound 2F (140 mg, 83%) as a white solid. M.S. found for $C_{18}H_{16}N_2O_4$: 325.07 $(M+H)^+$.

Example 3

Preparation of Intermediate Compound 3L

Step A—Synthesis of Compound 3B

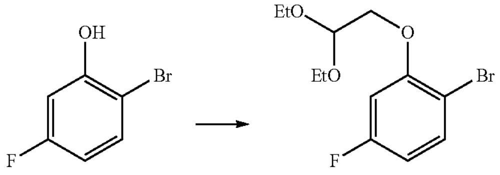

3A 3B

A solution of compound 3A, (228.00 g, 1.19 mmol), Potassium carbonate (247.47 g, 1.79 mol) in DMF (3.00 L) was treated with 2-Bromo-1,1-diethoxyethane (197.54 mL, 1.31 mol) and heated at 135° C. for 7 hours. The reaction mixture was concentrated in vacuo and extracted with EtOAc (3×2 L). The combined organic layers were washed with aqueous NaOH (2M, 4 L). The organic layer was dried ($MgSO_4$), filtered, concentrated in vacuo to provide compound 3B (362.00 g, 98%) which was used without further purification.

Step B—Synthesis of Compound 3C

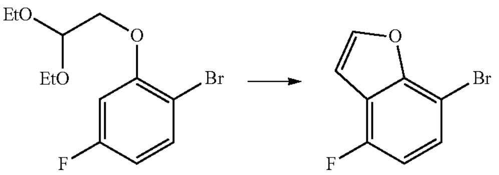

3B 3C

A solution of compound 3B (352.00 g, 1.15 mol) in toluene (2500 mL, 2.3 mol) was treated with polyphosphoric acid (370.00 g, 3.4 mol) and heated at reflux for 5 hours. The reaction mixture was concentrated in vacuo, diluted with water (3 L) and then extracted with EtOAc (4 L). The organic layer was washed with aqueous NaOH (2 L), filtered, concentrated in vacuo and purified using distillation at reduced pressure to provide compound 3C (125.00 g, 50.8%). Bp. 80° C. (1 mm/Hg) as a colorless liquid which solidified at room temperature. $^1$H NMR (400 MHz, $CDCl_3$) δ 7.67 (d, 1 H, J=2.2 Hz), 7.39 (dd, 1 H J=5.1 & 3.7 Hz), 6.94 (d, 1 H, J=2.2 Hz), 6.86 (t, 1 H, J=8.8 Hz).

Step C—Synthesis of Compound 3D

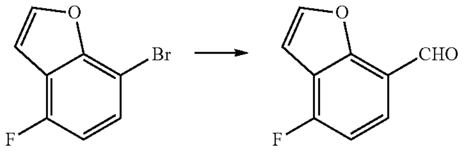

3C 3D

A solution of compound 3C (124.12 g, 577.25 mmol) in ether (2.0 L) was cooled to −78° C. and treated dropwise with a solution of 2.5 M of n-butyllithium in hexane (235.5 mL) and allowed to stir at −78° C. for 15 minutes. To this reaction mixture was added DMF (89.393 mL, 1.15 mol) and allowed to stir at −78° C. for 30 minutes. The reaction mixture was quenched with methanol (23.383 mL, 577.25 mmol) and warmed to room temperature. The reaction mixture was diluted with ether (300 mL) and the organic layer was washed with water (300 mL). The separated organic layer was dried ($MgSO_4$) filtered, concentrated in vacuo to provide compound 3D (89.00 g, 93.9%).

Step D—Synthesis of Compound 3E

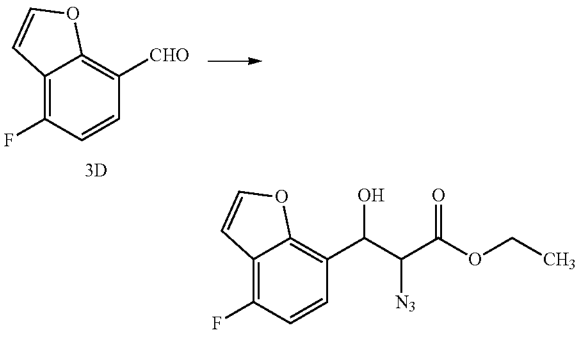

3D

3E

A solution of compound 3D (12.71 g, 77.45 mmol), lithium chloride (6.567 g, 154.9 mmol) and ethyl azidoacetate (20.00 g, 154.9 mmol; added as a 30% solution in $CH_2Cl_2$), diazabicyclo[5.4.0]undec-7-ene (23.16 mL, 154.9 mmol) and stirred for 2 hours. The completion of the reaction was followed by TLC (EtOAc/Hexanes 1:4). Upon completion, the reaction mixture was diluted with ethyl acetate (1 L) and washed with water and aqueous HCl (400 mL). The combined organic layers were dried ($MgSO_4$), filtered and concentrated in vacuo and the residue obtained was purified using flash column chromatography $SiO_2$ (EtOAc/Hexanes) to provide compound 3E (183 g, 80.6%) as a colorless oil.

Step E—Synthesis of Compound 3F

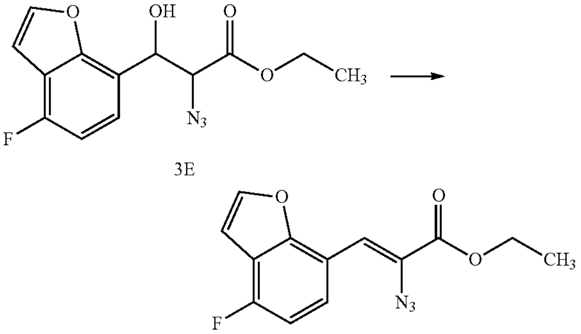

3E

3F

A solution of compound 3E (15.7 g, 53.5 mmol) and methanesulfonyl chloride (8.29 mL, 107 mmol) in methylene chloride (87.7 mL, 1.37 mmol) at −30° C. was treated dropwise with a solution of triethylamine (52.2 mL, 375.0 mmol) in methylene chloride (100 mL). The reaction mixture was allowed to stir at −30° C. for 3 hours, diluted with aqueous saturated sodium bicarbonate and methylene chloride (400 mL). The organic layer was separated and washed with water, aqueous HCl and brine. The organic layer was dried ($M_2SO_4$), filtered, concentrated in vacuo, and purified using flash column chromatography ($SiO_2$, 10% EtOAc in (1:1) Hexanes $CH_2Cl_2$) to provide compound 3F (12.6 g, 85.5%).

Step F—Synthesis of Compound 3G

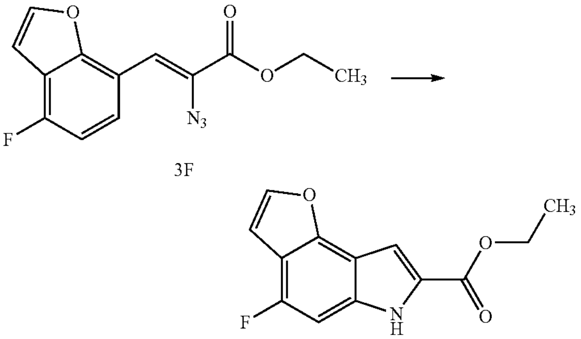

3F

3G 150 mL of xylenes was heated at 165° C. To this boiling solution was added dropwise a solution of compound 3F (11.2 g, 40.7 mmol) in Xylenes (70 mL, 189.4 mmol). The reaction mixture was stirred for additional 20.0 minutes and allowed to cool to room temperature to provide compound 3G as a precipitate (7.00 g, 69.6%), which was filtered, washed with hexanes and dried in vacuo.

Step G—Synthesis of Compound 3H

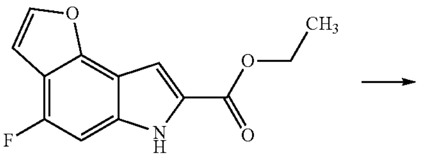

3G

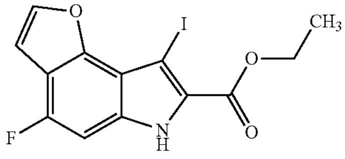

3H

To a solution of compound 3G (15.88 g, 64.23 mmol) in DMF (100 mL) was added N-iodosuccinimide (15.90 g, 70.66 mmol) and allowed to stir at room temperature, for 2 hours. The reaction mixture was diluted with water (1000 mL) and extracted in EtOAc (1000 mL). The organic layer was washed with water (1000 mL), aqueous sodium thiosulfate (5% aqueous soln. 1 L) and dried ($MgSO_4$). The organic layer was dried ($MgSO_4$), filtered, concentrated in vacuo to provide compound 3H (22.30 g, 93.04%) as a solid.

Step H—Synthesis of Compound 3I

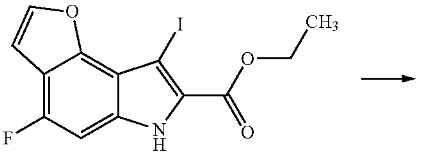

3H

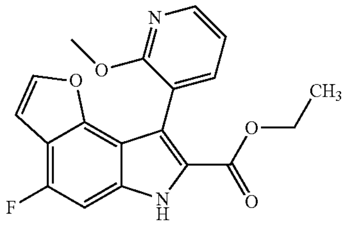

3I

A solution of compound 3H (22.000 g, 58.962 mmol), 2-methoxypyridin-3-ylboronic acid (13.527 g, 88.444 mmol), $(PPh_3)_2PdCl_2$ (4.13 g, 5.88 mmol) in 1,2-dimethoxyethane (250.0 mL) was degassed for 2 min and allowed to stir at room temperature, for 15 minutes. The orange reaction mixture was treated with a solution of potassium carbonate (30.53 g, 220.9 mmol) in water (250.0 mL) and allowed to stir at 90° C. for 3 hours. The yellow reaction turned orange dark with the disappearance of starting material (TLC). The reaction mixture was diluted with EtOAc (1000 mL) and washed with aqueous NaOH (500 mL, 1M), dried ($MgSO_4$), filtered, concentrated in vacuo, and purified using flash column chromatography $SiO_2$ (THF/Hexanes 0-->60%) to provide compound 3I (16.65 g, 79.7%) as pale brown solid.

Step I—Synthesis of compound 3J

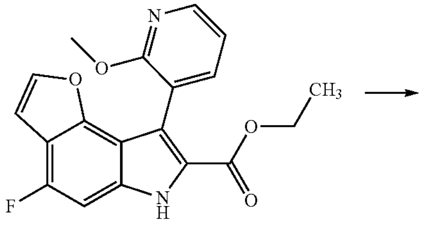

3I

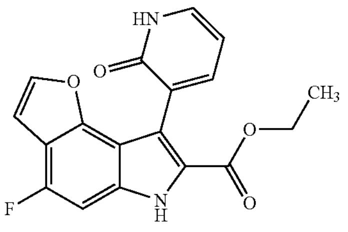

3J

A solution of compound 3I (4.50 g, 12.7 mmol) in methanol (10 mL, 246.9 mmol) was treated with a solution of 4 M HCl in dioxane (100 mL) and heated at 90° C. for 3 hours in a pressure tube. The reaction mixture was concentrated in vacuo and the residue obtained was purified using flash column chromatography ($SiO_2$, THF/Hexanes 0-->100%) to provide compound 3J as a colorless solid.

Step J—Synthesis of Compound 3K

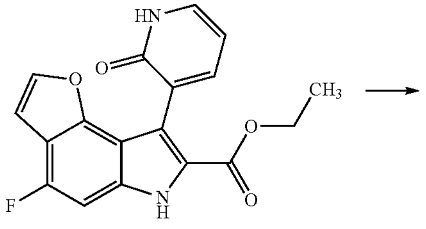

3J

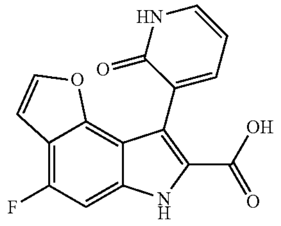

3K

A solution of compound 3J (810.00 mg, 2.38 mmol) in water (25 mL), THF (25 mL) and methanol (25 mL, 780.2 mmol) was treated with lithium hydroxide monohydrate (499.41 mg, 11.901 mmol) and heated at 80° C. for 1 hour. The reaction mixture was then acidified using 1N HCl, filtered and dried in vacuo to provide compound 3K (627.00 mg, 84.4%) as colorless solid.

Step K—Synthesis of compound 3L

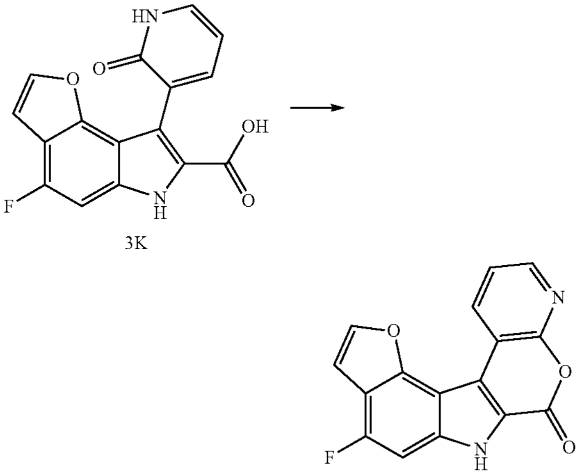

3K

3L

To a suspension of compound 3K (8.00 g, 25.6 mmol) and N-(3-dimethylaminopropyl)-N'-ethylcarbodiimide hydrochloride (9.82 g, 51.2 mmol) in DMF (153.85 mL) was added triethylamine (35.71 mL, 256.2 mmol) and the reaction was stirred overnight at room temperature. The reaction mixture was concentrated in vacuo and the resulting residue was diluted with methanol (100 mL). The resulting precipitate was filtered and dried to provide compound 3L (5.90 g, 78.3%)

Example 4

Preparation of Intermediate Compound 4D

Step A—Synthesis of Compound 4A

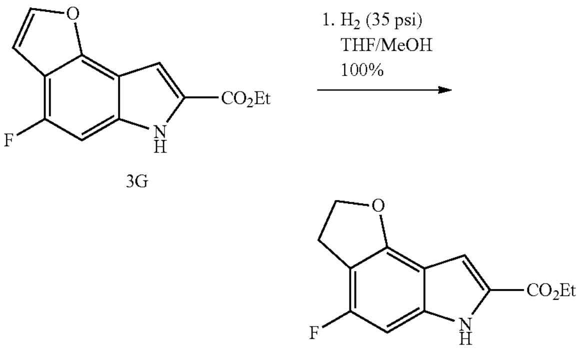

3G

4A

A solution of 3G (5.0 g; 20.22 mmol) in 220 mL of a 2:1 MeOH/THF mixture was treated with a catalytic amount of 10% palladium on carbon (5 mol %, 1.07 g). The mixture was hydrogenated at 35 psi for 18 hours. NMR of an aliquot showed complete conversion into product. The mixture was diluted with dichloromethane (300 mL) and the solids were removed by filtration through a short path of celite. The filtrate was concentrated in vacuo to provide the product 4A (5.03 g; 99%) as a white solid.

Step B—Synthesis of Compound 4B

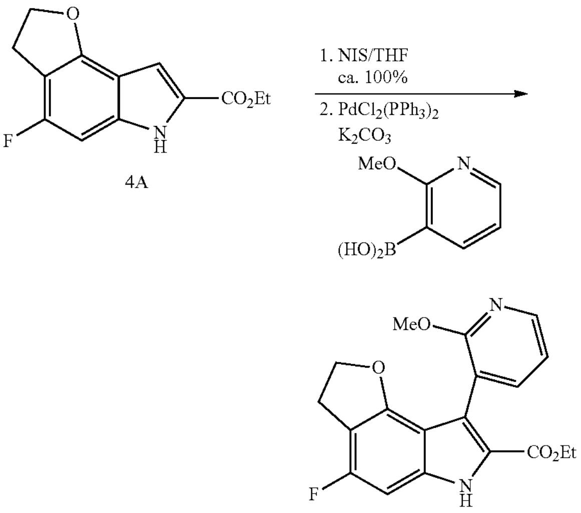

4A

4B

A solution of 4A (7.81 g; 31.34 mmol) in 300 mL of THF was cooled to −78° C. and treated with a solution of N-iodosuccinimide (1.1 eq, 7.75 g in 100 mL of THF). The mixture was stirred for 20 min and TLC (25% THF in hexanes) showed complete consumption of starting material. The reaction was quenched by addition of aqueous saturated sodium bicarbonate soln (100 mL). The mixture was allowed to reach room temperature and the product was dissolved in ethyl acetate (800 mL). The organic layer was washed with aqueous saturated sodium bicarbonate (100 mL) and brine (80 mL). The organic layer was dried over magnesium sulfate, filtered and concentrated in vacuo. The crude product (ca. 100%, 11.75 g) was used directly in the next reaction.

The product above (11.75 g; 40.44 mmol) was dissolved in 400 mL of 1,2-dimethoxyethane was treated with 2-methoxypyridine-3-boronic acid (2.0 eq, 12.3 g) and bis(triphenylphosphine)palladium(II) chloride (0.1 eq, 2.8 g). The mixture was stirred for 10 min followed by addition of aqueous potassium carbonate (4.0 eq, 80.8 mL of 2 M soln). The mixture was stirred at 90° C. and the progress of the reaction was followed by TLC (25% THF in hexanes). The reaction was completed after ~2 hours, then the mixture was diluted with ethyl acetate (600 mL) and washed with aqueous saturated sodium bicarbonate (2×200 mL) and brine (200 mL). The organic layer was dried over magnesium sulfate, filtered and concentrated in vacuo to provide the crude product as a brown solid. The crude product was treated with acetonitrile (200 mL) and stirred in an oil bath at 90° C. Acetonitrile was added in portions (50 mL) until the mixture became a homogeneous dark solution (approx. 300 mL). The heating bath was removed and the mixture was allowed to reach room temp. The mixture was then placed in a freezer (−20° C.) overnight. The mother liquor was removed (decantation) and the solids were washed with ether (50 mL). The crystallized product 4B was dried under high vacuum (11.66 g, 82%) to provide a slightly yellow powder.

Step C—Synthesis of Compound 4C

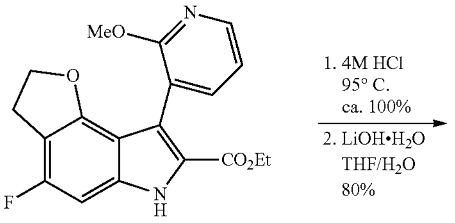

4B

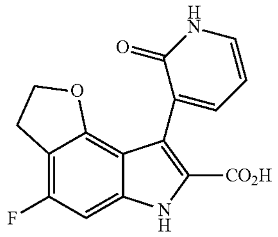

4C

Compound 4B was divided into two batches and treated separately. Each batch was dissolved in 4 M HCl solution in dioxane (100 mL) and methanol (25 mL). The homogeneous solution was heated in a sealed tube (95° C.) until all starting material had been consumed. After 3 hour, the mixture was concentrated to dryness in vacuo to provide the crude product (ca 100%, 7.97 g) as a slightly yellow solid which was used without further purification.

An aliqiout of the product above (780 mg, 2.278 mmol) was dissolved in 40 mL of 1:1 THF/MeOH and water was added (10 mL). The resulting solution was treated with lithium hydroxide monohydrate (5.0 eq, 478 mg) and heated to 50° C. for 3 hours. TLC (50% THF in dichloromethane) showed complete disappearence of the starting material. The mixture was treated with 15 mL of aqueous 1 M HO and the volatiles were removed in vacuo. The crude product was diluted with aqueous 1 M HCl (20 mL) and the solids recovered by filtration (whatman #1) and washed with ether (30 mL): to provide the product 4C (560 mg; 78%) as a slightly yellow solid.

Step D—Synthesis of Compound 4D

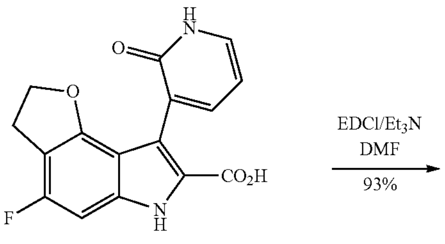

4C

-continued

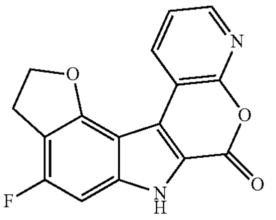

4D

Compound 4C (4.75 g, 15.11 mmol) was suspended in 150 mL of dry DMF and treated with EDCI (2.0 eq, 5.79 g) and triethylamine (10 eq, 21.2 mL, d 0.720). The mixture was stirred overnight at room temp. All the volatiles were removed in vacuo (high vacuum pump) and the residue was treated with methanol (30 mL). The product precipitated as a slightly yellow solid which was recovered by filtration. The product was washed with methanol (10 mL) and hexanes (20 mL) and concentrated in vacuo to provide 4D (4.2 g; 93%) as a slightly yellow solid.

Example 5

Preparation of Intermediate Compound 5G

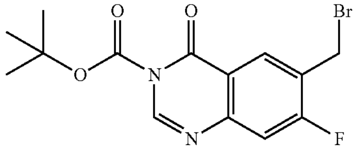

5F

Step A—Synthesis of 5B

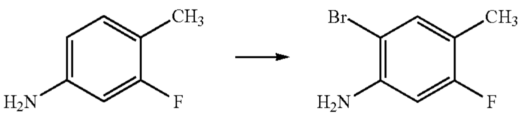

5A 5B

A mixture of compound 5A (6.00 g, 47.9 mmol) and anhydrous potassium carbonate (6.70 g, 48.5 mmol) in anhydrous dichloromethane (130 mL) was cooled to −15° C. in a salt-ice bath and then added dropwise to a solution of bromine (7.70 g, 48.2 mmol) in anhydrous dichloromethane (80 mL). After addition was complete, the reaction was allowed to stir at −15° C. for 1 hour. Ice water (100 mL) was added to the reaction mixture and the aqueous layer was extracted with dichloromethane (2×100 mL). The combined organic layers were dried over $MgSO_4$ and concentrated in vacuo to provide compound 5B (11.0 g, quant.), which was used without further purification.

Step B—Synthesis of compound 5C

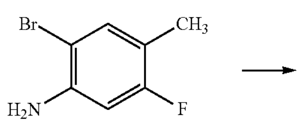

5B

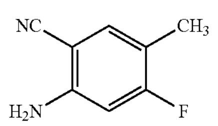

5C

Compound 5B was dissolved in DMF (150 mL) and to this solution was added copper (I) cyanide (11.0 g, 123 mmol). The mixture was heated to 160° C. and allowed to stir at this temperature for 20 hours. After being cooled to room temperature, with water (200 mL), iron (III) chloride (42.0 g, 155 mmol) and concentrated hydrochloric acid (20 mL) were added to the reaction mixture and the resulting reaction was stirred for 45 minutes. The reaction mixture was then basified to pH>10 using commercial ammonium hydroxide solution. The basic solution was then extracted with ethyl acetate (4×400 mL). The combined organic extracts were washed with water, dried over magnesium sulfate, filtered and concentrated in vacuo. The residue obtained was purified using flash chromatography to provide compound 5C (5.82 g, 81%). $^1$H NMR (400 MHz, $d_6$-DMSO): δ 7.34 (d, J=8.4 Hz, 1H), 6.52 (d, J=12.4 Hz, 1H), 6.10 (s, 2 H), 2.08 (s, 3 H).

Step C—Synthesis of Compound 5D

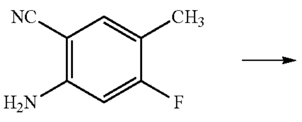

5C

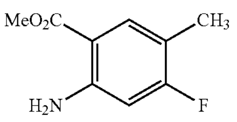

5D

To the solution of 5C (2.0 g, 13.3 mmol) in anhydrous methanol (15 mL) at room temperature was added concentrated sulfuric acid (4.0 mL). The reaction mixture was heated to 70° C. and stirred for four days. After cooled to room temperature, it was poured into with ice water. The mixture was then diluted with ethyl acetate (200 mL) and was made basic (pH>10) with commercial ammonium hydroxide solution. The layers were separated. The aqueous layer was extracted with ethyl acetate (2×100 mL). The combined organic solution was dried over $MgSO_4$ and concentrated in vacuo to provide the crude product which, was purified using flash chromatography to provide compound 5D (1.0 g, 41%) and some recovered 5C. $^1$H NMR (400 MHz, $d_6$-DMSO): δ 7.61 (d, J=8.8 Hz, 1H), 6.69 (s, 2 H). 6.51 (d, J=12.0 Hz, 1 H), 3.77 (s, 3 H), 2.06 (s, 3 H).

Step D—Synthesis of Compound 5E

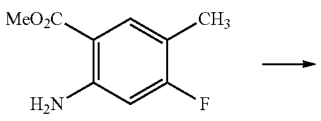

5D

-continued

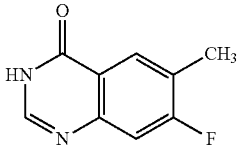

5E

The solution of compound 5D (500 mg, 2.73 mmol) in formamide (6.0 mL) was heated to 150° C. in an oil bath and stirred for 18 hours. After cooled to room temperature, ethyl acetate (100 mL) and water (100 mL) were added and the layers were separated. The organic solution was washed with water (2×60 mL), dried over $MgSO_4$ and concentrated in vacuo to provide the crude product 5E (0.50 g, quant.) which, was used without further purification. MS found for $C_9H_7FN2O$: 179.0 $(M+H)^+$.

Step E—Synthesis of Compound 5F

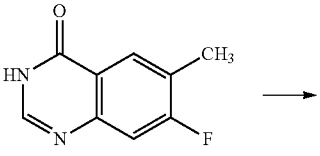

5E

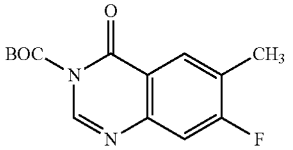

5F

To the solution of 5E (from Step 4) in anhydrous THF (20 mL) at room temperature was added di-tert-butyl dicarbonate (1.84 g, 8.43 mmol), 4-dimethylaminopyridine (350 mg, 2.86 mmol) and triethyl amine (0.40 mL, 2.87 mmol). The reaction mixture was stirred for 18 hours. Ethyl acetate (100 mL) and water (100 mL) were added and the layers were separated. The aqueous layer was extracted with ethyl acetate (2×50 mL). The combined organic solution was dried over $MgSO_4$ and concentrated in vacuo to provide the crude product which, was purified using flash chromatography to provide compound 5F (285 mg, 36%). MS found for $C_{14}H_{15}FN2O_3$: 179.0 $(M+H-100)^+$.

Step F—Synthesis of compound 5G

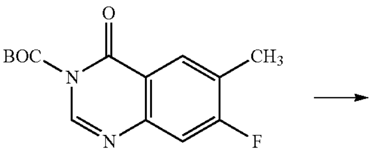

5F

-continued

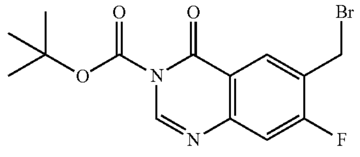

5G

The mixture of 5F (282 mg, 1.01 mmol), NBS (253 mg, 1.42 mmol) and AIBN (58 mg, 0.353 mmol) in anhydrous carbon tetrachloride (60 mL) was heated to 90° C. in an oil bath and stirred for 4 hours. After cooled to room temperature and concentrated in vacuo, the residue was dissolved in ethyl acetate (100 mL) and water (100 mL). The layers were separated. The organic solution was washed with water (100 mL), dried over $MgSO_4$ and concentrated in vacuo to provide the crude product 5G (453 mg, quant.) which, was used without further purification.

Example 6

Preparation of Intermediate Compound 6B

6B

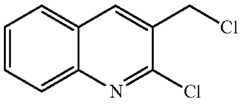

Step A—Synthesis of Compound 6A

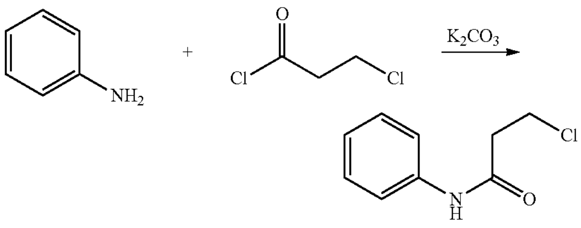

6A

A mixture of aniline (65.04 mL, 713.8 mmol), potassium carbonate (54.4 g, 394 mmol) and water (300 mL) were added to a 2000 mL flask. The resulting reaction was kept at room temperature using a room temperature water bath and stirred with a mechanic stirrer. 3-Chloro-propionyl chloride (75.18 mL, 787.6 mmol) was added dropwise via additional funnel and the resulting suspension was allowed to stir at room temperature for 3 hours. The reaction mixture was filtered and the collected solid was washed sequentially with water (300 mL), aq. HCl (1M, 2×300 mL), and water (300 mL), then dried to provide compound 6A, which was used without purification (114.5 g, 87%).

Step B—Synthesis of Compound 68

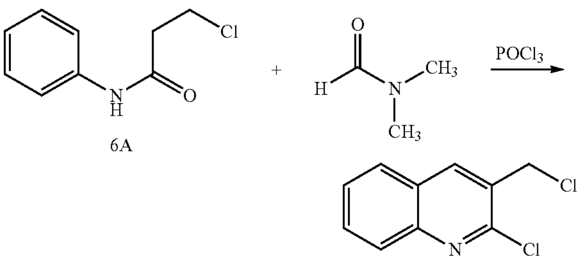

6A

6B

N,N-Dimethylformamide (53.7 mL, 694 mmol) was charged into a three necked flask and cooled to 0° C. and treated with phosphoryl chloride (177.7 mL, 1906 mmol) dropwise. The reaction was stirred at that temperature for 10 min and treated with 3-Chloro-N-phenylpropanamide 6A (50.00 g, 272.3 mmol) and stirred at room temperature, for 30 minutes. The reaction mixture was heated at 80° C. for 3 h and slowly poured into ice. The solid separating out was filtered and washed extensively with water (2×1000 mL), aq. saturated sodium bicarbonate (500 mL), and taken in EtOAc (1 L), The solution was dried ($MgSO_4$) filtered concentrated in vacuo and the residue obtained was recrystallized from boiling hexanes to provide compound 6B (20 g).

Example 7

Preparation of Intermediate Compound 7E

7E

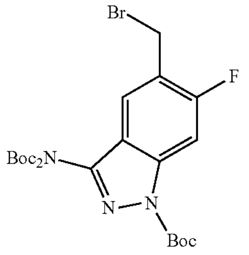

Step A—Synthesis of Compound 7A

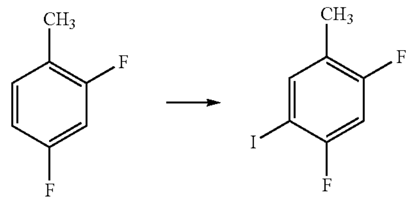

7A

A solution of 2,4-difluorotoluene (4.72 g, 36.8 mmol) in trifluoroacetic acid (12.29 mL, 159.5 mmol) was cooled to 0° C., then N-Iodosuccinimide (9.59 g, 42.6 mmol) was added and the resulting reaction was allowed to stir at room temperature for about 15 hours. The reaction mixture was then concentrated in vacuo and the residue obtained was dissolved in hexanes (100 mL), washed with aquesous sodium thiosulfate (100 mL), brine (100 mL), then dried ($MgSO_4$), filtered and concentrated in vacuo. The resulting residue was purified using bulb-to-bulb distillation to provide compound 7A (7.2 g, 77%) as a colorless oil.

Step B—Synthesis of Compound 7B

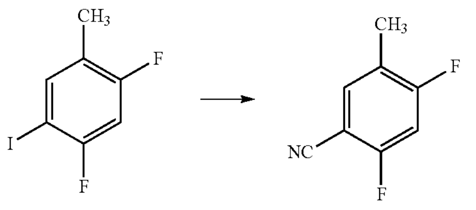

7A 7B

A solution of compound 7A (7.11 g, 28.0 mmol), zinc cyanide (1.97 g, 16.8 mmol) and tetrakis(triphenylphosphine) palladium(0) (3.23 g, 2.80 mmol) in DMF (30 mL) was heated to 90° C. and allowed to stir at this temperature for 1.5 hours. The reaction mixture was concentrated in vacuo and the residue obtained was taken up in water (400 mL) and extracted with ether (400 mL). The organic extract was washed with aqueous ammonium hydroxide solution (1N). The organic layer was dried ($MgSO_4$) filtered, concentrated in vacuo to provide a residue that was purified using flash column chromatography ($SiO_2$, EtOAc/Hexanes) to provide a mixture that contained product and triphenylphosphine. This mixture was further purified using sublimation at 1 mm/Hg at 45° C. to provide compound 7B (1.8 g; Yield=42%).

Step C—Synthesis of Compound 7C

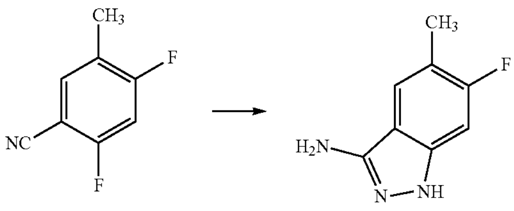

7B 7C

A solution of compound 7B (1.400 g, 9.154 mmol) and hydrazine (0.700 mL, 22.3 mmol) in isopropyl alcohol (50 mL, 653.1 mmol), was heated to reflux and allowed to stir at this temperature for 24 hours. The reaction mixture was cooled to room temperature, concentrated in vacuo and the residue obtained was purified using flash column chromatography ($SiO_2$, Acetone/Hexanes 0→50%) to provide compound 7C (330 mg, 22%).

Step D—Synthesis of Compound 7D

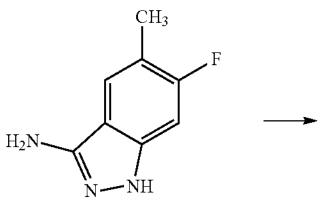

7C

-continued

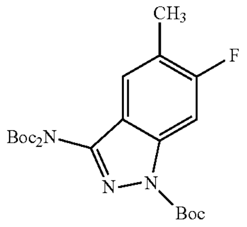

7D

A solution of compound 7C (330.00 mg, 1.998 mmol), di-tert-butyldicarbonate (2.6163 g, 11.98 mmol) and 4-dimethylaminopyridine (48.817 mg, 0.39959 mmol) in acetonitrile (15 mL, 287.2 mmol) was heated to reflux and allowed to stir at this temperature for 2 hours. The reaction mixture was cooled to room temperature, concentrated in vacuo, and the resulting residue was purified using flash column chromatography ($SiO_2$, EtOAc/Hexanes 0-20%) to provide compound 70 (640.00 mg, 68%) as a colorless oil.

Step E—Synthesis of Compound 7E

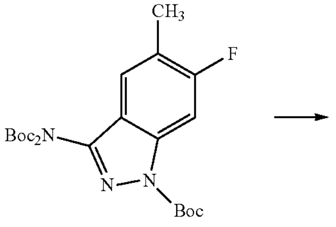

7D

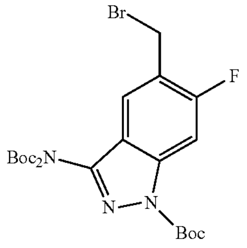

7E

A solution of compound 70 (630.00 mg, 1.3533 mmol), N-bromosuccinimide (337.22 mg, 1.8947 mmol) and benzoyl peroxide (65.563 mg, 0.27067 mmol) in carbon tetrachloride (20 mL) was heated to reflux and allowed to stir at this temperature for 3 hours. The reaction mixture was cooled to room temperature, concentrated in vaeuo and the residue obtained was dissolved in EtOAc (300 mL). The resulting solution was washed with aqueous sodium thiosulfate (100 mL), brine (100 mL), dried ($MgSO_4$), filtered, and concentrated in vacuo. The residue obtained was purified using flash column chromatography ($SiO_2$, EtOAc/Hexanes) to provide compound 7E as a colorless oil.

Example 8

Preparation of Intermediate Compounds 8E and 8F

8E

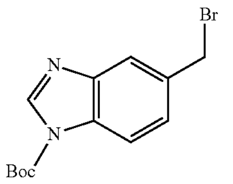

8F

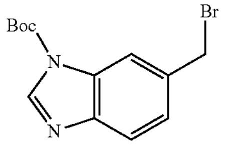

Step A—Synthesis of Compound 8B

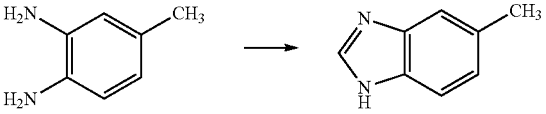

8A 8B

A solution of compound 8A (3 g, 24.5 mmol) in trimethyl orthoformate (15 mL) was treated with 2 drops conc. HC1 and heated to 80° C. for 2 hours. The reaction mixture was cooled to room temperature and concentrated in vacuo to provide compound 8B (3.65 g), which was used without further purification. M.S. found for $C_8H_8N_2$: 133.2 $(M+H)^+$.

Step B—Synthesis of compounds 8C and 8D

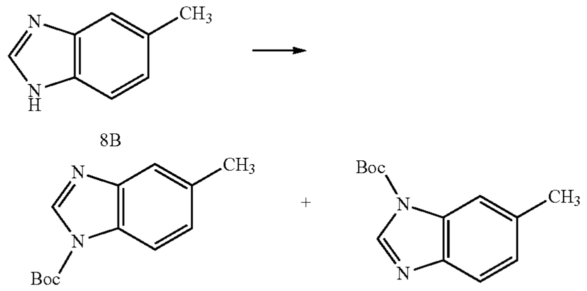

8B 8C 8D

To a solution of compound 88 (24.5 mmol) in $CH_3CN$ (65 mL) was added di-tertbutyl dicarbonate (5.89 g, 27.0 mmol), triethylamine (3.76 mL, 27.0 mmol) and 4-dimethylamino pyridine (300 mg, 2.45 mmol) and the resulting reaction was heated to 80° C. and allowed to stir at this temperature for 1.5 hours. The reaction mixture was cooled to room temperature, concentrated in vacuo, and the residue obtained was purified using flash column chromatography (silica gel, EtOAc/Hexanes 5-20%) to provide a mixture of isomeric compounds 8C and 8D (5.38 g, 94.3% yield over steps A and B).

Step C—Synthesis of Compounds 8E and 8F

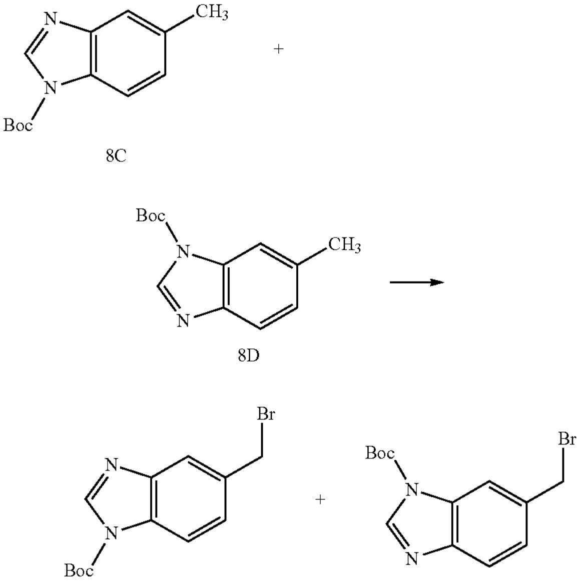

8C

8D 8E 8F

To a solution of compounds 8C and 8D (2 g, 8.61 mmol) in carbon tetrachloride (40 mL) was added N-bromosuccinimide (1.6 g, 9.04 mmol) and dibenzoyl peroxide (41.7 mg, 0.1722 mmol) and the resulting reaction was heated to 90° C. and allowed to stir at this temperature for 12 hours. The reaction was cooled to room temperature, solids were filtered off and the filtrate was washed with water, dried over sodium sulfate and concentrated in vacuo to provide compounds 8E and 8F (2.58 g) which was used without further purification. M.S. found for $C_{13}H_{15}BrN_2O_2$: 334.7 $(M+Na)^+$.

Example 9

Preparation of Intermediate Compound 9B

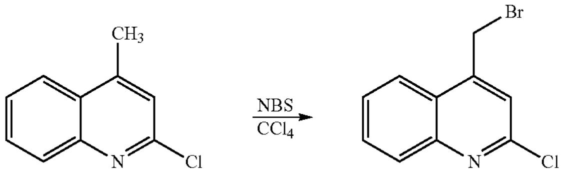

9A 9B

A mixture of compound 9A (1.5 g, 8.44 mmol), NBS (1.8 g, 10.11 mmol) in carbon tetrachloride (50 mL) was heated to reflux, then benzoyl peroxide (0.21 g, 0.866 mmol) was added. The resulting suspension was allowed to stir at reflux for 19 hours, then cooled to room temperature and filtered. The filtrate was washed with saturated sodium carbonate, dried over sodium sulfate and concentrated in vacuo to provide a mixture (1.7 g) which contains about 50% of compound 9B, and was used without further purification.

Example 10

Preparation of Intermediate Compound 10D

Step A—Synthesis of Compound 10B

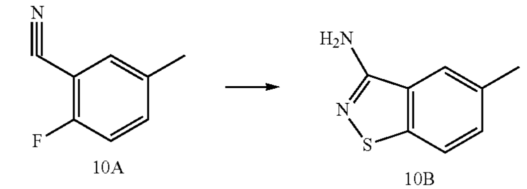

10A 10B

A mixture of 2-fluoro-5-methylbenzonitrile (10A, 2.0 g; 14.799 mmol) and sodium sulfide (1.0 eq, 1.15 g) was dissolved in 150 mL of DMSO and heated at 70®C overnight. The mixture was placed in an ice-water bath and treated with concentrated aqueous ammonium hydroxide (20 mL) and aqueous sodium hypochlorite (20 mL). The reaction mixture was allowed to warm to room temperature and stirred for 5 hours. The mixture was diluted with ethyl acetate (300 mL) and washed with water (2×60 mL) and brine (50 mL). The organic layer was dried over magnesium sulfate, filtered and concentrated in vacuo. The residue was adsorbed on silica gel and purified on a Biotage 40-M silica gel column (gradient: 0 to 30% acetone in hexanes) to provide the product 10B (860 mg; 36%) as a white solid. $^1$H-NMR ($CDCl_3$; 400 MHz): δ 7.68 (1H, d, J=8.54 Hz), 7.48 (1H, s), 7.33 (1H, d, J=8.54 Hz), 4.89 (2H, broad s), 2.50 (3H, s).

Step B—Synthesis of Compound 10C

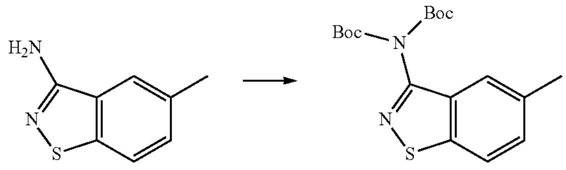

10B 10C

A solution of 5-methylbenzo[d]isothiazol-3-ylamine, (10B, 850 mg; 5.176 mmol) in dry acetonitrile (50 mL) was treated with Boc-anhydride (2.1 eq, 2.37 g) and heated to 50° C. All starting material had been consumed after 2 h and the mixture was concentrated in vacuo to one third of its volume. The residue was dissolved in ethyl acetate (100 mL) and washed with aqueous sodium hydrogen sulfate (20 mL), and brine (20 mL). The organic layer was dried over magnesium sulfate, filtered and concentrated in vacuo. The residue was adsorbed on silica gel and purified on a Biotage 40-M silica gel column (gradient: 0 to 10% ethyl acetate in hexanes) to provide the product 10C (1.7 g; 91%) as a white powder. $^1$H-NMR ($CDCl_3$; 400 MHz): δ 7.77 (1H, d, J=8.54 Hz), 7.55 (1H, s), 7.38 (1H, dd, J=1.83, 8.54 Hz), 2.51 (3H, s), 1.36 (18H, s). LR-MS (ESI): caldc for $C_{18}H_{25}N_2O_4S$ $[M+H]^+$ 365.15; found 365.23.

Step C—Synthesis of Compound 10D

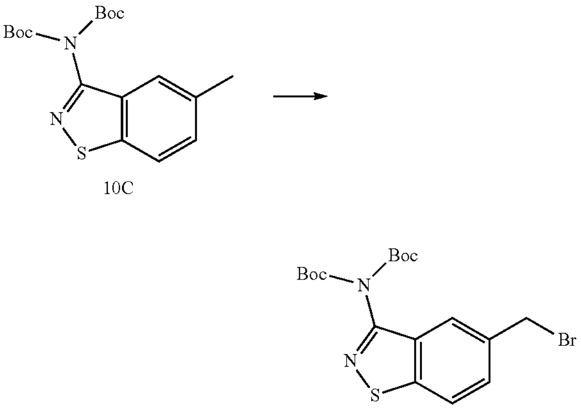 [SMILES: Cc1ccc2snc(N(C(=O)OC(C)(C)C)C(=O)OC(C)(C)C)c2c1 ; CC(C)(C)OC(=O)N(C(=O)OC(C)(C)C)c1nsc2ccc(CBr)cc12]

10C

A solution of N,N-bis-Boc-5-methyl-benzo{d}isothiazol-3-ylamine (10C, 500 mg; 1.371 mmol) in 15 mL of carbon tetrachloride was treated N-bromosuccinimide (1.05 eq, 256 mg) and benzoyl peroxide (10 mol %; 33 mg). The solution was degassed (vacuum/argon flush) and then heated to 75° C. for 5 hours. The reaction mixture was concentrated to one third of its volume in vacuo and the residue was dissolved in ethyl acetate (50 mL). The solution was washed with aqueous saturated sodium bicarbonate soln (2×10 mL) and brine (10 mL). The organic layer was dried over magnesium sulfate, filtered and concentrated in vacuo. The residue was adsorbed on silica gel and purified on a Biotage 40-S silica gel column (gradient: hexanes then 0 to 10% ethyl acetate in hexanes) to provide the product 10D (396 mg; 69%) as a white solid. $^1$H-NMR ($CDCl_3$; 400 MHz): δ 7.87 (1H, d, J=8.54 Hz), 7.78 (1H, s), 7.58 (1H, dd, J=1.83, 8.54 Hz), 4.63 (2H, s), 1.37 (18H, s). LR-MS (ESI): caldc for $C_{18}H_{24}BrN_2O_4S$ $[M+H]^+$ 445.06; found 445.24.

Example 11

Preparation of Compound 24

Step A—Synthesis of Compound 11A

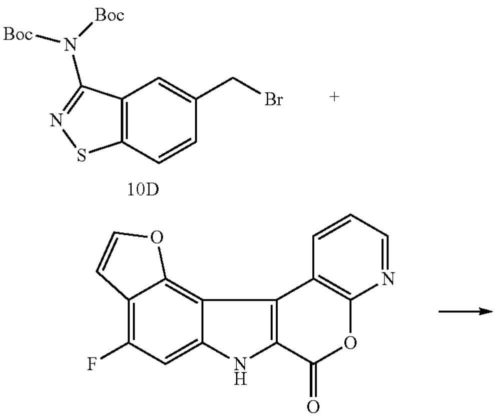

10D

3L

-continued

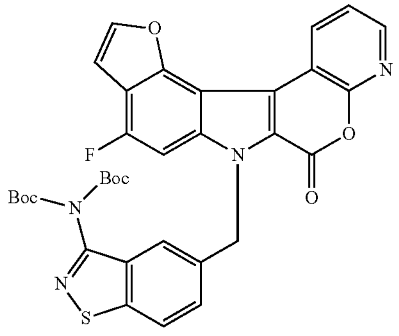

11A

A mixture of lactone 3L (215 mg; 0.733 mmol) and N,N-bis-Boc-5-bromomethyl-benzo[d]isothiazol-3-ylamine 10D (1.2 eq, 390 mg) was suspended in dry DMF (7 mL) and treated with cesium carbonate (2.0 eq, 477 mg). The slurry was stirred overnight. The mixture was treated with water (10 mL) and the product was recovered by filtration (whatman #1). The solids were washed with water (2×5 mL) to provide the product 11A (480 mg; 99%) as a white solid which did not require further purification. $^1$H-NMR (dmso-$d_6$; 400 MHz): δ 9.28 (1H, dd, J=1.83, 7.93 Hz), 8.50 (1H, dd, J=1.22, 4.88 Hz), 8.28 (1H, d, J=2.44 Hz), 8.20 (1H, d, J=8.54 Hz), 7.75 (1H, d, J=10.37 Hz), 7.66 (2H, m), 7.36 (1H, s), 7.28 (1H, d, J=1.83 Hz), 6.25 (2H, s), 1.12 (18H, s).

Step B—Synthesis of Compound 11B

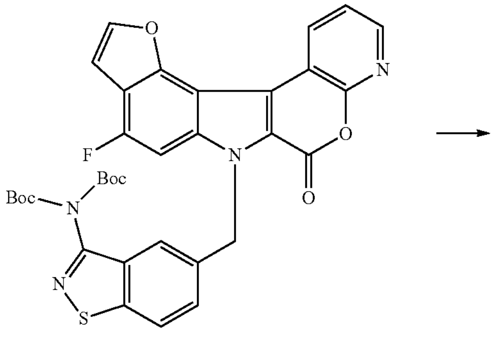

11A

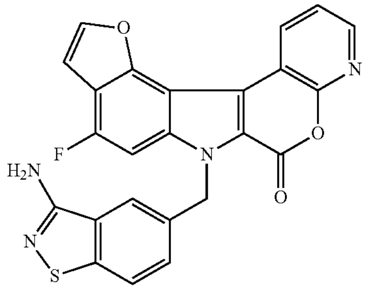

11B

The N,N-bis-Boc protected aminoisothiazole 11A (480 mg; 0.730 mmol) was treated with 4 M HCl in dioxane (15 mL). The resulting slurry was stirred for 3 h at which point no more starting material remained according to TLC (50% ethyl acetate in hexanes). The mixture was concentrated in vacuo to provide the crude product 11B (ca. 99%; 333 mg) as a slightly yellow solid which was used without further purification. $^1$H-NMR (dmso-$d_6$; 400 MHz): δ 9.28 (1H, dd, J=1.83, 7.93 Hz), 8.50 (1H, dd, J=1.83, 4.88 Hz), 8.28 (1H, d, J=2.44 Hz), 7.95 (1H, d, J=8.54 Hz), 7.77 (1H, s), 7.70 (2H, broad s), 7.65 (1H, dd, J=4.88, 7.93 Hz), 7.61 (1H, d, J=10.37 Hz), 7.58 (1H, dd, J=1.83, 8.54 Hz), 7.28 (1H, d, J=1.83 Hz), 6.14 (2H, s).

Step C—Synthesis of Compound 24

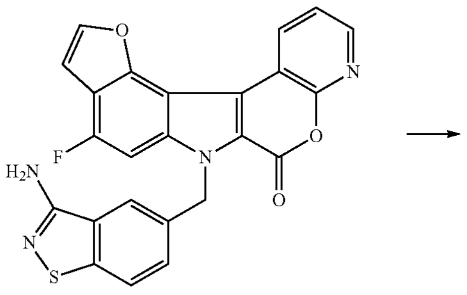

11B

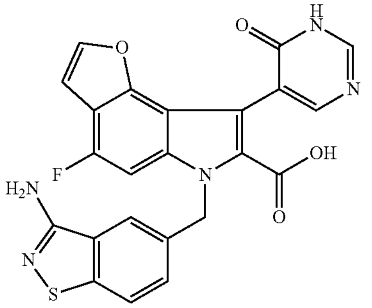

24

The lactone 11B (100 mg; 0.219 mmol) was suspended in 3 mL of THF and 1 mL of water followed by addition of lithium hydroxide monohydrate (5.0 eq, 46 mg). The reaction mixture was stirred for 2 h and TLC (50% acetone in dichloromethane showed no more starting material left. Aqueous 1 M HCl was added (0.5 mL) and the THF was removed in vacuo. The residue was dissolved in DMF (8 mL) and injected into a semi-prep HPLC system using the following conditions: Delta Pak Column, C18, 5 micrometer, 300 A; 300×30 mm I.D.; Flow rate: 25 mL/min; Gradient: 5% THF in water (0.01% TFA) for 5 min then increase to 90% over 45 minutes. The fractions containing the product (37-39 min) according to MS were combined and concentrated in vacuo to provide the title compound 24 (48 mg; 48%) as a white solid. $^1$H-NMR (dmso-$d_6$; 400 MHz): δ 12.90 (1H, broad s), 11.75 (1H, broad s), 7.91 (1H, d, J=2.44 Hz), 7.89 (1H, s), 7.80 d, J=8.54 Hz), 7.66 (1H, dd, J=2.44, 6.71 Hz), 7.46 (1H, d, J=10.98 Hz), 7.40 (1H, dd, J=1.83, 6.71 Hz), 7.10 (1H, d, J=8.54 Hz), 7.06 (1H, d, J=2.44 Hz), 6.73 (2H, broad s), 6.32 (1H, t, J=6.71 Hz), 5.96 (2H, s). LR-MS (ESI): calcd for $C_{24}H_{16}FN_4O_4S$ $[M+H]^+$ 475.09; found 475.27.

Example 12

Preparation of Intermediate Compound 12F

Step A—Synthesis of Compound 12B

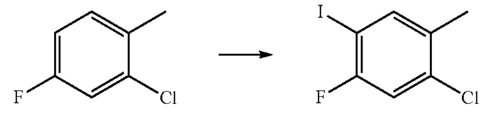

12A 12B

N-iodosuccinimide (1.1 eq; 17.1 g) was added to a solution of 2,4-difluoro toluene (12A, 10.0 g; 69.17 mmol; Alfa Aesar) in trifluoroacetic acid (46 mL). The reaction was set to stir for 12 hours. The volatiles were removed under reduced pressure; the remaining slurry was diluted with ether (400 mL) and washed with 5% aq sodium thiosulfate (5×40 mL), water (2×30 mL), and brine (40 mL). The organic layer was collected, dried over magnesium sulfate, filtered, and concentrated under reduced pressure. The reaction was purified via bulb to bulb distillation to provide product 12B as a colorless liquid (17 g; 91%)

Step B—Synthesis of Compound 12C

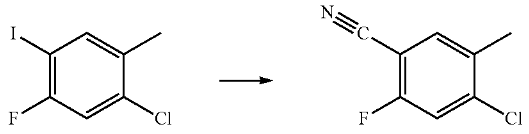

12B 12C

A solution of intermediate 12B (13.0 g; 48.06 mmol) and zinc cyanide (1 eq; 5.644 g) in N,N-dimethlyformamide (50 mL) was treated with tetrakis (triphenylphosphine) palladium (0) (0.1 eq; 5.55 g) and heated at 90° C. for 12 hours. The reaction mixture was diluted with ether (600 mL) and ammonium hydroxide (1:1 concentrated ammonium hydroxide: water 200 mL). The organic layer was separated and washed with water (100 mL) and brine (100 mL), dried over magnesium sulfate, filtered, concentrated under reduced pressure, and purified over silica gel first eluting with hexanes, then with 20% ethyl acetate/hexanes. Product 12C (4.48 g; 33%) was afforded as a clear oil.

Step C—Synthesis of Compound 12D

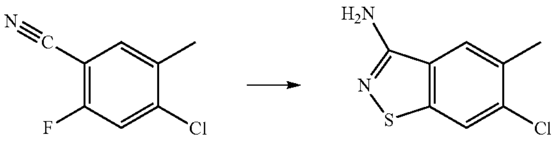

12C 12D

A solution of 12C (2.25 g; 13.27 mmol) and sodium sulfide (1 eq; 1.035 g) was prepared in DMSO (130 mL) and heated at 70° C. overnight. The mixture was placed in an ice water bath and treated with concentrated aqueous ammonium hydroxide (30 mL) and aqueous sodium hypochlorite (30 mL). The reaction mixture was stirred for 5 h (temp from 0 to 25° C.). The mixture was diluted with ethyl acetate (400 mL) and washed with water (2×40 mL) and brine (50 mL). The organic layer was dried over magnesium sulfate, filtered and concentrated in vacuo. The residue was adsorbed on silica gel and purified on an ISCO 330G column (gradient: 0-30% acetone in hexanes), affording product 12D (800 mg; 30.3%) as a white solid.

Step D—Synthesis of Compound 12E

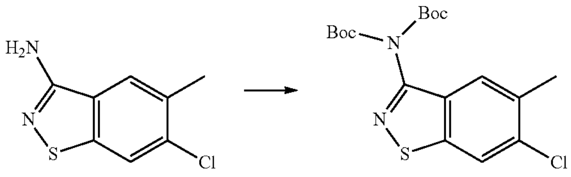

12D 12E

A solution of intermediate 12D (780 mg; 3.93 mmol) in dry acetonitrile (39 mL) was treated with Boc-anhydride (2.2 eq; 1.885 g) and heated to 50° C. All starting material had been consumed after 2 h and the mixture was concentrated in vacuo to one third of its volume. The residue was dissolved in ethyl acetate (100 mL) and washed with aqueous sodium hydrogen sulfate (20 mL) and brine (20 mL). The organic layer was dried over magnesium sulfate, filtered and concentrated in vacuo. The residue was adsorbed on silica gel and purified on a ISCO 80 gram column (gradient: 0 to 10% ethyl acetate in hexanes) to provide the product 12E (1.03 g; 66% yield) as a white solid.

Step E—Synthesis of Compound 12F

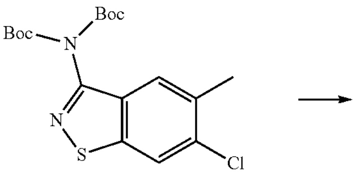

12E

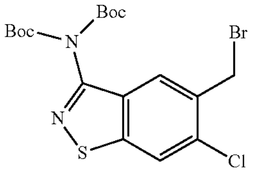

12F

A solution of intermediate 12E (400 mg; 1.003 mmol), N-Bromosuccinimide (1.05 eq; 187.4 mg), and benzoyl peroxide (0.1 eq; 24.3 mg) in dry carbon tetrachloride (10 mL) was prepared and heated at reflux for 12 hours. TLC (30% ethyl acetate in hexanes) revealed the reaction had partially progressed. The reaction mixture was concentrated under reduced pressure, diluted with ethyl acetate (100 mL), washed with saturated aqueous sodium bicarbonate (25 mL) and brine (25 mL), dried over magnesium sulfate, filtered, and concentrated under reduced pressure. The residue was then diluted with dichloromethane, adsorbed onto silica gel, and purified on ISCO (25-M Column; 0-40% ethyl acetate in hexanes). The fractions containing product were concentrated under reduced pressure affording intermediate 12F (278 mg; 58%) as a clear yellow oil.

Example 13

Preparation of Compound 105

Step A—Synthesis of Compound 13A

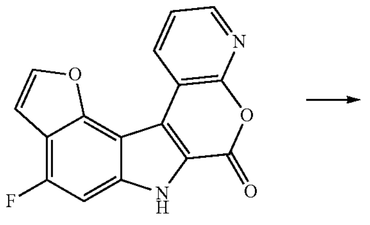

3L

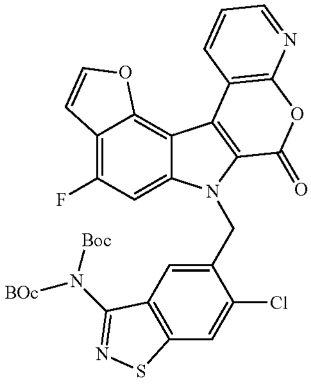

13A

A mixture of lactone 3L (163.05 mg, 0.554 mmol) in 10 mL of dry DMF was prepared and treated with N,N-bis-Boc-5-bromomethyl-6-chloro-benzo[d]isothiazol-3-ylamine 12F (1.05 eq; 278 mg) and cesium carbonate (3.0 eq, 541.5 mg). The slurry was set to stir overnight. The mixture was treated with water (10 mL) and the product was recovered by filtration (watmann #1). The solid was washed with 1:1 hexanes: diethyl ether (15 mL) and dried under reduced pressure. The product 13A was afforded as an off white solid (344.6 mg; 90%).

Step B—Synthesis of Compound 13B

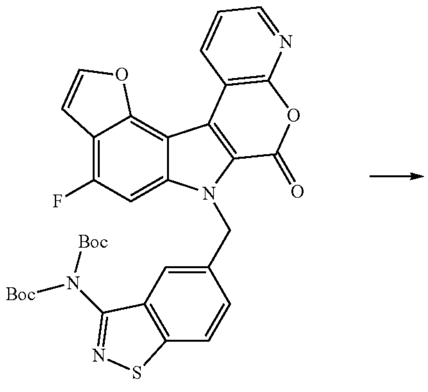

13A

-continued

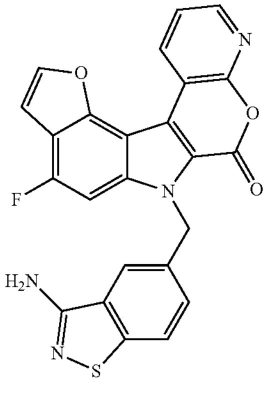

13B

Compound 13A (330 mg; 0.477 mmol) was treated with a 1:1 solution of trifluoroacetic acid:dichloromethane (8 mL). The resulting solution was set to stir for 30 minutes. TLC (60% ethyl acetate in hexanes) revealed that the reaction was complete. The volatiles were removed under reduced pressure to provide crude product 13 B (241 mg; 103%) as a slightly yellow solid which was used without further purification.

Step C—Synthesis of Compound 105

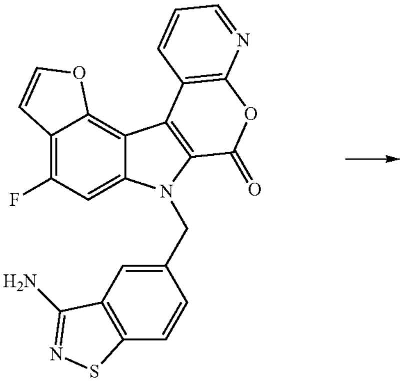

13B

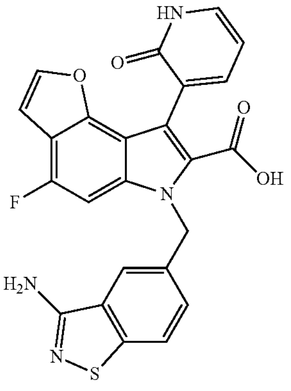

105

Lithium hydroxide monohydrate (4 eq; 51.3 mg) was added to a slurry of lactone 13B (150 mg; 0.306 mmol) in 4:1 THF:$H_2O$ (5 mL). The mixture was stirred for 2 hours. The reaction became a homogeneous solution and was quenched with 5 drops aqueous HCl (1N). The solution was concentrated to near dryness and diluted with 8 mL DMF. The compound was quickly taken into syringe, filtered, and injected into HPLC under the following conditions; Column: Delta Pak, C18, 5 micrometer, 300 A; 300×30 mm I.D.; Flow rate: 30 mL/min; gradient: 10% THF in water (0.01% TFA) for 10 ruin isocratic, increase to 95% THF in water from 10 min to 60 minutes. Isocratic from min 60 to min 65 at 95% THF in water. The fractions containing product 105 (80 mg; 51.4%) were collected and concentrated under reduced pressure to provide a white solid. MS (M+H)=475.5

Example 14

Preparation of Intermediate Compound 14G

Step A—Synthesis of Compound 14B

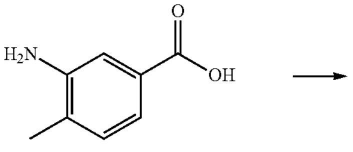

14A

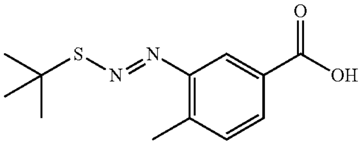

14B

To a stirred solution of aqueous HCl (15 mL of cone HCl in 50 mL of water) was added 3-amino-4-methyl benzoic acid (14 A, 5.0 g; 33.0 mmol). The mixture was cooled in an ice-water bath followed by slow addition of a solution of sodium nitrite (1.1 eq, 2.50 g) in water (12 mL). The mixture was stirred for 30 min at which point the mixture was a homogeneous dark solution. A saturated aqueous solution of sodium acetate was added until pH 6 was attained. Sodium t-butylthiolate (0.5 eq, 1.85 g) was added in one portion. The reaction was stirred for 2 h and the resulting precipitate was collected by filtration (whatman #1), washed with water (20 mL) and concentrated in vacuo to provide the product 14B (2.7 g; 64%) as a tan solid.

Step B—Synthesis of Compound 14C

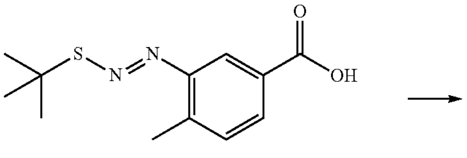

14B

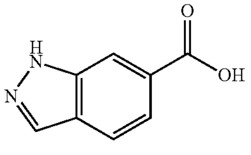

14C

To a stirred solution of potassium tert-butoxide (10.0 eq, 12.0 g) in DMSO (50 mL) was added a solution of t-butyl-diazaenyl benzoic acid 14B (2.7 g; 10.70 mmol) in DMSO (30 mL). The mixture was stirred for 6 h and then diluted with ice and acidified with aqueous 1 M HCl until pH 5-6 was attained. The mixture was extracted with ethyl acetate (3×50 mL) and the combined organic layers were washed with water (20 mL) and brine (20 mL). The organic layer was dried over magnesium sulfate, filtered and concentrated in rotavap to provide the crude product 14C as a slightly yellow solid which was used without further purification.

Step C—Synthesis of Compound 14D

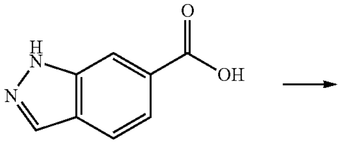

14C

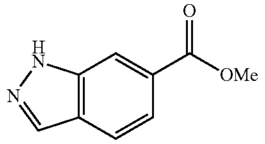

14D

A solution of 1H-indazole-6-carboxylic acid 14C (1.73 g; 10.70 mmol) in toluene (80 mL) and methanol (30 mL) was treated with a solution of TMS-diazomethane (2 M soln in ether) until evolution of gas stopped. The reaction mixture was concentrated in vacuo and the residue was adsorbed on silica gel. The product was purified on a Biotage 40-M silica gel column (gradient: 0 to 20% acetone in hexanes) to provide the product 14D (950 mg; 50% for two steps) as a slightly yellow solid. $^1$H-NMR ($CDCl_3$; 400 MHz): δ 8.28 (1H, s), 8.16 (1H, s), 7.86 (1H, d, J=8.54 Hz), 7.81 (1H, d, J=8.54 Hz), 3.98 (3H, s). LR-MS (EST): caldc for $C_9H_9N_2O_2$ $[M+H]^+$ 177.07; found 177.20.

Step D—Synthesis of Compound 14E

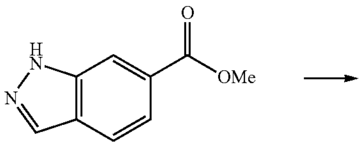

14D

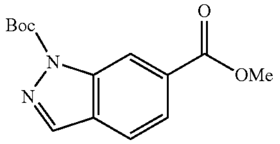

14E

A solution of 1H-indazole-6-carboxylic acid methyl ester 140 (840 mg; 4.76 mmol) in 25 mL of acetonitrile was treated with Boc-anhydride (1.05 eq, 1.09 g) and a catalytic amount of DMAP (tip of spatula). The mixture was stirred at 60° C. for 3 hours. The mixture was concentrated to half its volume in rotavap and then diluted with ethyl acetate (100 mL) and washed with aqueous saturated sodium bicarbonate (20 mL) and brine (20 mL). The organic layer was dried over magnesium sulfate, filtered and concentrated in rotavap. The residue was purified on a Biotage 40-M silica gel column (gradient: 0 to 20% ethyl acetate in hexanes) to provide the product 14E (1.2 g; 93%) as a colorless oil. $^1$H-NMR ($CDCl_3$; 400 MHz): δ 8.91 (1H, s), 8.22 (1H, s), 7.99 (1H, dd, J=1.22, 8.54 Hz), 7.78 (1H, d, J=8.54 Hz), 3.97 (3H, s), 1.74 (9H, s).

Step E—Synthesis of Compound 14F

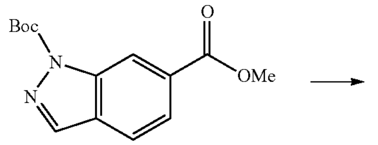

14E

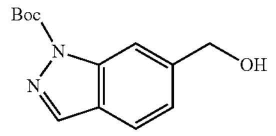

14F

A solution of indazole 14E (460 mg; 1.66 mmol) in 16 mL of dry THF was cooled to −78° C. and treated with lithium triethylborohydride (2.5 eq, 4.15 mL of a 1 M soln in THF). The reaction mixture was stirred at −78° C. and followed by TLC (25% ethyl acetate in hexanes). The reaction was completed in about 1 h and quenched by addition of aqueous saturated sodium hydrogen sulfate (3 mL). The mixture was extracted with ethyl acetate (100 mL) and washed with water (20 mL) and brine (20 mL). The organic layer was dried over magnesium sulfate, filtered and concentrated in rotavap to provide the crude product as a colorless oil. The residue was chromatographed on a Biotage 40-S silica gel column (0 to 40% ethyl acetate in hexanes) to provide the following: des-Boc starting material (70 mg); alcohol product 14F (160 mg; 40%). $^1$H-NMR ($CDCl_3$; 400 MHz): δ 8.19 (1H, s), 8.13 (1H, s), 7.67 (1H, d, J=7.93 Hz), 7.30 (1H, d, J=7.93 Hz), 5.13 (2H, s), 1.71 (9H, s).

Step F—Synthesis of Compound 14G

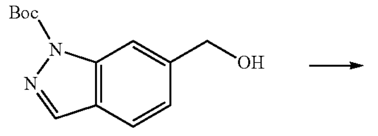

14F

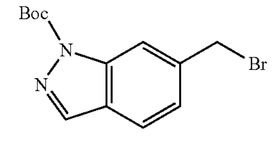

14G

A solution of alcohol 14F (160 mg; 0.644 mmol) in dry chloroform (12 mL) was placed in an ice-water bath and treated with pyridine (4.0 eq, 0.208 mL, d 0.978) and a solution of thionyl bromide (1.2 eq, 0.060 mL, d 2.683) in 1 mL of chloroform. The ice-water bath was removed and the reaction mixture was stirred at room temp for 30 minutes. TLC (30% ethyl acetate in hexanes) showed about 40% conversion and more thionyl bromide was added (0.2 eq). The mixture was heated to 70° C. for 10 minutes. Upon cooling the mixture was diluted with ethyl acetate (30 mL) and washed with aqueous saturated sodium bicarbonate (5 mL), aqueous sodium hydrogen sulfate (5 mL) and brine (5 mL). The organic layer was dried over magnesium sulfate, filtered and concentrated in rotavap. The residue was purified on a Biotage 25-S silica gel column (gradient: 0 to 40% ethyl acetate in hexanes) to provide the product 14G (76 mg; 38%) as a colorless oil along with unreacted starting material (25 mg; 24%). $^1$H-NMR ($CDCl_3$; 400 MHz): δ 8.23 (1H, s), 8.14 (1H, s), 7.72 (1H, d, J=8.54 Hz), 7.32 (1H, dd, J=1.22, 8.54 Hz), 5.21 (1H, d, J=12.20 Hz), 5.09 (1H, d, J=12.20 Hz), 1.71 (9H, s).

Example 15

Preparation of Compound 1

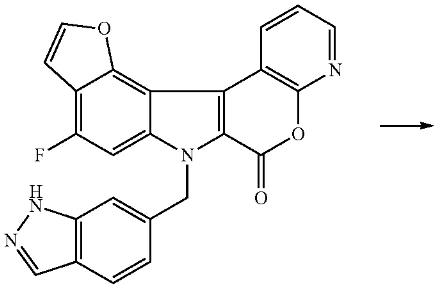

15A

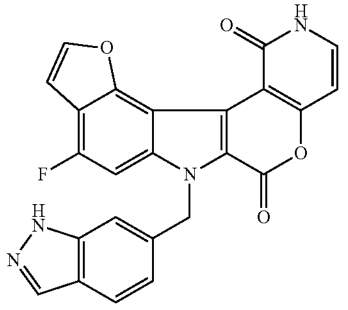

1

The lactone 15A (0.213 mmol) was dissolved in 3 mL of THF and 1 mL of water followed by addition of lithium hydroxide monohydrate (4.0 eq, 36 mg). The reaction mixture was stirred for 3 hours. Aqueous 1 M HCl was added (0.5 mL) and the THF was removed in rotavap. The residue was dissolved in DMF (15 mL) and injected into a semi-prep HPLC system using the following conditions: Delta Pak Column, C18, 5 micrometer, 300 A; 300×30 mm I.D.; Flow rate: 25 mL/min; Gradient: 5% THF in water (0.01% TFA) for 5 min then increase to 90% over 45 minutes. The fractions containing the product (31 & 32 min) according to MS were combined and concentrated in rotavap to provide the product 1 (16 mg; 17%) as a white solid. $^1$H-NMR (dmso-$d_6$; 400 MHz): δ 12.90 (2H, broad s), 11.74 (1H, broad s), 7.98 (1H, s), 7.91 (1H, d, J=2.44 Hz), 7.67 (1H, d, J=8.54 Hz), 7.65 (1H, dd, J=1.83, 6.71 Hz), 7.47 (1H, d, J=10.98 Hz), 7.40 (1H, dd, J=1.83, 6.71 Hz), 7.10 (1H, s), 7.05 (1H, d, J=2.44 Hz), 6.95 (1H, dd, J=1.22, 8.54 Hz), 6.32 (1H, dd, J=6.10, 6.71 Hz), 6.00 (2H, s). LR-MS (ESI): caldc for $C_{24}H_{16}FN_4O_4$ [M+H]$^+$ 443.12; found 443.28.

Example 16

Preparation of Intermediate Compound 16E

Step A—Synthesis of Compound 16B

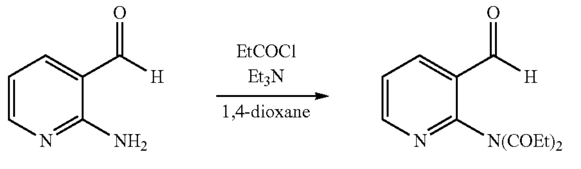

16A 16B

To a solution of 16A (7.2 g, 58.8 mmol) in 1,4-dioxane (39 mL) at 0° C. was added propionyl chloride (15.8 ml, 176.5 mmol) and $Et_3N$ (24.6 mL, 176.5 mmol) with stirring. The reaction mixture was stirred at room temperature for overnight. The solvent was removed under reduced pressure, and the resulting residue was taken up in EtOAc. The organic phase was washed with water, dried over $MgSO_4$, filtered, and concentrated in vacuo to provide a crude residue of 16B.

Step B—Synthesis of Compound 16C

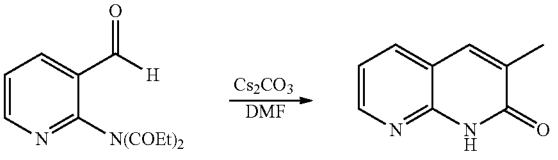

16B 16C

To a suspension of 16B (crude residue from above) in DMF (60 mL) was added cesium carbonate (38 g, 117.6 mmol), and the resulting mixture was heated at 65° C. for overnight. Reaction was cooled to room temperature, and the bulk of DMF was removed under reduced pressure. Water was then added to the crude residue and the mixture was filtered. The filter-cake was washed with water and EtOAc. 5.2 g of 16C was collected as a pale yellow solid.

Step C—Synthesis of Compound 16D

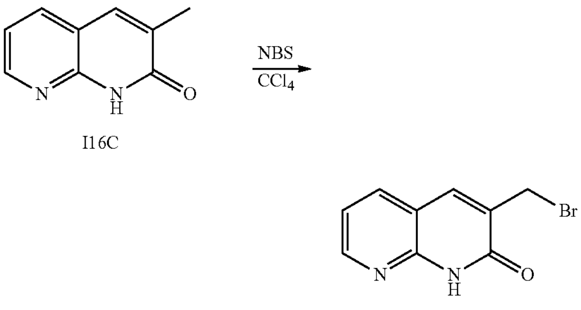

I16C

16D

To a suspension of 16C (0.8 g, 5 mmol) in $CCl_4$ (25 mL) was added NBS (38 g, 117.6 mmol), and benzoyl peroxide (61 mg, 0.25 mmol), and the resulting mixture was then heated at 90° C. for 4 hours. Cooled the reaction to room temperature, and 300 mL of $CH_2Cl_2$ was added. The mixture was filtered, and filtrate was dried over $MgSO_4$, filtered, and concentrated in vacuo to provide 2 g of crude residue of 16D.

Step D—Synthesis of Compound 16E

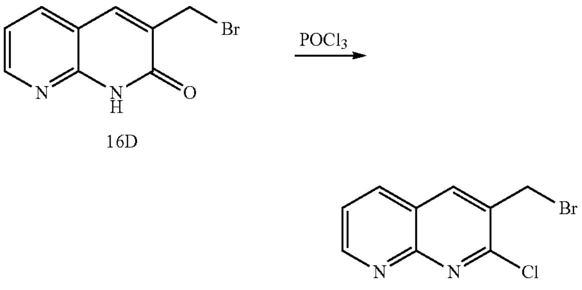

16D

16E $POCl_3$ was added to a 100 mL round bottom flask containing crude 16D. The resulting suspension was then heated at 88° C. for 4 hours. Cooled the reaction to room temperature, and then poured into a 1 liter beaker containing ice. The resulting solution was neutralized to ph 8 using 6 N NaOH solution. Solid that precipitated from the solution was collected to provide 0.82 g of crude residue which was purified using column chromatography on silica get (ISCO Combi-Flash Rf; gradient: 5 to 50% ethyl acetate in hexanes) to provide 330 mg of compound 16E.

Example 17

Preparation of Intermediate Compound 17D

Step A—Synthesis of Compound 17B

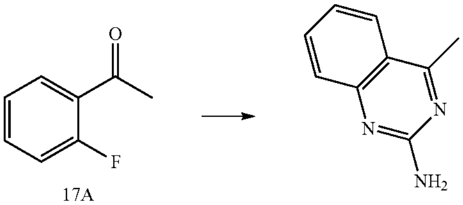

17A 17B

A mixture of ortho-fluoroacetophenone (17A, 3.45 g; 25 mmol) and guanidine carbonate (2 eq; 9.0 g) was prepared in 250 mL of N,N-dimethyl acetamide, set to stir, and heated at 135° C. under nitrogen purge overnight. The solvent was removed under reduced pressure and diluted with ethyl acetate (600 mL). The solution was washed with water (2×100 mL) and brine (40 mL). The organic layer was separated, dried over magnesium sulfate, filtered, and concentrated under reduced pressure. The solid was dissolved in methylene dichloride, loaded on silica gel and dried under reduced pressure. The material was purified on ISCO (80 g column; 0-70% THF in Hexanes). Fractions containing product were collected and concentrated under reduced pressure to provide product 17B as a crème colored solid (880 mg; 22%)

Step B—Synthesis of Compound 17C

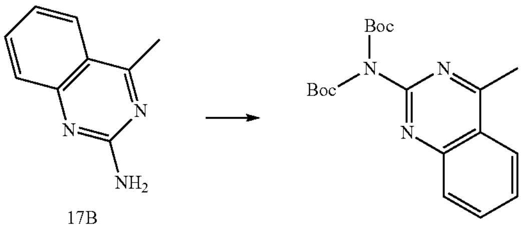

17B 17C

A solution of 4-Methyl-quinazolin-2-ylamine 17B (640 mg; 4.02 mmol) in 10 mL of dry acetonitrile was treated with a solution of Boc-anhydride (2.5 eq; 2.19 g) in 10.0 mL of dry acetonitrile. The resulting solution was treated with DMAP (0.2 eq; 98.2 mg). The mixture was set to stir overnight. TLC (50% THF in hexanes) showed a complete reaction. The mixture was diluted with ethyl acetate (500 mL) and washed with water (3x30 mL), and Brine (40 mL). The organic layer was dried over magnesium sulfate, filtered and concentrated in rotavap. The residue was adsorbed on silica gel and purified on an ISCO column (120 g) (0% to 60% THF in hexanes). The fractions with product were collected and concentrated under reduced pressure to provide product 17C as a light yellow-white solid (1.3 g; 90%).

Step C—Synthesis of Compound 17D

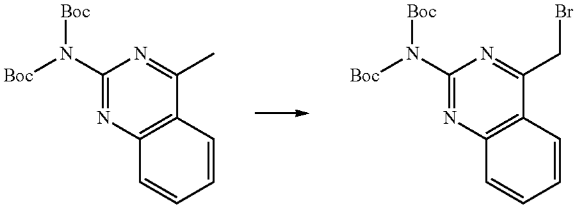

17C 17D

Intermediate 17C (1.11 g; 3.09 mmol), N-Bromosuccinimide (1.05 eq; 577 mg), and benzoyl peroxide (0.1 eq; 75 mg) were combined in round bottom and diluted with dry carbon tetrachloride (31 mL). The reaction was stirred at room temperature for 10 minutes and then heated at reflux overnight. TLC (30% ethyl acetate in hexanes) revealed the reaction has partially progressed. The reaction mixture was concentrated under reduced pressure, diluted with ethyl acetate (300 mL), and washed with sat. aqueous sodium bicarbonate (40 mL) and brine 0-40 mL), dried over magnesium sulfate, filtered, concentrated under reduced pressure, diluted with methylene dichloride, adsorbed onto silica gel, and purified on MO (25-M Column; 0-40% ethyl acetate in hexanes). The fractions containing product were concentrated under reduced pressure and afforded product as a clear oil in a 2:1 mixture of pure product 17D and starting material (Total: 440 mg; 33%).

Example 18

Preparation of Compound 18

Step A—Synthesis of Compound 18A

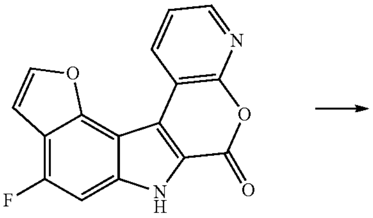

3L

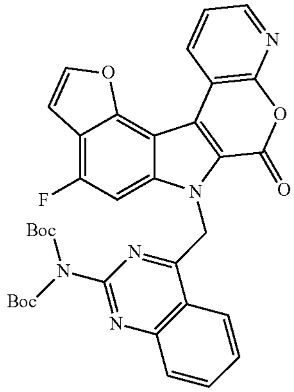

18A

A solution of lactone 3L (244.1 mg, 0.83 mmol) in 10 mL of dry DMF was treated with N,N-bis-Boc-4-bromomethyl-quinazolin-2-ylamine 086951-092-36 (1.1 eq; 400 mg) and cesium carbonate (3.0 eq, 811 mg). The slurry was set to stir overnight. The reaction was quenched with water (5 mL), stirred for 10 minutes and dried under reduced pressure and heat. The residual paste was diluted with ethyl acetate (400 mL) and washed with water (2x30 mL) and brine (2x30 mL). The organic layer was separated, dried over magnesium sulfate, filtered, and concentrated under reduced pressure. Product 18A was afforded as a crude yellow gum and was not purified further (300 mg; 55%).

Step B—Synthesis of Compound 18B

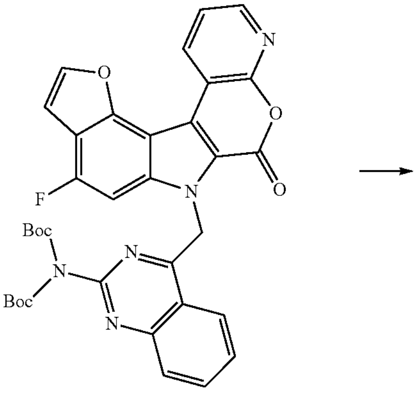

18A

-continued

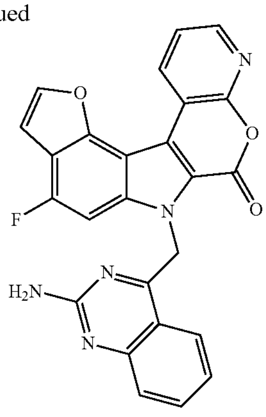

18B

Lactone 18A (380 mg; 0.631 mmol) was diluted with 5 mL methylene dichloride to which 5 mL difluoro acetic acid was added. The reaction was stirred for 3 hours. The reaction mixture was dried under reduced pressure and set to dry further under vacuum for 48 hours. Intermediate 18B was used as is in the next reaction.

Step C—Synthesis of Compound 18

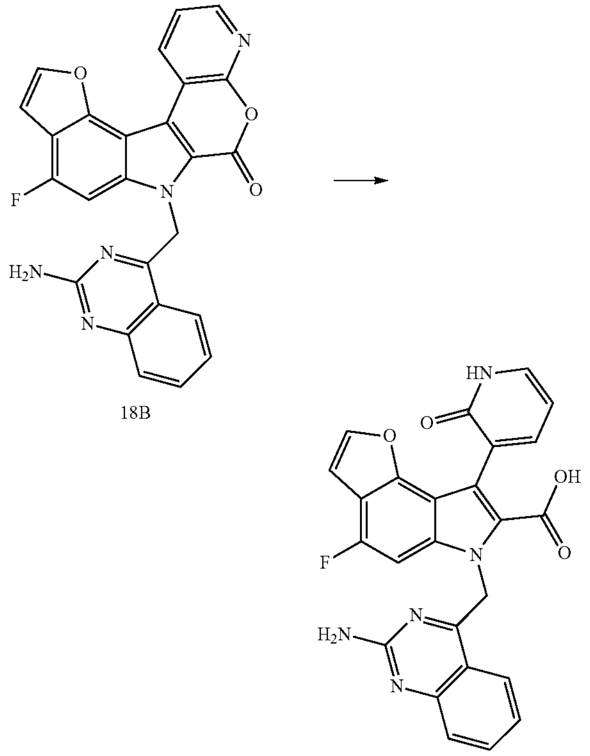

18B

18

Lactone 18B (150 mg; 0.332 mmol) was diluted with 5 mL THF:water. Lithium Hydroxide monohydrate (2 eq, 27.9 mg) was added and the mixture was allowed to stir for 2 hrs. The reaction was quenched with 5 drops of HCl (1N). The solution was concentrated to near dryness and diluted with 8 mL DMF. The solution was quickly taken into syringe and injected into HPLC under the following conditions; Column: Delta Pak, C18, 5 micrometer, 300 A; 300×30 mm I.D.; Flow rate: 30 mL/min; gradient: 10% THF in water (0.01% TFA) for 10 min isocratic, increase to 95% THF in water from 10 min to 60 minutes. Isocratic from min 60 to min 65 at 95%. THF in water. The fractions containing product were collected and concentrated under reduced pressure to provide the title compound 18 as an off-white solid (30 mg; 20%).

Example 19

Preparation of Intermediate Compound 19C

Step A—Synthesis of Compound 19B

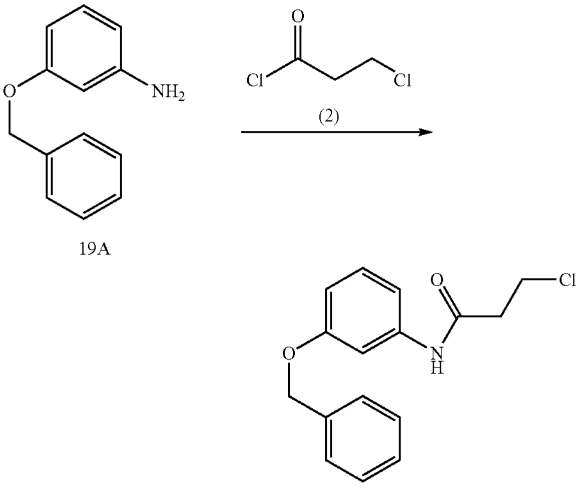

19A

19B

Compound 19A (commercially available) (10.0 g, 50.25 mmol) was dissolved in water at room temperature and to resulting suspension $K_2CO_3$ (3.8 g, 27.64 mmol) was added. 3-Chloro propionylchloride (7.0 g, 55.28 mmol) was added dropwise for 30 minutes and stirred for 2 hours at room temperature The precipitate was filtered and washed with water, 1 N HCl, dried at 50° C. under vacuum overnight to provide 7.2 g of the product 19B.

Step B—Synthesis of compound 19C

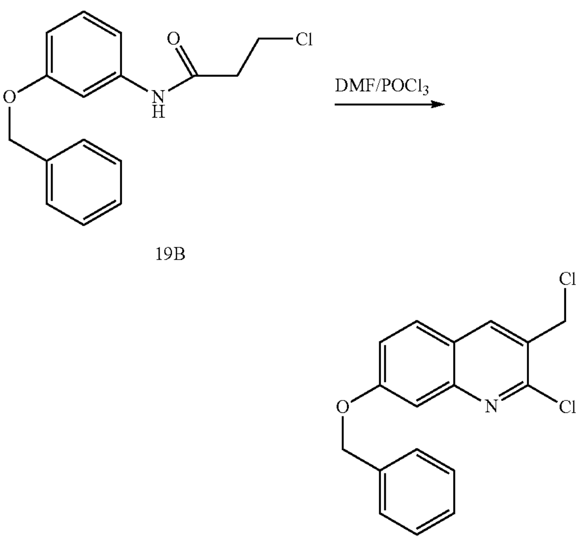

19B

19C

To N,N-Dimethylformamide (3.6 g, 49.66 mmol) at 0° C. was added drop wise $POCl_3$ (26.6 g, 173.8 mmol) and stirred for 60 minutes, white precipitate was formed. The 7.2 g of the compound 19B was added by portion in reaction mixture and stirred for 24 hours at room temperature. Reaction mixture was diluted with ethyl acetate and slowly added to a beaker with ice, after ice was melted, organic layer was separated and washed with 0.5 N NaOH and water, brine, dried over sodium sulfate, and concentrated in vacuum, purified using flash chromatography, to provide compound 19C (5.5 g, 34% after two steps). M.S. found: 318.04 $(M+H)^+$.

Example 20

Preparation of Compound 55

Step A—Synthesis of Compound 20A

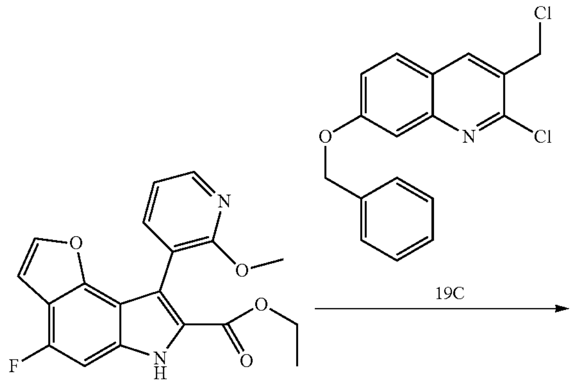

31

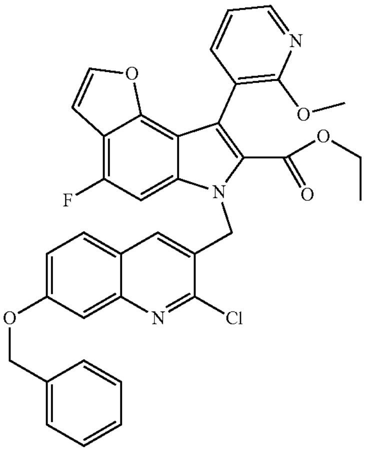

20A

To a solution of compound 31 (0.30 g, 0.85 mmol) in DMF (5 mL) was added cesium carbonate (0.28 g, 0.85 mmol) and chloride 19C (0.27 g, 0.85 mmol) and the resulting reaction was allowed to stir at room temperature for 24 hours. The reaction mixture was diluted with EtOAc and washed with water, brine. The combined organic layers were dried ($Na_2SO_4$), filtered, and concentrated in vacuo, and purified using flash chromatography, to provide compound 20A (0.42 g, 77%).

Step B—Synthesis of Compound 20B

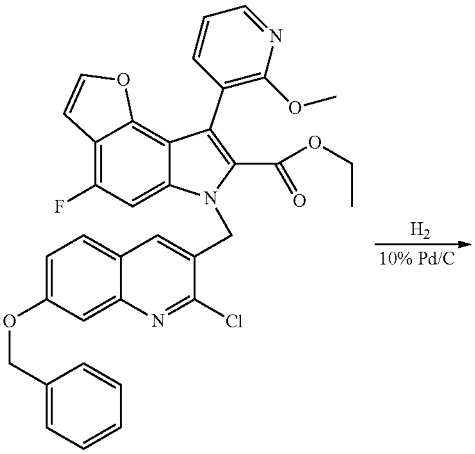

20A

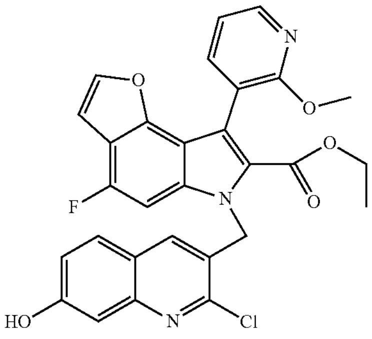

20B

To solution of the compound 20A (0.42 g, 0.66 mM) in THF was added 10% Pd/C and treated with hydrogen in balloon for 24 hours. Reaction mixture was diluted with ethyl acetate and filtered through celite, concentrated in vacuo, purified using flash chromatography, to provide compound 20B (0.2 g, 55%).

Step C—Synthesis of Compound 20C

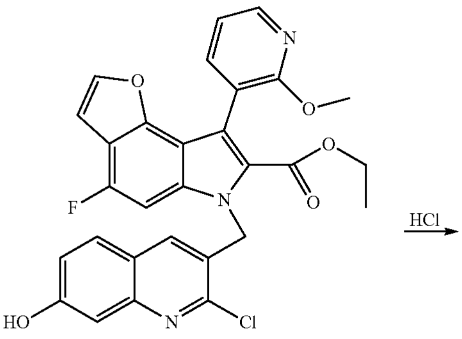

20B

-continued

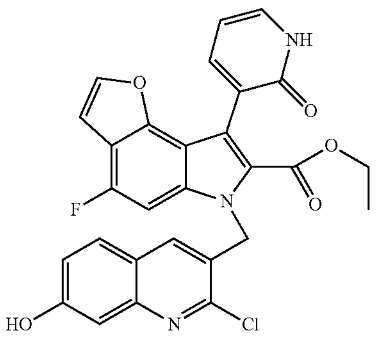

20C

Compound 208 (200 mg, 0.37 mmol) was dissolved in 3 mL dioxane and 3 mL 4N HCl and the resulting reaction mixture was heated to 90° C. and allowed to remain at this temperature for 5 hours. The reaction mixture was cooled to room temperature, and then concentrated in vacuo to provide a crude product which was purified using flash chromatography, to provide compound 20C (150 mg, 77%).

Step D—Synthesis of Compound 55

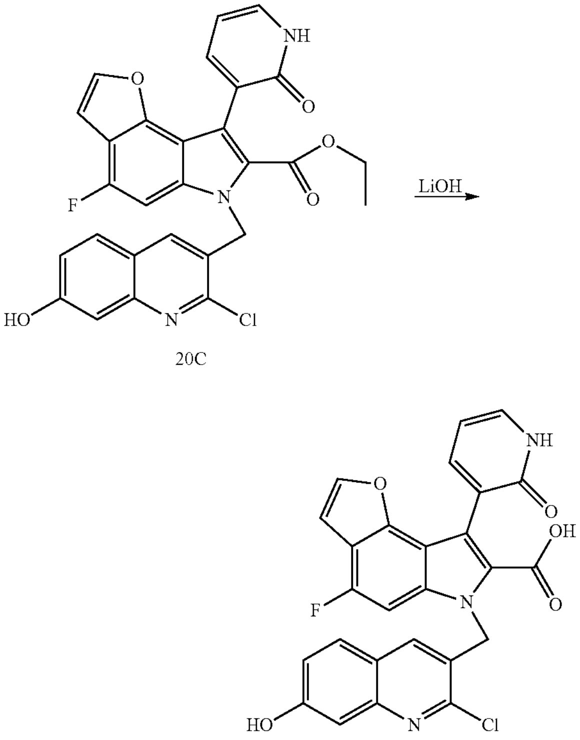

20C

55

To a solution of compound 20C (150 mg, 0.28 mmol) in water (5 mL)/THF (10 mL) was added lithium hydroxide (68 mg, 10 mmol) and the resulting reaction was allowed to stir at 65° C. for 5 hours. The reaction mixture was diluted with aqueous HCl and extracted into ethyl acetate. The combined organic layers were dried with $Na_2SO_4$, filtered, and concentrated in vacuo to provide 50 mg of the product 55. M.S. found: 504.3 $(M+H)^+$; $^1H$ NMR (500 MHz, DMSO): δ 10.41 (s, 1H), 7.97 (m, 1H), 7.74 (m, 1H), 7.62 (d, J=9.1 Hz, 1H), 7.52 (d, J=11.0 Hz, 1H), 7.44 (s, 1H), 7.16 (m, 1H), 7.11 (m, 1H), 7.08 (m, 1H), 7.05 (s, 1H), 6.36 (t, J=6.9 Hz, 1H), 5.97 (s, 2H).

Example 21

Preparation of Compound 60

Step A—Synthesis of Compound 21A

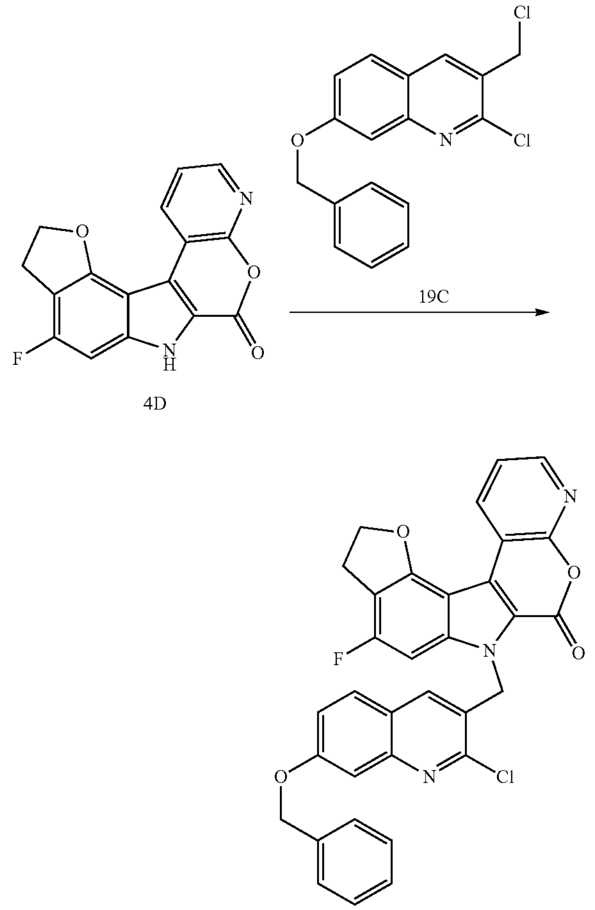

4D

21A

To a solution of compound 4D (0.65 g, 2.2 mmol) in DMF (10 mL) was added cesium carbonate (0.72 g, 2.2 mmol) and compound 19C (0.71 g, 2.2 mmol) and the resulting reaction was allowed to stir at room temperature for 24 hours. The reaction mixture was diluted with EtOAc and washed with water, brine. The combined organic layers were dried ($Na_2SO_4$), filtered, and concentrated in vacuo, and purified using flash chromatography, to provide compound 21A (0.8 g, 68%).

Step B—Synthesis of Compound 21B

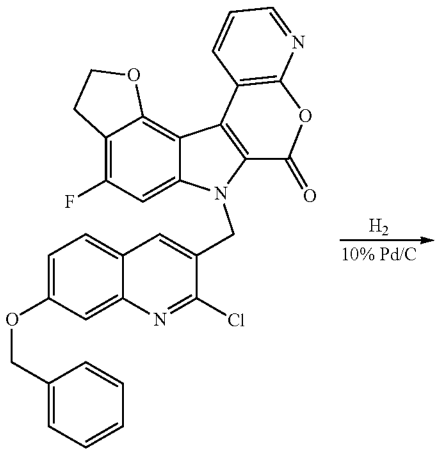

21A

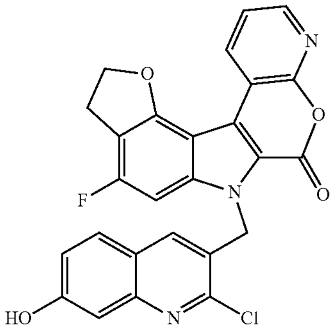

21B

To solution of the compound MA (0.2 g, 0.35 mmol) in THF was added 10% Pd/C and treated with hydrogen in balloon for 24 hours. Reaction mixture was diluted with Ethyl Acetate and filtered through celite, concentrated in vacuo, purified using flash chromatography, to provide compound 21B (0.12 g, 71%).

Step C—Synthesis of Compound 60

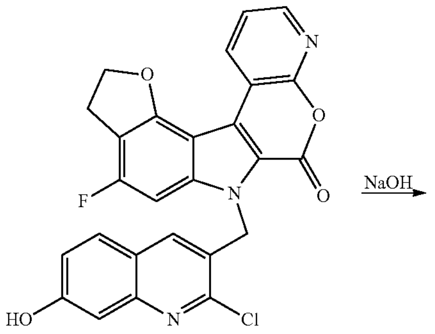

21B

-continued

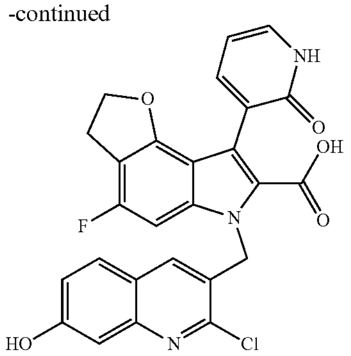

60

Compound 21B (120 mg, 0.25 mmol) was dissolved in 5 mL THE and 2 mL 0.5N NaOH and stirred at room temperature. The reaction mixture was diluted with EtOAc and washed with water, brine. The combined organic layers were dried ($Na_2SO_4$), filtered, and concentrated in vacuo, product was washed with methanol, concentrated in vacuo to provide compound 60 (5 mg, 4%). M.S. found: 506.3 $(M+H)^+$; $^1H$ NMR (500 MHz, DMSO): δ 10.39 (s, 1H), 7.64 (d, J=8.8 Hz, 1H), 7.54 (m, 1H), 7.36 (m, 1H), 7.16 (s, 1H), 7.10 (m, 1H), 7.06 (s, 1H), 6.97 (m, 1H), 5.83 (s, 2H), 4.67 (t, J=8.5 Hz, 2H), 3.23 (t, J=8.5 Hz, 2H).

Example 22

Preparation of Compound 92

Step A—Synthesis of Compound 22B

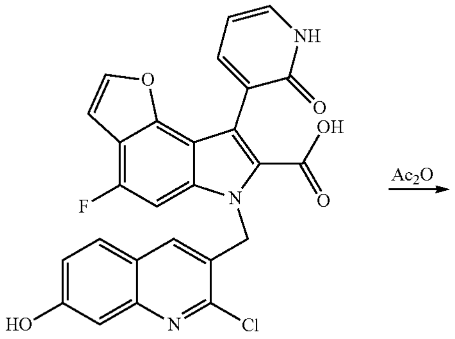

22A

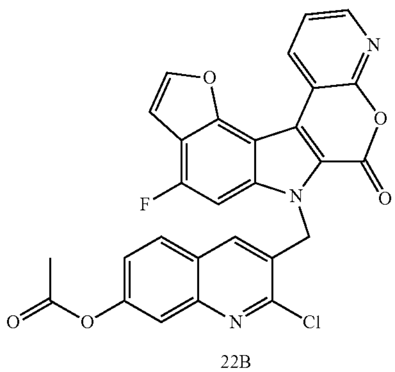

22B

Compound 22A (200 mg 0.4 mmol) was dissolved in 5 mL DMF at room temperature and 1 mL acetic anhydride. 1 mL triethyl amine was added and stirred for 1 hour at 60° C. The reaction mixture was diluted with ethyl acetate and washed with water, brine. The combined organic layers were dried ($Na_2SO_4$), filtered, and concentrated in vacuo, product was washed with methanol, dried in vacuum for 24 hours to provide compound 22B (77 mg, 37%).

Step B—Synthesis of Compound 92

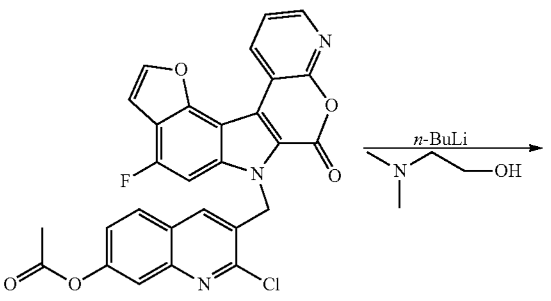

22B

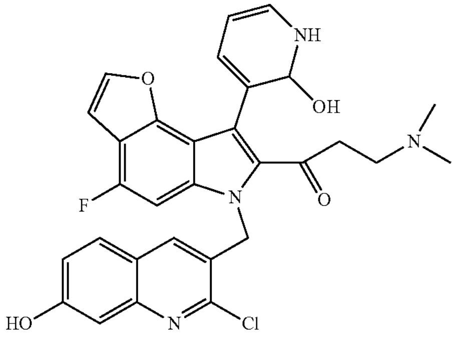

92

To solution of 22B (77 mg, 0.15 mM) in 4 mL THF was added dropwise 1.6M n-BuLi (0.5 ml, 0.75 mmol) at −70° C. and stirred for 10 minutes, reaction mixture was cooled to 0° C. and solution of the N,N-dimethylethanol (80 mg, 0.90 mmol) in 4 mL THF was added and stirred for 1 hour. Solvent was evaporated, reaction mixture was separated on preparative HPLC to produce product 92 (14 mg, 17%). M.S. found: 576 $(M+H)^+$, $^1H$ NMR (500 MHz, $CD_3OD$): δ 8.13 (dd, 1.9 Hz, J=6.9 Hz, 1H), 7.76 (d, J=2.2 Hz, 1H), 7.68 (dd, 1.9 Hz, J=6.9 Hz, 1H), 7.56 (d, J=8.8 Hz, 1H), 7.29 (s, 1H), 7.22 (m, 2H), 7.10 (dd, J=2.5 Hz, J=8.8 Hz, 1H), 7.04 (d, J=2.2 Hz, 1H), 6.77 (t, J=6.6 Hz, 1H), 6.03 (s, 2H), 4.55 (t, J=5.0 Hz, 2H), 3.36 (t, J=5.0 Hz, 2H), 2.88 (s, 6H).

Example 23

Synthesis of Compound 99

Step A—Synthesis of Compound 23A

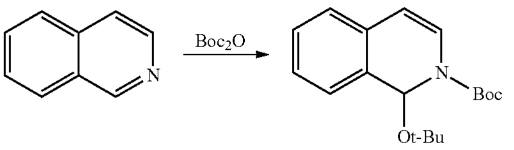

23A

As per Ref: Tetrahedron, 2006, 62, 11599-11607, isoquinoline (3.8 g, 29.5 mmol) and di-tert-butyl dicarbonate (7.7 g, 35.4 mmol) were mixed in hexane and stirred at room temperature for 15 hours. Formed precipitate was filtered and concentrated in vacuo to produce product 23A (BBDI) (2.5 g). This was used as the coupling reagent in the next step.

Step B—Synthesis of Compound 23C

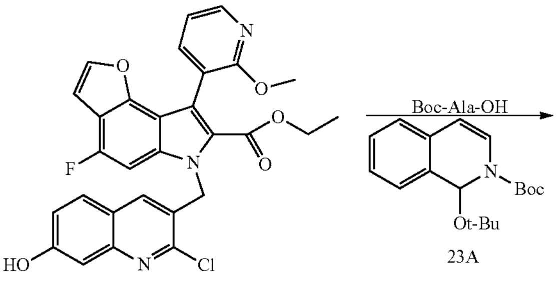

23A

23B

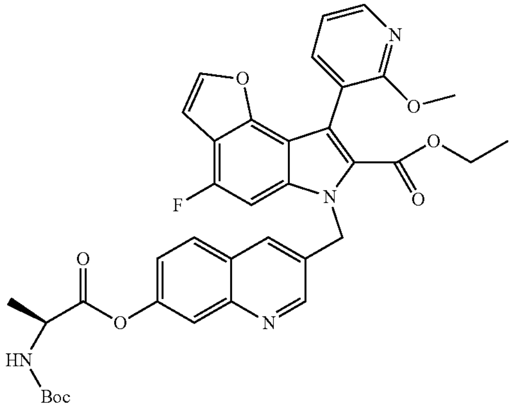

23C

Compound 23B (200 mg 0.36 mmol) was dissolved in 5 ml dioxane at room temperature and compound 23A (327 mg 1.08 mM) was added and stirred for 30 minutes. Boc-Ala-OH (204 mg, 1.08 mmol) was added and stirred for 10 hours at room temperature. The reaction mixture was diluted with ethyl acetate and washed with 1N HCl, water, brine. The combined organic layers were dried ($Na_2SO_4$), filtered, and concentrated in vacuo, product was purified on flash chromatography, dried in vacuum for 24 hours to provide compound 23C (160 mg, 61%).

Step C—Synthesis of Compound 99

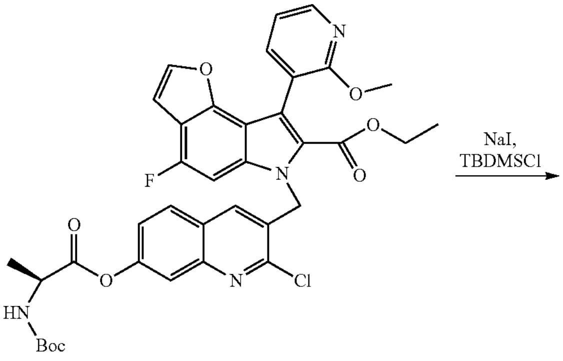

23C

-continued

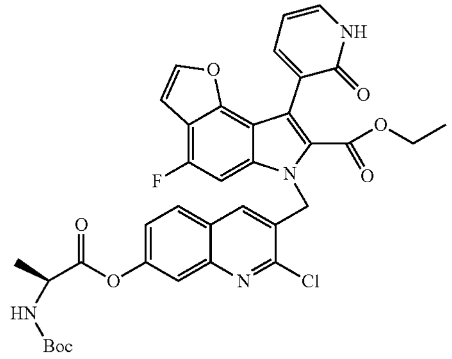

99

To solution of the 23C (160 mg, 0.22 mmol) in 5 mL acetonitrile at 0° C. were added sodium iodide (1.5 eqv.) and tert-butyldimethylsilyl chloride (2 eqv.) and stirred at room temperature for 24 hours. Solvent was evaporated, reaction mixture was separated on flash LC to produce product 99 (70 mg, 45%). M.S. found: 703.4 $(M+H)^+$; $^1$H NMR (500 MHz, $CD_3OD$): δ 7.9 (dd, J=1.9 Hz, J=6.9 Hz, 1H), 7.8 (d, J=8.8 Hz, 1H), 7.73 (d, J=2.2 Hz, 1H), 7.72 (m, 1H), 7.57 (dd, J=2.2 Hz, J=6.3 Hz, 1H), 7.51 (s, 1H), 7.33 (m, 1H), 7.19 (d, 10.4 Hz, 1H), 7.00 (d, J=2.2 Hz, 1H), 6.62 (t, J=6.6 Hz, 1H), 6.08 (s, 2H), 4.41 (m, 1H), 4.11 (q, J=7.3 Hz, 3H), 1.55 (d, J=7.3 Hz, 3H), 1.48 (s, 9H), 1.04 (t, J=7.3 Hz, 3H).

Example 24

Preparation of Intermediate Compound 24C

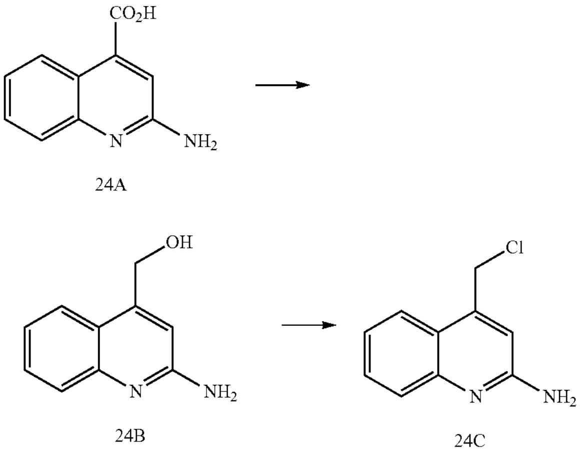 [SMILES: Nc1cc(C(=O)O)c2ccccc2n1 ; Nc1cc(CO)c2ccccc2n1 ; Nc1cc(CCl)c2ccccc2n1]

24A

24B

24C

The starting materials 24A (2.0 g, 10.6 mmol), lithium aluminum hydride (2.0 g, 52.7 mmol), and THF (100 ml) were added to a 250 ml round-bottomed flask. The resulting suspension was stirred at room temperature for 18 hours. The reaction was quenched with 10 ml of saturated ammonium chloride solution followed by 200 ml of ethyl acetate. After filtration, the organic layer was washed with brine (2×100 ml), dried over sodium sulfate, and concentrated under vacuum to provide 24B as a yellowish solid (1.05 g, 59%).

A 250 ml round-bottomed flask was charged with 24B (1.05 g, 6.03 mmol) and thionyl chloride (10 ml). The resulting mixture was stirred at 60° C. for 4 hours before cooled to room temperature. After removal of excess of thionyl chloride, the residue was concentrated in vacuo to provide 24C as an orange solid (1.45 g). This crude material was used without further purification.

Example 25

Preparation of Compound 15

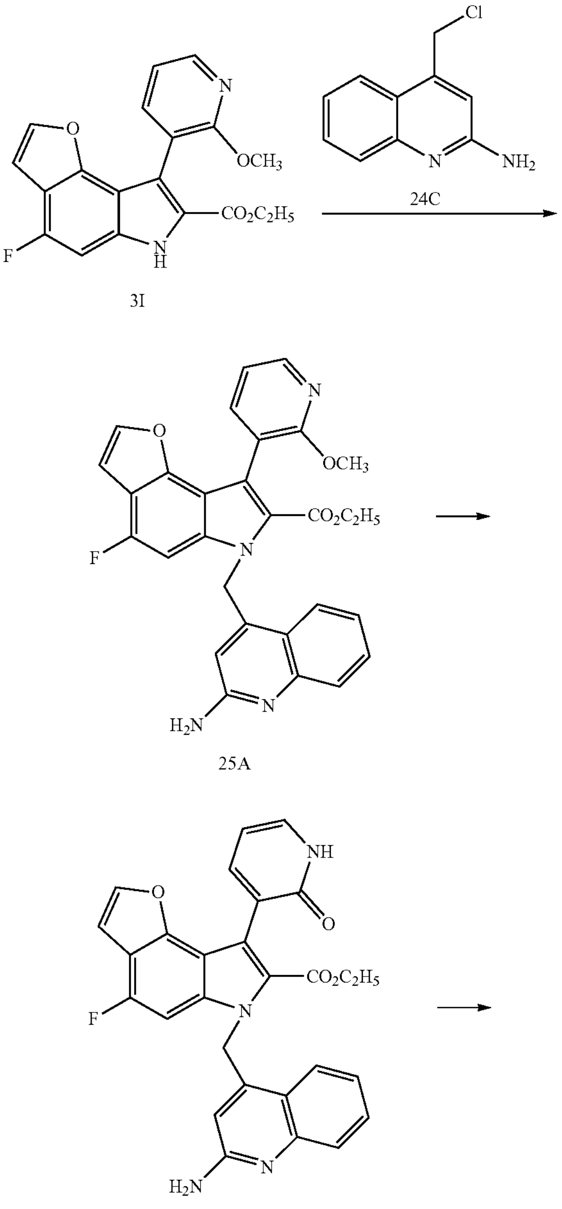

3I

24C

25A

25B

-continued

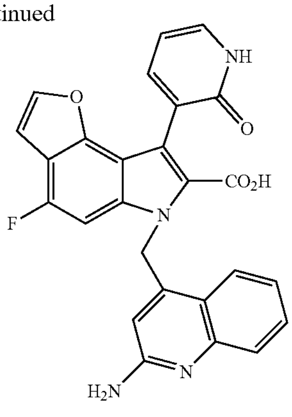

15

The suspension of 3I (1.0 g, 2.8 mmol), crude 24C (0.5 g, ~2.6 mmol), cesium carbonate (2.0 g, 6.16 mmol) and DMF (10 ml) was stirred at room temperature for 16 hours, diluted with ethyl acetate (100 ml), and washed with brine (3×40 ml). The organic solution was dried over sodium sulfate and concentrated. The residue was purified using flash chromatography on silica gel using 0-5% methanol in dichloromethane as eluent to provide 15A as an orange solid (0.88 g, 62%). MS found 511.3 for $C_{29}H_{23}FN_4O_4$ Compound 25A (0.88 g, 1.72 mmol) was dissolved in a 4.0 M solution of HCl in 1,4-dioxane (30.0 ml, 120 mmol) in a 75 ml pressure vessel. The resulting solution was stirred at 90° C. for 18 hours before cooled to room temperature. The mixture was transferred to a 250 ml round-bottomed flask and concentrated in vacuo. The residue was washed with methanol (2×5 ml) and dried on house vacuum to provide 25B as a white solid (0.62 g, 73%). MS found 497.3 for $C_{28}H_{21}FN_4O_4H^+$.

To the stirring mixture of 25B (0.62 g, 1.25 mmol) in THF (12 ml) in a 100 ml round-bottomed flask was added with a solution of lithium hydroxide (5.0 ml of 1 M, 5.0 mmol). The resulting solution was maintained refluxing for 1 day before cooled to room temperature. After concentration in vacuo, the residue was dissolved in methanol (20 ml), neutralized with 1.0 M HCl aqueous solution (5 ml, 5.0 mmol) and then concentrated again. The residue was washed with water (2×50 ml) and dried on house vacuum to provide title compound 15 as a pale solid (0.55 g, 94%). MS found 469.3 for $C_{26}H_{17}FN_4O_4+H^+$. $^1$H NMR (DMSO-$d_6$) δ 8.20 (d, 1H, J=9.5 Hz), 8.01 (d, 1H, J=2.2 Hz), 7.80-7.76 (m, 1H), 7.71-7.67 (m, 2H), 7.57-7.40 (m, 3H), 7.13 (d, 1H, J=2.2 Hz), 6.40 (t, 1H, J=6.3 Hz), 6.31 (s, 2H), 5.84 (s, 1H).

Example 26

Preparation of Compound 39

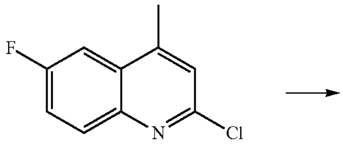

26A

-continued

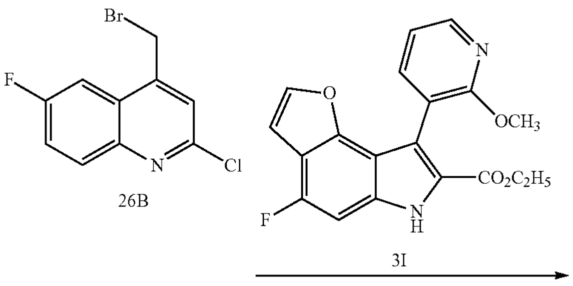

26B

3I

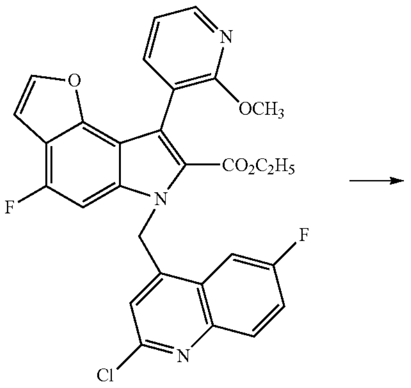

26C

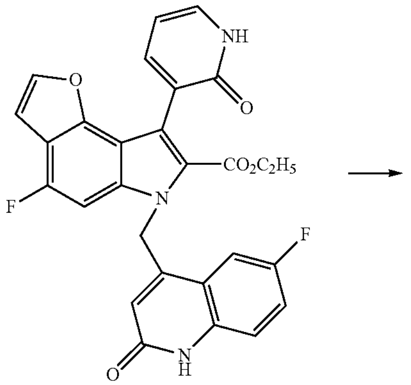

26D

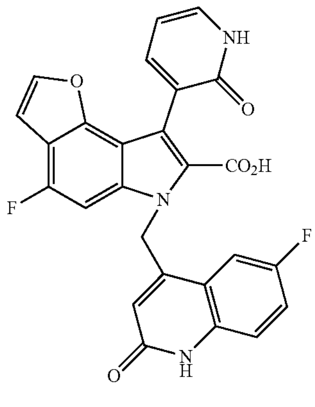

39

Compound 26A (3.0 g, 15.34 mmol), NBS (3.3 g, 18.54 mmol), and benzoyl peroxide (0.34 g, 1.4 mmol) were diluted with carbon tetrachloride (100 ml). The resulting mixture was refluxed for 15 hours before cooled to room temperature. After filtration, the filtrate was washed with saturated sodium carbonate solution, dried over sodium sulfate, and concentrated to deliver 26B as a gel (4.1 g). This material was used for the next step without further purification.

The suspension of 3I (270 mg, 0.76 mmol), crude 26B (1 g, ~2.5 mmol), cesium carbonate (0.5 g, 1.54 mmol) and DMF (3 ml) was stirred at room temperature for 16 hours, diluted with ethyl acetate (100 ml), and washed with brine (3×40 ml). The organic solution was dried over sodium sulfate and concentrated. The residue was purified using flash chromatography on silica gel using 0-20% ethyl acetate in hexanes as eluent to deliver 26C as solid (130 mg, 31%). MS found 548.3 for $C_{29}H_{20}ClF_2N_3O_4$+$H^+$.

The starting material 26C (130 mg, 0.237 mmol) was dissolved in a 4.0 M solution of HCl in 1,4-dioxane (10.0 ml, 40 mmol) in a 75 ml pressure vessel. The resulting solution was stirred at 90° C. for 17 hours before cooled to room temperature. The mixture was transferred to a 250 ml round-bottomed flask and concentrated in vacuo. The residue was washed with methanol (2×5 ml) and dried on house vacuum to provide 26D as a white solid (120 mg, 98%). MS found 516.3 for $C_{28}H_{19}F_2N_3O_5$+$H^+$.

To the stirring mixture of 261) (120 mg, 0.232 mmol) in THF (10 ml) in a 100 ml round-bottomed flask was added with a solution of lithium hydroxide (3.0 ml of 1 M, 3.0 mmol). The resulting solution was maintained refluxing for 19 hours before cooled to room temperature. After neutralization with 1.0 M HCl aqueous solution (3 ml, 3.0 mmol), the solution was concentrated in vacuo, washed with water (3×10 ml), and dried on house vacuum to provide 39 as a white solid (103 mg, 91%). MS found 488.3 for $C_{26}H_{15}F_2N_3O_5H$. $^1H$ NMR (CD3OD) δ 10.18-10.12 (m, 2H), 9.97 (d, 1H, J=2.2 Hz), 9.80-9.71 (m, 3H), 9.32 (d, 1H, J=10.4 Hz), 9.24 (d, 1H, J=2.2 Hz), 8.84 (t, 1H, J=6.6 Hz), 8.62 (s, 2H), 8.02 (s, 1H).

Example 27

Preparation of Compound 116

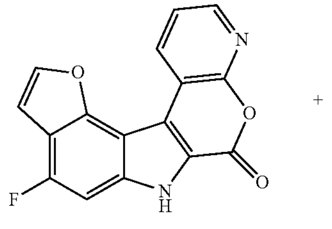

3L

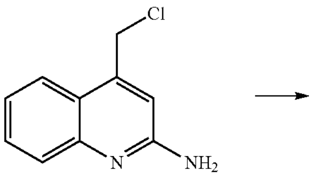

27A

-continued

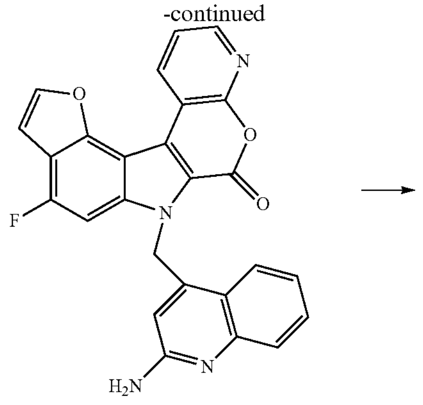

27B

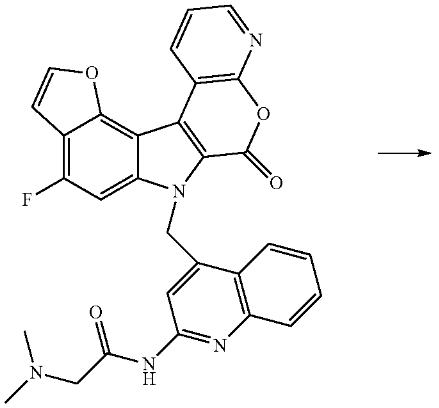

27C

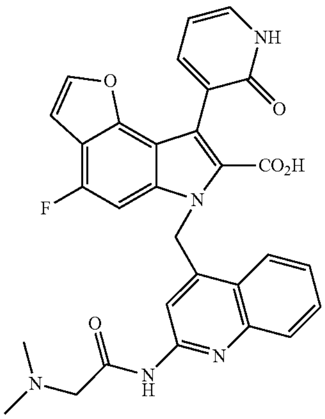

116

The suspension of 3L (305 mg, 1.04 mmol), 27A (300 mg, 1.57 mmol), cesium carbonate (1.97 g, 6.04 mmol) and DMF (5 ml) was stirred at room temperature for 20 hours. Water (10 mL) was added to the reaction mixture before filtration. The cake was washed with MeOH (2×1 ml), dried by air and then on house vacuum to provide 27B as a light yellow powder (280 mg, 60%). This crude product is pure enough for the next reaction without further purification.

A solution of 27B (40 mg, 0.089 mmol), dimethylaminoacetyl chloride hydrochloride (147 mg, 0.93 mmol) and triethylamine (0.26 ml, 1.87 mmol) in THF (5 ml) in a 25 ml round-bottomed flask was stirred at room temperature for 72 hours. After evaporating off the solvents, water (3 mL) was added to the flask before filtration. The cake was washed with MeOH (2×1 mL), dried by air and then on house vacuum to provide 27C as a yellow solid (36 mg, 75%). This crude product is pure enough for the next reaction without further purification.

To the stirring mixture of 27C (36 mg, 0.067 mmol) in THF (5 ml) in a 25 ml round-bottomed flask was added with a solution of lithium hydroxide (0.34 ml of 1 M, 0.34 mmol). The resulting solution was stirred at room temperature for 2 hours. Before concentration under vacuum, the reaction mixture was neutralized with 1.0 M HCl aqueous solution (0.34 ml, 0.34 mmol). Water (3 ml) was added to the flask before filtration. The cake was washed with MeOH (2×1 mL), dried by air and then on house vacuum to provide title compound 116 as a yellow solid (34 mg, 92%). MS found 554.3 for $C_{30}H_{24}FN_5O_5$+$H^+$.

Example 28

Preparation of Compound 87

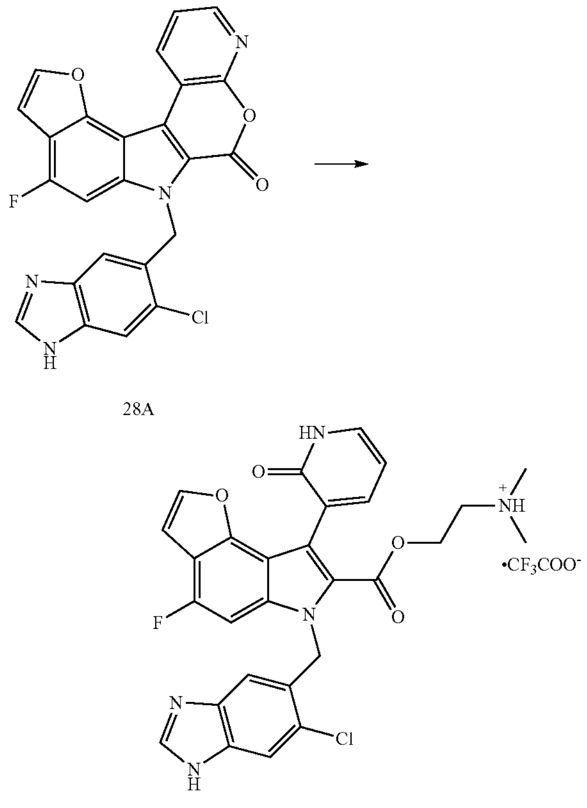

28A

87

A solution of N,N-dimethylaminoethanol (0.134 g, 1.50 mmol) in anhydrous tetrahydrofuran (10.00 mL, 49.3 mmol) was cooled to −20° C. and treated dropwise with n-butyl lithium in hexane (2.5 M solution, 0.500 mL) and stirred for 10 minutes. To this mixture was added a solution of 6-((5-chloro-1H-benzo[d]imidazol-6-yl)methyl)-4-fluorofuro[2,3-e]pyrido[3',2':5,6]pyrano[3,4-b]indol-7(6H)-one (28A, 0.115 g, 0.250 mmol) in THF (4.00 mL, 49.3 mmol) and stirred at room temperature for 1 h. The reaction mixture was quenched with trifluoroacetic acid (200 uL), concentrated in vacuo and the residue taken in DMF and purified using HPLC (C18-reverse phase) using following conditions: THF and water with 0.01% TFA to obtained 2-(dimethylamino)ethyl 6-((5-chloro-1H-benzo[d]imidazol-6-yl)methyl)-4-fluoro-8-(2-oxo-1,2-dihydropyridin-3-yl)-6H-furo[2,3-e]indole-7-carboxylate (Title compound 87) (52.00 mg; Yield=38.0%) as colorless solid. $^1$H NMR (500 MHz, $d_6$-DMSO), δ, 12.09 (s, 1H), 9.59 (s, 1H), 8.64 (s, 1H), 8.02 (d, 1H, J=2.0 Hz), 7.59 (dd, 1H, J=5.0 & 7.0 Hz), 7.91 (s, 2H), 7.58 (dd, 1H, & 6.0 Hz), 7.48 (d, 1H, J=11.0 Hz), 7.15 (d, 1H, J=2.0 Hz), 6.55 (s, 1H), 6.51 (t, 1H, J=7.0 Hz), 6.00 (s, 2H), 4.42-4.40 (m, 2 H), 3.29-3.27 (m, 2H), 2.74 (s, 6H).

Example 29

Preparation of Intermediate Compound 29G

Step A—Synthesis of Compound 29B

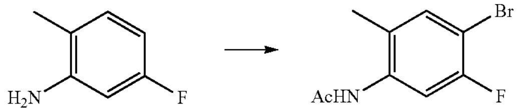

29A 29B

A solution of 5-fluoro-2-methylaniline (29A, 25 g, 200 mmol) in toluene (250 mL) was treated with acetic anhydride (25 mL, 226 mmol) heated at reflux for 1 hour. The reaction mixture was cooled when a colorless solid precipitated out which was filtered and washed with a mixture of ether and hexanes. The colorless solid was taken in acetic acid (150 mL) and treated dropwise with a solution of bromine (9.6 mL, 186 mmol) in acetic acid (20 mL) and stirred at room temperature for 12 hours. The solution was diluted with water and the solid separating out was filtered and washed to yield N-(4-bromo-5-fluoro-2-methylphenyl)acetamide (29B, 40 g) as a colorless solid.

Step B—Synthesis of Compound 29C

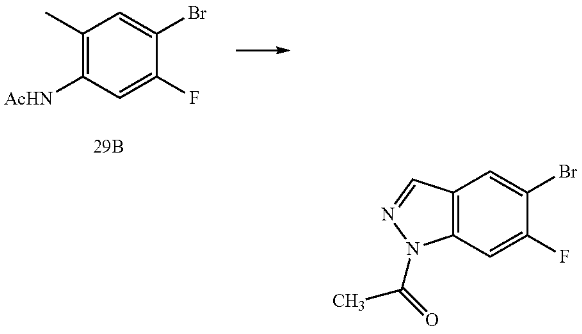

29B

29C

A solution of N-(4-bromo-5-fluoro-2-methylphenyl)acetamide (29B, 10.00 g, 40.64 mmol) in chloroform (100 mL) was treated with acetic anhydride (11.5 mL, 122.0 mmol), potassium acetate (8.00 g, 81.5 mmol), and 18-Crown-6 (540.00 mg, 2.0430 mmol) and then with isoamyl nitrite (12.3 mL, 871 mmol) and heated at 65° C. for 12 hours. The reaction mixture was cooled to room temperature and treated with EtOAc (500 mL), washed with water, dried ($MgSO_4$), filtered, and then concentrated in vacuo. A pale yellow solid of 1-(5-bromo-6-fluoro-1H-indazol-1-yl)ethanone (29C) precipitated out. The initial filtrate was concentrated and the residue was purified using chromatography ($SiO_2$, EtOAc/Hexanes) to yield more of product 29C.

Step C—Synthesis of Compound 290

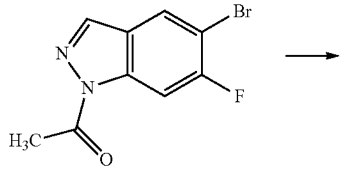

29C

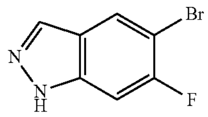

29D

A solution of 1-(5-bromo-6-fluoro-1H-indazol-1-yl)ethanone (29C, 5.0 g, 19.5 mmol) was treated with aq HCl (3M soln., 100 mL) and methanol (20 mL) and heated at 90° C. for 3 h, when the reaction turns homogenous. The reaction mixture was cooled to room temperature and basified with aq. NaOH. A colorless solid precipitated out which was filtered and dried to yield 5-bromo-6-fluoro-1H-indazole (29D)

Step D—Synthesis of Compound 29E

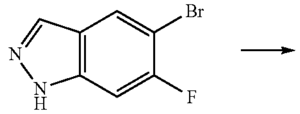

29D

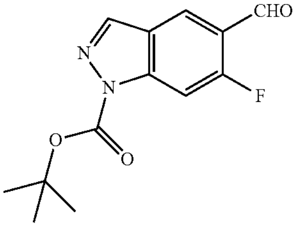

29E

A solution of 5-bromo-6-fluoro-1H-indazole (29D, 3.50 g, 16.28 mmol) in tetrahydrofuran (200.00 mL) was treated with sodium hydride (60% in mineral oil, 1.172 g) at 0° C. and stirred at room temperature for 20 minutes. The reaction mixture was cooled to −78° C. (dry ice and acetone) and treated with 2.5 M of n-butyl lithium in hexane (8.2 mL, 20.3 mmol) dropwise. The reaction mixture was stirred at that temperature for 20 minutes and treated with DMF (5.06 mL, 65.11 mmol). The reaction mixture was slowly warmed to room temperature when the viscous solution turn fluidic and stirring was efficient. Analysis of TLC (40% EtOAc/Hexanes) indicated complete conversion of starting material to product. The reaction mixture was acidified with aq. HCl taken up in EtOAc (500 mL) washed with aq. HCl (100 mL), brine (100 mL), dried ($MgSO_4$), filtered, concentrated in vacuo and used as it is in next step. A solution of product 6-fluoro-1H-indazole-5-carbaldehyde (2.3 g) in THF (100 mL) was treated with di-tort-butyldicarbonate (3.56 g, 16.28 mmol) and DMAP (300 mg) and stirred at room temperature for 3 hours. The reaction mixture was concentrated in vacuo and the residue was purified using chromatography ($SiO_2$, EtOAc/Hexanes gradient 0-40%) to yield [2e] tert-butyl 6-fluoro-5-formyl-1H-indazole-1-carboxylate (29E, 3.5 g; Yield=81%) as a colorless solid.

Step E—Synthesis of Compound 29F

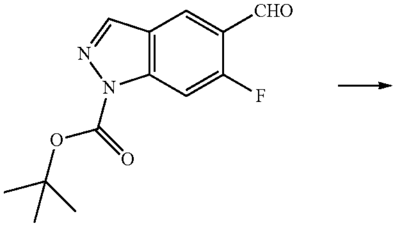

29E

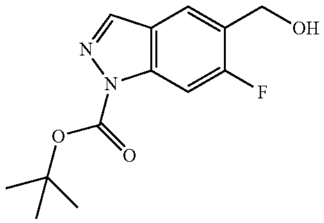

29F

A solution of tert-butyl 6-fluoro-5-formyl-1H-indazole-1-carboxylate (29E, 3.55 g, 13.4 mmol) in methanol (50.00 mL) was treated with $NaBH_4$ (1.02 g, 26.9 mmol) at 0° C. and stirred for 1 h. The reaction mixture was diluted with water and EtOAc (500 mL). The organic layer was separated and washed with aq. HCl (1M, 200 mL), aq. NaOH (1M, 200 mL) brine (200 mL) dried ($MgSO_4$), filtered, concentrated in vacuo and residue was purified using chromatography ($SiO_2$, EtOAc/hexanes) to yield tert-butyl 5-(hydroxymethyl)-6-fluoro-1H-indazole-1-carboxylate (29F, 3.00 g; Yield=83.9%) as a colorless solid.

Step F—Synthesis of Compound 29G

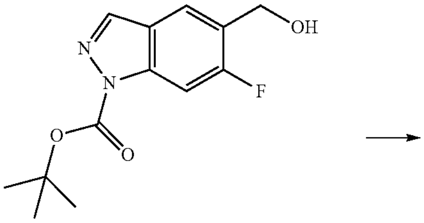

29F

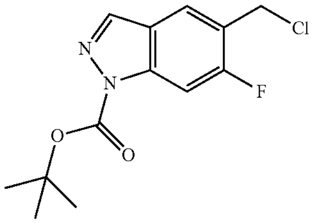

29G

A solution of tert-butyl 5-(hydroxymethyl)-6-fluoro-1H-indazole-1-carboxylate (29F, 3.0 g, 11.27 mmol) in methylene chloride (50.00 mL, 780.0 mmol) at room temperature was treated with pyridine (4.56 mL, 56.33 mmol) and methanesulfonyl chloride (1.31 mL) and stirred at room temperature for 16 hours. The reaction mixture was concentrated in vacuo and the residue was dissolved in EtOAc (300 mL) washed with aq HCl (100 mL), brine (100 mL), dried ($MgSO_4$), filtered, concentrated in vacuo, and purified using chromatography ($SiO_2$, EtOAc/Hexanes) to yield tert-butyl 5-(chloromethyl)-6-fluoro-1H-indazole-1-carboxylate (29G, 1.9 g; Yield=59%)

Example 30

Preparation of Compound 12

Step A—Synthesis of Compound 30A

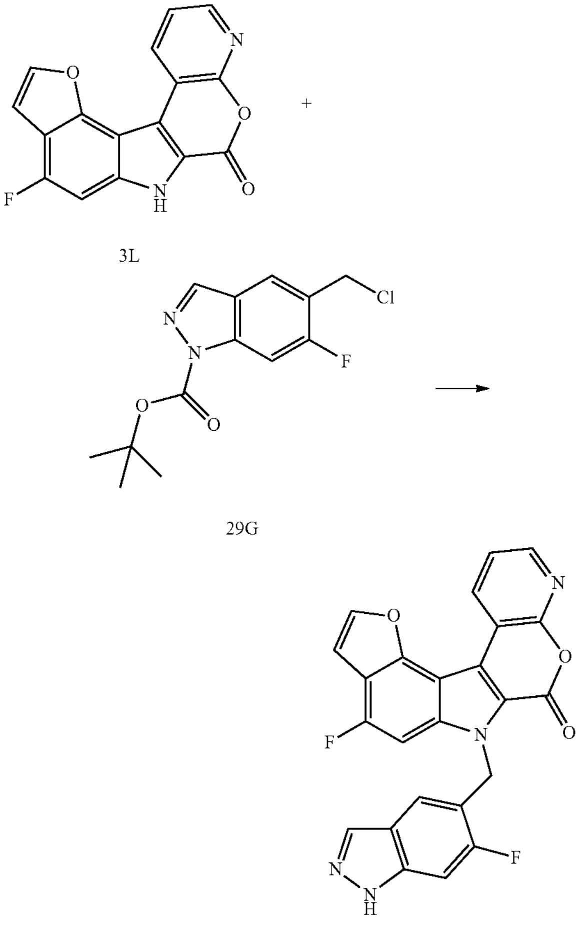

3L

29G

30A

A solution of 3L (900 mg, 106 mmol) in DMF (40.00 mL, 516.6 mmol) was treated with 29G (1.09 g, 3.84 mmol) and cesium carbonate (1.50 g, 4.59 mmol) and stirred at room temperature overnight. The reaction mixture was concentrated, diluted with $CH_2Cl_2$ (600 mL), washed with water, dried ($MgSO_4$), filtered, concentrated in vacuo and purified using chromatography (THF/Hexanes) to yield alkylated product (1.6 g; Yield=96%; The purified solid was dissolved in $CH_2Cl_2$ (40 mL) and TFA (40 mL) and stirred at room temperature for 1 hour. The reaction mixture was concentrated and treated with ether and the resulting solid 30A was filtered and dried.

Step B—Synthesis of Compound 12

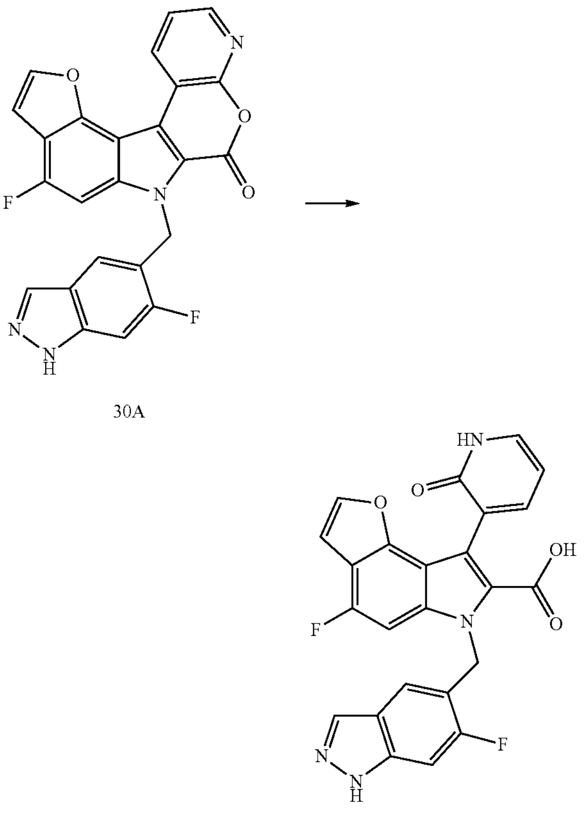

30A

12

A suspension of 30A (900 mg, 2.04 mmol) in THF (40 mL, 493 mmol) and water (40 mL,) was treated with lithium hydroxide monohydrate (427 mg, 10.2 mmol) and stirred at room temperature for 3.5 h when the reaction mixture turns clear. The reaction mixture was acidified with aq HCl and concentrated in vacuo. The solid separating out was filtered and purified using HPLC (reverse phase, $C_{18}$ column, Water/THF) to yield title compound 12. $^1H$ NMR (500 MHz, $D_6$-dmso), δ, 13.11 (s, 1 H), 12.96 (s, 1 H), 11.77 (s, 1 H), 7.96 (s, 1 H), 7.94 (d, 1 H, J=2.0 Hz), 7.69 (dd, 1 H, J=1.6 & 7.0 Hz), 7.50 (d, 1 H, J=11.0 Hz), 7.43 (d, 1 H, J=6.5 Hz), 7.39 (d, 1H, 11.0 Hz), 7.09 (d, 1H, J=2.0 Hz), 7.04 (d, 1 H, J=7.5 Hz), 6.35 (t, 1 H, J=7.0 Hz), 6.00 (s, 2 H).

Example 31

Preparation of Intermediate Compound 31C

Step A—Synthesis of Compound 31A

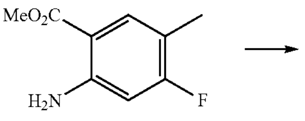

5D

-continued

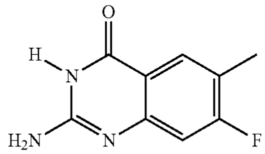

31A

A solid mixture of 5D (2.66 g, 14.5 mmol), chloroformamidinium hydrochloride (2.6 g, 22.6 mmol) and methyl sulfone (8.5 g, 90.3 mmol) was heated to 150-160° C. in an oil bath with vigorous stirring. It became a clear solution after about 10 minutes. Heating was continued for a total of 2 hours. When cooled to room temperature, it became a solid. The material was taken up with water (200 mL), basified with commercial ammonium hydroxide. After stirred for 1 hour, the solid was collected through filtration. It was washed with water (20 mL) and concentrated in vacuo to provide crude product 31A (2.93 g, quant.). MS found for $C_9H_8FN_3O$: 194.2 $(M+H)^+$.

Step B—Synthesis of Compound 31B

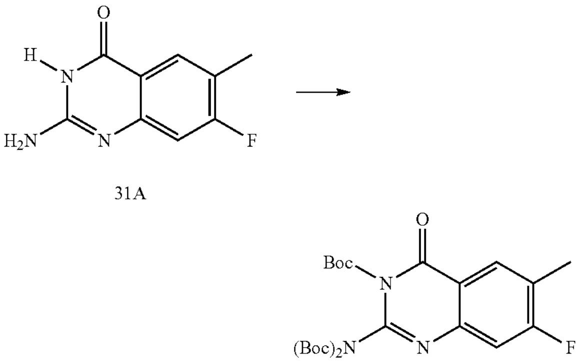

31A

31B

Compound 31B was prepared from 31A according the procedures described above for the preparation of compound 5F, and using 4 equivalents of $(Boc)_2O$. MS found for $C_{24}H_{32}FN_3O_7$: 394.3 $(M+H-100)^+$.

Step C—Synthesis of Compound 31C

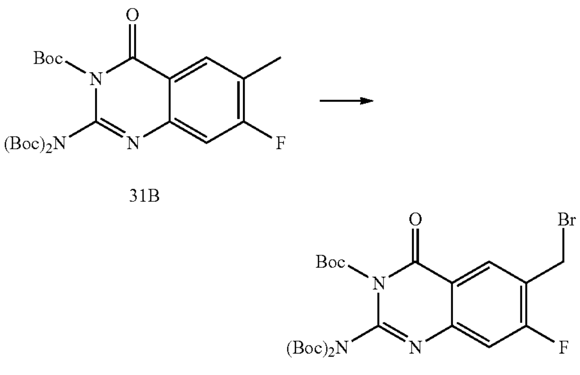

31B

31C

A solution of compound 318 (4.83 g, 9.8 mmol), N-bromosuccinimide (2.70 g, 15.2 mmol) and benzoyl peroxide (600 mg, 2.48 mmol) in carbon tetrachloride (300 mL) was heated to reflux and allowed to stir at this temperature for 18 hours. The reaction mixture was cooled to room temperature, concentrated in vacuo and the residue obtained was dissolved in EtOAc (300 mL). The resulting solution was washed with aqueous sodium thiosulfate (100 mL), brine (100 mL), dried ($MgSO_4$), filtered, and concentrated in vacuo to provide intermediate compound 31C, which was used without further purification. MS found for $C_{24}H_{31}BrFN_3O_7$: 472.3 $(M+H-100)^+$.

Example 32

Preparation of Intermediate Compound 32C

Step A—Synthesis of Compound 32A

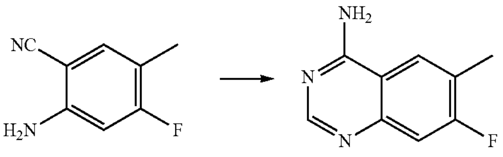

5C

32A

A solution of 5C (0.20 g, 1.33 mmol) in formamide (15 mL) was heated to 150° C. and stirred for 18 hours. After cooled to room temperature, ethyl acetate (60 mL) and water (30 mL) were added and the layers were separated. The organic solution was washed with water (3×20 mL), dried ($MgSO_4$), filtered, and concentrated in vacuo to provide the crude product 32A (0.22 g, 93%). MS found for $C_9H_8FN_3$: 178.2 $(M+H)^+$.

Step B—Synthesis of Compound 32B

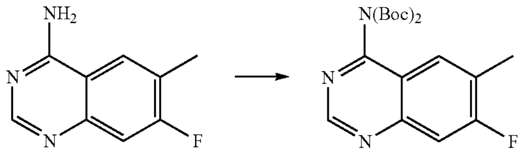

32A

32B

Compound 32B was prepared from 32A according the procedures described above for the preparation of compound 5F, except that 3.0 equivalent of $(Boc)_2O$ was used in this reaction. MS found for $C_{19}H_{24}FN_3O_4$: 378.4 $(M+H)^+$.

Step C—Synthesis of Compound 32C

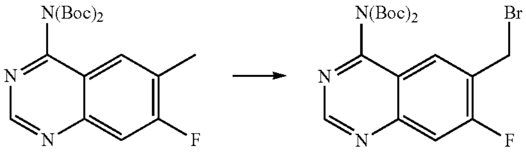

32B

32C

Compound 32C was prepared from 32B according the procedures described above for the preparation of compound 5G. MS found for $C_{19}H_{23}BrFN_3O_4$: 458.3 $(M+H)^+$.

Example 33

Preparation of Intermediate Compound 33D

33D

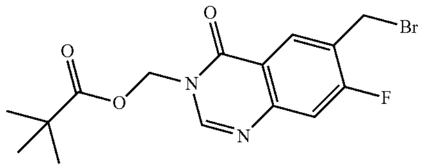

Step A—Synthesis of Compound 33B

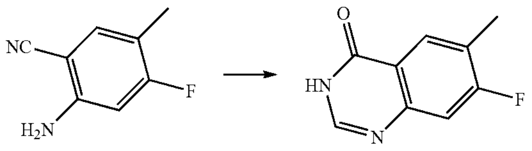

33A 33B

To a suspension of compound 33A (3.4 g, 22.7 mmol) in 98% formic acid (60 mL) was slowly added fuming sulfuric acid slowly (1 mL) and the resulting mixture was heated to reflux and allowed to stir at this temperature for 5 hours. The reaction mixture was cooled to room temperature then concentrated in vacuo and the residue obtained was diluted with EtOAc (300 mL) and water (300 mL). The layers were separated, and the aqueous solution was basified to pH 10 using with aqueous ammonium hydroxide solution. The basic solution was extracted with ethyl acetate (2×200 mL) and the combined organic extracts were washed with saturated aqueous sodium bicarbonate solution (2×400 mL), dried over magnesium sulfate, filtered and concentrated in vacuo to provide the compound 33B (3.17 g, 78%), which was used without further purification.

Step B—Synthesis of Compound 33C

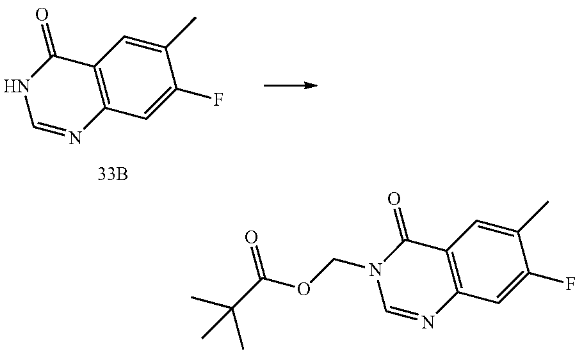

33B

33C

A suspension of compound 33B (1.34 g, 7.52 mmol), chloromethyl pivalate (1.65 mL, 11.4 mmol) and anhydrous cesium carbonate (4.8 g, 14.8 mmol) in anhydrous DMF (60 mL) was allowed to stir at room temperature for 18 hours. The reaction mixture was then diluted with EtOAc and water (150 mL each) and the layers were separated. The aqueous phase was extracted with ethyl acetate (2×100 mL) and the combined organic extracts were washed with water (2×300 mL), dried over magnesium sulfate, filtered and concentrated in vacuo to provide a crude residue which was purified using flash column chromatography on silica gel (0-60% ethyl acetate/hexanes) to provide compound 33C (1.67 g, 76%).

Step C—Synthesis of Compound 33D

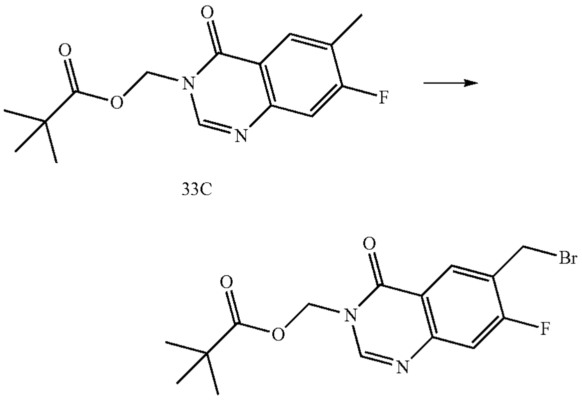

33C

33D

A solution of compound 33C (1.65 g, 5.64 mmol), N-bromosuccinimide (1.41 g, 7.92 mmol) and benzoyl peroxide (410 mg, 1.69 mmol) in anhydrous carbon tetrachloride (150 mL) was heated to 85° C. and allowed to stir at this temperature for 8 hours. The reaction mixture was allowed to cool to room temperature and was concentrated in vacuo to provide a crude residue which was dissolved in ethyl acetate (200 mL). To the resulting solution was added water (200 mL) and the mixture was transferred to a separatory funnel. The organic phase was collected and washed with water (2×150 mL), dried over $MgSO_4$ and concentrated in vacuo. The residue obtained was purified using flash chromatography (0-60% ethyl acetate/hexanes) to provide compound 330 (1.77 g, 85%).

Example 34

Preparation of Intermediate Compound 89

89

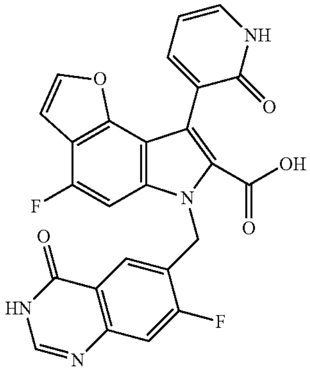

Step A—Synthesis of Compound 34A

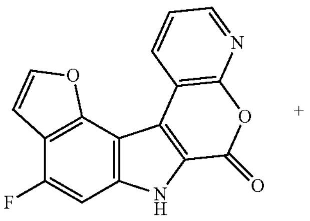

3L

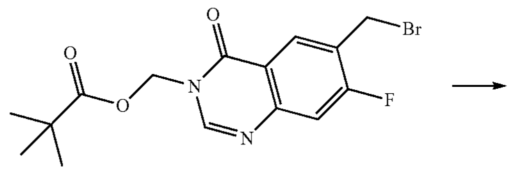

33D

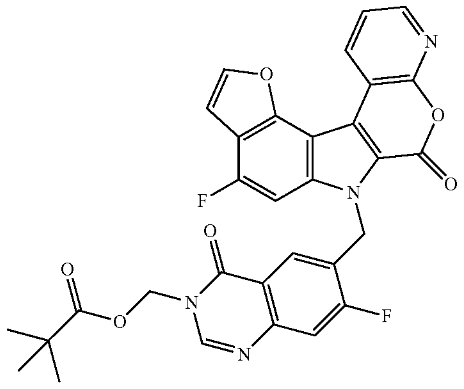

34A

To a solution of compound 3L (6.0 g, 20.4 mmol) and compound 33D (7.95 g, 21.1 mmol) in DMF (500 mL) was added cesium carbonate (14.0 g, 43.0 mmol). The resulting reaction was allowed to stir at room temperature for 19 hours, then was diluted with ethyl acetate (200 mL) and water (200 mL). A precipitate formed and the mixture was filtered through a fritted funnel and the reaction flask was rinsed with additional EtOAc and water (1:1, total 600 mL), which was then also filtered. The filter cake was washed with EtOAc (200 mL) and water (150 mL) and dried under vacuum to provide a tan solid. The collected filtrate was separated and the aqueous layer was extracted with EtOAc (2×500 mL). The combined organic extracts were washed with water (3×1.0 L), dried ($MgSO_4$), filtered and concentrated in vacuo to provide a yellow solid residue. The yellow residue and the tan solid filter cake were combined to provide compound 34A (12.1 g, quantitative), which was used in the next step without further purification. MS found for $C_{29}H_{23}F_2N_5O_5$: 585.5 $(M+H)^+$.

Step B—Synthesis of Compound 34B

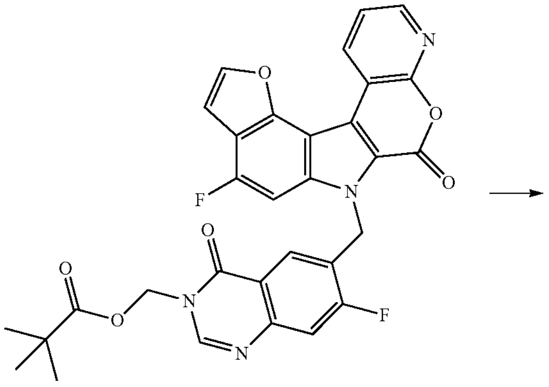

34A

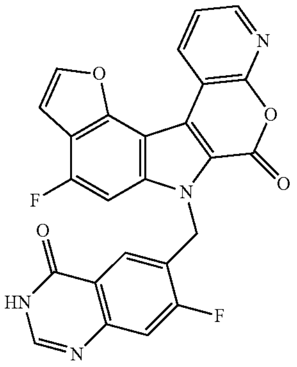

34B

A solution of compound 34A (11.6 g, 19.8 mmol) in a mixture of 4 M HCl in 1,4-dioxane and water (600 mL, 3:1 ratio, pre-mixed and cooled) was heated to 85° C. and allowed to stir at this temperature for 3 hours. During the progress of the reaction, the reaction mixture turned from a suspension to a clear solution in about 5 minutes, then over the 3 hour reaction period, a large amount of white solid precipitate formed. The reaction mixture was cooled to room temperature and the resulting suspension was filtered through filter paper. The collected solid was washed with EtOAc, then water, and dried in vacuo to provide compound 34B (8.99 g, 97%), which was used without further purification.

Step C—Synthesis of Compound 34C

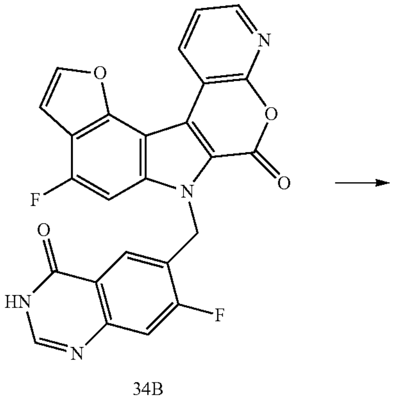

34B

-continued

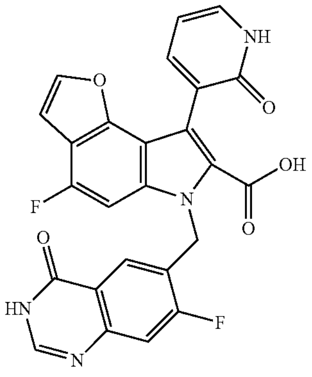

34C

To a solution compound 34B (3.50 g, 7.44 mmol) in THF (100 mL) and water (100 mL) was added aqueous LiOH solution (22.0 mL, 1.0 M, 22.0 mmol). The resulting reaction was allowed to stir at room temperature for 3 hours, then was acidified to pH 5-6 using 1 N aqueous HCl solution (25 mL). The acidic solution was extracted with ethyl acetate (3×150 mL) and the combined organic extracts were dried over magnesium sulfate, filtered and concentrated in vacuo to provide a crude residue which was purified using reverse-phase HPLC (10-100% acetonitrile/water (with 0.1% trifluoroacetic acid)) to provide compound 34C (3.60 g, 99%). $^1$H NMR (500 MHz, $d_6$-DMSO): δ 13.0 (bs, 1H), 12.3 (bs, 1 H), 11.8 (bs, 1 H), 8.08 (s, 1 H), 7.96 (s, 1 H), 7.68-7.66 (m, 1 H), 7.53 (dd, J4.0, 11.0 Hz, 2 H), 7.42-7.41 (m, 2 H), 7.10 (s, 1 H), 6.34 (t, J=6.8 Hz, 1 H), 6.01 (s, 2 H). MS found for $C_{25}H_{14}F_2N_4O_5$: 489.0 $(M+H)^+$.

Step D—Synthesis of Compound 89

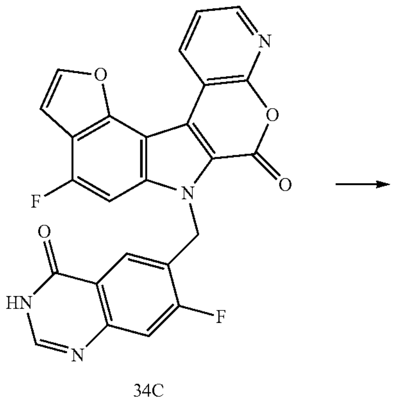

34C

-continued

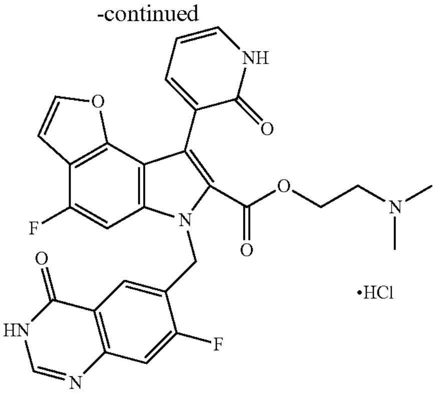

89

A solution of N,N-dimethylethanolamine (5.80 mL, 57.7 mmol) in 300 mL THF in a flame-dried flask was cooled to at −30° C. and n-BuLi (1.6 M, 31.0 mL, 49.6 mmol) was added. The resulting reaction was allowed to stir for 10 minutes, then compound 34C (4.50 g, 9.57 mmol) was added as a solid powder to the cold reaction mixture in one portion. The resulting suspension was allowed to stir at −30° C. for 20 minutes, then the cooling bath was removed and the reaction mixture was allowed to warm to room temperature on its own and stir at this temperature for an additional 1 hour. The reaction mixture was then cooled to 0° C. and HCl (4 M solution in dioxane, 30 mL) was added in one portion and a precipitate formed. The resulting solution was allowed to rest until the solid material settled at the bottom of the flask and the upper, clear solution was removed via pipette. The remaining solid material was triturated with water at a ratio of 4 mL/g to provide a white suspension, which was filtered through filter paper. The collected white solid material (3.5 g, 65%) was then purified via one of two separate methods. The first method uses reverse-phase HPLC (C-18 column, 10-100% acetonitrile/water/0.1% trifluoroacetic acid) wherein two molar equivalents of 1 N aqueous HCl solution were added to the combined HPLC fractions containing compound 89 prior to concentration to provide compound 89 as its hydrochloride salt. In the second purification method, the product is recrystallized from acetone/water (1:1, containing 2 molar equivalent of aqueous 1N HCl) to provide compound 89 as its hydrochloride salt. Compound 89 must be prepared as its HCl salt to prevent conversion back to compound 34C.

Example 35

Spectroscopic Data for Illustrative Tricyclic Indole Derivatives

Mass spectrometry and $^1$H NMR data was obtained for illustrative compounds of the present invention, using the instrumentation described above in the General Methods section. Data is presented in the tables below. Compound numbering refers to the compound numbering indicated in the above specification

| No. | LR-MS (M + H) | $^1$H NMR |
|---|---|---|
| 1 | 443.28 | 1H-NMR (dmso-d6; 400 MHz): δ 12.90 (2H, broad s), 11.74 (1H, broad s), 7.98 (1H, s), 7.91 (1H, d, J = 2.44 Hz), 7.67 (1H, d, J = 8.54 Hz), 7.65 (1H, dd, J = 1.83, 6.71 Hz), 7.47 (1H, d, J = 10.98 Hz), 7.40 (1H, dd, J = 1.83, 6.71 Hz), 7.10 (1H, s), 7.05 (1H, d, J = 2.44 Hz), 6.95 (1H, dd, J = 1.22, 8.54 Hz), 6.32 (1H, dd, J = 6.10, 6.71 Hz), 6.00 (2H, s). LR-MS (ESI): calcd for C24H16FN4O4 [M + H] + 443.12; found 443.28 |

-continued

| No. | LR-MS (M + H) | $^1$H NMR |
|---|---|---|
| 2 | 443.41 | 1H NMR (500 MHz, D6-dmso), δ 12.98 (s, 1 H), 11.78 (s, 1 H), 11.72 (s, 1 H), 8.04 (d, 1 H, J = 8.0 Hz), 7.89 (d, 1 H, J = 2.5 Hz), 7.75 (dd, 1 H, J = 2.0 & 6.5 Hz), 7.61 (bt, 1 H, J = 7.0 Hz), 7.58 (d, 1 H, J = 9.0 Hz), 7.46-7.43 (m, 2 H), 739 (d, 1 H, J = 8.5 Hz), 7.33 (t, 1 H, J = 8.0 Hz), 7.01 (d, 1 H, J = 2.0 Hz), 6.38 (t, 1 H, J = 6.5 Hz), 6.20 (s, 2 H), 5.14 (s, 1 H |
| 3 | 444.39 | NA |
| 4 | 444.39 | NA |
| 5 | 450.42 | 1H NMR (400 MHz, D6-dmso, HCl salt), δ 11.77 (s, 1 H), 8.22 (s, 3 H), 7.92 (d, 1 H, J = 2.4 Hz), 7.65 (dd, 1 H, J = 1.6 & 6.4 Hz), 7.45-7.39 (m, 3 H), 7.30 (t, 1 H, J = 8.8 Hz), 7.07 (dd, 1 H, J = 0.4 & 2.4 Hz), 6.80 (dd, 1 H, J = 2.0 & 7.2 Hz), 6.33 (t, 1 H, J = 6.8 Hz), 5.92 (s, 2 H), 3.82 (q, 2 H, J = 5.6 Hz |
| 6 | 452.35 | 1H-NMR (400 MHz, in dmso-d6): δ 11.72 (1H, broad s), 7.90 (1H, d, J = 2.20 Hz), 7.86 (1H, s), 7.64 (1H, d, J = 10.98 Hz), 7.60 (1H, dd, J = 2.20, 7.32 Hz), 7.52 (1H, d, J = 3.66 Hz), 7.39 (1H, d, J = 4.39 Hz), 7.29 (1H, s), 7.08 (1H, d, J = 3.66 Hz), 7.06 (1H, d, J = 2.20 Hz), 6.30 (1H, t = 6.59 Hz), 6.02 (2H, s); LR-MS (ESI): calcd. for C22H15FN3O5S [M + H] + 452.07, found 452.35 |
| 7 | 453.45 | NA |
| 8 | 454.43 | NA |
| 9 | 458.42 | 1H NMR (400 MHz, D6-dmso), δ 12.84 (s, 1 H), 11.75 (s, 1 H), 11.44 (s, 1 H), 7.82 (d, 1 H, J = 2.4 Hz), 7.69 (dd, 1 H, J = 2.0 & 6.4 Hz), 7.52 & 7.45 (AB, 2 H, J = 8.8 Hz), 7.40 (dd, 1 H, J = 1.6 & 6.4 Hz), 7.14 (d, 1 H, J = 7.2 Hz), 7.00 (d, 1 H, J = 11.2 Hz), 6.95 (d, 1 H, J = 2.4 Hz), 6.34 (t, 1 H, J = 6.8 Hz), 5.92 (s, 2 H), 5.32 (bs, 2 H). |
| 10 | 459.25 | 1H-NMR (dmso-d6; 400 MHz): δ 12.96 (2H, broad s), 11.75 (1H, broad s), 7.93 (2H, m), 7.74 (1H, d, J = 5.49 Hz), 7.67 (1H, dd, J = 1.83, 6.71 Hz), 7.59 (1H, s), 7.50 (1H, d, J = 10.98 Hz), 7.42 (1H, dd, J = 1.83, 6.71 Hz), 7.38 (1H, d, J = 5.49 Hz), 7.15 (1H, d, J = 8.54 Hz), 7.07 (1H, d, J = 2.44 Hz), 6.34 (1H, dd, J = 6.10, 6.71 Hz), 6.00 (2H, s), LR-MS (ESI): caldc for C25H16FN2O4S [M + H] + 459.08; found 459.25 |
| 11 | 459.86 | NA |
| 12 | 461.40 | 1H NMR (500 MHz, D6-dmso), δ 13.11 (s, 1 H), 12.96 (s, 1 H), 11.77 (s, 1 H), 7.96 (s, 1 H), 7.94 (d, 1 H, J = 2.0 Hz), 7.69 (dd, 1 H, J = 1.6 & 7.0 Hz), 7.50 (d, 1 H, J = 11.0 Hz), 7.43 (d, 1 H, J = 6.5 Hz), 7.39 (d, 1H, J = 11.0 Hz), 7.09 (d, 1H, J = 2.0 Hz), 7.04 (d, 1 H, J = 7.5 Hz), 6.35 (t, 1 H, J = 7.0 Hz), 6.00 (s, 2 H). |
| 13 | 461.30 | 1H-NMR (400 MHz, in dmso-d6): δ 11.66 (1H, Broad s), 8.80 (1H, s), 7.91 (1H, s), 7.52 (1H, dd, J = 1.95, 6.84 Hz), 7.35 (1H, dd, J = 1.95, 6.35 Hz), 7.13 (1H, d, J = 8.3 Hz), 6.85 (1H, d, J = 8.79 Hz), 6.51 (1H, s), 6.29 (1H, dd, J = 6.35, 6.84 Hz), 5.90 (2H, s), 4.56 (2H, t, J = 8.79 Hz), 3.16 (2H, t, J = 8.79 Hz); LR-MS (ESI): calcd. for C24H18ClN4O4 [M + H] + 461.10, found 461.30 |
| 14 | 463.42 | NA |
| 15 | 469.3 | $^1$H NMR (DMSO-d6) δ 8.20 (d, 1H, J = 9.5 Hz), 8.01 (d, 1H, J = 2.2 Hz), 7.80-7.76 (m, 1H), 7.71-7.67 (m, 2H), 7.57-7.40 (m, 3H), 7.13 (d, 1H, J = 2.2 Hz), 6.40 (t, 1H, J = 6.3 Hz), 6.31 (s, 2H), 5.84 (s, 1H). |
| 16 | 470.43 | NA |
| 17 | 470.44 | NA |
| 18 | 470.36 | 1H-NMR (400 MHz, in dmso-d6): δ 12.76 (1H, broad s), 11.76 (1H, broad s), 8.37 (1H, d, J = 8.30 Hz), 7.92 (1H, d, J = 2.44 Hz), 7.92 (1H, m), 7.65 (1H, dd, J = 2.44, 6.84 Hz), 7.61 (1H, d, J = 8.30 Hz), 7.52 (1H, d, J = 11.23 Hz), 7.52 (1H, m), 7.42 (1H, dd, J = 1.47, 6.35 Hz), 7.07 (1H, d, J = 2.44 Hz), 6.45 (2H, s), 6.34 (1H, dd, J = 6.35, 6.84 Hz); LR-MS (ESI): calcd. for C25H17FN5O4 [M + H] + 470.13, found 470.36 |
| 19 | 471.42 | NA |
| 20 | 471.46 | NA |
| 21 | 472.42 | NA |
| 22 | 472.95 | 1H-NMR (dmso-d6; 400 MHz): δ 12.84 (1H, broad s), 11.69 (2H, broad s), 7.95 (1H, d, J = 7.93 Hz), 7.58 (1H, dd, J = 7.32, 7.93 Hz), 7.52 (1H, dd, J = 1.83, 6.71 Hz), 7.36 (2H, m), 7.29 (1H, dd, J = 7.32, 7.93 Hz), 6.94 (1H, d, J = 9.76 Hz), 6.28 (1H, t, J = 6.71 Hz), 6.03 (2H, s), 5.10 (1H, s), 4.66 (2H, dd, J = 8.54, 9.15 Hz), 3.22 (2H, dd, J = 8.54, 9.15 Hz). LR-MS (ESI): caldc for C26H19FN3O5 [M + H] + 472.13; found 471.95 |
| 23 | 473.44 | 1H-NMR (dmso-d6; 400 MHz): δ 12.95 (1H, broad s), 12.31 (1H, d, J = 3.05 Hz), 11.67 (1H, broad s), 8.08 (1H, d, J = 3.66 Hz), 7.51 (1H, d, J = 11.59 Hz), 7.49 (1H, dd, J = 2.44, 7.32 Hz), 7.41 (1H, d, J = 7.93 Hz), 7.35 (1H, d, J = 6.10 Hz), 7.18 (1H, d, J = 8.54 Hz), 7.02 (1H, d, J = 8.54 Hz), 6.28 (1H, t, J = 6.71 Hz), 5.89 (2H, s), 4.56 (2H, t, J = 8.54 Hz), 3.18 (2H, t, J = 8.54 Hz) |
| 24 | 475.27 | 1H-NMR (dmso-d6; 400 MHz): δ 12.90 (1H, broad s), 11.75 (1H, broad s), 7.91 (1H, d, J = 2.44 Hz), 7.89 (1H, s), 7.80 (1H, d, J = 8.54 Hz), 7.66 (1H, dd, J = 2.44, 6.71 Hz), 7.46 (1H, d, J = 10.98 Hz), 7.40 (1H, dd, J = 1.83, 6.71 Hz), 7.10 (1H, d, J = 8.54 Hz), 7.06 (1H, d, J = 2.44 Hz), 6.73 (2H, broad s), 6.32 (1H, t, J = 6.71 Hz), 5.96 (2H, s). LR-MS (ESI): caldc for C24H16FN4O4S [M + H] + 475.09; found 475.27 |

-continued

| No. | LR-MS (M + H) | $^1$H NMR |
|---|---|---|
| 25 | 475.47 | NA |
| 26 | 476.42 | 1H NMR (500 MHz, D6-dmso), δ 13.01 (s, 1H), 11.79 (s, 1 H), 11.24 (s, 1 H), 7.94(d, 1 H, J = 2.0 Hz), 7.67 (dd, 1 H, J = 2 & 7.0 Hz), 7.50 (d, 1 H, J = 11.0 Hz), 7.45 (d, 1 H, J =10.5 Hz), 7.44-7.42 (m, 1 H), 7.08 (d, 1 H, J = 2.0 Hz), 6.34 (dd, 2 H, J = 6.5 & 10.5 Hz), 5.98 (s, 2 H), 5.39 (b, 2 H). |
| 27 | 477.40 | NA |
| 28 | 477.34 | 1H-NMR (400 MHz, in dmso-d6): δ 12.84 (1H, Broad s), 11.64 (1H, Broad s), 7.89 (1H, s), 7.79 (1H, d, J = 8.3 Hz), 7.46 (1H, dd, J = 1.95, 6.84 Hz), 7.33 (1H, dd, J = 1.95, 6.35 Hz), 7.06 (1H, dd, J = 0.98, 8.3 Hz), 6.94 (1H, d, J = 10.25 Hz), 6.74 (2H, broad s), 6.25 (1H, dd, J = 6.84, 6.84 Hz), 5.81 (2H, s), 4.61 (2H, t, J = 8.79 Hz), 3.18, (2H, t, J = 8.79 Hz); LR-MS (ESI): calcd. for C24H18FN4O4S [M + H] + 477.10, found 477.34 |
| 29 | 477.85 | NA |
| 30 | 478.43 | 1H NMR (500 MHz, D6-dmso), δ, 12.86 (s, 1 H), 11.70 (s, 1 H), 7.50 (dd, 1 H, J = 2.0 & 6.5 Hz), 7.35 (dd, 1 H, J = 2.0 & 6.5 Hz), 7.15 (d, 1 H, J = 7.5 Hz), 7.03 (d, 1 H, J = 11.0 Hz), 6.90 (d, 1 H, J = 10.0 Hz), 6.27 (t, 1 H, J = 6.5 Hz), 5.77 (s, 2 H), 4.62 (t, 2 H, J = 9.0 Hz), 3.20 (t, 2 H, J = 9.0 Hz); 13C NMR (125 MHz, D6-dmso), d, 162.5, 161.5, 160.7, 158.8, 158.4, 156.5, 155.0, 154.9, 148.4, 140.6, 140.6, 140.5, 139.3, 139.2, 133.7, 127.2, 127.2, 125.7, 119.6, 119.6. 116.4, 116.3, 115.7, 110.4, 109.0, 105.0, 104.8, 104.8, 95.1, 94.8, 88.9, 88.7, 72.7, 42.8, 42.8, 25.8, |
| 31 | 478.43 | 1H NMR (400 MHz, D6-dmso), d, 13.06 (s, 1 H), 11.67 (s, 1 H), 11.29 (s, 1 H), 7.49-7.45 (m, 2 H), 7.33 (dd, 1 H, J = 2.0 & 6.8 Hz), 6.90 (d, 1 H, J = 10.0 Hz), 6.31 (d, 1 H, J = 6.0 Hz), 6.26 (t, 1 H, J = 6.4 Hz), 5.82 (s, 2 H), 4.63 (t, 2 H), 3.19 (t, 2 H). |
| 32 | 479.87 | NA |
| 33 | 481.84 | NA |
| 34 | 482.42 | NA |
| 35 | 483.48 | NA |
| 36 | 484.46 | NA |
| 37 | 487.42 | NA |
| 38 | 488.42 | NA |
| 39 | 488.3 | $^1$H NMR (CD3OD) δ 10.18-10.12 (m, 2H), 9.97 (d, 1H, J = 2.2 Hz), 9.80-9.71 (m, 3H), 9.32 (d, 1H, J = 10.4 Hz), 9.24 (d, 1H, J = 2.2 Hz), 8.84 (t, 1H, J = 6.6 Hz), 8.62 (s, 2H), 8.02 (s, 1H). |
| 40 | 488.42 | NA |
| 41 | 488.42 | 1H-NMR (400 MHz, in dmso-d6): δ 11.74 (1H, broad s), 8.44 (1H, dd, J = 5.86, 8.79 Hz), 7.92 (1H, d, J = 1.95 Hz), 7.78 (2H, broad s), 7.65 (1H, dd, J = 1.95, 6.84 Hz), 7.51 (1H, d, J= 11.23 Hz), 7.42 (1H, dd, J = 1.95, 6.35 Hz), 7.37 (1H, ddd, J = 1.95, 8.79, 9.28 Hz), 7.30 (1H, dd, J = 2.44, 10.25 Hz), 7.07 (1H, d, J = 1.95 Hz), 6.41 (2H, s), 6.33 (1H, dd, J = 6.84, 6.35 Hz); LR-MS (ESI): calcd. for C25H16F2N5O4 [M + H] + 488.12, found 488.42 |
| 42 | 488.88 | NA |
| 43 | 488.88 | NA |
| 44 | 489.45 | NA |
| 45 | 489.87 | $^1$H NMR (500 MHz, $d_6$-DMSO) δ 12.9 (s, 1H), 11.80 (s, 1H), 9.06 (m, 1H), 8.36 (d, J = 8.2 Hz, 1H), 7.99 (s, 1H), 7.73 (d, J = 6.6 Hz, 1H), 7.61 (s, 1H), 7.58 (s, 1H), 7.45 (d, J = 6.0 Hz, 1H), 7.33 (s, 1H), 7.12 (s, 1H), 6.37 (t, J = 6.6 Hz, 1H), 6.06 (s, 2H). |
| 46 | 490.44 | NA |
| 47 | 490.44 | 1H NMR (400 MHz, D6-dmso), δ 12.87 (s, 1 H), 11.76 (d, 1 H, J = 2.4 Hz), 7.92 ( d, 1 H, J = 2.4 Hz), 7.67 (dd, 1 H, J = 2.0 & 6.8 Hz), 7.43 (d, 1 H, J = 10.8 Hz), 7.43-7.42 (m, 1 H), 7.23 (d, 1 H, J = 11.6 Hz), 7.10 (d, 1 H, J = 7.2 Hz), 7.07 (d, 1 H, J = 2.0 Hz), 6.35 (t, 1 H, J = 6.4 Hz), 5.91 (s, 2 H), 5.57 (bs, 2 H), 3.65 (s, 3H). |
| 48 | 491.43 | $^1$H NMR (400 MHz, $d_6$-DMSO): δ 12.3 (bs, 1 H), 11.7 (bs, 1 H), 8.09 (s, 1 H), 7.51 (d, J = 11.2 Hz, 1H), 7.47 (d, J = 5.6 Hz, 1 H), 7.35 (d, J = 5.2 Hz, 1 H), 7.00 (d, J = 10.0 Hz, 1 H), 6.27 (t, J = 6.6 Hz, 1 H), 5.87 (s, 2 H), 4.65 (t, J = 8.6 Hz, 2 H), 3.22 (t, J = 8.6 Hz, 2 H). MS found for $C_{25}H_{16}F_2N_4O_5$: 491.0 $(M + H)^+$. |
| 49 | 492.48 | NA |
| 50 | 497.50 | NA |
| 51 | 500.91 | NA |
| 52 | 503.44 | NA |
| 53 | 503.44 | NA |
| 54 | 504.43 | NA |
| 55 | 504.88 | $^1$H NMR (500 MHz, DMSO): δ 10.41 (s, 1H), 7.97 (m, 1H), 7.74 (m, 1H), 7.62 (d, J = 9.1 Hz, 1H), 7.52 (d, J = 11.0 Hz, 1H), 7.44 (s, 1H), 7.16 (m, 1H), 7.11 (m, 1H), 7.08 (m, 1H), 7.05 (s, 1H), 6.36 (t, J = 6.9 Hz, 1H), 5.97(s, 2H). |
| 56 | 504.88 | NA |

-continued

| No. | LR-MS (M + H) | $^1$H NMR |
|---|---|---|
| 57 | 505.41 | $^1$H NMR (500 MHz, $d_6$-DMSO): δ 13.0 (bs, 1 H), 11.8 (bs, 1 H), 11.3 (bs, 1 H), 11.2 (bs, 1 H), 7.94 (d, J = 2.5 Hz, 1H), 7.64 (dd, J = 6.8, 1.8 Hz, 1 H), 7.49 (d, J = 11.0 Hz, 1 H), 7.42 (d, J = 5.0 Hz, 1 H), 7.33 (d, J = 8.0 Hz, 1 H), 7.09 (d, J = 2.5 Hz, 1 H), 6.94 (d, J = 10.5 Hz, 1 H), 6.33 (t, J = 6.5 Hz, 1 H), 5.90 (s, 2 H). |
| 58 | 506.3 | $^1$H NMR (500 MHz, DMSO): δ 12.94 (s, 1H), 11.79 (s, 1H), 8.05 (dd, 1H, J = 5.67 Hz, 5.04 Hz), 7.98(t, J = 1.57 Hz, 1.89 Hz, 1H), 7.72(m, 3H), 7.57 (d, 1H, J = 10.7 Hz), 7.45 (d, 1H, J = 6 Hz), 7.21 (s, 1H), 7.12 (t, 1H, J = 1.57 Hz, 1.89 Hz ), 6.36 (t, 1H, J = 6.6, 6.9 Hz), 6.03 (bs, 2H), M.S. found: 506.3 $(M + H)^+$. |
| 59 | 506.87 | $^1$H NMR (500 MHz, $CD_3OD$): δ 7.88-7.80 (m, 2H), 7.65 (d, J = 2.2 Hz, 1H), 7.58 (dd, J = 2.5 Hz, J = 9.8 Hz, 1H), 7.52 (s, 1H), 7.45 (dd, J = 1.9 Hz, J = 6.6 Hz, 1H), 7.33 (m, 1H), 6.98 (d, J = 10.4 Hz, 1H), 6.91 (d, J-2.2 Hz, 1H), 6.51 (t, J = 6.6 Hz, 1H), 6.14 (s, 2H). |
| 60 | 506.89 | $^1$H NMR (500 MHz, DMSO): δ 10.39 (s, 1H), 7.64 (d, J = 8.8 Hz, 1H), 7.54 (m, 1H), 7.36 (m, 1H), 7.16 (s, 1H), 7.10 (m, 1H), 7.06 (s, 1H), 6.97 (m, 1H), 5.83 (s, 2H), 4.67 (t, J = 8.5 Hz, 2H), 3.23 (t, J = 8.5 Hz, 2H). |

| # | LR-MS (M + H) | $^1$H NMR DATA |
|---|---|---|
| 61 | 508.48 | |
| 62 | 508.88 | $^1$H NMR (500 MHz, DMSO): δ 7.92-7.86 (m, 1H), 7.77 (d, J = 10.1 Hz, 1H), 7.54-7.40 (m, 3H), 7.25 (s, 1H), 6.72 (m, 1H), 6.30 (m, 1H), 5.96 (s, 2H), 4.57 (t, J = 8.5 Hz, 2H), 3.17 (t, J = 8.5 Hz, 2H). |
| 63 | 510.49 | NA |
| 64 | 510.50 | NA |
| 65 | 516.93 | NA |
| 66 | 516.98 | NA |
| 67 | 517.47 | NA |
| 68 | 517.47 | NA |
| 69 | 517.47 | NA |
| 70 | 517.47 | NA |
| 71 | 518.26 | 1H-NMR (400 MHz, in dmso-d6): δ13.00 (1H, broad s), 11.76 (1H, broad s), 7.92 (1H, d, J = 2.44 Hz), 7.65 (1H, dd, J = 1.95, 6.84 Hz), 7.54 (1H, m), 7.50 (1H, d, J = 10.74 Hz), 7.41 (1H, dd, J = 1.95, 6.84 Hz), 7.08 (1H, d, J = 2.44 Hz), 7.04 (1H, d, J = 7.81 Hz), 6.31 (1H, dd, J = 6.35, 6.84 Hz), 5.86 (2H, s); LR-MS (ESI): calcd. for C23H13BrF3N2O4 [M + H] + 517.00, found 517.20 |
| 72 | 520.92 | NA |
| 73 | 523.32 | NA |
| 74 | 524.48 | NA |
| 75 | 524.3 | $^1$H NMR (500 MHz, DMSO): δ 12.94 (s, 1H), 11.79 (s, 1H), □ 8.05 (m, 2H), 7.98 (t, J = 1.89 Hz, 1H), 7.73 (d, 1H, J = 6.62 Hz), 7.57 (d, J = 11 Hz, 1H), 7.45 (d, 1H, J = 5.67 Hz), 7.25 (s, 1H), 7.12 (t, J = 1.89 Hz, 1H), ), 6.36 (t, 1H, J = 6.2 Hz), 6.02 (bs, 2H), M.S. found: 524.3 $(M + H)^+$. |
| 76 | 532.52 | NA |
| 77 | 532.93 | NA |
| 78 | 532.93 | NA |
| 79 | 534.45 | 1H NMR (400 MHz, D6-dmso), δ 12.93 (s, 1 H), 12.62 (s, 1 H), 11.74 (s, 1 H), 9.70 (s, 1 H), 7.90 (d, 1 H, J = 2.4 Hz), 7.64 (dd, 1 H, J = 2.0 & 6.8 Hz), 7.47 (d, 1 H, J = 10.8 Hz), 7.40 (dd, 1 H, J = 2.0 & 6.4 Hz), 7.24 (d, 1 H, J = 10.8 Hz), 7.17 (bd, 1 H, J = 5.6 Hz), 7.05 (d, 1 H, J = 2.4 Hz), 6.32 (t, 1 H, J = 6.8 Hz), 5.96 (s, 2 H), 3.48 (S, 3 H). |
| 80 | 534.97 | NA |
| 81 | 535.94 | NA |
| 82 | 536.90 | $^1$H NMR (500 MHz, $CD_3OD$): δ 7.84 (dd, J = 1.9 Hz, J = 6.9 Hz, 1H), 7.65 (d, J = 2.5 Hz, 1H), 7.50-7.38 (m, 4H), 6.95 (d, J = 10.4 Hz, 1H), 6.91 (d, J = 2.2 Hz, 1H), 6.51 (t, J = 6.6 Hz, 1H), 6.12 (s, 2H), 4.02 (s, 3H). |
| 83 | 536.90 | NA |
| 84 | 536.99 | NA |
| 85 | 541.51 | NA |
| 86 | 546.96 | NA |
| 87 | 548.98 | 1H NMR (500 MHz, d6-DMSO, TFA salt), δ 12.09 (s, 1 H), 9.59 (s, 1 H), 8.64 (s, 1 H), 8.02 (d, 1 H, J = 2.0 Hz), 7.59 (dd, 1 H, J = 5.0 & 7.0 Hz), 7.91 (s, 2 H), 7.58 (dd, 1 H, J = 2.0 & 6.0 Hz), 7.48 (d, 1 H, J = 11.0 Hz), 7.15 (d, 1 H, J = 2.0 Hz), 6.55 (s, 1 H), 6.51 (t, 1H, J = 7.0 Hz), 6.00 (s, 2 H), 4.42-4.40 (m, 2 H), 3.29-3.27 (m, 2 H), 2.74 (s, 6 H). |
| 88 | 554.55 | NA |

-continued

| # | LR-MS (M + H) | $^1$H NMR DATA |
|---|---|---|
| 89 | 560.53 | $^1$H NMR (400 MHz, $d_6$-DMSO): δ 12.2 (bs, 1 H), 10.4 (bs, 1 H), 8.20 (s, 1 H), 8.04 (d, J = 2.0 Hz, 1H), 7.90 (dd, J = 7.4, 2.2 Hz, 1 H), 7.62 (d, J = 11.2 Hz, 1 H), 7.57 (d, J = 10.8 Hz, 1 H), 7.90 (dd, J = 6.6, 2.2 Hz, 1 H), 7.49(d, J = 8.8 Hz, 1 H), 7.14 (d, J = 2.0 Hz, 1 H), 6.47 (t, J = 7.0 Hz, 1 H), 5.98 (s, 2 H), 4.46 (m, 2 H), 3.27 (m, 2 H), 2.71 (s, 3 H), 2,70 (s, 3 H). |
| 90 | 563.01 | 1H NMR (400 MHz, D6-dmso), δ, 12.10 (s, 1 H), 9.38 (s, 1 H), 8.43 (s, 1 H), 8.00 (d, 1 H, J = 3.2 Hz), 7.95 (dd, 1 H, J = 4.8 & 6.8 Hz), 7.85 (s, 1 H), 7.57 (d, 1 H, J = 6.4 Hz), 7.47 (d, 1 H, J = 10.8 Hz), 7.13 (d, 1 H, J = 2.4 Hz), 6.51 (t, 1 H, J = 6.4 Hz), 6.46 (s, 1 H), 5.95 (d, 2 H, J = 3.2 Hz), 5.37-5.30 (m, 1 H), 3.27-3.21 (m, 1 H), 3.10-3.04 (m, 1 H), 2.76 (s, 6 H), 1.02 (d, 3 H, J = 6.4 Hz). |
| 91 | 575.96 | $^1$H NMR (500 MHz, $CD_3OD$): δ 7.90-7.85 (m, 2H), 7.80 (d, J = 2.5 Hz, 1H), 7.72 (d, J = 2.2 Hz, 1H), 7.59-7.55 (m, 2H), 7.39 (dd, J = 2.2 Hz, J = 8.8 Hz, 1H), 7.15 (d, J = 10.4 Hz, 1H), 6.98 (d, J = 2.2 Hz, 1H), 6.62 (t, J = 6.6 Hz, 1H), 6.09 (s, 2H), 4.49 (q, J = 7.3 Hz, 1H), 1.77(d, J = 7.3 Hz, 3H), |
| 92 | 576.00 | $^1$H NMR (500 MHz, $CD_3OD$): δ 8.13 (dd, J = 1.9 Hz, J = 6.9 Hz, 1H), 7.76 (d, J = 2.2 Hz, 1H), 7.68 (dd, J = 1.9 Hz, J = 6.9 Hz, 1H), 7.56 (d, J = 8.8 Hz, 1H), 7.29 (s, 1H), 7.22 (m, 2H), 7.10 (dd, J = 2.5 Hz, J = 8.8 Hz, 1H), 7.04 (d, J = 2.2 Hz, 1H), 6.77 (t, , J = 6.6 Hz, 1H), 6.03 (s, 2H), 4.55 (t, J = 5.0 Hz, 2H), 3.36 (t, J = 5.0 Hz. 2H), 2.88 (s, 6H). |
| 93 | 589.3 | $^1$H NMR (500 MHz, $CD_3OD$): δ 8.13 (dd, J = 1.89 Hz, 1.89 Hz, 1H), 7.76 (d, J = 2.2 Hz, 1H), 7.68 (dd, J = 1.89 Hz, 1.89 Hz, 1H), 7.60 (d, J = 9.14 Hz, 1H), 7.33 (m, 2H), 7.24 (d, J = 10 Hz, 1H), 7.17 (dd, J = 2.52 Hz, 2.52 Hz, 1H), ), 7.03 (d, J = 2.2 Hz, 1H), 6.76 (t, J = 6.62 Hz, 6.93 Hz, 1H), 6.04 (bs, 2H), 4.55 (m, 2H), 3.95 (s, 3H), 3.37 (m, 2H), 2.88 (s, 6H). M.S. found: 589.3 $(M + H)^+$. |
| 94 | 591.02 | NA |
| 95 | 591.55 | NA |
| 96 | 603.56 | $^1$H NMR (500 MHz, $d_6$-DMSO): δ 11.8 (bs, 1 H), 8.46 (s, 1 H), 7.96 (d, J = 2.4 Hz, 1H), 7.67-7.65 (m, 1 H), 7.59 (d, J = 11.2 Hz, 1 H), 7.55 (d, J = 10.0 Hz, 1 H), 7.47 (d, J = 8.0 Hz, 1 H), 7.43 (d, J = 7.2 Hz, 1 H), 7.10 (d, J = 2.4 Hz, 1 H), 6.34 (t, J = 7.0 Hz, 1 H), 6.03 (s, 2 H), 5.80 (s, 2 H), 1.07 (s, 9 H). MS found for $C_{31}H_{24}F_2N_4O_7$: 603.7 $(M + H)^+$. |
| 97 | 604.01 | NA |
| 98 | 604.54 | NA |
| 99 | 704.13 | $^1$H NMR (500 MHz, $CD_3OD$): δ 7.9 (dd, J = 1.9 Hz, J = 6.9 Hz, 1H), 7.8 (d, J = 8.8 Hz, 1H), 7.73 (d, J = 2.2 Hz, 1H), 7.72 (m, 1H), 7.57 (dd, J = 2.2 Hz, J = 6.3 Hz, 1H), 7.51 (s, 1H), 7.33 (m, 1H), 7.19 (d, J = 10.4 Hz, 1H), 7.00 (d, J = 2.2 Hz, 1H), 6.62 (t, J = 6.6 Hz, 1H), 6.08 (s, 2H), 4.41 (m, 1H), 4.11 (q, J = 7.3 Hz, 3H), 1.55 (d, J = 7.3 Hz, 3H), 1.48 (s, 9H), 1.04 (t, J = 7.3 Hz, 3H). |
| 100 | 704.66 | NA |
| 101 | 812.87 | NA |
| 102 | 820.29 | NA |
| 106 | 532.5 | $^1$HNMR (500 MHz, $D_6$-dmso), d 12.09 (s, 1 H), 9.52 (s, 1 H), 7.99 (d, 1 H, J = 2.0 Hz), 7.99 (s, 1 H), 7.94 (dd, 1 H, J = 2.0 & 6.5 Hz) 7.61 (d, 1 H, J = 10.5 Hz), 7.56 (dd, 1 H, J = 2.0 & 6.5 Hz), 7.40 (d, 1 H, J = 11.0 Hz), 7.16 (d, 1 H, J = 7.0 Hz), 7.13 (d, 1 H, J = 2.0 Hz), 6.51 (t, 1 H, J = 6.5 Hz), 5.95 (s, 2 H), 4.47 (bt, 2 H, J = 5.0 Hz), 3.36-3.31 (m, 2 H), 2.77 (s, 3 H), 2.76 (s, 3 H). |

wherein NA = not available

| No. | LR-MS (M + H) |
|---|---|
| 125 | 666.7 |
| 126 | 697.7 |
| 127 | 442.4 |
| 128 | 445.4 |
| 129 | 446.4 |
| 130 | 447.4 |
| 131 | 449.4 |
| 132 | 451.4 |
| 133 | 454.4 |
| 134 | 454.8 |
| 135 | 456.8 |
| 136 | 457.4 |
| 137 | 459.5 |
| 138 | 460.4 |
| 139 | 461.4 |

-continued

| No. | LR-MS (M + H) |
|---|---|
| 140 | 461.4 |
| 141 | 463.4 |
| 142 | 463.4 |
| 143 | 464.4 |
| 144 | 468.8 |
| 145 | 471.4 |
| 146 | 473.3 |
| 147 | 474.4 |
| 148 | 475.4 |
| 149 | 477.4 |
| 150 | 477.9 |
| 151 | 477.9 |
| 152 | 478.4 |
| 153 | 478.8 |

-continued

| No. | LR-MS (M + H) |
|---|---|
| 154 | 479.4 |
| 155 | 479.9 |
| 156 | 479.9 |
| 157 | 479.9 |
| 158 | 483.5 |
| 159 | 483.5 |
| 160 | 485.5 |
| 161 | 488.4 |
| 162 | 491.9 |
| 163 | 491.9 |
| 164 | 505.9 |
| 165 | 507.4 |
| 166 | 509.5 |
| 167 | 511.9 |
| 168 | 519.4 |
| 169 | 519.9 |
| 170 | 521.3 |
| 171 | 526.5 |
| 172 | 528.6 |
| 173 | 532.5 |
| 174 | 534.5 |
| 175 | 539.5 |
| 176 | 540.6 |
| 177 | 540.6 |
| 178 | 543.5 |
| 179 | 547.5 |
| 180 | 549.6 |
| 181 | 733.7 |
| 182 | 555.5 |
| 183 | 555.6 |
| 184 | 556.8 |
| 185 | 559.5 |
| 186 | 562.5 |
| 187 | 563.0 |
| 188 | 566.6 |
| 189 | 574.6 |
| 190 | 574.6 |
| 191 | 575.5 |
| 192 | 575.5 |
| 193 | 576.5 |
| 194 | 578.0 |
| 195 | 578.6 |
| 196 | 579.6 |
| 197 | 580.0 |
| 198 | 582.6 |
| 199 | 583.6 |
| 200 | 588.6 |
| 201 | 589.6 |
| 202 | 594.0 |
| 203 | 597.1 |
| 204 | 603.6 |
| 205 | 619.6 |
| 206 | 631.6 |
| 207 | 633.7 |

Example 36

HCV NS5B Polymerase Inhibition Assay

An in vitro transcribed heteropolymeric RNA known as D-RNA or DCoH has been shown to be an efficient template for HCV NS5B polymerase (S.-E. Behrens et al., EMBO J. 15: 12-22 (1996); WO 96/37619). A chemically synthesized 75-mer version, designated DCoH75, whose sequence matches the 3'-end of D-RNA, and DCoH75ddC, where the 3'-terminal cytidine of DCoH75 is replaced by dideoxycytidine, were used for assaying the NS5B enzyme activity as described in Ferrari et al., 12th *International Symposium on HCV and Related Viruses*, P-306 (2005). The sequence of the template RNA was: 5'-UGU GCC GGU CUU UCU GAA CGG GAU AUA AAC CUG GCC AGC UUC AUC GAA CAA GUU GCC GUG UCU AUG ACA UAG AUC-3' (SEQ.ID. NO. 1). A soluble C-terminal 21-amino acid truncated NS5B enzyme form (NS5BΔCT21, from HCV-Con 1 isolate, genotype 1b, Genbank accession number AJ238799) was produced and purified from *Escherichia coli* as C-teiuiinal polyhistidine-tagged fusion protein as described in Ferrari et al., *J. Virol.* 73:1649-1654 (1999). A typical assay contained 20 mM Hepes pH 7.3, 10 mM $MgCl_2$, 60 mM NaCl, 100 μg/ml BSA, 20 units/ml RNasin, 7.5 mM DTT, 0.1 μM ATP/GTP/UTP, 0.026 μM CTP, 0.25 mM GAU, 0.03 μM RNA template, 20 μCi/ml [$^{33}$P]-CTP, 2% DMSO, and 30 or 150 nM NS5B enzyme. Reactions were incubated at 22° C. for 2 hours, then stopped by adding 150 mM EDTA, washed in DE81 filter plate in 0.5M di-basic sodium phosphate buffer, pH 7.0, and counted using Packard TopCount after the addition of scintillation cocktail. Polynucleotide synthesis was monitored by the incorporation of radiolabeled CTP. The effect of the Compounds of Formula (I) on the polymerase activity was evaluated by adding various concentrations of a Compound of Formula (I), typically in 10 serial 2-fold dilutions, to the assay mixture. The starting concentrations ranged from 200 μM to 1 μM. An $IC_{50}$ value for the inhibitor, defined as the compound concentration that provides 50% inhibition of polymerase activity, was determined by fitting the cpm data to the Hill equation Y=100/(1+10^((LogIC50−X)*HillSlope)), where X is the logarithm of compound concentration, and Y is the % inhibition. Ferrari et al., 12th *International Symposium on HCV and Related Viruses*, P-306 (2005) described in detail this assay procedure. It should be noted that such an assay as described is exemplary and not intended to limit the scope of the invention. The skilled practitioner can appreciate that modifications including but not limited to RNA template, primer, nucleotides, NS5B polymerase form, buffer composition, can be made to develop similar assays that yield the same result for the efficacy of the compounds and compositions described in the invention.

NS5B polymerase inhibition data was calculated for selected compounds of the present invention using this method. All compounds tested demonstrated $IC_{50}$ values of between 1 nM and 1 mM.

Example 37

Cell-Based HCV Replicon Assay

To measure cell-based anti-HCV activity of the a Compound of Formula (I), replicon cells were seeded at 5000 cells/well in 96-well collagen I-coated Nune plates in the presence of the Compound of Formula (I). Various concentrations of a Compound of Formula (I), typically in 10 serial 2-fold dilutions, were added to the assay mixture, with the starting concentration ranging from 250 μM to 1 μM. The final concentration of DMSO was 0.5%, fetal bovine serum was 5%, in the assay media. Cells were harvested on day 3 by the addition of 1× cell lysis buffer (Ambion cat #8721). The replicon RNA level was measured using real time PCR (Taqman assay). The amplicon was located in 5B. The PCR primers were: 5B.2F, ATGGACAGGCGCCCTGA (SEQ. ID. NO. 2); 5B.2R, TTGATGGGCAGCTTGGTTTC (SEQ. ID. NO. 3);the probe sequence was FAM-labeled CACGCCATGCGCTGCGG (SEQ. ID. NO. 4). GAPDH RNA was used as endogenous control and was amplified in the same reaction as NS5B (multiplex PCR) using primers and VIC-labeled probe recommended by the manufacturer (PE Applied Biosystem). The real-time RT-PCR reactions were run on ABI PRISM 7900HT Sequence Detection System using the following program: 48° C. for 30 minutes, 95° C. for 10 minutes, 40 cycles of 95° C. for 15 sec, 60° C. for 1 minute. The ΔCT values ($CT_{5B}$-$CT_{GAPDH}$) were plotted against the concentration of test compound and fitted to the sigmoid dose-response model using XLfit4 (MDL). $EC_{50}$ was defined as the concentration of inhibitor necessary to achieve $\Delta CT=1$ over the projected baseline; $EC_{90}$ the concentration necessary to achieve $\Delta CT=3.2$ over the baseline. Alternatively, to quantitate the absolute amount of replicon RNA, a standard curve was established by including serially diluted T7 transcripts of replicon RNA in the Taqman assay. All Taqman reagents were from PE Applied Biosystems. Such an assay procedure was described in detail in e.g. Malcolm et al., *Antimicrobial Agents and Chemotherapy* 50: 1013-1020 (2006).

HCV replicon assay data was calculated for selected compounds of the present invention using this method. Numerous compounds of the present invention were tested and all demonstrated $EC_{50}$ values less than 0.5 micromolar (μM). Compounds 89, 129, 131, 136, 150, 157, 161, 162, 164, 165, 170, 172, 174, 177, 185, 188 and 189 each demonstrated EC90 values less than 0.1 μM in this assay.

Uses of the Tricyclic Indole Derivatives

The Tricyclic Indole Derivatives are useful in human and veterinary medicine for treating or preventing a viral infection or a virus-related disorder in a patient. In accordance with the invention, the Tricyclic Indole Derivatives can be administered to a patient in need of treatment or prevention of a viral infection or a virus-related disorder.

Accordingly, in one embodiment, the invention provides methods for treating a viral infection in a patient comprising administering to the patient an effective amount of at least one Tricyclic Indole Derivative or a pharmaceutically acceptable salt, solvate, ester or prodrug thereof. In another embodiment, the invention provides methods for treating a virus-related disorder in a patient comprising administering to the patient an effective amount of at least one Tricyclic Indole Derivative or a pharmaceutically acceptable salt, solvate, ester or prodrug thereof.

Treatment or Prevention of a Viral Infection

The Tricyclic indole Derivatives can be used to treat or prevent a viral infection. In one embodiment, the Tricyclic Indole Derivatives can be inhibitors of viral replication. In a specific embodiment, the Tricyclic Indole Derivatives can be inhibitors of HCV replication. Accordingly, the Tricyclic Indole Derivatives are useful for treating viral diseases and disorders related to the activity of a virus, such as HCV polymerase.

Examples of viral infections that can be treated or prevented using the present methods, include but are not limited to, hepatitis A infection, hepatitis B infection and hepatitis C infection.

In one embodiment, the viral infection is hepatitis C infection.

In one embodiment, the hepatitis C infection is acute hepatitis C. In another embodiment, the hepatitis C infection is chronic hepatitis C.

The compositions and combinations of the present invention can be useful for treating a patient suffering from infection related to any HCV genotype. HCV types and subtypes may differ in their antigenicity, level of viremia, severity of disease produced, and response to interferon therapy as described in Holland et al., *Pathology,* 30(2):192-195 (1998). The nomenclature set forth in Simmonds et al., *J Gen Virol,* 74(Pt11):2391-2399 (1993) is widely used and classifies isolates into six major genotypes, 1 through 6, with two or more related subtypes, e.g., 1a, 1b. Additional genotypes 7-10 and 11 have been proposed, however the phylogenetic basis on which this classification is based has been questioned, and thus types 7, 8, 9 and 11 isolates have been reassigned as type 6, and type 10 isolates as type 3 (see Lamballerie et al, *J Gen Virol,* 78(Pt1):45-51 (1997)). The major genotypes have been defined as having sequence similarities of between 55 and 72% (mean 64.5%), and subtypes within types as having 75%-86% similarity (mean 80%) when sequenced in the NS-5 region (see Simmonds et al., *J Gen Virol,* 75(Pt 5):1053-1061 (1994)).

Treatment or Prevention of a Virus-Related Disorder

The Tricyclic Indole Derivatives can be used to treat or prevent a virus-related disorder. Accordingly, the Tricyclic Indole Derivatives are useful for treating disorders related to the activity of a virus, such as liver inflammation or cirrhosis. Virus-related disorders include, but are not limited to, RNA-dependent polymerase-related disorders and disorders related to HCV infection.

Treatment or Prevention of a RNA-Dependent Polymerase-Related Disorder

The Tricyclic Indole Derivatives are useful for treating or preventing a RNA dependent polymerase (RdRp) related disorder in a patient. Such disorders include viral infections wherein the infective virus contains a RdRp enzyme.

Accordingly, in one embodiment, the present invention provides a method for treating a RNA dependent polymerase-related disorder in a patient, comprising administering to the patient an effective amount of at least one Tricyclic Indole Derivative or a pharmaceutically acceptable salt, solvate, ester or prodrug thereof.

Treatment or Prevention of a Disorder Related to HCV Infection

The Tricyclic Indole Derivatives can also be useful for treating or preventing a disorder related to an HCV infection. Examples of such disorders include, but are not limited to, cirrhosis, portal hypertension, ascites, bone pain, varices, jaundice, hepatic encephalopathy, thyroiditis, porphyria cutanea tarda, cryoglobulinemia, glomerulonephritis, sicca syndrome, thrombocytopenia, lichen planus and diabetes mellitus.

Accordingly, in one embodiment, the invention provides methods for treating an HCV-related disorder in a patient, wherein the method comprises administering to the patient a therapeutically effective amount of at least one Tricyclic Indole Derivative, or a pharmaceutically acceptable salt, solvate, ester or prodrug thereof.

Combination Therapy

In another embodiment, the present methods for treating or preventing a viral infection or a virus-related disorder can further comprise the administration of one or more additional therapeutic agents which are not Tricyclic Indole Derivatives.

In one embodiment, the additional therapeutic agent is an antiviral agent.

In another embodiment, the additional therapeutic agent is an immunomodulatory agent, such as an immunosuppressive agent.

Accordingly, in one embodiment, the present invention provides methods for treating a viral infection in a patient, the method comprising administering to the patient: (i) at least one Tricyclic Indole Derivative, or a pharmaceutically acceptable salt, solvate, ester or prodrug thereof, and (ii) at least one additional therapeutic agent that is other than a Tricyclic Indole Derivative, wherein the amounts administered are together effective to treat or prevent a viral infection.

When administering a combination therapy of the invention to a patient, therapeutic agents in the combination, or a pharmaceutical composition or compositions comprising therapeutic agents, may be administered in any order such as, for example, sequentially, concurrently, together, simultaneously and the like. The amounts of the various actives in such combination therapy may be different amounts (different dosage amounts) or same amounts (same dosage amounts). Thus, for non-limiting illustration purposes, a Tricyclic Indole Derivative and an additional therapeutic agent may be present in fixed amounts (dosage amounts) in a single dosage unit (e.g., a capsule, a tablet and the like). A commercial example of such single dosage unit containing fixed amounts of two different active compounds is VYTORIN (available from Merck Schering-Plough Pharmaceuticals, Kenilworth, N.J.).

In one embodiment, the at least one Tricyclic Indole Derivative is administered during a time when the additional therapeutic agent(s) exert their prophylactic or therapeutic effect, or vice versa.

In another embodiment, the at least one Tricyclic Indole Derivative and the additional therapeutic agent(s) are administered in doses commonly employed when such agents are used as monotherapy for treating a viral infection.

In another embodiment, the at least one Tricyclic Indole Derivative and the additional therapeutic agent(s) are administered in doses lower than the doses commonly employed when such agents are used as monotherapy for treating a viral infection.

In still another embodiment, the at least one Tricyclic Indole Derivative and the additional therapeutic agent(s) act synergistically and are administered in doses lower than the doses commonly employed when such agents are used as monotherapy for treating a viral infection.

In one embodiment, the at least one Tricyclic Indole Derivative and the additional therapeutic agent(s) are present in the same composition. In one embodiment, this composition is suitable for oral administration. In another embodiment, this composition is suitable for intravenous administration. In another embodiment, this composition is suitable for subcutaneous administration. In still another embodiment, this composition is suitable for parenteral administration.

Viral infections and virus-related disorders that can be treated or prevented using the combination therapy methods of the present invention include, but are not limited to, those listed above.

In one embodiment, the viral infection is HCV infection.

The at least one Tricyclic Indole Derivative and the additional therapeutic agent(s) can act additively or synergistically. A synergistic combination may allow the use of lower dosages of one or more agents and/or less frequent administration of one or more agents of a combination therapy. A lower dosage or less frequent administration of one or more agents may lower toxicity of therapy without reducing the efficacy of therapy.

In one embodiment, the administration of at least one Tricyclic Indole Derivative and the additional therapeutic agent(s) may inhibit the resistance of a viral infection to these agents.

Non-limiting examples of additional therapeutic agents useful in the present compositions and methods include an interferon, an immunomodulator, a viral replication inhibitor, an antisense agent, a therapeutic vaccine, a viral polymerase inhibitor, a nucleoside inhibitor, a viral protease inhibitor, a viral helicase inhibitor, a virion production inhibitor, a viral entry inhibitor, a viral assembly inhibitor, an antibody therapy (monoclonal or polyclonal), and any agent useful for treating an RNA-dependent polymerase-related disorder.

In one embodiment, the additional therapeutic agent is a viral protease inhibitor.

In another embodiment, the additional therapeutic agent is a viral replication inhibitor.

In another embodiment, the additional therapeutic agent is an HCV NS3 protease inhibitor.

In another embodiment, the additional therapeutic agent is an HCV NS5B polymerase inhibitor.

In another embodiment, the additional therapeutic agent is a nucleoside inhibitor.

In another embodiment, the additional therapeutic agent is an interferon.

In one embodiment, the additional therapeutic agent is an HCV replicase inhibitor.

In another embodiment, the additional therapeutic agent is an antisense agent.

In another embodiment, the additional therapeutic agent is a therapeutic vaccine.

In a further embodiment, the additional therapeutic agent is a virion production inhibitor.

In another embodiment, the additional therapeutic agent is an antibody therapy.

In another embodiment, the additional therapeutic agent is an HCV NS2 inhibitor.

In another embodiment, the additional therapeutic agent is an HCV NS4A inhibitor.

In another embodiment, the additional therapeutic agent is an HCV NS4B inhibitor.

In another embodiment, the additional therapeutic agent is an HCV NS5A inhibitor.

In another embodiment, the additional therapeutic agent is an HCV NS3 helicase inhibitor.

In another embodiment, the additional therapeutic agent is an HCV IRES inhibitor.

In another embodiment, the additional therapeutic agent is an HCV p7 inhibitor.

In another embodiment, the additional therapeutic agent is an HCV entry inhibitor.

In another embodiment, the additional therapeutic agent is an HCV assembly inhibitor.

In one embodiment, the additional therapeutic agents comprise a protease inhibitor and a polymerase inhibitor.

In still another embodiment, the additional therapeutic agents comprise a protease inhibitor and an immunomodulatory agent.

In yet another embodiment, the additional therapeutic agents comprise a polymerase inhibitor and an immunomodulatory agent.

In another embodiment, the additional therapeutic agents comprise a protease inhibitor and a nucleoside.

In another embodiment, the additional therapeutic agents comprise an immunomodulatory agent and a nucleoside.

In one embodiment, the additional therapeutic agents comprise a protease inhibitor and a NS5A inhibitor.

In another embodiment, the additional therapeutic agents comprise a nucleoside and a NS5A inhibitor.

In another embodiment, the additional therapeutic agents comprise a protease inhibitor, an immunomodulatory agent and a nucleoside.

In still another embodiment, the additional therapeutic agents comprise a protease inhibitor, a nucleoside and a NS5A inhibitor.

In a further embodiment, the additional therapeutic agents comprise a protease inhibitor, a polymerase inhibitor and an immunomodulatory agent.

In another embodiment, the additional therapeutic agent is ribavirin.

HCV polymerase inhibitors useful in the present compositions and methods include, but are not limited to, VP-19744 (Wyeth/ViroPharma), PSI-7851 (Pharmasset), R7128 (Roche/Pharmasset), PF-868554/filibuvir (Pfizer), VCH-759 (ViroChem Pharma), HCV-796 (Wyeth/ViroPharma), IDX-184 (Idenix), IDX-375 (Idenix), NM-283 (Idenix/Novartis), R-1626 (Roche), MK-0608 (Isis/Merck), INX-8014 (Inhibitex), INX-8018 (Inhibitex), INX-189 (Inhibitex), GS 9190 (Gilead), A-848837 (Abbott), ABT-333 (Abbott), ABT-072 (Abbott), A-837093 (Abbott), BI-207127 (Boehringer-Ingelheim), BILB-1941 (Boehringer-Ingelheim), MK-3281 (Merck), VCH222 (ViroChem), VCH916 (ViroChem), VCH716(ViroChem), GSK-71185 (Glaxo SmithKline), ANA598 (Anadyr), GSK-625433 (Glaxo SmithKline), XTL-2125 (XTL Biopharmaceuticals), and those disclosed in Ni et al., *Current Opinion in Drug Discovery and Development,* 7(4):446 (2004); Tan et al., *Nature Reviews,* 1:867 (2002); and Beaulieu et al., *Current Opinion in Investigational Drugs,* 5:838 (2004).

Other HCV polymerase inhibitors useful in the present compositions and methods include, but are not limited to, those disclosed in International Publication Nos. WO 08/082,484, WO 08/082,488, WO 08/083,351, WO 08/136,815, WO 09/032,116, WO 09/032,123, WO 09/032,124 and WO 09/032,125.

Interferons useful in the present compositions and methods include, but are not limited to, interferon alfa-2a, interferon alfa-2b, interferon alfacon-1 and PEG-interferon alpha conjugates. "PEG-interferon alpha conjugates" are interferon alpha molecules covalently attached to a PEG molecule. Illustrative PEG-interferon alpha conjugates include interferon alpha-2a (Roferon™, Hoffman La-Roche, Nutley, N.J.) in the form of pegylated interferon alpha-2a (e.g., as sold under the trade name Pegasys™), interferon alpha-2b (Intron™, from Schering-Plough Corporation) in the form of pegylated interferon alpha-2b (e.g., as sold under the trade name PEG-Intron™ from Schering-Plough Corporation), interferon alpha-2b-XL (e.g., as sold under the trade name PEG-Intron™), interferon alpha-2c (Berofor Alpha™, Boehringer Ingelheim, Ingelheim, Germany), PEG-interferon lambda (Bristol-Myers Squibb and ZymoGenetics), interferon alfa-2b alpha fusion polypeptides, interferon fused with the human blood protein albumin (Aibuferon™, Human Genome Sciences), Omega Interferon (Intarcia), Locteron controlled release interferon (Biolex/OctoPlus), Biomed-510 (omega interferon), Peg-IL-29 (ZymoGenetics), Locteron CR (Octoplus), IFN-α-2b-XL (Flamel Technologies), and consensus interferon as defined by determination of a consensus sequence of naturally occurring interferon alphas (Infergen™, Amgen, Thousand Oaks, Calif.).

Antibody therapy agents useful in the present compositions and methods include, but are not limited to, antibodies specific to IL-10 (such as those disclosed in US Patent Publication No. US2005/0101770, humanized 12G8, a humanized monoclonal antibody against human IL-10, plasmids containing the nucleic acids encoding the humanized 12G8 light and heavy chains were deposited with the American Type Culture Collection (ATCC) as deposit numbers PTA-5923 and PTA-5922, respectively), and the like).

Examples of viral protease inhibitors useful in the present compositions and methods include, but are not limited to, a HCV protease inhibitor.

HCV protease inhibitors useful in the present compositions and methods include, but are not limited to, those disclosed in U.S. Pat. Nos. 7,494,988, 7,485,625, 7,449,447, 7,442,695, 7,425,576, 7,342,041, 7,253,160, 7,244,721, 7,205,330, 7,192,957, 7,186,747, 7,173,057, 7,169,760, 7,012,066, 6,914,122, 6,911,428, 6,894,072, 6,846,802, 6,838,475, 6,800,434, 6,767,991, 5,017,380, 4,933,443, 4,812,561 and 4,634,697; U.S. Patent Publication Nos. US20020068702, US20020160962, US20050119168, US20050176648, US20050209164, US20050249702 and US20070042968; and International Publication Nos. WO 03/006490, WO 03/087092, WO 04/092161 and WO 08/124,148.

Additional HCV protease inhibitors useful in the present compositions and methods include, but are not limited to, SCHSO3034 (Boceprevir, Schering-Plough), SCH900518 (Schering-Plough), VX-950 (Telaprevir, Vertex), VX-500 (Vertex), VX-813 (Vertex), VBY-376 (Virobay), BI-201335 (Boehringer Ingelheim), TMC-435 (Medivir/Tibotec), ABT-450 (Abbott), MK-7009 (Merck), TMC-435350 (Medivir), ITMN-191/R7227 (InterMune/Roche), EA-058 (Abbott/Enanta), EA-063 (Abbott/Enanta), GS-9132 (Gilead/Achillion), ACH-1095 (Gilead/Achillon), IDX-136 (Idenix), IDX-316 (Idenix), ITMN-8356 (InterMune), ITMN-8347 (InterMune), ITMN-8096 (InterMune), ITMN-7587 (InterMune), PHX1766 (Phenomix), amprenavir, atazanavir, fosemprenavir, indinavir, lopinavir, ritonavir, nelfinavir, saquinavir, tipranavir, Kaletra (a combination of ritonavir and lopinavir) and TMC114.

Additional examples of HCV protease inhibitors useful in the present compositions and methods include, but are not limited to, those disclosed in Landro et al., *Biochemistry,* 36(30:9340-9348 (1997); Ingallinella et al., *Biochemistry,* 37(25):8906-8914 (1998); Llinàs-Brunet et al., *Bioorg Med Chem Lett,* 8(13):1713-1718 (1998); Martin et al., *Biochemistry,* 37(33):11459-11468 (1998); Dimasi et al., *J Virol,* 71(10):7461-7469 (1997); Martin et al., *Protein Eng,* 10(5):607-614 (1997); Elzouki et al., *J Hepat,* 27(1):42-48 (1997); *BioWorld Today,* 9(217):4 (Nov. 10, 1998); U.S. Patent Publication Nos. US2005/0249702 and US 2007/0274951; and International Publication Nos, WO 98/14181, WO 98/17679, WO 98/17679, WO 98/22496 and WO 99/07734 and WO 05/087731.

Further examples of HCV protease inhibitors useful in the present compositions and methods include, but are not limited to, the following compounds:

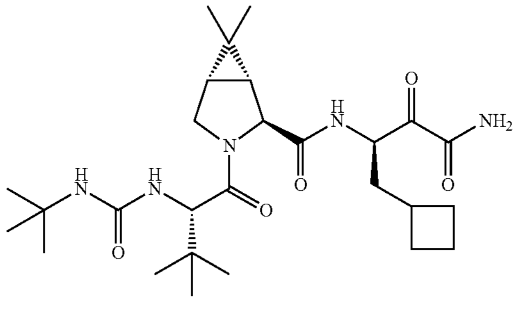

-continued
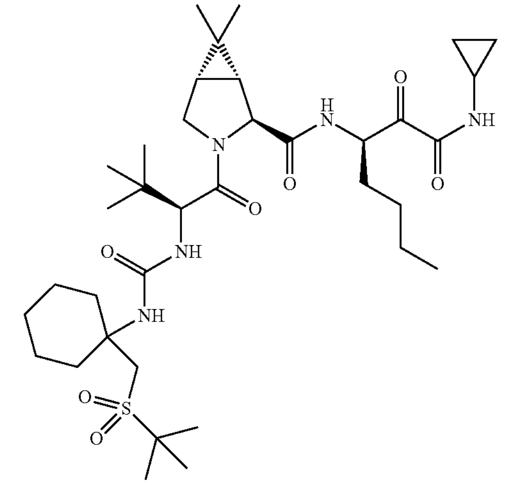
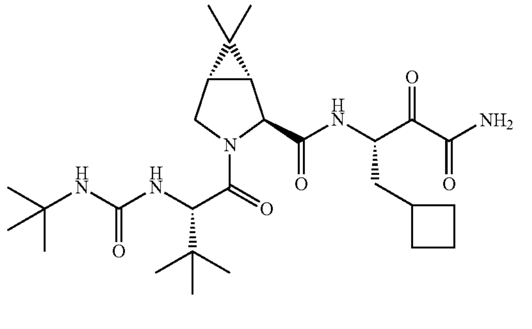
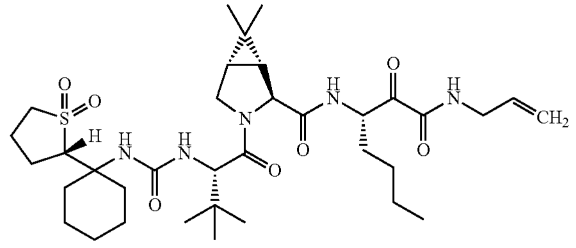
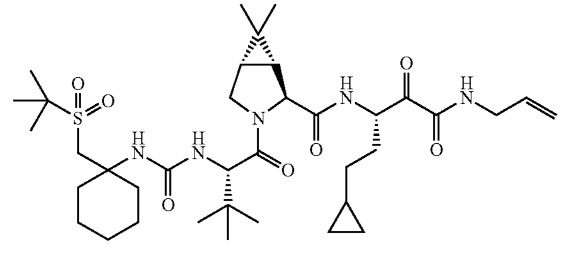
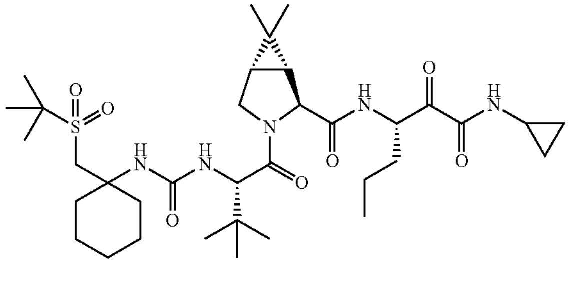
-continued
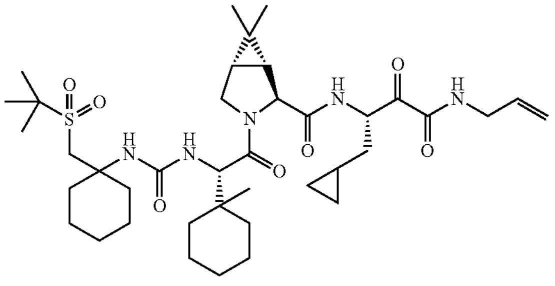
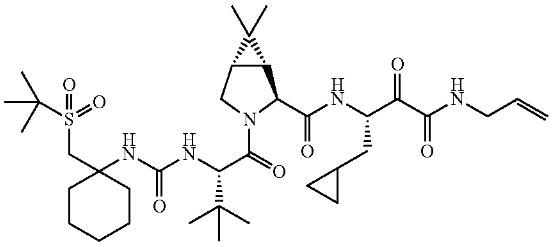
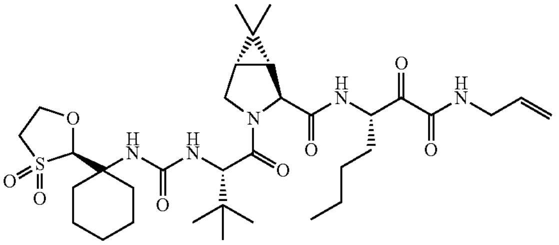
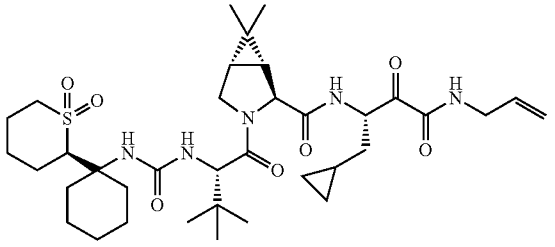
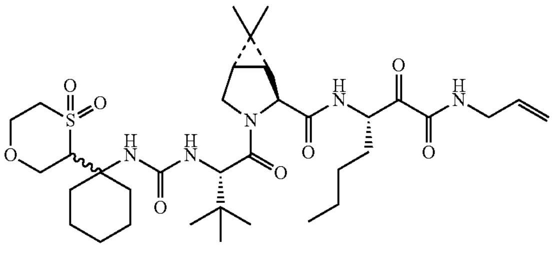
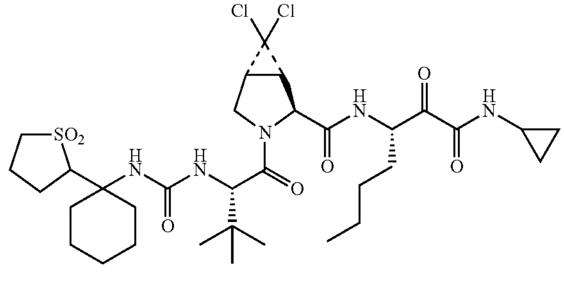

-continued

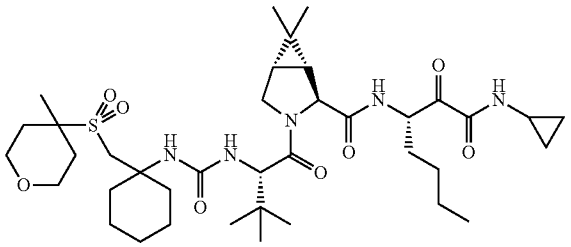

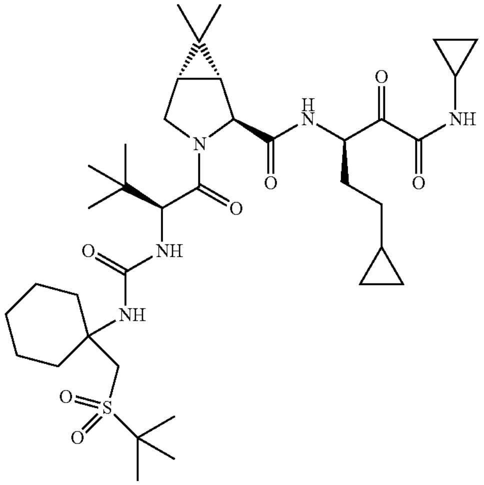

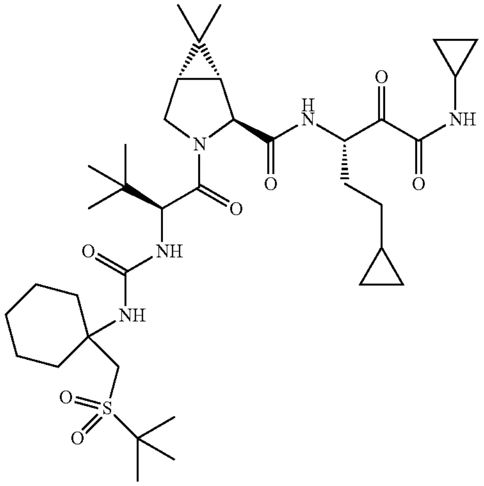

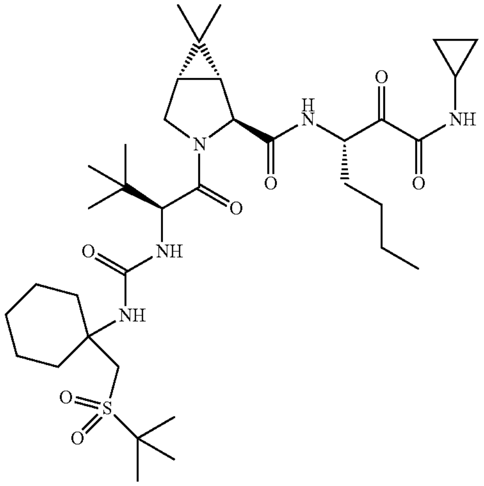

-continued

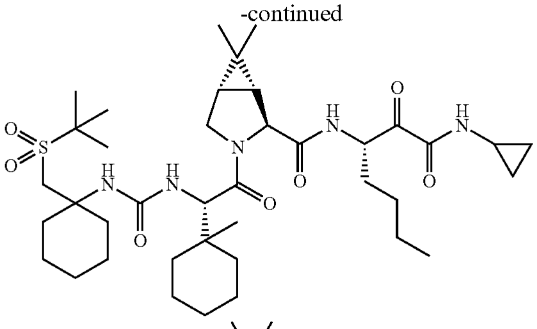

and

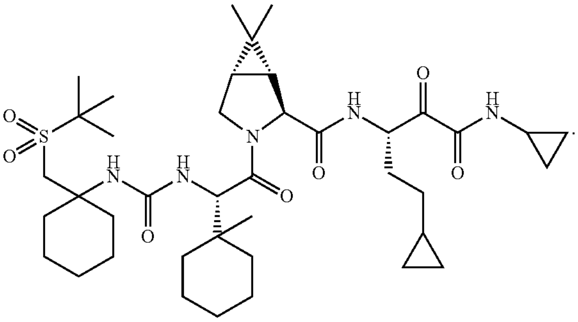

.

Viral replication inhibitors useful in the present compositions and methods include, but are not limited to, HCV replicase inhibitors, IRES inhibitors, NS4A inhibitors, NS3 helicase inhibitors, NS5A inhibitors, ribavirin, AZD-2836 (Astra Zeneca), BMS-790052 (Bristol-Myers Squibb), viramidine, A-831 (Arrow Therapeutics); an antisense agent or a therapeutic vaccine.

In one embodiment, viral replication inhibitors useful in the present compositions and methods include, but are not limited to, HCV replicase inhibitors, IRES inhibitors, NS4A inhibitors, NS3 helicase inhibitors and NS5A inhibitors.

HCV NS4A inhibitors useful in the useful in the present compositions and methods include, but are not limited to, those disclosed in U.S. Pat. Nos. 7,476,686 and 7,273,885; U.S. Patent Publication No. US20090022688; and International Publication Nos. WO 2006/019831 and WO 2006/019832. Additional HCV NS4A inhibitors useful in the useful in the present compositions and methods include, but are not limited to, AZD2836 (Astra Zeneca and ACH-806 (Achillon Pharmaceuticals, New Haven, Conn.).

HCV replicase inhibitors useful in the useful in the present compositions and methods include, but are not limited to, those disclosed in U.S. Patent Publication No. US20090081636.

Therapeutic vaccines useful in the present compositions and methods include, but are not limited to, IC41 (Intercell Novartis), CSL123 (Chiron/CSL), GI 5005 (Globeimmune), TG-4040 (Transgene), GNI-103 (GENimmune), Hepavaxx C (ViRex Medical), ChronVac-C (Inovio/Tripep), PeviPRO™ (Pevion Biotect), HCV/MF59 (Chiron/Novartis) and Civacir (NABI).

Examples of further additional therapeutic agents useful in the present compositions and methods include, but are not limited to, TT033 (Benitec/Tacere Bio/Pfizer), Sirna-034 (Sirna Therapeutics), GNI-104 (GENimmune), GI-5005 (GlobeImmune), IDX-102 (Idenix), Levovirin™ (ICN Pharmaceuticals, Costa Mesa, Calif.); Humax (Genmab), ITX-2155 (Ithrex/Novartis), PRO206 (Progenies), HepaCide-I (NanoVirocides), MX3235 (Migenix), SCY-635 (Scynexis); KPE02003002 (Kemin Pharma), Lenocta (VioQuest Pharmaceuticals), IET—Interferon Enhancing Therapy (Transition Therapeutics), Zadaxin (SciClone Pharma), VP 50406™ (Viropharma, Incorporated, Exton, Pa.); Taribavirin (Valeant Pharmaceuticals); Nitazoxanide (Romark); Debio 025 (Debiopharm); GS-9450 (Gilead); PF-4878691 (Pfizer); ANA773 (Anadys); SCV-07 (SciClone Pharmaceuticals); NIM-881 (Novartis); ISIS 14803™ (ISIS Pharmaceuticals, Carlsbad, Calif.); Heptazyme™ (Ribozyme Pharmaceuticals, Boulder, Colo.); Thymosin™ (SciClone Pharmaceuticals, San Mateo, Calif.); Maxamine™ (Maxim Pharmaceuticals, San Diego, Calif.); NKB-122 (JenKen Bioscience Inc., North Carolina); Alinia (Romark Laboratories), INFORM-1 (a combination of R7128 and ITMN-191); and mycophenolate mofetil (Hoffman-LaRoche, Nutley, N.J.).

The doses and dosage regimen of the other agents used in the combination therapies of the present invention for the treatment or prevention of a viral infection or virus-related disorder can be determined by the attending clinician, taking into consideration the approved doses and dosage regimen in the package insert; the age, sex and general health of the patient; and the type and severity of the viral infection or related disease or disorder. When administered in combination, the Tricyclic Indole Derivative(s) and the other agent(s) can be administered simultaneously (i.e., in the same composition or in separate compositions one right after the other) or sequentially. This is particularly useful when the components of the combination are given on different dosing schedules, e.g., one component is administered once daily and another every six hours, or when the preferred pharmaceutical compositions are different, e.g., one is a tablet and one is a capsule. A kit comprising the separate dosage forms is therefore advantageous.

Generally, a total daily dosage of the at least one Tricyclic Indole Derivative(s) alone, or when administered as combination therapy, can range from about 1 to about 2500 mg per day, although variations will necessarily occur depending on the target of therapy, the patient and the route of administration. In one embodiment, the dosage is from about 10 to about 1000 mg/day, administered in a single dose or in 2-4 divided doses. In another embodiment, the dosage is from about 1 to about 500 mg/day, administered in a single dose or in 2-4 divided doses. In still another embodiment, the dosage is from about 1 to about 100 mg/day, administered in a single dose or in 2-4 divided doses. In yet another embodiment, the dosage is from about 1 to about 50 mg/day, administered in a single dose or in 2-4 divided doses. In another embodiment, the dosage is from about 500 to about 1500 mg/day, administered in a single dose or in 2-4 divided doses. In still another embodiment, the dosage is from about 500 to about 1000 mg/day, administered in a single dose or in 2-4 divided doses. In yet another embodiment, the dosage is from about 100 to about 500 mg/day, administered in a single dose or in 2-4 divided doses.

In one embodiment, when the additional therapeutic agent is INTRON-A interferon alpha 2b (commercially available from Schering-Plough Corp.), this agent is administered by subcutaneous injection at 3MIU(12 mcg)/0.5 mL/TIW for 24 weeks or 48 weeks for first time treatment.

In another embodiment, when the additional therapeutic agent is PEG-INTRON interferon alpha 2b pegylated (commercially available from Schering-Plough Corp.), this agent is administered by subcutaneous injection at 1.5 mcg/kg/week, within a range of 40 to 150 mcg/week, for at least 24 weeks.

In another embodiment, when the additional therapeutic agent is ROFERON A interferon alpha 2a (commercially available from Hoffmann-La Roche), this agent is administered by subcutaneous or intramuscular injection at 3MIU (11.1 mcg/mL)/TIW for at least 48 to 52 weeks, or alternatively 6MIU/TIW for 12 weeks followed by 3MIU/TIW for 36 weeks.

In still another embodiment, when the additional therapeutic agent is PEGASUS interferon alpha 2a pegylated (commercially available from Hoffmann-La Roche), this agent is administered by subcutaneous injection at 180 mcg/1 mL or 180 mcg/0.5 mL, once a week for at least 24 weeks.

In yet another embodiment, when the additional therapeutic agent is INFERGEN interferon alphacon-1 (commercially available from Amgen), this agent is administered by subcutaneous injection at 9 mcg/TIW is 24 weeks for first time treatment and up to 15 mcg/TIW for 24 weeks for non-responsive or relapse treatment.

In a further embodiment, when the additional therapeutic agent is Ribavirin (commercially available as REBETOL ribavirin from Schering-Plough or COPEGUS ribavirin from Hoffmann-La Roche), this agent is administered at a daily dosage of from about 600 to about 1400 mg/day for at least 24 weeks.

In one embodiment, one or more compounds of the present invention are administered with one or more additional therapeutic agents selected from a HCV protease inhibitor, a HCV replication inhibitor, a nucleoside, an interferon, a pegylated interferon and ribavirin. The combination therapies can include any combination of these additional therapeutic agents.

In another embodiment, one or more compounds of the present invention are administered with one additional therapeutic agent selected from a HCV protease inhibitor, a HCV replication inhibitor, a nucleoside, an interferon, a pegylated interferon and ribavirin.

In another embodiment, one or more compounds of the present invention are administered with two additional therapeutic agents selected from a HCV protease inhibitor, a HCV replication inhibitor, a nucleoside, an interferon, a pegylated interferon and ribavirin.

In a specific embodiment, one or more compounds of the present invention are administered with a HCV protease inhibitor and ribavirin. In another specific embodiment, one or more compounds of the present invention are administered with a pegylated interferon and ribavirin.

In another embodiment, one or more compounds of the present invention are administered with three additional therapeutic agents selected from a HCV protease inhibitor, a HCV replication inhibitor, a nucleoside, an interferon, a pegylated interferon and ribavirin.

In one embodiment, one or more compounds of the present invention are administered with one or more additional therapeutic agents selected from a HCV polymerase inhibitor, a viral protease inhibitor, an interferon, and a viral replication inhibitor. In another embodiment, one or more compounds of the present invention are administered with one or more additional therapeutic agents selected from a HCV polymerase inhibitor, a viral protease inhibitor, an interferon, and a viral replication inhibitor. In another embodiment, one or more compounds of the present invention are administered with one or more additional therapeutic agents selected from a HCV polymerase inhibitor, a viral protease inhibitor, an interferon, and ribavirin.

In one embodiment, one or more compounds of the present invention are administered with one additional therapeutic agent selected from a HCV polymerase inhibitor, a viral protease inhibitor, an interferon, and a viral replication inhibitor. In another embodiment, one or more compounds of the present invention are administered with ribavirin.

In one embodiment, one or more compounds of the present invention are administered with two additional therapeutic agents selected from a HCV polymerase inhibitor, a viral protease inhibitor, an interferon, and a viral replication inhibitor.

In another embodiment, one or more compounds of the present invention are administered with ribavirin, interferon and another therapeutic agent.

In another embodiment, one or more compounds of the present invention are administered with ribavirin, interferon and another therapeutic agent, wherein the additional therapeutic agent is selected from a HCV polymerase inhibitor, a viral protease inhibitor, and a viral replication inhibitor.

In still another embodiment, one or more compounds of the present invention are administered with ribavirin, interferon and a viral protease inhibitor.

In another embodiment, one or more compounds of the present invention are administered with ribavirin, interferon and an HCV protease inhibitor.

In another embodiment, one or more compounds of the present invention are administered with ribavirin, interferon and boceprevir or telaprevir.

In a further embodiment, one or more compounds of the present invention are administered with ribavirin, interferon and an HCV polymerase inhibitor.

Compositions and Administration

Due to their activity, the Tricyclic Indole Derivatives are useful in veterinary and human medicine. As described above, the Tricyclic Indole Derivatives are useful for treating or preventing a viral infection or a virus-related disorder in a patient in need thereof.

When administered to a patient, the Tricyclic Indole Derivatives can be administered as a component of a composition that comprises a pharmaceutically acceptable carrier or vehicle. The present invention provides pharmaceutical compositions comprising an effective amount of at least one Tricyclic Indole Derivative and a pharmaceutically acceptable carrier. In the pharmaceutical compositions and methods of the present invention, the active ingredients will typically the administered in admixture with suitable carrier materials suitably selected with respect to the intended form of administration, i.e., oral tablets, capsules (either solid-filled, semi-solid filled or liquid filled), powders for constitution, oral gels, elixirs, dispersible granules, syrups, suspensions, and the like, and consistent with conventional pharmaceutical practices. For example, for oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Solid form preparations include powders, tablets, dispersible granules, capsules, cachets and suppositories. Powders and tablets may be comprised of from about 0.5 to about 95 percent inventive composition. Tablets, powders, cachets and capsules can be used as solid dosage forms suitable for oral administration.

Moreover, when desired or needed, suitable binders, lubricants, disintegrating agents and coloring agents may also be incorporated in the mixture. Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, and the like. Disintegrants include starch, methylcellulose, guar gum, and the like. Sweetening and flavoring agents and preservatives may also be included where appropriate.

Liquid form preparations include solutions, suspensions and emulsions and may include water or water-propylene glycol solutions for parenteral injection.

Liquid form preparations may also include solutions for intranasal administration.

Aerosol preparations suitable for inhalation may include solutions and solids in powder form, which may be in combination with a pharmaceutically acceptable carrier, such as an inert compressed gas.

Also included are solid form preparations which are intended to be converted, shortly before use, to liquid form preparations for either oral or parenteral administration. Such liquid forms include solutions, suspensions and emulsions.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

The Tricyclic Indole Derivatives of the present invention may also be deliverable transdermally. The transdermal compositions can take the form of creams, lotions, aerosols and/or emulsions and can be included in a transdermal patch of the matrix or reservoir type as are conventional in the art for this purpose.

Additionally, the compositions of the present invention may be formulated in sustained release form to provide the rate controlled release of any one or more of the components or active ingredients to optimize therapeutic effects, i.e., antiviral activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

In one embodiment, the one or more Tricyclic Indole Derivatives are administered orally.

In another embodiment, the one or more Tricyclic Indole Derivatives are administered intravenously.

In another embodiment, the one or more Tricyclic Indole Derivatives are administered topically.

In still another embodiment, the one or more Tricyclic Indole Derivatives are administered sublingually.

In one embodiment, a pharmaceutical preparation comprising at least one Tricyclic Indole Derivative is in unit dosage form. In such form, the preparation is subdivided into unit doses containing effective amounts of the active components.

Compositions can be prepared according to conventional mixing, granulating or coating methods, respectively, and the present compositions can contain, in one embodiment, from about 0.1% to about 99% of the Tricyclic Indole Derivative(s) by weight or volume. In various embodiments, the present compositions can contain, in one embodiment, from about 1% to about 70% or from about 5% to about 60% of the Tricyclic Indole Derivative(s) by weight or volume.

The quantity of Tricyclic Indole Derivative in a unit dose of preparation may be varied or adjusted from about 1 mg to about 2500 mg. In various embodiment, the quantity is from about 10 mg to about 1000 mg, 1 mg to about 500 mg, 1 mg to about 100 mg, and 1 mg to about 100 mg.

For convenience, the total daily dosage may be divided and administered in portions during the day if desired. In one embodiment, the daily dosage is administered in one portion. In another embodiment, the total daily dosage is administered in two divided doses over a 24 hour period. In another embodiment, the total daily dosage is administered in three divided doses over a 24 hour period. In still another embodiment, the total daily dosage is administered in four divided doses over a 24 hour period.

The amount and frequency of administration of the Tricyclic Indole Derivatives will be regulated according to the judgment of the attending clinician considering such factors as age, condition and size of the patient as well as severity of the symptoms being treated. Generally, a total daily dosage of the Tricyclic Indole Derivatives range from about 0.1 to about 2000 mg per day, although variations will necessarily occur depending on the target of therapy, the patient and the route of administration. In one embodiment, the dosage is from about 1 to about 200 mg/day, administered in a single dose or in 2-4 divided doses. In another embodiment, the dosage is from about 10 to about 2000 mg/day, administered in a single dose or in 2-4 divided doses. In another embodiment, the dosage is from about 100 to about 2000 mg/day, administered in a single dose or in 2-4 divided doses. In still another embodiment, the dosage is from about 500 to about 2000 mg/day, administered in a single dose or in 2-4 divided doses.

The compositions of the invention can further comprise one or more additional therapeutic agents, selected from those listed above herein. Accordingly, in one embodiment, the present invention provides compositions comprising: (i) at least one Tricyclic Indole Derivative or a pharmaceutically acceptable salt, solvate, ester or prodrug thereof; (ii) one or more additional therapeutic agents that are not a Tricyclic Indole Derivative; and (iii) a pharmaceutically acceptable carrier, wherein the amounts in the composition are together effective to treat a viral infection or a virus-related disorder.

Kits

In one aspect, the present invention provides a kit comprising a therapeutically effective amount of at least one Tricyclic Indole Derivative, or a pharmaceutically acceptable salt, solvate, ester or prodrug of said compound and a pharmaceutically acceptable carrier, vehicle or diluent.

In another aspect the present invention provides a kit comprising an amount of at least one Tricyclic Indole Derivative, or a pharmaceutically acceptable salt, solvate, ester or prodrug of said compound and an amount of at least one additional therapeutic agent listed above, wherein the amounts of the two or more active ingredients result in a desired therapeutic effect. In one embodiment, the one or more Tricyclic Indole Derivatives and the one or more additional therapeutic agents are provided in the same container. In one embodiment, the one or more Tricyclic Indole Derivatives and the one or more additional therapeutic agents are provided in separate containers.

The present invention is not to be limited by the specific embodiments disclosed in the examples that are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

A number of references have been cited herein, the entire disclosures of which are incorporated herein by reference.

---

What is claimed is:

1. A compound having the formula:

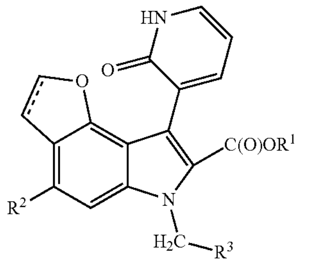

(I)

and pharmaceutically acceptable salts thereof,
wherein the dotted line represents an optional and additional bond, and wherein:

$R^1$ is -alkylene-OC(O)-alkyl or aminoalkyl;

$R^2$ is H, F, Cl or —$CH_3$;

$R^3$ is phenyl, naphthyl, nitrogen-containing heterocycloalkyl, nitrogen-containing heterocycloalkenyl or nitrogen-containing heteroaryl, any of which can be optionally substituted with up to 3 groups, which can be the same or different, and are selected from methyl, t-butyl, allyl, F, Cl, Br, —CN, —O—$CH_2CH_3$, —S(O)$CH_3$, —S(O)$_2CH_3$, —$NH_2$, —OH, —$CH_2NH_2$, —C(O)$NH_2$, —C(O)$NHCH_3$, —C(O)NH-cyclopropyl, hydroxyalkyl, —C(O)H, —C(O)$CH_3$, —C(O)O-isopropyl, —C(O)O-t-butyl, —$CH_2$C(O)-t-butyl, —$OCH_3$, —$NHCH_3$, —$SCH_3$, —C(O)$NHCH_3$, —NHC(O)$OCH_3$, —NHC(O)O-isopropyl, —$CH_2N(CH_3)_2$, —OC(O)CH($CH_3$)NHC(O)O-t-butyl, —OC(O)CH($CH_3$)$NH_2$, —C(O)O-t-butyl, —$CH_2$C(O)O-t-butyl, —$OCH_2CH_2N(CH_3)_2$, morpholinyl, —$CH_2$OC(O)-t-butyl, —CH(=NOH), —CH(=$NOCH_3$), —NHC(O)$CH_2N(CH_3)_2$ and —NHC(O)O-t-butyl.

2. The compound of claim 1, wherein $R^1$ is H or aminoalkyl.

3. The compound of claim 2, wherein $R^1$ is —$CH_2CH_2NH_2$, —$CH_2CH(NH_2)CH_3$, —$CH_2CH_2CH_2NH_2$, —$CH_2CH_2NHCH_3$, —$CH_2CH_2N(CH_3)_2$, —$CH_2CH(N(CH_3)_2)CH_3$, or —$CH_2CH_2CH_2N(CH_3)_2$.

4. The compound of claim 3, wherein $R^1$ is —$CH_2CH_2N(CH_3)_2$.

5. The compound of claim 1, wherein $R^2$ is H or F.

6. The compound of claim 2, wherein $R^2$ is H or F.

7. The compound of claim 1, wherein $R^3$ is nitrogen-containing heteroaryl or nitrogen-containing heterocycloalkenyl.

8. The compound of claim 7, wherein $R^3$ is nitrogen-containing heteroaryl.

9. The compound of claim 8, wherein $R^3$ is:

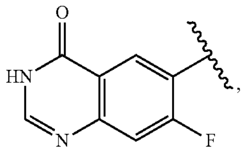
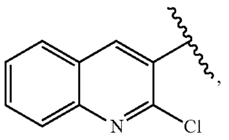
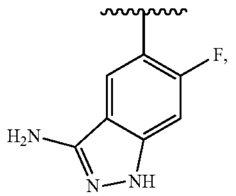
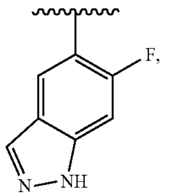
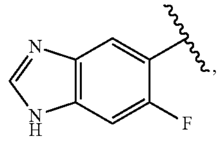
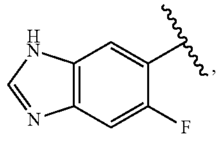
or
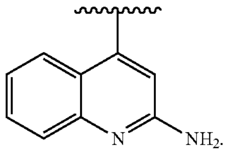

10. The compound of claim 6, wherein $R^3$ is nitrogen-containing heteroaryl or nitrogen-containing heterocycloalkenyl.

11. The compound of claim 10, wherein $R^3$ is nitrogen-containing heteroaryl.

12. The compound of claim 11, wherein $R^3$ is:

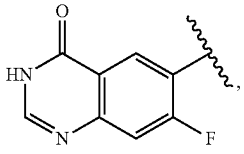
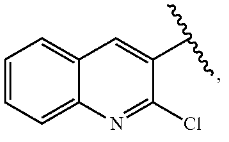
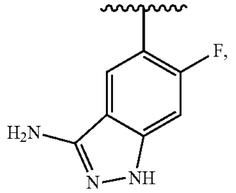
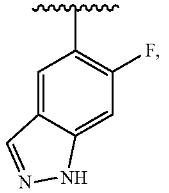

-continued
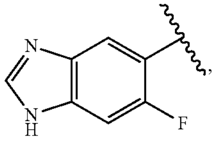
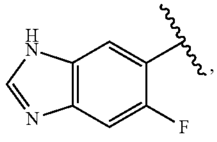
or
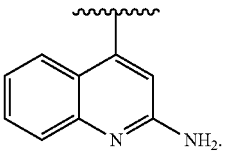
13. The compound of claim 4, wherein $R^2$ is F.
14. The compound of claim 13, wherein $R^3$ is:
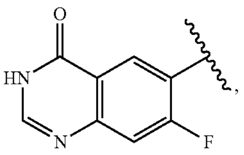
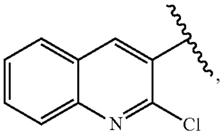
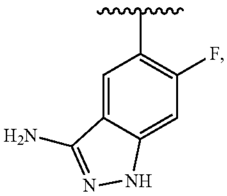
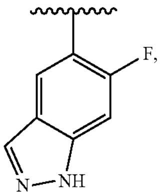
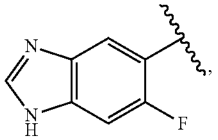
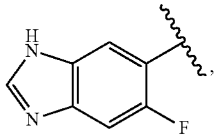
or
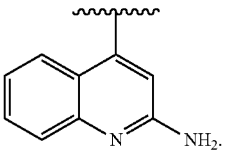
15. A compound having the structure:
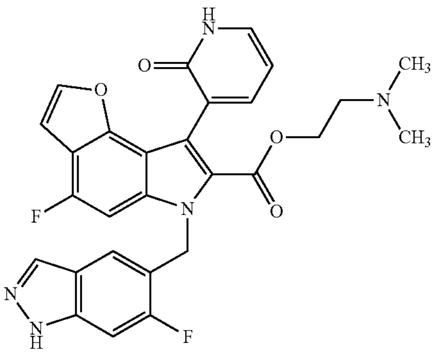
-continued
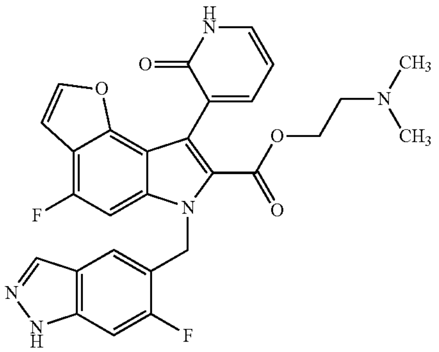
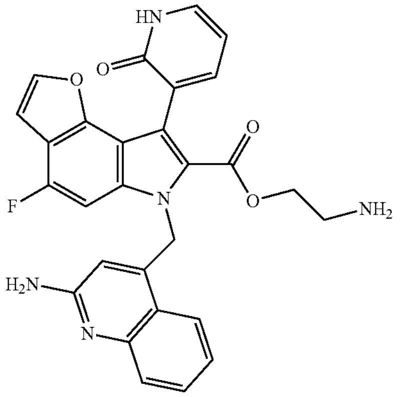
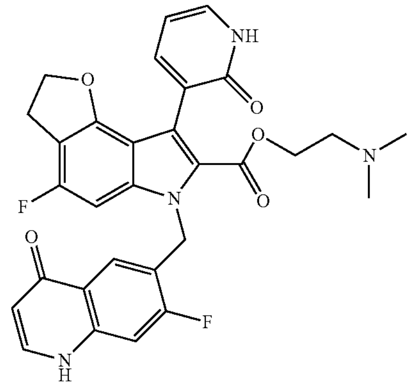
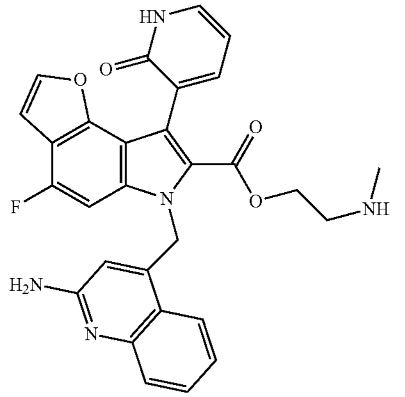

-continued
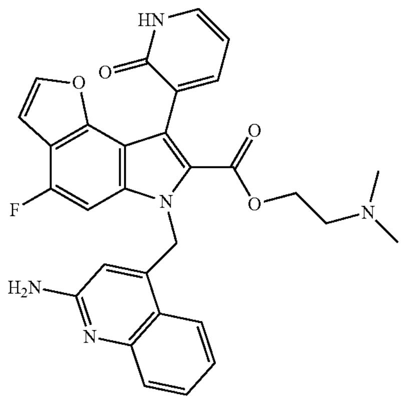
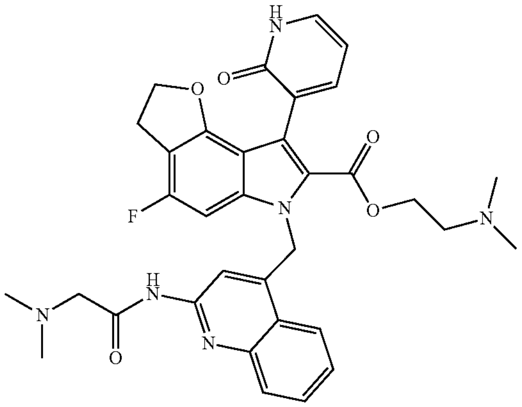
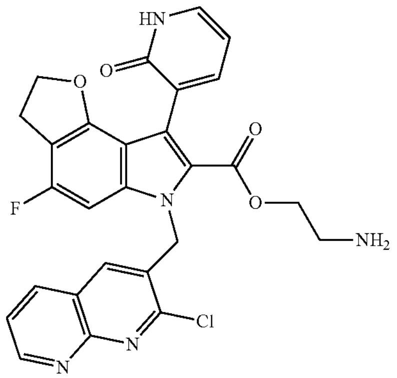
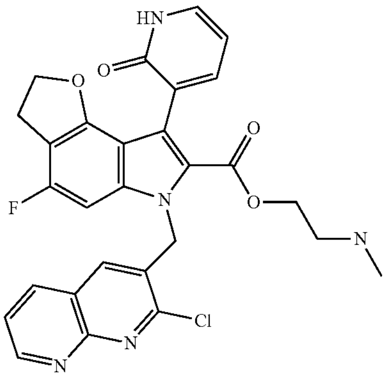
-continued
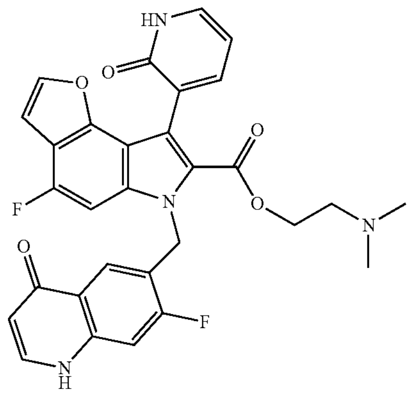
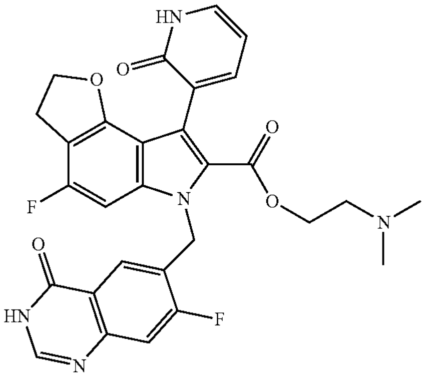
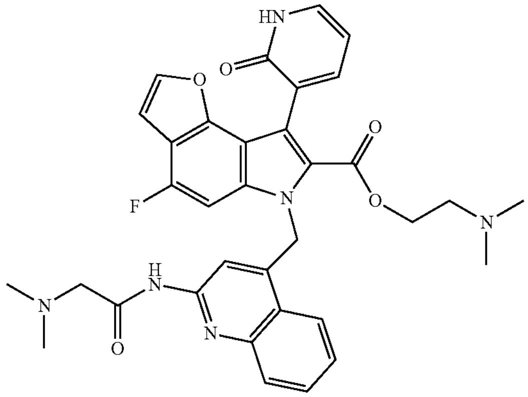
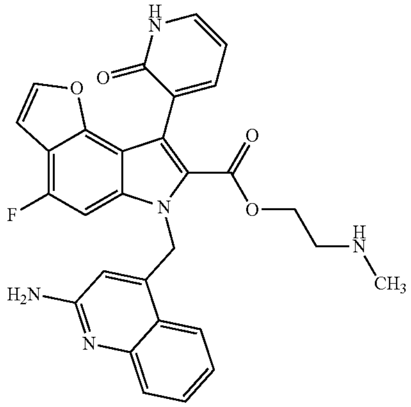 [SMILES: CNCCOC(=O)c1c(-c2ccc[nH]c2=O)c2c3occc3c(F)cc2n1Cc1cc(N)nc2ccccc12]

-continued
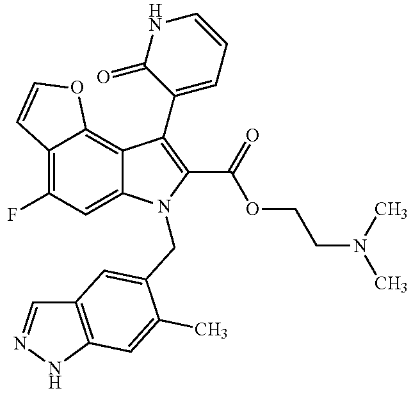 [SMILES: Cc1cc2[nH]ncc2cc1Cn1c(C(=O)OCCN(C)C)c(-c2ccc[nH]c2=O)c2c3occc3c(F)cc21]
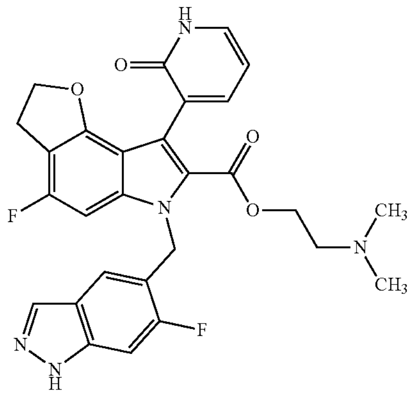 [SMILES: CN(C)CCOC(=O)c1c(-c2ccc[nH]c2=O)c2c3c(c(F)cc2n1Cc1cc2cn[nH]c2cc1F)CCO3]
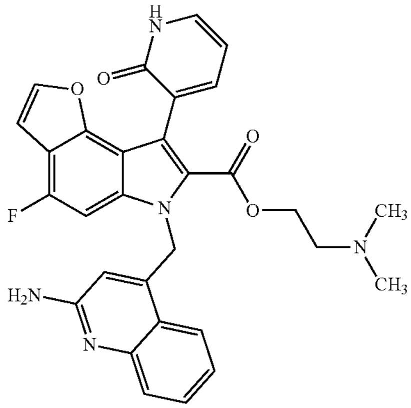 [SMILES: CN(C)CCOC(=O)c1c(-c2ccc[nH]c2=O)c2c3occc3c(F)cc2n1Cc1cc(N)nc2ccccc12]
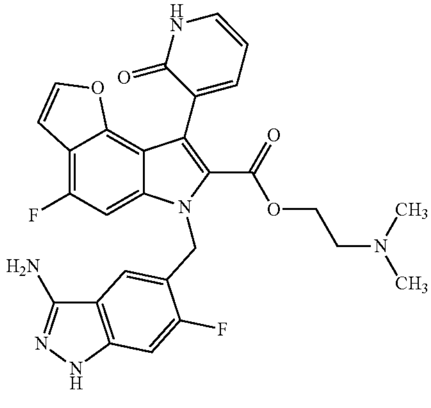 [SMILES: CN(C)CCOC(=O)c1c(-c2ccc[nH]c2=O)c2c3occc3c(F)cc2n1Cc1cc2c(N)n[nH]c2cc1F]
-continued
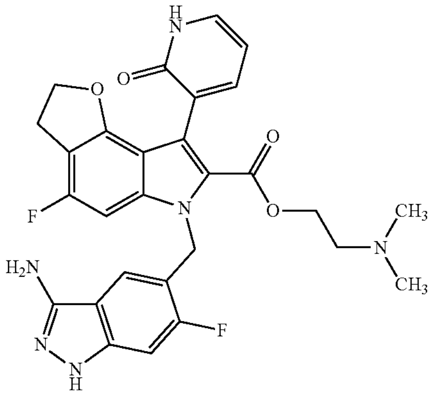
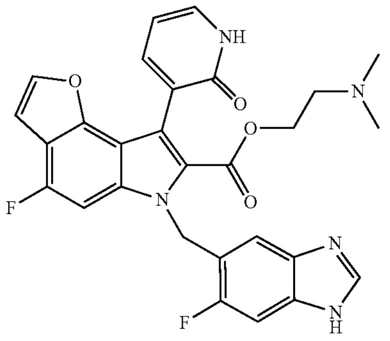
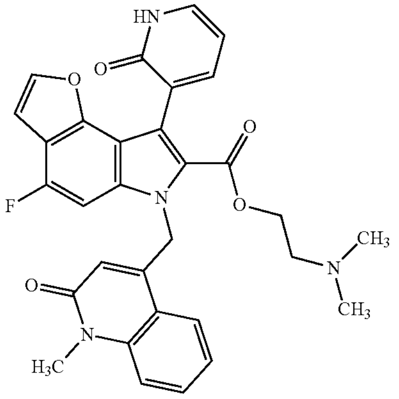 [SMILES: CN(C)CCOC(=O)c1c(-c2ccc[nH]c2=O)c2c3occc3c(F)cc2n1Cc1cc(=O)n(C)c2ccccc12]
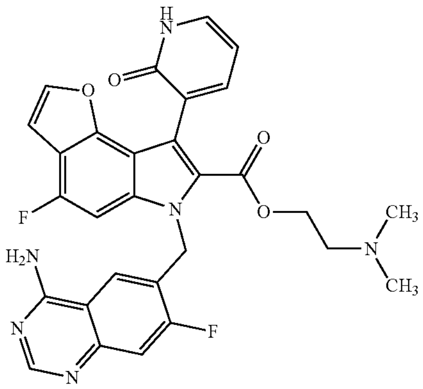 [SMILES: CN(C)CCOC(=O)c1c(-c2ccc[nH]c2=O)c2c3occc3c(F)cc2n1Cc1cc2c(N)ncnc2cc1F]

-continued
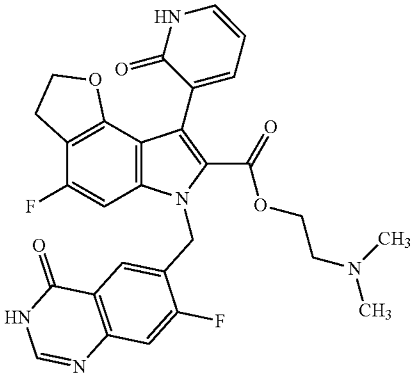
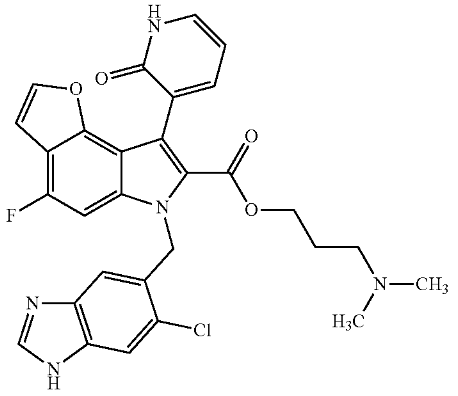
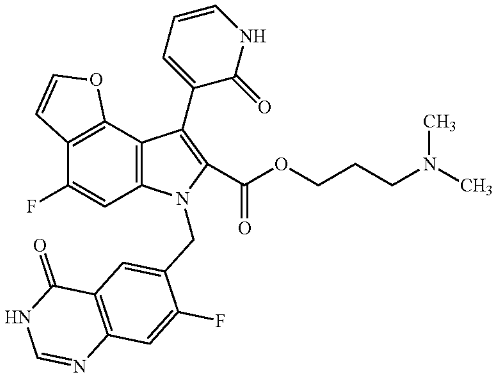 [SMILES: CN(C)CCCOC(=O)c1c(-c2ccc[nH]c2=O)c2c3occc3c(F)cc2n1Cc1cc2c(=O)[nH]cnc2cc1F]
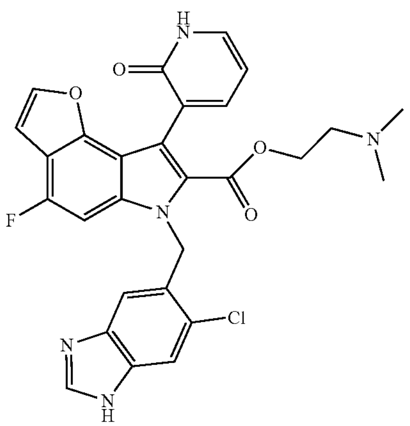
-continued
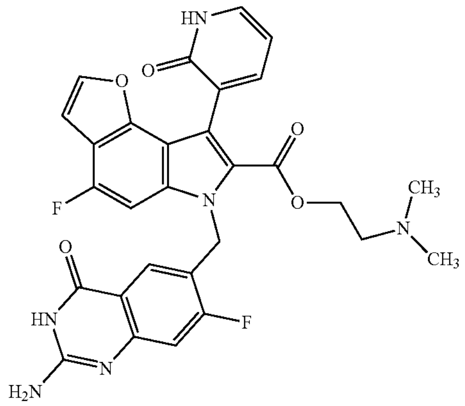
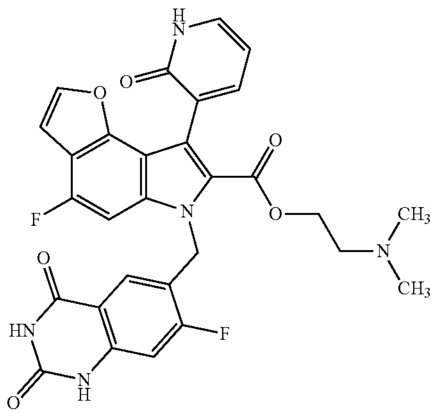
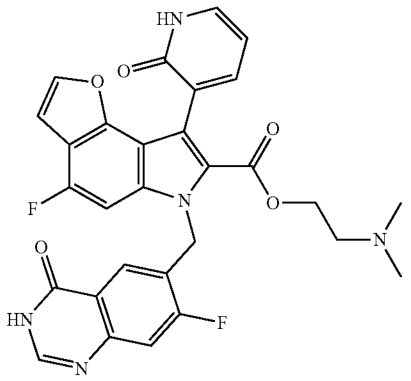
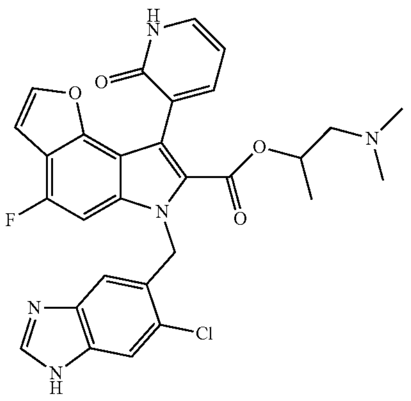

-continued

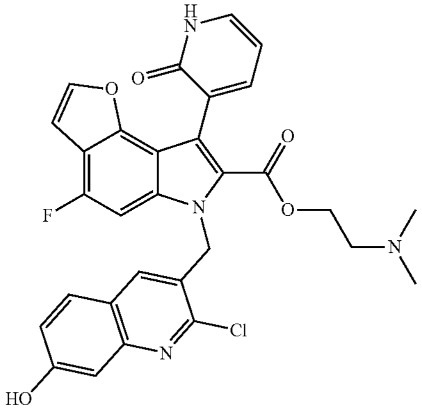 [SMILES: CN(C)CCOC(=O)c1c(-c2ccc[nH]c2=O)c2c3occc3c(F)cc2n1Cc1cc2ccc(O)cc2nc1Cl]

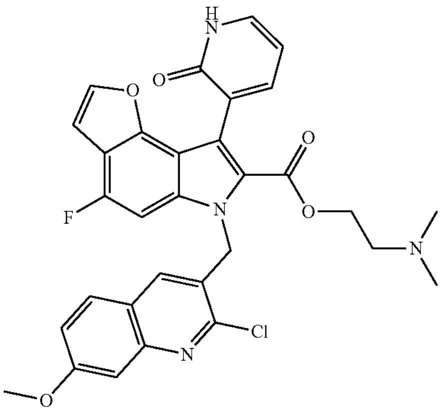

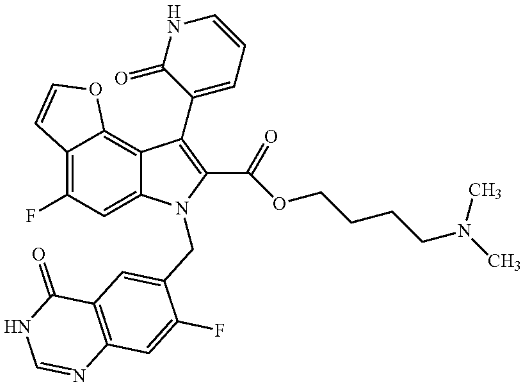 [SMILES: CN(C)CCCCOC(=O)c1c(-c2ccc[nH]c2=O)c2c3occc3c(F)cc2n1Cc1cc2c(=O)[nH]cnc2cc1F]

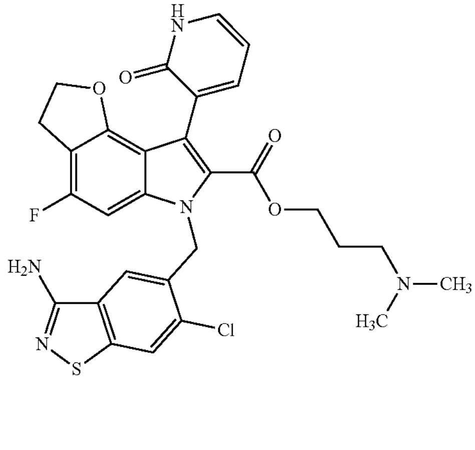 [SMILES: CN(C)CCCOC(=O)c1c(-c2ccc[nH]c2=O)c2c3c(c(F)cc2n1Cc1cc2c(N)nsc2cc1Cl)CCO3]

-continued

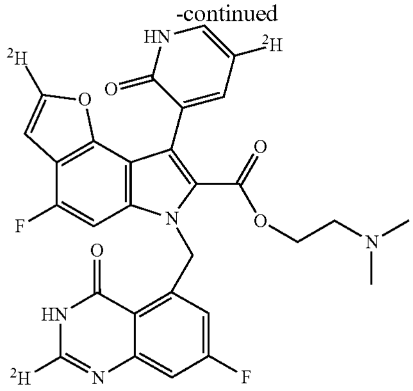

or

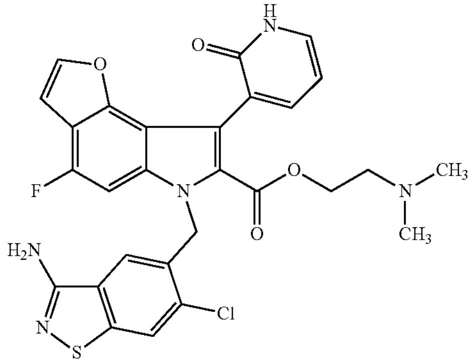 [SMILES: CN(C)CCOC(=O)c1c(-c2ccc[nH]c2=O)c2c3occc3c(F)cc2n1Cc1cc2c(N)nsc2cc1Cl]

or a pharmaceutically acceptable salt thereof.

16. A pharmaceutical composition comprising at least one compound of claim 1 or a pharmaceutically acceptable salt thereof, and at least one pharmaceutically acceptable carrier.

17. The pharmaceutical composition of claim 16, further comprising at least one additional antiviral agent, wherein the additional agent is not a compound of claim 1, and wherein the additional antiviral agents) are selected from: an HCV polymerase inhibitor; an interferon; a RNA replication inhibitor; an antisense agent; a therapeutic vaccine; a protease inhibitor; an antibody therapy (monoclonal or polyclonal); and ribavirin.

18. A compound having the structure

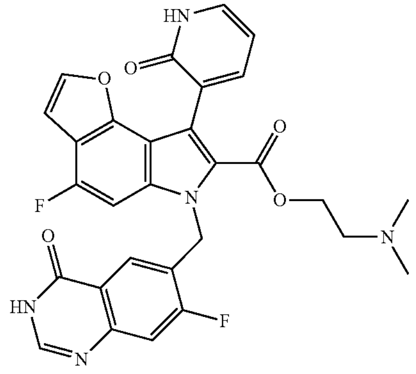 [SMILES: CN(C)CCOC(=O)c1c(-c2ccc[nH]c2=O)c2c3occc3c(F)cc2n1Cc1cc2c(=O)[nH]cnc2cc1F]

or a pharmaceutically acceptable salt thereof.

19. A pharmaceutical composition comprising the compound of claim 18 or a pharmaceutically acceptable salt thereof, and at least one pharmaceutically acceptable carrier.

* * * * *